US011408006B2

(12) United States Patent
Tsuge et al.

(10) Patent No.: US 11,408,006 B2
(45) **Date of Patent: *Aug. 9, 2022**

(54) METHOD FOR PREPARING DNA UNIT COMPOSITION, AND METHOD FOR CREATING CONCATENATED DNA

(71) Applicant: Synplogen Co., Ltd., Kobe (JP)

(72) Inventors: Kenji Tsuge, Tsuruoka (JP); Mitsuhiro Itaya, Tsuruoka (JP)

(73) Assignee: SYNPLOGEN CO., LTD., Kobe (JP)

( * ) Notice: Subject to any disclaimer, the term of this patent is extended or adjusted under 35 U.S.C. 154(b) by 131 days.

This patent is subject to a terminal disclaimer.

(21) Appl. No.: 16/876,956

(22) Filed: May 18, 2020

(65) Prior Publication Data

US 2021/0010007 A1 Jan. 14, 2021

Related U.S. Application Data

(63) Continuation of application No. 15/113,222, filed as application No. PCT/JP2014/073579 on Sep. 5, 2014, now Pat. No. 10,655,133.

(30) Foreign Application Priority Data

Jan. 21, 2014 (JP) ............................ JP2014-008690

(51) Int. Cl.

*C12N 15/64* (2006.01)
*C12N 15/66* (2006.01)
*C12N 15/10* (2006.01)

(52) U.S. Cl.

CPC ............ *C12N 15/64* (2013.01); *C12N 15/10* (2013.01); *C12N 15/66* (2013.01)

(58) Field of Classification Search

CPC ......... C12N 15/10; C12N 15/64; C12N 16/66

See application file for complete search history.

(56) References Cited

U.S. PATENT DOCUMENTS 10,655,133 B2 * 5/2020 Tsuge .................... C12N 15/64
2002/0137134 A1 9/2002 Gerngroww (Continued)

FOREIGN PATENT DOCUMENTS

JP 2004129654 A 4/2004
JP 2006503583 A 2/2006

(Continued)

OTHER PUBLICATIONS

Hiroe et al. Applied and Environmental Microbiology (Year: 2012).*

(Continued)

*Primary Examiner* — Ethan C Whisenant
(74) *Attorney, Agent, or Firm* — Cantor Colburn LLP

(57) ABSTRACT

Provided are: a method for preparing a DNA unit composition in which the mol number of a plurality of DNA units is more uniform, and a method for creating concatenated DNA. The method for preparing a DNA unit composition has: a step for preparing solutions which contain a plurality of DNA units to which an added sequence is linked, and preparing a solution for each type of DNA unit and a step for, after preparing each of the solutions, measuring the concentration of the DNA unit in each of the solutions in a state where the added sequence is linked to the DNA unit, and on the basis of the results thereof, fractionating each of the solutions and making the mol number of the DNA unit in each of the solutions closer to being identical to one another.

16 Claims, 23 Drawing Sheets

Specification includes a Sequence Listing.

(56) References Cited

U.S. PATENT DOCUMENTS

| | | | |
|---|---|---|---|
| 2003/0148420 A1 | 8/2003 | Suzanne et al. |
| 2007/0031920 A1 | 2/2007 | Prentice |
| 2011/0263024 A1 | 10/2011 | Marillonnet et al. |
| 2018/0010156 A1 | 1/2018 | Nomura et al. |

FOREIGN PATENT DOCUMENTS

| | | |
|---|---|---|
| JP | 4479199 B2 | 6/2010 |
| WO | 0214490 A2 | 2/2002 |

OTHER PUBLICATIONS

Itaya et al., Bottom-up genome assembly using the *Bacillus subtilis* genome vector. Nature Methods 5(1) : 41 (Year: 2008).*
Itaya et al., Ch. 4 in the book Microbial Production :From Genome Design to Cell Eng. Springer Japan (Jan. 2014) (Year: 2014).*
Juhas et al. Critical Reviews in Biotechnology37(3):277 (Year: 2017).*
Ninh et al. Biotechnology and Bioengineering 112(1) : 189 (Year: 2015).*
Nishizaki et al., Applied and Environmental Microbiology 73(4) :1355 (Year: 2007).*
Tsuge et al., Nucleic Acids Research 31(21) : e133 (Year: 2003).*
Tsuge et al., J. of Biotechnology 129: 592 (Year: 2007).*
Tsuge et al., Scientific Reports 5 : 10655 (Year: 215).*
Edited by Takaaki Tamura, 4 DNA no Kenshutsu, Kaitei Idenshi Kogaku Jikken Note 1st volume, DNA o Eru [Toriatsukai no Kihon to Chushutsu Seisei Bunri], 2nd edition, 6th print, Yodosha Co., Ltd., 2006, pp. 28 to 29, with partial English translation.
Edited by Yasuko Nishino, Researcher Interview No. 3 Koshi Kenji Tsuge, Keio IAB Research Digest, 2009, vol. 2, pp. 8 to 11.
Hiromichi Sawaki et al., "Development of quantitative PCR array for studying human glycogens expression profiling", Japan Journal of Molecular Tumor Marker Research, 2009, vol. 24, p. 29, with English abstract.
Itaya, M. et al., Construction and Manipulation of Giant DNA by a Genome Vector, Methods in Enzymology, 2011, vol. 498, pp. 427-447, 4.4.
Kenji Tsuge et al., "Genome Builder Oyobi Genome Designer to shite no Kosokin", Journal of the Society for Bioscience and Bioengineering, Japan, 2012, vol. 90, No. 6, pp. 281 to 284.
Mitsuhiro Itaya et al., "Chosa DNA no Gosei to Gosei Seibutsu Kogaku deno Katsuyo", Journal of the Society for Bioscience and Bioengineering, Japan, 2013, vol. 91, No. 6, pp. 319 to 321.
Tsuge, K. et al.. Production of the non-ribosomal peptide plipastatin in Bacillus subtilis regulated by three relevant gene blocks assembled in a single movable DNA segment, Journal of Biotechnology, 2007, vol. 129, pp. 592-603.
International Search Report corresponding to Application No. PCT/JP2014/073579; dated Dec. 9, 2014, with English translation.
Extended European Search Report corresponding to Application No. 14879862.2-1404/3098310 PCT/JP2014073579; dated May 12, 2017.
K. Tsuge et al., "Method of preparing an equimolar DNA mixture for one-step DNA assembly of over 50 fragments," Scientific Reports, May 20, 2015, vol. 5, No. 1, pp. 1-11.
K. Tsuge et al., "One step assembly of multiple DNA fragments with a designed order and orientation in Bacillus subtilis plasmid," Nucleic Acids Research, Information Retrieved Ltd., vol. 31, No. 21, Nov. 1, 2003, pp. 1-8.
R. Godiska et al., "Linear plasmid vector for cloning of repetitive or unstable sequences in *Escherichia coli*," Nucleic Acids Research, Dec. 29, 2009, vol. 38, No. 6, pp. 1-9.
U.S. Final Office Action for U.S. Appl. No. 15/113,222 dated Sep. 24, 2018.
U.S. Non-Final Office Action for U.S. Appl. No. 15/113,222 dated Jun. 27, 2018.
Engler et al., "Golden Gate Shuffling: A One-Pot DNA Shuffling Method Based on Type IIs Restriction Enzymes." PLoS One vol. 4 (Issue 5): e5553 (Year 2009); 9 pages.
Engler et al., "A One Pot, One Step, Precision Cloning Method with High Throughput Capability", PLoS One, vol. 3 (Issue 11); e3647. (Year 2008); 7 pages.
Stemmer et al., "Single-Step assembly of a gene and entire plasmid from large numbers of oligodeoxyribonucleotides" Elsevier Science V.B, SSDI 0378-1119 (95) GO511-0, Gene 164: pp. 49-53 (Year: 1995).
CNIPA First Office Action and Search Report for corresponding CN Application No. 201811310437.X; dated Oct. 20, 2021.
CN Second Office Action for corresponding CN Application No. 201811310437.X; dated May 17, 2022.

* cited by examiner

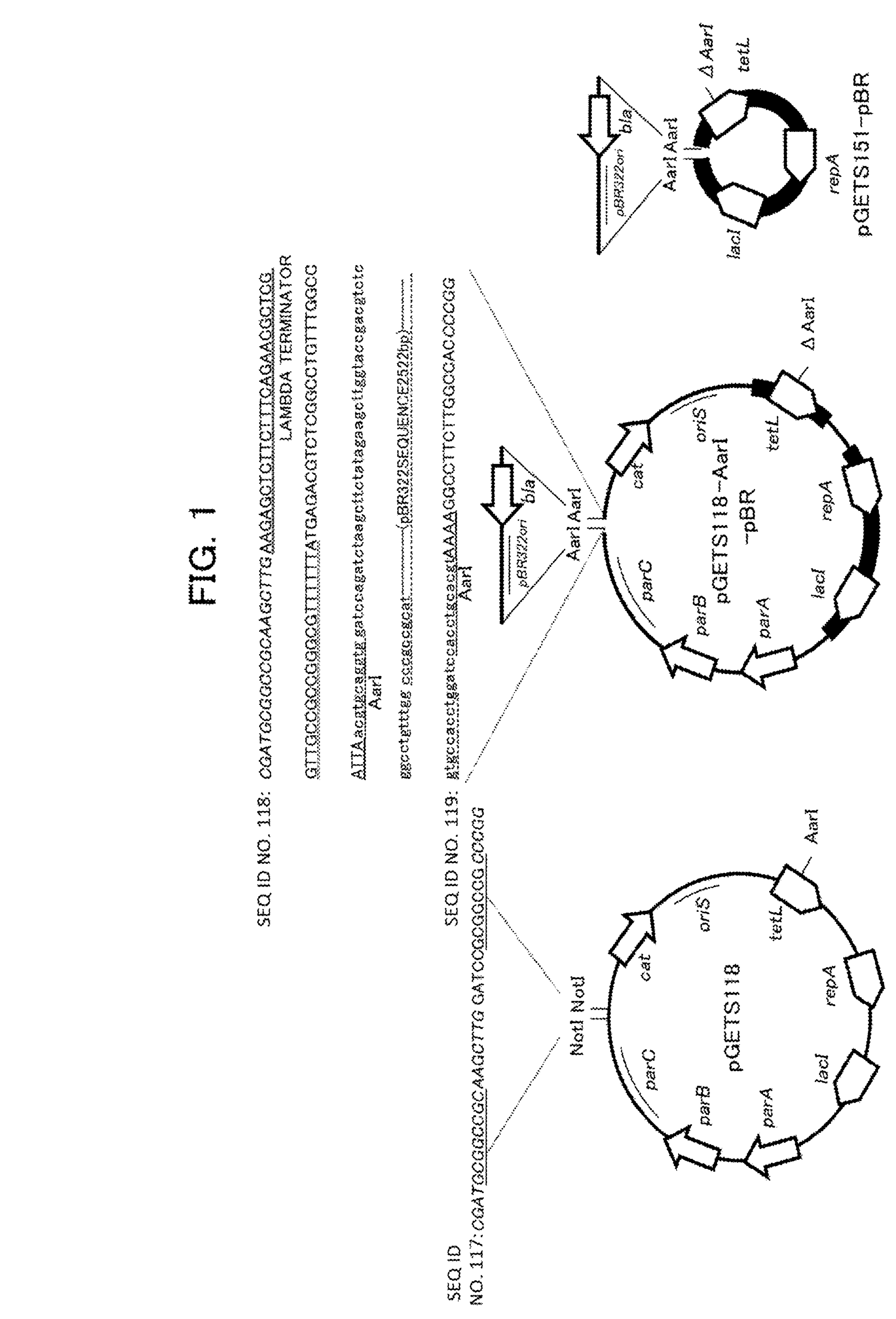

FIG. 1

SEQ ID NO. 118: CGATGCGGCCGCAAGCTTG AAGAGCTCTTCTTTGAGAAGGCTCG
LAMBDA TERMINATOR
GTTGCCGGGGAGGTTTTTATGAGACGTCTCGGCCTGTTTGGCG
ATTAacgtccagatcgatccaagctctagaagcttggtaccgacgtctc
AarI
ggcctgtttgg cccgcgcat ------ (pBR322SEQUENCE2522bp) ------
gtgccacttggatccacttgcagtAAAAGGCCTTCTTGGGCCACCCCGG
AarI SEQ ID NO. 119: gtgccacttggatccacttgcagtAAAAGGCCTTCTTGGGCCACCCCGG

SEQ ID NO. 117: CGATGCGGCCGCAAGCTTG GATCCGCGGGGCGG CCCGG

WILD-TYPE SEQUENCE

```
           9510      9520
SEQ ID NO. 120: ttccagccGgagggcgta
                F  Q  P  E  G  V
```

VARIANT WITH SYNONYMOUS CODON SUBSTITUTION (J02459.1:g.9515G>C)

```
           9510      9520
SEQ ID NO. 121: ttccagccGgagggcgta
                F  Q  P  E  G  V
                       AvaI
```

FIG. 15
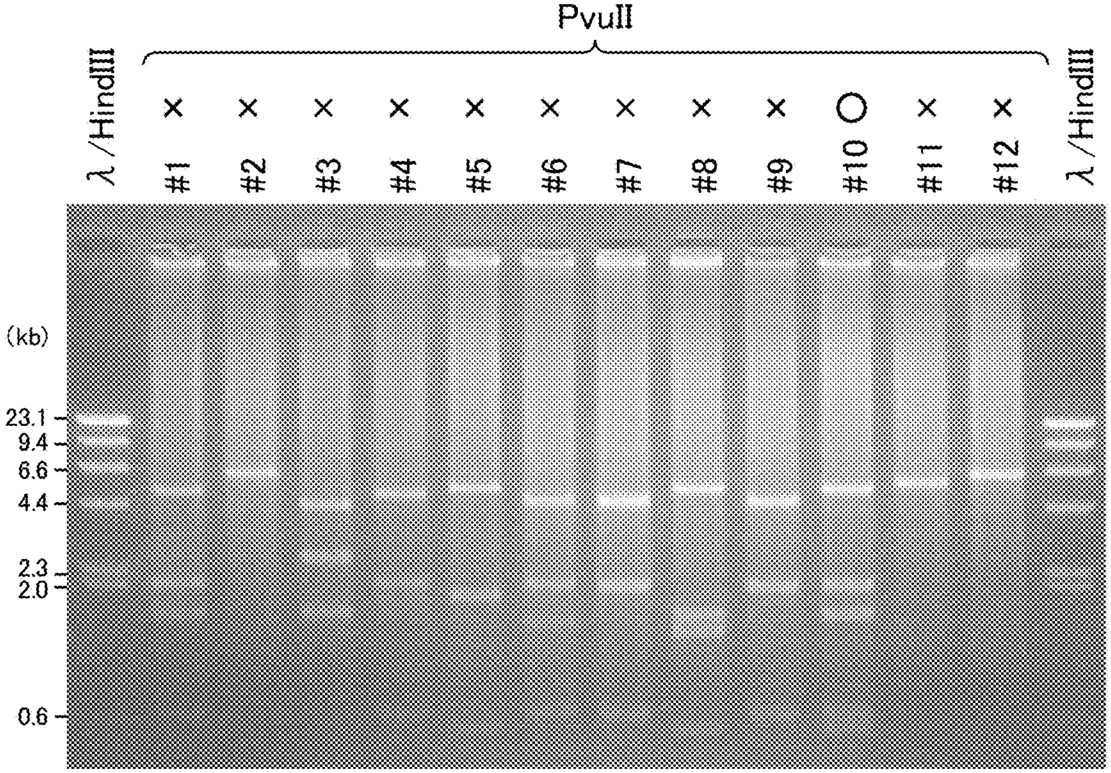
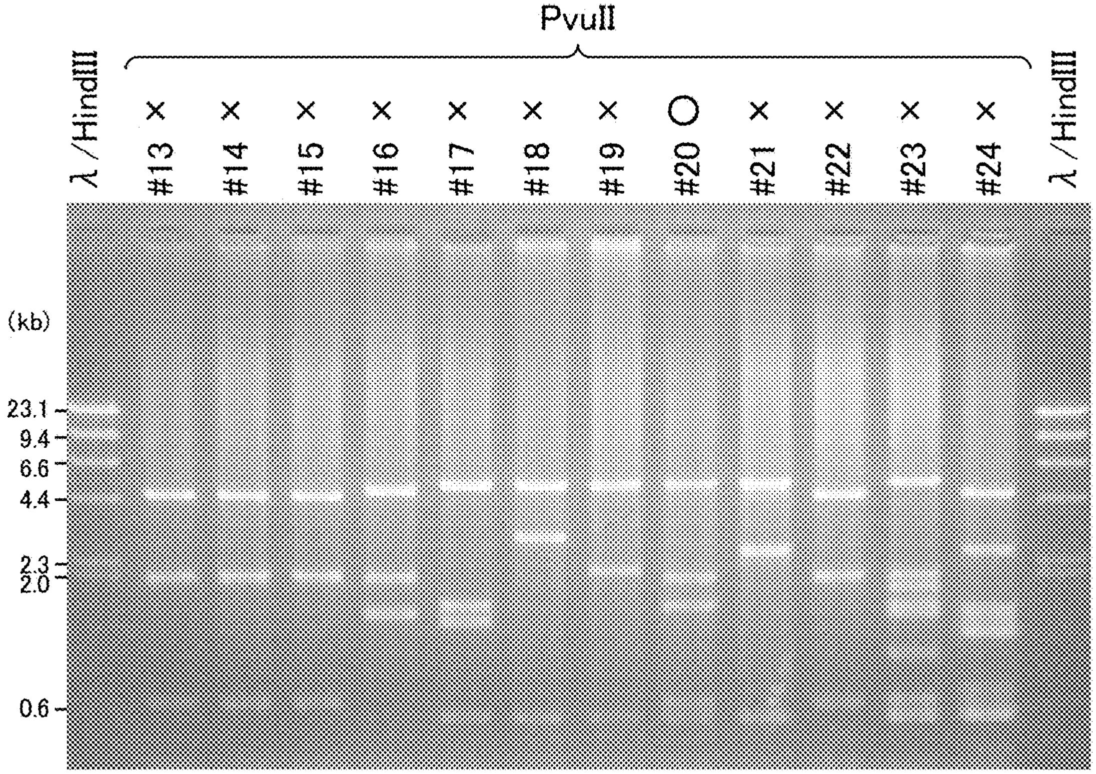

FIG. 18
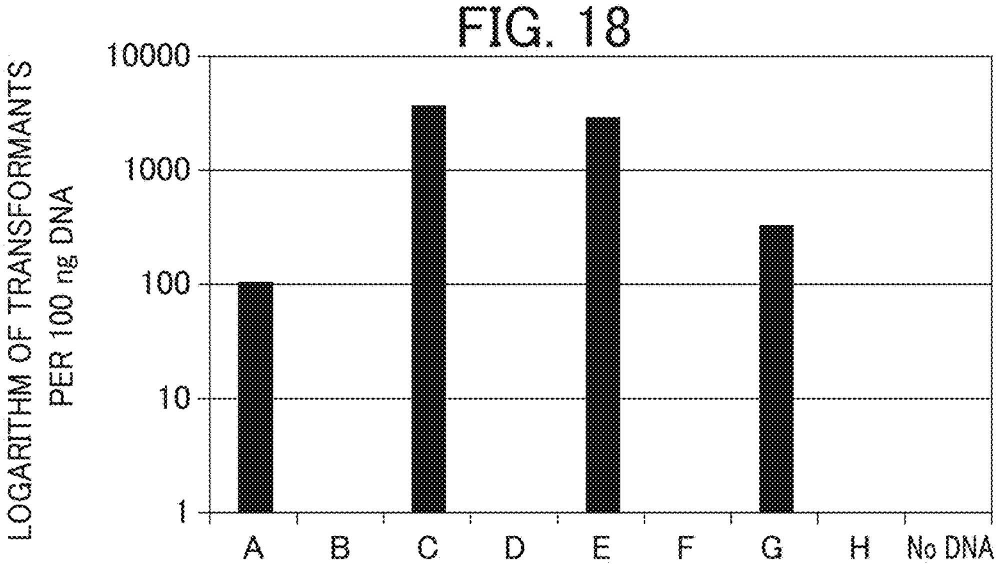
FIG. 19A
FIG. 19B
FIG. 19C
FIG. 19D
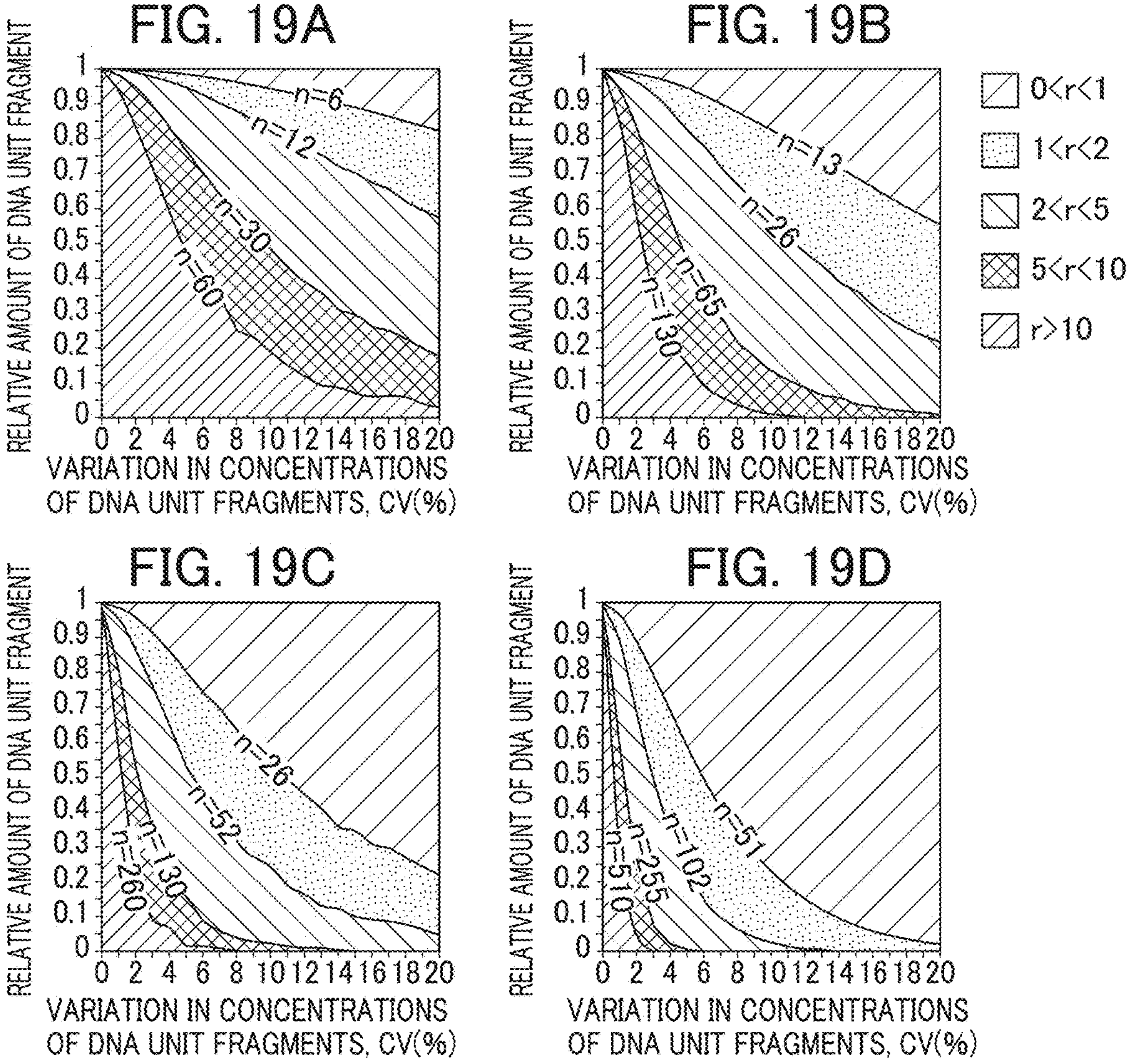

```
                        SEQUENCE LISTING

<160> NUMBER OF SEQ ID NOS: 121

<210> SEQ ID NO 1
<211> LENGTH: 17749
<212> TYPE: DNA
<213> ORGANISM: Artificial Sequence
<220> FEATURE:
<223> OTHER INFORMATION: Artificial plasmid

<400> SEQUENCE: 1

gcggccgcaa gcttgaagag ctcttctttc agaacgctcg gttgccgccg ggcgtttttt      60

atgagacgtc tcggcctgtt tggccattaa cgtgcaggtg gatccagatc taagcttcta     120

tagaagcttg gtaccgacgt ctcggcctgt ttggcccgcc gcatccatac cgccagttgt     180

ttaccctcac aacgttccag taaccgggca tgttcatcat cagtaacccg tatcgtgagc     240

atcctctctc gtttcatcgg tatcattacc cccatgaaca gaaatccccc ttacacggag     300

gcatcagtga ccaaacagga aaaaaccgcc cttaacatgg cccgctttat cagaagccag     360

acattaacgc ttctggagaa actcaacgag ctggacgcgg atgaacaggc agacatctgt     420

gaatcgcttc acgaccacgc tgatgagctt taccgcagct gcctcgcgcg tttcggtgat     480

gacggtgaaa acctctgaca catgcagctc ccgaagacgg tcacagcttg tctgtaagcg     540

gatgccggga gcagacaagc ccgtcagggc gcgtcagcgg gtgttggcgg gtgtcggggc     600

gcagccatga cccagtcacg tagcgatagc ggagtgtata ctggcttaac tatgcggcat     660

cagagcagat tgtactgaga gtgcaccata tgcggtgtga aataccgcac agatgcgtaa     720
```

-continued ggagaaaata ccgcatcagg cactcttccg cttcctcgct cactgactcg ctgcgctcgg 780
tcgttcggct gcggcgagcg gtatcagctc actcaaaggc ggtaatacgg ttatccacag 840
aatcagggga taacgcagga aagaacatgt gagcaaaagg ccagcaaaag gccaggaacc 900
gtaaaaaggc cgcgttgctg gcgtttttcc ataggctccg cccccctgac gagcatcaca 960
aaaatcgacg ctcaagtcag aggtggcgaa acccgacagg actataaaga taccaggcgt 1020
ttccccctgg aagctccctc gtgcgctctc ctgttccgac cctgccgctt accggatacc 1080
tgtccgcctt tctcccttcg ggaagcgtgg cgctttctca tagctcacgc tgtaggtatc 1140
tcagttcggt gtaggtcgtt cgctccaagc tgggctgtgt gcacgaaccc cccgttcagc 1200
ccgaccgctg cgccttatcc ggtaactatc gtcttgagtc caacccggta agacacgact 1260
tatcgccact ggcagcagcc actggtaaca ggattagcag agcgaggtat gtaggcggtg 1320
ctacagagtt cttgaagtgg tggcctaact acggctacac tagaaggaca gtatttggta 1380
tctgcgctct gctgaagcca gttaccttcg gaaaaagagt tggtagctct tgatccggca 1440
aacaaaccac cgctggtagc ggtggttttt ttgtttgcaa gcagcagatt acgcgcagaa 1500
aaaaaggatc tcaagaagat cctttgatct tttctacggg gtctgacgct cagtggaacg 1560
aaaactcacg ttaagggatt ttggtcatga gattatcaaa aaggatcttc acctagatcc 1620
ttttaaatta aaaatgaagt tttaaatcaa tctaaagtat atatgagtaa acttggtctg 1680
acagttacca atgcttaatc agtgaggcac ctatctcagc gatctgtcta tttcgttcat 1740
ccatagttgc ctgactcccc gtcgtgtaga taactacgat acgggagggc ttaccatctg 1800
gccccagtgc tgcaatgata ccgcgagacc cacgctcacc ggctccagat ttatcagcaa 1860
taaaccagcc agccggaagg gccgagcgca gaagtggtcc tgcaacttta tccgcctcca 1920
tccagtctat taattgttgc cgggaagcta gagtaagtag ttcgccagtt aatagtttgc 1980
gcaacgttgt tgccattgct gcaggcatcg tggtgtcacg ctcgtcgttt ggtatggctt 2040
cattcagctc cggttcccaa cgatcaaggc gagttacatg atcccccatg ttgtgcaaaa 2100
aagcggttag ctccttcggt cctccgatcg ttgtcagaag taagttggcc gcagtgttat 2160
cactcatggt tatggcagca ctgcataatt ctcttactgt catgccatcc gtaagatgct 2220
tttctgtgac tggtgagtac tcaaccaagt cattctgaga atagtgtatg cggcgaccga 2280
gttgctcttg cccggcgtca acacgggata ataccgcgcc acatagcaga actttaaaag 2340
tgctcatcat tggaaaacgt tcttcggggc gaaaactctc aaggatctta ccgctgttga 2400
gatccagttc gatgtaaccc actcgtgcac ccaactgatc ttcagcatct tttactttca 2460
ccagcgtttc tgggtgagca aaaacaggaa ggcaaaatgc cgcaaaaaag ggaataaggg 2520
cgacacggaa atgttgaata ctcatactct tcctttttca atattattga agcatttatc 2580
agggttattg tctcatgagc ggatacatat ttgaatgtat ttagaaaaat aaacaaatag 2640
gggttccgcg cacatttccc cgaaaagtgc cacctggatc cacctgcacg taaaaggcct 2700
tcttggccac cccgggccgt cgaccaattc tcatgtttga cagcttatca tcgaatttct 2760
gccattcatc cgcttattat cacttattca ggcgtagcaa ccaggcgttt aagggcacca 2820
ataactgcct taaaaaaatt acgccccgcc ctgccactca tcgcagtact gttgtaattc 2880
attaagcatt ctgccgacat ggaagccatc acaaacggca tgatgaacct gaatcgccag 2940
cggcatcagc accttgtcgc cttgcgtata atatttgccc atggtgaaaa cgggggcgaa 3000
gaagttgtcc atattggcca cgtttaaatc aaaactggtg aaactcaccc agggattggc 3060
tgagacgaaa aacatattct caataaaccc tttagggaaa taggccaggt tttcaccgta 3120

```
acacgccaca tcttgcgaat atatgtgtag aaactgccgg aaatcgtcgt ggtattcact   3180
ccagagcgat gaaaacgttt cagtttgctc atggaaaacg gtgtaacaag ggtgaacact   3240
atcccatatc accagctcac cgtctttcat tgccatacgg aattccggat gagcattcat   3300
caggcgggca agaatgtgaa taaaggccgg ataaaacttg tgcttatttt tctttacggt   3360
ctttaaaaag gccgtaatat ccagctgaac ggtctggtta taggtacatt gagcaactga   3420
ctgaaatgcc tcaaaatgtt ctttacgatg ccattgggat atatcaacgg tggtatatcc   3480
agtgattttt ttctccattt tagcttcctt agctcctgaa aatctcgata actcaaaaaa   3540
tacgcccggt agtgatctta tttcattatg gtgaaagttg gaacctctta cgtgccgatc   3600
aacgtctcat tttcgccaaa agttggccca gggcttcccg gtatcaacag ggacaccagg   3660
atttatttat tctgcgaagt gatcttccgt cacaggtatt tattcgcgat aagctcatgg   3720
agcggcgtaa ccgtcgcaca ggaaggacag agaaagcgcg gatctgggaa gtgacggaca   3780
gaacggtcag gacctggatt ggggaggcgg ttgccgccgc tgctgctgac ggtgtgacgt   3840
tctctgttcc ggtcacacca catacgttcc gccattccta tgcgatgcac atgctgtatg   3900
ccggtatacc gctgaaagtt ctgcaaagcc tgatgggaca taagtccatc agttcaacgg   3960
aagtctacac gaaggttttt gcgctggatg tggctgcccg gcaccgggtg cagtttgcga   4020
tgccggagtc tgatgcggtt gcgatgctga aacaattatc ctgagaataa atgccttggc   4080
ctttatatgg aaatgtggaa ctgagtggat atgctgtttt tgtctgttaa acagagaagc   4140
tggctgttat ccactgagaa gcgaacgaaa cagtcgggaa aatctcccat tatcgtagag   4200
atccgcatta ttaatctcag gagcctgtgt agcgtttata ggaagtagtg ttctgtcatg   4260
atgcctgcaa gcggtaacga aaacgatttg aatatgcctt caggaacaat agaaatcttc   4320
gtgcggtgtt acgttgaagt ggagcggatt atgtcagcaa tggacagaac aacctaatga   4380
acacagaacc atgatgtggt ctgtcctttt acagccagta gtgctcgccg cagtcgagcg   4440
acagggcgaa gccctcgagt gagcgaggaa gcaccaggga acagcactta tatattctgc   4500
ttacacacga tgcctgaaaa aacttccctt ggggttatcc acttatccac ggggatattt   4560
ttataattat ttttttata gtttttagat cttctttttt agagcgcctt gtaggccttt   4620
atccatgctg gttctagaga aggtgttgtg acaaattgcc ctttcagtgt gacaaatcac   4680
cctcaaatga cagtcctgtc tgtgacaaat tgcccttaac cctgtgacaa attgccctca   4740
gaagaagctg ttttttcaca aagttatccc tgcttattga ctcttttta tttagtgtga   4800
caatctaaaa acttgtcaca cttcacatgg atctgtcatg gcggaaacag cggttatcaa   4860
tcacaagaaa cgtaaaaata gcccgcgaat cgtccagtca aacgacctca ctgaggcggc   4920
atatagtctc tcccgggatc aaaaacgtat gctgtatctg ttcgttgacc agatcagaaa   4980
atctgatggc accctacagg aacatgacgg tatctgcgag atccatgttg ctaaatatgc   5040
tgaaatattc ggattgacct ctgcggaagc cagtaaggat atacggcagg cattgaagag   5100
tttcgcgggg aaggaagtgg ttttttatcg ccctgaagag gatgccggcg atgaaaaagg   5160
ctatgaatct ttccttggt ttatcaaacg tgcgcacagt ccatccagag ggctttacag   5220
tgtacatatc aacccatatc tcattccctt ctttatcggg ttacagaacc ggtttacgca   5280
gtttcggctt agtgaaacaa aagaaatcac caatccgtat gccatgcgtt tatacgaatc   5340
cctgtgtcag tatcgtaagc cggatggctc aggcatcgtc tctctgaaaa tcgactggat   5400
catagagcgt taccagctgc ctcaaagtta ccagcgtatg cctgacttcc gccgccgctt   5460
```

-continued cctgcaggtc tgtgttaatg agatcaacag cagaactcca atgcgcctct catacattga 5520
gaaaaagaaa ggccgccaga cgactcatat cgtattttcc ttccgcgata tcacttccat 5580
gacgacagga tagtctgagg gttatctgtc acagatttga gggtggttcg tcacatttgt 5640
tctgacctac tgagggtaat ttgtcacagt tttgctgttt ccttcagcct gcatggattt 5700
tctcatactt tttgaactgt aatttttaag gaagccaaat ttgagggcag tttgtcacag 5760
ttgatttcct tctctttccc ttcgtcatgt gacctgatac gcgtgctacc ttaagagagt 5820
caattcgccc ttcccggtcg atatgaacag cttatttaca taattcacgt tattggtagt 5880
tataaatgaa attcctaata tcggttatga agtgaaattg aatttctact tgatctttct 5940
ctctattttt gtaaaataaa attaagaata tttaaatatt caatgattca tttttgcaga 6000
aatcggagga agaagaatat atgaaaacat ttaacatttc tcaacaagat ccccccatat 6060
tgttgtataa gtgatgaaat actgaattta aaacttagtt tatatgtggt aaaatgtttt 6120
aatcaagttt aggaggaatt aattatgaag tgtaatgaat aatgaatgta acagggttca 6180
attaaaagag ggaagcgtat cattaaccct ataaactacg tctgccctca ttattggagg 6240
gtgaaatgtg aatacatcct attcacaatc gaatttacga cacaaccaaa ttttaatttg 6300
gctttgcatt ttatcttttt ttagcgtatt aaatgaaatg gttttgaacg tctcattacc 6360
tgatattgca aatgatttta ataaaccacc agcgagtaca aactgggtga acacagcctt 6420
tatgttaacc ttttccattg gaacagctgt atatggaaag ctatctgatc aattaggcat 6480
caaaaggtta ctcctatttg gaattataat aaattgtttc gggtcggtaa ttgggtttgt 6540
tggccattct ttcttttcct tacttattat ggctcgtttt attcaagggg ctggtgcagc 6600
tgcatttcca gcactcgtaa tggttgtagt tgcgcgctat attccaaagg aaaatagggg 6660
taaagcattt ggtcttattg gatcgatagt agccatggga gaaggagtcg gtccagcgat 6720
tggtggaatg atagcccatt atattcattg gtcctatctt ctactcattc ctatgataac 6780
aattatcact gttccgtttc ttatgaaatt attaaagaaa gaagtaagga taaaaggtca 6840
ttttgatatc aaaggaatta tactaatgtc tgtaggcatt gtatttttta tgttgtttac 6900
aacatcatat agcatttctt ttcttatcgt tagcgtgctg tcattcctga tatttgtaaa 6960
acatatcagg aaagtaacag atcctttgt tgatcccgga ttagggaaaa atataccttt 7020
tatgattgga gttctttgtg gggaattat atttggaaca gtagcagggt ttgtctctat 7080
ggttccttat atgatgaaag atgttcacca gctaagtact gccgaaatcg gaagtgtaat 7140
tattttccct ggaacaatga gtgtcattat tttcggctac attggtggga tacttgttga 7200
tagaagaggt cctttatacg tgttaaacat cggagttaca tttcttttctg ttagcttttt 7260 aactgcttcc tttcttttag aaacaacatc atggttcatg acaattataa tcgtatttgt 7320
tttaggtggg ctttcgttca ccaaaacagt tatatcaaca attgtttcaa gtagcttgaa 7380
acagcaggaa gctggtgctg gaatgagttt gcttaacttt accagctttt tatcagaggg 7440
aacaggtatt gcaattgtag gtggtttatt atccataccc ttacttgatc aaaggttgtt 7500
acctatggaa gttgatcagt caacttatct gtatagtaat ttgttattac ttttttcagg 7560
aatcattgtc attagttggc tggttacctt gaatgtatat aaacattctc aaagggattt 7620
ctaaatcgtt aagggatcaa ctttgggaga gagttcaaaa ttgatccttt ttttataaca 7680
ggaattgggc atcaaataaa acgaaaggct cagtcgaaag actgggcctt tcgttttatc 7740
tgttgtttgt cggtgaacgc tctcctgagt aggacaaatc cgccgggagc ggatttgaac 7800
gttgcgaagc aacggcccgg agggtggcgg gcaggacgcc cgccataaac tgccaggcat 7860

```
caaattaagc agaaggccat cctgacggat ggccttttg cgtttctaca aactcttcct   7920
gtcgtcatat ctacaattct acacagccca gtccagacta ttcggcactg aaattatggg   7980
tgaagtggtc aagacctcac taggcacctt aaaaatagcg caccctgaag aagatttatt   8040
tgaggtagcc cttgcctacc tagcttccaa gaaagatatc ctaacagcac aagagcggaa   8100
agatgttttg ttctacatcc agaacaacct ctgctaaaat tcctgaaaaa ttttgcaaaa   8160
agttgttgac tttatctaca aggtgtggca taatgtgtgg aattgtgagc ggataacaat   8220
taagctaatt ctatggtaaa agcattcctg aacccaatat ccttattttt agtggacaag   8280
gccttgttct catatggttg cttgagccag tgccttacaa ggctcttccg ctttggcagg   8340
ctgttcaaaa ttatttatta gagcaactca aggaactagg cggagatcca aaagcaaccg   8400
atgcagcacg tgtttttcgg attgctggga gcgtcaatag taagaatgga gcggaagtaa   8460
gagcggaata tcggcacgat tacagatatg agttaaggca gattcaattt gattaccttc   8520
cagaactcaa tgaggttatt aatcccgctc cacaaaagaa aaaacggggg cgtaaaaaga   8580
aagtagttca gttattcaat acctacaaac tccattacgc tcgcctattg gatatagtga   8640
aattggtgga actacgaaat tatgaggtaa ctggatacag ggaaatcatt tgctttttat   8700
accgttattg gttgtgctgt tacacgaacg accctgtaga ggctttaaat caaacacaga   8760
cacttaattt acagttcact gagcctttac ccttaaaaga ggttgaaagg gctacacgga   8820
gcgcagaaaa ggcgtgggaa gcacgaaata acgaagaggc taaccggatt gcaatcgaaa   8880
aaggatatcc cagtgctgga tacaatatta gcaataaaaa gttgattgaa tggctagata   8940
tcacaccaga agaacagaag catttacaga cgattataga cgctaatgag aaacggagaa   9000
gaaagcggga aagggatagg atttatcaag aacaaaaacg tcgtgagcgg ggagatatga   9060
cccgacagga gtatattaag caacaacagg ataaaacaga tgataaatta tttaaattgc   9120
aggagttatt agaacagaat cccaaaatct caaaaattaa attagcaaaa atacttggtg   9180
tagataaatc gcacttatac agactgctga aacaactata actggaaaaa attagtgtct   9240
catggttcgt cgcccttata ttatgggcgt tagcctgctt gctaattgga taggtgttat   9300
tgtcatttca acgtcggacg ttttggtaga tgaacgtcgg acgttatttg cttcaataga   9360
ttgttgatgt attaagggtt gcagtgaatc gacaagcaaa aagttatgac gttgtgaaaa   9420
aattgaatag aaaattggaa attacgtcgg acgttctaac ttaaaaaccc tgttatatca   9480
atgatttaaa aggaaattaa cgtcataaaa gacctttctg caacaaaagt ttttctggaa   9540
gagttgaggt tattttatag gtattatgga cttttgtaga ctttttgtgt actttttgtg   9600
gactccacac tcgctggtat cgtgttattt tttaattgag atatgaatat ggaaattaaa   9660
cgttttaggc gttggtttgg tgatgacaaa aaaataagag tacccgctca caacggatac   9720
tctttcgaga aatgtacgaa acgctataaa taaaaaataa ctagatacat ttacattgta   9780
tcacgtttcg tacatttctc caataacaaa ttgattggag gaatgcaaag tgaataatga   9840
accagtaaaa cgtggtaaga agaacagatg ggaattaaac ctacctataa tgacttatgt   9900
agtagctgat gattggattg ataaactagg acacgaaacg tttactttat ggttgaggtt   9960
ccatacttgg gtagatagag aagatgaact ccgagattat gatcgcatac ctagaagttt  10020
tgagaacata tataaaaaga cactaggaat ctcaaaaagt aagttttata gattgataaa  10080
acctttatgg gaatatggat taatagacat catagaatac gaagaatcta accgtaattc  10140
tactaaacct aaaaatataa ttgtttatga gtatccttta cacgaaatag aaagaaagta  10200
```

-continued

```
taaaccacta gaaaaattaa gagattggga taaagactat aattccgttt ctaaagaatt  10260
aggtaaaaca ggtggtagac caaggaaaaa agatagtgaa gaagaacccg aaaagaaacc  10320
cgaagaagta actaaaaaga aacgtaaata taagttaaaa agagttatcc acaacggttt  10380
caaaaatgaa acggtggagg gtttcaaaaa tgaaacggtg gagggtttca aaaatgaaac  10440
ggtgaccgtt tcaaaaataa aacccaataa ttattcaaat atctttaata acttatcaaa  10500
tatttctact aatgtttcaa ataatttatt aattgatgat gatgaggaaa tcgaaaatga  10560
accaactggt cgtacaataa ataggtcatt actttttttca caagaagata ttaaacaggc  10620
ctatcaattt attaatagat tttcagttat acagttacgt gaaaacttta gctttgataa  10680
acactttgaa gaacggttgg tatgttattt atggaaagca gggatttcta ctttttacac  10740
gcacgaaatc agtaaaatga taaaaaaaat agcagactat gaaaaatcta aaaaaggtag  10800
attaaaccca atacgtgacc gagccttata tatggtaaat ggtcttgtaa tgaatagagc  10860
ttcttcccaa agtgaacatg ctacttataa actaaaccaa tataaaaaac agaaggaaca  10920
ggaaaaacaa caacaggagc aacaaagatc aagagtaccg ttctataatt ggttggagga  10980
aagagaagaa caaaccgaag gtcaactacc caccacttaa agcctaacgg cttttgaagt  11040
ggggcttgta aaaagcccta gttgactacc ccaagtcttt cgaggactac gttggaaagg  11100
tcatgacacc tacaaatgct cctctagttc gtagccactg tcgttgatgg ttaaaagtcc  11160
tgatgggtag ggacggtgct gtcaacatca caagcccttc caacatgggg gaagaggaag  11220
aacactccga gaaaggaggg ggctgtcgta cacgccttgt tcgtgtacgt gatttttaac  11280
acttttatct ctaatataat ctctccttga gttagcagag actaagaata aaacacatta  11340
ggatttttta tctacataag gaggttcaat acatgcctac tatttcgttt aagggaaagt  11400
cttttgtaca aaatcatcac ttgactgtaa aatatcatga attgatccca gaaccagaaa  11460
aaagtctgac cgataaagtt agtcttcatg acaatcttat cattcatggg gacaatttaa  11520
aggcgttgaa agctctacta cctacatatg ctggtaagat agattgcatc tatattgacc  11580
caccatacaa tactggaact gaaaaatgga tttataatga taatgtcaac tccccaatga  11640
ttagggaatg gcttggaaaa gtggtagaca aagaagactt atcccgacat gataagtggc  11700
tttgtatgat gatgccgagg ttaaaactgt tgaaagagtt gttgtcagaa gacggagtga  11760
tatttgtaag cattgactac aatgaaatac accatcttac gtgccttatg aacgaaatat  11820
tcggtgagga gaattttcgt gacgctatta tcattcgtag aggagtaaaa aatgttcaag  11880
cgcaatttga cacaattgat tctctttcaa atggttatga gtctattttg gtttacacta  11940
aacagccatc tcgacgattt aataaggttt atgaagatgt agaagaaaag cctggtagtt  12000
ggaataatca ttggagaggt acagaccgta aaactatgag atatgaatta tttggggtta  12060
ctccgacaga aggtcaatgg agatggggga aagaacgtag tctccaggct attgaaaact  12120
atcaaatgat gttagatgaa cttagacaaa aaggcattac taatccaact caagaggata  12180
ttgataaatg gtatcttgaa tatgtagaaa ataatgggga agatattgac ttgttacgac  12240
aaaatgataa tggcacgatt gagcactttg ttccaccgac tagcaaaaag ttgttaagta  12300
atgcctggtt tgacttaaaa cccaacggtt ctagtcaatt aaagaagata tttggaagga  12360
aggttttcga taaccctaaa tcaattgatt tggtaaaaag actaatacaa tttgcgactg  12420
aaaacaaaga agcgattgta cttgactcat ttgcagggag tggcactact gctcatgcag  12480
tattatcgct taacaaacaa gatggaggga atcgtcgttt catccttatt gagatggaag  12540
aatatgcaca tgagattacc gcagaacgcg gatctttatc gatttgcatg caagctaatt  12600
```

cggtggaaac gaggtcatca tttccttccg aaaaaacggt tgcatttaaa tcttacatat 12660
gtaatacttt caaagactac atttgtaaga tttgatgttt gagtcggctg aaagatcgta 12720
cgtaccaatt attgtttcgt gattgttcaa gccataacac tgtagggata gtggaaagag 12780
tgcttcatct ggttacgatc aatcaaatat tcaaacggag ggagacgatt ttgatgaaac 12840
cagtaacgtt atacgatgtc gcagagtatg ccggtgtctc ttatcagacc gtttcccgcg 12900
tggtgaacca ggccagccac gtttctgcga aaacgcggga aaaagtggaa gcggcgatgg 12960
cggagctgaa ttacattccc aaccgcgtgg cacaacaact ggcgggcaaa cagtcgttgc 13020
tgattggcgt tgccacctcc agtctggccc tgcacgcgcc gtcgcaaatt gtcgcggcga 13080
ttaaatctcg cgccgatcaa ctgggtgcca gcgtggtggt gtcgatggta gaacgaagcg 13140
gcgtcgaagc ctgtaaaacg gcggtgcaca atcttctcgc gcaacgcgtc agtgggctga 13200
tcattaacta tccgctggat gaccaggatg ccattgctgt ggaagctgcc tgcactaatg 13260
ttccggcgtt atttcttgat gtctctgacc agacacccat caacagtatt attttctccc 13320
atgaagacgg tacgcgactg ggcgtggagc atctggtcgc attgggtcac cagcaaatcg 13380
cgctgttagc gggcccatta agttctgtct cggcgcgtct gcgtctggct ggctggcata 13440
aatatctcac tcgcaatcaa attcagccga tagcggaacg ggaaggcgac tggagtgcca 13500
tgtccggttt tcaacaaacc atgcaaatgc tgaatgaggg catcgttccc actgcgatgc 13560
tggttgccaa cgatcagatg gcgctgggcg caatgcgcgc cattaccgag tccgggctgc 13620
gcgttggtgc ggatatctcg gtagtgggat acgacgatac cgaagacagc tcatgttata 13680
tcccgccgtt aaccaccatc aaacaggatt ttcgcctgct ggggcaaacc agcgtggacc 13740
gcttgctgca actctctcag ggccaggcgg tgaagggcaa tcagctgttg cccgtctcac 13800
tggtgaaaag aaaaaccacc ctggcgccca atacgcaaac cgcctctccc cgcgcgttgg 13860
ccgattcatt aatgcagctg gcacgacagg tttcccgact ggaaagcggg cagtgagcgc 13920
aacgcaatta atgtgagtta ggatcgctac cttaagagag acgcgttatc ggggggttagt 13980 tcgtcatcat tgatgagggt tgattatcac agtttattac tctgaattgg ctatccgcgt 14040
gtgtacctct acctggagtt tttcccacgg tggatatttc ttcttgcgct gagcgtaaga 14100
gctatctgac agaacagttc ttctttgctt cctcgccagt tcgctcgcta tgctcggtta 14160
cacggctgcg gcgagcgcta gtgataataa gtgactgagg tatgtgctct tcttatctcc 14220
ttttgtagtg ttgctcttat tttaaacaac tttgcggttt tttgatgact ttgcgatttt 14280
gttgttgctt tgcagtaaat tgcaagattt aataaaaaaa cgcaaagcaa tgattaaagg 14340
atgttcagaa tgaaactcat ggaaacactt aaccagtgca taaacgctgg tcatgaaatg 14400
acgaaggcta tcgccattgc acagtttaat gatgacagcc cggaagcgag gaaaataacc 14460
cggcgctgga gaataggtga agcagcggat ttagttgggg tttcttctca ggctatcaga 14520
gatgccgaga aagcagggcg actaccgcac ccggatatgg aaattcgagg acgggttgag 14580
caacgtgttg gttatacaat tgaacaaatt aatcatatgc gtgatgtgtt tggtacgcga 14640
ttgcgacgtg ctgaagacgt atttccaccg gtgatcgggg ttgctgccca taaaggtggc 14700
gtttacaaaa cctcagtttc tgttcatctt gctcaggatc tggctctgaa ggggctacgt 14760
gttttgctcg tggaaggtaa cgacccccag ggaacagcct caatgtatca cggatgggta 14820
ccagatcttc atattcatgc agaagacact ctcctgcctt tctatcttgg ggaaaaggac 14880
gatgtcactt atgcaataaa gcccacttgc tggccggggc ttgacattat tccttcctgt 14940

-continued

```
ctggctctgc accgtattga aactgagtta atgggcaaat ttgatgaagg taaactgccc  15000
accgatccac acctgatgct ccgactggcc attgaaactg ttgctcatga ctatgatgtc  15060
atagttattg acagcgcgcc taacctgggt atcggcacga ttaatgtcgt atgtgctgct  15120
gatgtgctga ttgttcccac gcctgctgag ttgtttgact acacctccgc actgcagttt  15180
ttcgatatgc ttcgtgatct gctcaagaac gttgatctta aagggttcga gcctgatgta  15240
cgtattttgc ttaccaaata cagcaatagt aatggctctc agtccccgtg gatggaggag  15300
caaattcggg atgcctgggg aagcatggtt ctaaaaaatg ttgtacgtga aacggatgaa  15360
gttggtaaag gtcagatccg gatgagaact gtttttgaac aggccattga tcaacgctct  15420
tcaactggtg cctggagaaa tgctctttct atttgggaac ctgtctgcaa tgaaattttc  15480
gatcgtctga ttaaaccacg ctgggagatt agataatgaa gcgtgcgcct gttattccaa  15540
aacatacgct caatactcaa ccggttgaag atacttcgtt atcgacacca gctgccccga  15600
tggtggattc gttaattgcg cgcgtaggag taatggctcg cggtaatgcc attactttgc  15660
ctgtatgtgg tcgggatgtg aagtttactc ttgaagtgct ccggggtgat agtgttgaga  15720
agacctctcg ggtatggtca ggtaatgaac gtgaccagga gctgcttact gaggacgcac  15780
tggatgatct catcccttct tttctactga ctggtcaaca gacaccggcg ttcggtcgaa  15840
gagtatctgg tgtcatagaa attgccgatg ggagtcgccg tcgtaaagct gctgcactta  15900
ccgaaagtga ttatcgtgtt ctggttggcg agctggatga tgagcagatg gctgcattat  15960
ccagattggg taacgattat cgcccaacaa gtgcttatga acgtggtcag cgttatgcaa  16020
gccgattgca gaatgaattt gctggaaata tttctgcgct ggctgatgcg gaaaatattt  16080
cacgtaagat tattacccgc tgtatcaaca ccgccaaatt gcctaaatca gttgttgctc  16140
tttttctca ccccggtgaa ctatctgccc ggtcaggtga tgcacttcaa aaagccttta  16200
cagataaaga ggaattactt aagcagcagg catctaacct tcatgagcag aaaaaagctg  16260
gggtgatatt tgaagctgaa gaagttatca ctcttttaac ttctgtgctt aaaacgtcat  16320
ctgcatcaag aactagttta agctcacgac atcagtttgc tcctggagcg acagtattgt  16380
ataagggcga taaaatggtg cttaacctgg acaggtctcg tgttccaact gagtgtatag  16440
agaaaattga ggccattctt aaggaacttg aaaagccagc accctgatgc gaccacgttt  16500
tagtctacgt ttatctgtct ttacttaatg tcctttgtta caggccagaa agcataactg  16560
gcctgaatat tctctctggg cccactgttc cacttgtatc gtcggtctga taatcagact  16620
gggaccacgg tcccactcgt atcgtcggtc tgattattag tctgggacca cggtcccact  16680
cgtatcgtcg gtctgattat tagtctggga ccacggtccc actcgtatcg tcggtctgat  16740
aatcagactg ggaccacggt cccactcgta tcgtcggtct gattattagt ctgggaccat  16800
ggtcccactc gtatcgtcgg tctgattatt agtctgggac cacggtccca ctcgtatcgt  16860
cggtctgatt attagtctgg aaccacggtc ccactcgtat cgtcggtctg attattagtc  16920
tgggaccacg gtcccactcg tatcgtcggt ctgattatta gtctgggacc acgatcccac  16980
tcgtgttgtc ggtctgatta tcggtctggg accacggtcc cacttgtatt gtcgatcaga  17040
ctatcagcgt gagactacga ttccatcaat gcctgtcaag ggcaagtatt gacatgtcgt  17100
cgtaacctgt agaacggagt aacctcggtg tgcggttgta tgcctgctgt ggattgctgc  17160
tgtgtcctgc ttatccacaa cattttgcgc acggttatgt ggacaaaata cctggttacc  17220
caggccgtgc cggcacgtta accgggctgc atccgatgca agtgtgtcgc tgtcgacgag  17280
ctcgcgagct cggacatgag gttgccccgt attcagtgtc gctgatttgt attgtctgaa  17340
```

gttgttttta cgttaagttg atgcagatca attaatacga tacctgcgtc ataattgatt 17400
atttgacgtg gtttgatggc ctccacgcac gttgtgatat gtagatgata atcattatca 17460
ctttacgggt cctttccggt gatccgacag gttacggggc ggcgacctcg cgggttttcg 17520
ctatttatga aaattttccg gtttaaggcg tttccgttct tcttcgtcat aacttaatgt 17580
ttttatttaa aataccctct gaaaagaaag gaaacgacag gtgctgaaag cgagcttttt 17640
ggcctctgtc gtttcctttc tctgtttttg tccgtggaat gaacaatgga agtccgagct 17700
catcgctaat aacttcgtat agcatacatt atacgaagtt atattcgat 17749

<210> SEQ ID NO 2
<211> LENGTH: 6912
<212> TYPE: DNA
<213> ORGANISM: Artificial Sequence
<220> FEATURE:
<223> OTHER INFORMATION: Artificial plasmid

<400> SEQUENCE: 2
gcggccgcaa gcttgaagag ctcttctttc agaacgctcg gttgccgccg ggcgtttttt 60
atgagacgtc tcggcctgtt tggccattaa cgtgcaggtg gatccagatc taagcttcta 120
tagaagcttg gtaccgacgt ctcggcctgt ttggcccgcc gcatcccatac cgccagttgt 180 ttaccctcac aacgttccag taaccgggca tgttcatcat cagtaacccg tatcgtgagc 240
atcctctctc gtttcatcgg tatcattacc cccatgaaca gaaatccccc ttacacggag 300
gcatcagtga ccaaacagga aaaaaccgcc cttaacatgg cccgctttat cagaagccag 360
acattaacgc ttctggagaa actcaacgag ctggacgcgg atgaacaggc agacatctgt 420
gaatcgcttc acgaccacgc tgatgagctt taccgcagct gcctcgcgcg tttcggtgat 480
gacggtgaaa acctctgaca catgcagctc ccgaagacgg tcacagcttg tctgtaagcg 540
gatgccggga gcagacaagc ccgtcagggc gcgtcagcgg gtgttggcgg gtgtcggggc 600
gcagccatga cccagtcacg tagcgatagc ggagtgtata ctggcttaac tatgcggcat 660
cagagcagat tgtactgaga gtgcaccata tgcggtgtga aataccgcac agatgcgtaa 720
ggagaaaata ccgcatcagg cactcttccg cttcctcgct cactgactcg ctgcgctcgg 780
tcgttcggct gcggcgagcg gtatcagctc actcaaaggc ggtaatacgg ttatccacag 840
aatcagggga taacgcagga aagaacatgt gagcaaaagg ccagcaaaag gccaggaacc 900
gtaaaaaggc cgcgttgctg gcgtttttcc ataggctccg cccccctgac gagcatcaca 960
aaaatcgacg ctcaagtcag aggtggcgaa acccgacagg actataaaga taccaggcgt 1020
ttccccctgg aagctccctc gtgcgctctc ctgttccgac cctgccgctt accggatacc 1080
tgtccgcctt tctcccttcg ggaagcgtgg cgctttctca tagctcacgc tgtaggtatc 1140
tcagttcggt gtaggtcgtt cgctccaagc tgggctgtgt gcacgaaccc cccgttcagc 1200
ccgaccgctg cgccttatcc ggtaactatc gtcttgagtc caacccggta agacacgact 1260
tatcgccact ggcagcagcc actggtaaca ggattagcag agcgaggtat gtaggcggtg 1320
ctacagagtt cttgaagtgg tggcctaact acggctacac tagaaggaca gtatttggta 1380
tctgcgctct gctgaagcca gttaccttcg gaaaaagagt tggtagctct tgatccggca 1440
aacaaaccac cgctggtagc ggtggttttt ttgtttgcaa gcagcagatt acgcgcagaa 1500
aaaaaggatc tcaagaagat cctttgatct tttctacggg gtctgacgct cagtggaacg 1560
aaaactcacg ttaagggatt ttggtcatga gattatcaaa aaggatcttc acctagatcc 1620

-continued

```
ttttaaatta aaaatgaagt tttaaatcaa tctaaagtat atatgagtaa acttggtctg   1680
acagttacca atgcttaatc agtgaggcac ctatctcagc gatctgtcta tttcgttcat   1740
ccatagttgc ctgactcccc gtcgtgtaga taactacgat acgggagggc ttaccatctg   1800
gccccagtgc tgcaatgata ccgcgagacc cacgctcacc ggctccagat ttatcagcaa   1860
taaaccagcc agccggaagg gccgagcgca gaagtggtcc tgcaacttta tccgcctcca   1920
tccagtctat taattgttgc cgggaagcta gagtaagtag ttcgccagtt aatagtttgc   1980
gcaacgttgt tgccattgct gcaggcatcg tggtgtcacg ctcgtcgttt ggtatggctt   2040
cattcagctc cggttcccaa cgatcaaggc gagttacatg atcccccatg ttgtgcaaaa   2100
aagcggttag ctccttcggt cctccgatcg ttgtcagaag taagttggcc gcagtgttat   2160
cactcatggt tatggcagca ctgcataatt ctcttactgt catgccatcc gtaagatgct   2220
tttctgtgac tggtgagtac tcaaccaagt cattctgaga atagtgtatg cggcgaccga   2280
gttgctcttg cccggcgtca acacgggata ataccgcgcc acatagcaga actttaaaag   2340
tgctcatcat tggaaaacgt tcttcggggc gaaaactctc aaggatctta ccgctgttga   2400
gatccagttc gatgtaaccc actcgtgcac ccaactgatc ttcagcatct tttactttca   2460
ccagcgtttc tgggtgagca aaaacaggaa ggcaaaatgc cgcaaaaaag ggaataaggg   2520
cgacacggaa atgttgaata ctcatactct tcctttttca atattattga agcatttatc   2580
agggttattg tctcatgagc ggatacatat ttgaatgtat ttagaaaaat aaacaaatag   2640
gggttccgcg cacatttccc cgaaaagtgc cacctggatc cacctgcacg taaaaggcct   2700
tcttggccgc ccttcccggt cgatatgaac agcttattta cataattcac gttattggta   2760
gttataaatg aaattcctaa tatcggttat gaagtgaaat tgaatttcta cttgatcttt   2820
ctctctattt ttgtaaaata aaattaagaa tatttaaata ttcaatgatt catttttgca   2880
gaaatcggag gaagaagaat atatgaaaac atttaacatt tctcaacaag atccccccat   2940
attgttgtat aagtgatgaa atactgaatt taaaacttag tttatatgtg gtaaaatgtt   3000
ttaatcaagt ttaggaggaa ttaattatga agtgtaatga ataatgaatg taacagggtt   3060
caattaaaag agggaagcgt atcattaacc ctataaacta cgtctgccct cattattgga   3120
gggtgaaatg tgaatacatc ctattcacaa tcgaatttac gacacaacca aattttaatt   3180
tggctttgca ttttatcttt ttttagcgta ttaaatgaaa tggttttgaa cgtctcatta   3240
cctgatattg caaatgattt taataaacca ccagcgagta caaactgggt gaacacagcc   3300
tttatgttaa cctttttccat tggaacagct gtatatggaa agctatctga tcaattaggc   3360
atcaaaaggt tactcctatt tggaattata ataaattgtt tcgggtcggt aattgggttt   3420
gttggccatt ctttctttc cttacttatt atggctcgtt ttattcaagg ggctggtgca   3480
gctgcatttc cagcactcgt aatggttgta gttgcgcgct atattccaaa ggaaaatagg   3540
ggtaaagcat ttggtcttat tggatcgata gtagccatgg gagaaggagt cggtccagcg   3600
attggtggaa tgatagccca ttatattcat tggtcctatc ttctactcat tcctatgata   3660
acaattatca ctgttccgtt tcttatgaaa ttattaaaga aagaagtaag gataaaaggt   3720
cattttgata tcaaaggaat tatactaatg tctgtaggca ttgtattttt tatgttgttt   3780
acaacatcat atagcatttc ttttcttatc gttagcgtgc tgtcattcct gatatttgta   3840
aaacatatca ggaaagtaac agatcctttt gttgatcccg gattagggaa aaatataccct   3900
tttatgattg gagttctttg tgggggaatt atatttggaa cagtagcagg gtttgtctct   3960
atggttcctt atatgatgaa agatgttcac cagctaagta ctgccgaaat cggaagtgta   4020
```

-continued

```
attattttcc ctggaacaat gagtgtcatt attttcggct acattggtgg gatacttgtt   4080
gatagaagag gtcctttata cgtgttaaac atcggagtta catttctttc tgttagcttt   4140
ttaactgctt cctttctttt agaaacaaca tcatggttca tgacaattat aatcgtattt   4200
gttttaggtg ggctttcgtt caccaaaaca gttatatcaa caattgtttc aagtagcttg   4260
aaacagcagg aagctggtgc tggaatgagt ttgcttaact ttaccagctt tttatcagag   4320
ggaacaggta ttgcaattgt aggtggttta ttatccatac ccttacttga tcaaaggttg   4380
ttacctatgg aagttgatca gtcaacttat ctgtatagta atttgttatt actttttttca  4440
ggaatcattg tcattagttg gctggttacc ttgaatgtat ataaacattc tcaaagggat   4500
ttctaaatcg ttaagggatc aactttggga gagagttcaa aattgatcct tttttataa    4560
caggaattgg gcatcaaata aaacgaaagg ctcagtcgaa agactgggcc tttcgtttta   4620
tctgttgttt gtcggtgaac gctctcctga gtaggacaaa tccgccggga gcggatttga   4680
acgttgcgaa gcaacggccc ggagggtggc gggcaggacg cccgccataa actgccaggc   4740
atcaaattaa gcagaaggcc atcctgacgg atggcctttt tgcgtttcta caaactcttc   4800
ctgtcgtcat atctacaatt ctacacagcc cagtccagac tattcggcac tgaaattatg   4860
ggtgaagtgg tcaagacctc actaggcacc ttaaaaatag cgcaccctga agaagattta   4920
tttgaggtag cccttgccta cctagcttcc aagaaagata tcctaacagc acaagagcgg   4980
aaagatgttt tgttctacat ccagaacaac ctctgctaaa attcctgaaa aattttgcaa   5040
aaagttgttg actttatcta caaggtgtgg cataatgtgt ggaattgtga gcggataaca   5100
attaagctaa taactggaaa aaattagtgt ctcatggttc gtcgccctta tattatgggc   5160
gttagcctgc ttgctaattg gataggtgtt attgtcattt caacgtcgga cgttttggta   5220
gatgaacgtc ggacgttatt tgcttcaata gattgttgat gtattaaggg ttgcagtgaa   5280
tcgacaagca aaaagttatg acgttgtgaa aaaattgaat agaaaattgg aaattacgtc   5340
ggacgttcta acttaaaaac cctgttatat caatgattta aaaggaaatt aacgtcataa   5400
aagacctttc tgcaacaaaa gtttttctgg aagagttgag gttattttat aggtattatg   5460
gacttttgta gactttttgt gtactttttg tggactccac actcgctggt atcgtgttat   5520
tttttaattg agatatgaat atggaaatta aacgttttag gcgttggttt ggtgatgaca   5580
aaaaaataag agtacccgct cacaacggat actctttcga gaaatgtacg aaacgctata   5640
aataaaaaat aactagatac atttacattg tatcacgttt cgtacatttc tccaataaca   5700
aattgattgg aggaatgcaa agtgaataat gaaccagtaa aacgtggtaa gaagaacaga   5760
tgggaattaa acctacctat aatgacttat gtagtagctg atgattggat tgataaacta   5820
ggacacgaaa cgtttacttt atggttgagg ttccatactt gggtagatag agaagatgaa   5880
ctccgagatt atgatcgcat acctagaagt tttgagaaca tatataaaaa gacactagga   5940
atctcaaaaa gtaagtttta tagattgata aaaccttttat gggaatatgg attaatagac  6000
atcatagaat acgaagaatc taaccgtaat tctactaaac ctaaaaatat aattgtttat   6060
gagtatcctt tacacgaaat agaaagaaag tataaaccac tagaaaaatt aagagattgg   6120
gataaagact ataattccgt ttctaaagaa ttaggtaaaa caggtggtag accaaggaaa   6180
aaagatagtg aagaagaacc cgaaaagaaa cccgaagaag taactaaaaa gaaacgtaaa   6240
tataagttaa aaagagttat ccacaacggt ttcaaaaatg aaacggtgga gggtttcaaa   6300
aatgaaacgg tggagggttt caaaaatgaa acggtgaccg tttcaaaaat aaaacccaat   6360
```

-continued

```
aattattcaa atatctttaa taacttatca aatatttcta ctaatgtttc aaataattta   6420

ttaattgatg atgatgagga aatcgaaaat gaaccaactg gtcgtacaat aaataggtca   6480

ttactttttt cacaagaaga tattaaacag gcctatcaat ttattaatag attttcagtt   6540

atacagttac gtgaaaactt tagctttgat aaacactttg aagaacggtt ggtatgttat   6600

ttatggaaag cagggatttc tactttttac acgcacgaaa tcagtaaaat gataaaaaaa   6660

atagcagact atgaaaaatc taaaaaaggt agattaaacc caatacgtga ccgagcctta   6720

tatatggtaa atggtcttgt aatgaataga gcttcttccc aaagtgaaca tgctacttat   6780

aaactaaacc aatataaaaa acagaaggaa caggaaaaac aacaacagga gcaacaaaga   6840

tcaagagtac cgttctataa ttggttggag gaaagagaag aacaaaccga aggtcaacta   6900

cccaccactt aa                                                       6912
```

<210> SEQ ID NO 3
<211> LENGTH: 48526
<212> TYPE: DNA
<213> ORGANISM: Bacteriophage lambda

<400> SEQUENCE: 3

```
attacggggc ggcgacctcg cgggttttcg ctatttatga aattttccg gtttaaggcg     60

tttccgttct tcttcgtcat aacttaatgt ttttatttaa aataccctct gaaaagaaag    120

gaaacgacag gtgctgaaag cgagcttttt ggcctctgtc gtttcctttc tctgtttttg    180

tccgtggaat gaacaatgga agtcaacaaa aagcagctgg ctgacatttt cggtgcgagt    240

atccgtacca ttcagaactg gcaggaacag ggaatgcccg ttctgcgagg cggtggcaag    300

ggtaatgagg tgctttatga ctctgccgcc gtcataaaat ggtatgccga aagggatgct    360

gaaattgaga acgaaaagct gcgccgggag gttgaagaac tgcggcaggc cagcgaggca    420

gatctccagc caggaactat tgagtacgaa cgccatcgac ttacgcgtgc gcaggccgac    480

gcacaggaac tgaagaatgc cagagactcc gctgaagtgg tggaaaccgc attctgtact    540

ttcgtgctgt cgcggatcgc aggtgaaatt gccagtattc tcgacgggct ccccctgtcg    600

gtgcagcggc gttttccgga actggaaaac cgacatgttg atttcctgaa acgggatatc    660

atcaaagcca tgaacaaagc agccgcgctg gatgaactga taccggggtt gctgagtgaa    720

tatatcgaac agtcaggtta acaggctgcg gcattttgtc cgcgccgggc ttcgctcact    780

gttcaggccg gagccacaga ccgccgttga atgggcggat gctaattact atctcccgaa    840

agaatccgca taccaggaag ggcgctggga aacactgccc tttcagcggg ccatcatgaa    900

tgcgatgggc agcgactaca tccgtgaggt gaatgtggtg aagtctgccc gtgtcggtta    960

ttccaaaatg ctgctgggtg tttatgccta ctttatagag cataagcagc gcaacaccct   1020

tatctggttg ccgacggatg gtgatgccga gaactttatg aaaacccacg ttgagccgac   1080

tattcgtgat attccgtcgc tgctggcgct ggccccgtgg tatggcaaaa agcaccggga   1140

taacacgctc accatgaagc gtttcactaa tgggcgtggc ttctggtgcc tgggcggtaa   1200

agcggcaaaa aactaccgtg aaaagtcggt ggatgtggcg ggttatgatg aacttgctgc   1260

ttttgatgat gatattgaac aggaaggctc tccgacgttc ctgggtgaca agcgtattga   1320

aggctcggtc tggccaaagt ccatccgtgg ctccacgcca aaagtgagag gcacctgtca   1380

gattgagcgt gcagccagtg aatccccgca ttttatgcgt tttcatgttg cctgcccgca   1440

ttgcggggag gagcagtatc ttaaatttgg cgacaaagag acgccgtttg gcctcaaatg   1500

gacgccggat gacccctcca gcgtgtttta tctctgcgag cataatgcct gcgtcatccg   1560
```

ccagcaggag ctggacttta ctgatgcccg ttatatctgc gaaaagaccg ggatctggac 1620
ccgtgatggc attctctggt tttcgtcatc cggtgaagag attgagccac ctgacagtgt 1680
gacctttcac atctggacag cgtacagccc gttcaccacc tgggtgcaga ttgtcaaaga 1740
ctggatgaaa acgaaagggg atacgggaaa acgtaaaacc ttcgtaaaca ccacgctcgg 1800
tgagacgtgg gaggcgaaaa ttggcgaacg tccggatgct gaagtgatgg cagagcggaa 1860
agagcattat tcagcgcccg ttcctgaccg tgtggcttac ctgaccgccg gtatcgactc 1920
ccagctggac cgctacgaaa tgcgcgtatg ggatgggggg ccgggtgagg aaagctggct 1980
gattgaccgg cagattatta tgggccgcca cgacgatgaa cagacgctgc tgcgtgtgga 2040
tgaggccatc aataaaacct atacccgccg gaatggtgca gaaatgtcga tatcccgtat 2100
ctgctgggat actggcggga ttgacccgac cattgtgtat gaacgctcga aaaaacatgg 2160
gctgttccgg gtgatcccca ttaaaggggc atccgtctac ggaaagccgg tggccagcat 2220
gccacgtaag cgaaacaaaa acggggttta ccttaccgaa atcggtacgg ataccgcgaa 2280
agagcagatt tataaccgct tcacactgac gccggaaggg gatgaaccgc ttcccggtgc 2340
cgttcacttc ccgaataacc cggatatttt tgatctgacc gaagcgcagc agctgactgc 2400
tgaagagcag gtcgaaaaat gggtggatgg caggaaaaaa atactgtggg acagcaaaaa 2460
gcgacgcaat gaggcactcg actgcttcgt ttatgcgctg gcggcgctgc gcatcagtat 2520
ttcccgctgg cagctggatc tcagtgcgct gctggcgagc ctgcaggaag aggatggtgc 2580
agcaaccaac aagaaaacac tggcagatta cgcccgtgcc ttatccggag aggatgaatg 2640
acgcgacagg aagaacttgc cgctgcccgt gcggcactgc atgacctgat gacaggtaaa 2700
cgggtggcaa cagtacagaa agacggacga agggtggagt ttacggccac ttccgtgtct 2760
gacctgaaaa aatatattgc agagctggaa gtgcagaccg gcatgacaca gcgacgcagg 2820
ggacctgcag gattttatgt atgaaaacgc ccaccattcc cacccttctg ggccggacg 2880 gcatgacatc gctgcgcgaa tatgccggtt atcacggcgg tggcagcgga tttggagggc 2940
agttgcggtc gtggaaccca ccgagtgaaa gtgtggatgc agccctgttg cccaacttta 3000
cccgtggcaa tgcccgcgca gacgatctgg tacgcaataa cggctatgcc gccaacgcca 3060
tccagctgca tcaggatcat atcgtcgggt ctttttttccg gctcagtcat cgcccaagct 3120
ggcgctatct gggcatcggg gaggaagaag cccgtgcctt ttcccgcgag gttgaagcgg 3180
catggaaaga gtttgccgag gatgactgct gctgcattga cgttgagcga aaacgcacgt 3240
ttaccatgat gattcgggaa ggtgtggcca tgcacgcctt taacggtgaa ctgttcgttc 3300
aggccacctg ggataccagt tcgtcgcggc ttttccggac acagttccgg atggtcagcc 3360
cgaagcgcat cagcaacccg aacaataccg gcgacagccg gaactgccgt gccggtgtgc 3420
agattaatga cagcggtgcg gcgctgggat attacgtcag cgaggacggg tatcctggct 3480
ggatgccgca gaaatggaca tggatacccc gtgagttacc cggcgggcgc gcctcgttca 3540
ttcacgtttt tgaacccgtg gaggacgggc agactcgcgg tgcaaatgtg ttttacagcg 3600
tgatggagca gatgaagatg ctcgacacgc tgcagaacac gcagctgcag agcgccattg 3660
tgaaggcgat gtatgccgcc accattgaga gtgagctgga tacgcagtca gcgatggatt 3720
ttattctggg cgcgaacagt caggagcagc gggaaaggct gaccggctgg attggtgaaa 3780
ttgccgcgta ttacgccgca gcgccggtcc ggctgggagg cgcaaaagta ccgcacctga 3840
tgccgggtga ctcactgaac ctgcagacgg ctcaggatac ggataacggc tactccgtgt 3900

-continued

```
ttgagcagtc actgctgcgg tatatcgctg ccgggctggg tgtctcgtat gagcagcttt   3960
cccggaatta cgcccagatg agctactcca cggcacgggc cagtgcgaac gagtcgtggg   4020
cgtactttat ggggcggcga aaattcgtcg catcccgtca ggcgagccag atgtttctgt   4080
gctggctgga agaggccatc gttcgccgcg tggtgacgtt accttcaaaa gcgcgcttca   4140
gttttcagga agcccgcagt gcctgggga actgcgactg gataggctcc ggtcgtatgg   4200
ccatcgatgg tctgaaagaa gttcaggaag cggtgatgct gatagaagcc ggactgagta   4260
cctacgagaa agagtgcgca aaacgcggtg acgactatca ggaaattttt gcccagcagg   4320
tccgtgaaac gatggagcgc cgtgcagccg gtcttaaacc gcccgcctgg gcggctgcag   4380
catttgaatc cgggctgcga caatcaacag aggaggagaa gagtgacagc agagctgcgt   4440
aatctcccgc atattgccag catggccttt aatgagccgc tgatgcttga acccgcctat   4500
gcgcgggttt tcttttgtgc gcttgcaggc cagcttggga tcagcagcct gacggatgcg   4560
gtgtccggcg acagcctgac tgcccaggag gcactcgcga cgctggcatt atccggtgat   4620
gatgacggac cacgacaggc ccgcagttat caggtcatga acggcatcgc cgtgctgccg   4680
gtgtccggca cgctggtcag ccggacgcgg gcgctgcagc cgtactcggg gatgaccggt   4740
tacaacggca ttatcgcccg tctgcaacag gctgccagcg atccgatggt ggacggcatt   4800
ctgctcgata tggacacgcc cggcgggatg gtggcggggg catttgactg cgctgacatc   4860
atcgcccgtg tgcgtgacat aaaaccggta tgggcgcttg ccaacgacat gaactgcagt   4920
gcaggtcagt tgcttgccag tgccgcctcc cggcgtctgg tcacgcagac cgcccggaca   4980
ggctccatcg gcgtcatgat ggctcacagt aattacggtg ctgcgctgga gaaacagggt   5040
gtggaaatca cgctgattta cagcggcagc cataaggtgg atggcaaccc ctacagccat   5100
cttccggatg acgtccggga gacactgcag tcccggatgg acgcaacccg ccagatgttt   5160
gcgcagaagg tgtcggcata taccggcctg tccgtgcagg ttgtgctgga taccgaggct   5220
gcagtgtaca gcggtcagga ggccattgat gccggactgg ctgatgaact tgttaacagc   5280
accgatgcga tcaccgtcat gcgtgatgca ctggatgcac gtaaatcccg tctctcagga   5340
gggcgaatga ccaaagagac tcaatcaaca actgtttcag ccactgcttc gcaggctgac   5400
gttactgacg tggtgccagc gacggagggc gagaacgcca gcgcggcgca gccggacgtg   5460
aacgcgcaga tcaccgcagc ggttgcggca gaaaacagcc gcattatggg gatcctcaac   5520
tgtgaggagg ctcacggacg cgaagaacag gcacgcgtgc tggcagaaac ccccggtatg   5580
accgtgaaaa cggcccgccg cattctggcc gcagcaccac agagtgcaca ggcgcgcagt   5640
gacactgcgc tggatcgtct gatgcagggg gcaccggcac cgctggctgc aggtaacccg   5700
gcatctgatg ccgttaacga tttgctgaac acaccagtgt aagggatgtt tatgacgagc   5760
aaagaaacct ttacccatta ccagccgcag ggcaacagtg acccggctca taccgcaacc   5820
gcgcccggcg gattgagtgc gaaagcgcct gcaatgaccc cgctgatgct ggacacctcc   5880
agccgtaagc tggttgcgtg ggatggcacc accgacggtg ctgccgttgg cattcttgcg   5940
gttgctgctg accagaccag caccacgctg acgttctaca agtccggcac gttccgttat   6000
gaggatgtgc tctggccgga ggctgccagc gacgagacga aaaaacggac cgcgtttgcc   6060
ggaacggcaa tcagcatcgt ttaactttac ccttcatcac taaaggccgc ctgtgcggct   6120
ttttttacgg gatttttta tgtcgatgta cacaaccgcc caactgctgg cggcaaatga   6180
gcagaaattt aagtttgatc cgctgtttct gcgtctcttt ttccgtgaga gctatccctt   6240
caccacggag aaagtctatc tctcacaaat tccgggactg gtaaacatgg cgctgtacgt   6300
```

-continued

```
ttcgccgatt gtttccggtg aggttatccg ttcccgtggc ggctccacct ctgaatttac   6360
gccgggatat gtcaagccga agcatgaagt gaatccgcag atgaccctgc gtcgcctgcc   6420
ggatgaagat ccgcagaatc tggcggaccc ggcttaccgc cgccgtcgca tcatcatgca   6480
gaacatgcgt gacgaagagc tggccattgc tcaggtcgaa gagatgcagg cagtttctgc   6540
cgtgcttaag ggcaaataca ccatgaccgg tgaagccttc gatccggttg aggtggatat   6600
gggccgcagt gaggagaata acatcacgca gtccggcggc acggagtgga gcaagcgtga   6660
caagtccacg tatgacccga ccgacgatat cgaagcctac gcgctgaacg ccagcggtgt   6720
ggtgaatatc atcgtgttcg atccgaaagg ctgggcgctg ttccgttcct tcaaagccgt   6780
caaggagaag ctggataccc gtcgtggctc taattccgag ctggagacag cggtgaaaga   6840
cctgggcaaa gcggtgtcct ataaggggat gtatggcgat gtggccatcg tcgtgtattc   6900
cggacagtac gtggaaaacg gcgtcaaaaa gaacttcctg ccggacaaca cgatggtgct   6960
ggggaacact caggcacgcg gtctgcgcac ctatggctgc attcaggatg cggacgcaca   7020
gcgcgaaggc attaacgcct ctgcccgtta cccgaaaaac tgggtgacca ccggcgatcc   7080
ggcgcgtgag ttcaccatga ttcagtcagc accgctgatg ctgctggctg accctgatga   7140
gttcgtgtcc gtacaactgg cgtaatcatg gcccttcggg gccattgttt ctctgtggag   7200
gagtccatga cgaaaagatga actgattgcc cgtctccgct cgctgggtga acaactgaac   7260
cgtgatgtca gcctgacggg gacgaaagaa gaactggcgc tccgtgtggc agagctgaaa   7320
gaggagcttg atgacacgga tgaaactgcc ggtcaggaca cccctctcag ccgggaaaat   7380
gtgctgaccg gacatgaaaa tgaggtggga tcagcgcagc cggataccgt gattctggat   7440
acgtctgaac tggtcacggt cgtggcactg gtgaagctgc atactgatgc acttcacgcc   7500
acgcgggatg aacctgtggc atttgtgctg ccgggaacgg cgtttcgtgt ctctgccggt   7560
gtggcagccg aaatgacaga gcgcggcctg gccagaatgc aataacggga ggcgctgtgg   7620
ctgatttcga taacctgttc gatgctgcca ttgcccgcgc cgatgaaacg atacgcgggt   7680
acatgggaac gtcagccacc attacatccg gtgagcagtc aggtgcggtg atacgtggtg   7740
tttttgatga ccctgaaaat atcagctatg ccggacaggg cgtgcgcgtt gaaggctcca   7800
gcccgtccct gtttgtccgg actgatgagg tgcggcagct gcggcgtgga gacacgctga   7860
ccatcggtga ggaaaatttc tgggtagatc gggtttcgcc ggatgatggc ggaagttgtc   7920
atctctggct tggacggggc gtaccgcctg ccgttaaccg tcgccgctga aagggggatg   7980
tatggccata aaaggtcttg agcaggccgt tgaaaacctc agccgtatca gcaaaacggc   8040
ggtgcctggt gccgccgcaa tggccattaa ccgcgttgct tcatccgcga tatcgcagtc   8100
ggcgtcacag gttgcccgtg agacaaaggt acgccggaaa ctggtaaagg aaagggccag   8160
gctgaaaagg gccacggtca aaaatccgca ggccagaatc aaagttaacc ggggggattt   8220
gcccgtaatc aagctgggta atgcgcgggt tgtcctttcg cgccgcaggc gtcgtaaaaa   8280
ggggcagcgt tcatccctga aaggtggcgg cagcgtgctt gtggtgggta accgtcgtat   8340
tcccggcgcg tttattcagc aactgaaaaa tggccggtgg catgtcatgc agcgtgtggc   8400
tgggaaaaac cgttacccca ttgatgtggt gaaaatcccg atggcggtgc cgctgaccac   8460
ggcgtttaaa caaaatattg agcggatacg gcgtgaacgt cttccgaaag agctgggcta   8520
tgcgctgcag catcaactga ggatggtaat aaagcgatga aacatactga actccgtgca   8580
gccgtactgg atgcactgga gaagcatgac accggggcga cgtttttga tggtcgcccc   8640
```

-continued

```
gctgtttttg atgaggcgga ttttccggca gttgccgttt atctcaccgg cgctgaatac   8700
acgggcgaag agctggacag cgatacctgg caggcggagc tgcatatcga agttttcctg   8760
cctgctcagg tgccggattc agagctggat gcgtggatgg agtcccggat ttatccggtg   8820
atgagcgata tcccggcact gtcagatttg atcaccagta tggtggccag cggctatgac   8880
taccggcgcg acgatgatgc gggcttgtgg agttcagccg atctgactta tgtcattacc   8940
tatgaaatgt gaggacgcta tgcctgtacc aaatcctaca atgccggtga aaggtgccgg   9000
gaccaccctg tgggtttata aggggagcgg tgacccttac gcgaatccgc tttcagacgt   9060
tgactggtcg cgtctggcaa aagttaaaga cctgacgccc ggcgaactga ccgctgagtc   9120
ctatgacgac agctatctcg atgatgaaga tgcagactgg actgcgaccg ggcaggggca   9180
gaaatctgcc ggagatacca gcttcacgct ggcgtggatg cccggagagc aggggcagca   9240
ggcgctgctg gcgtggttta atgaaggcga tacccgtgcc tataaaatcc gcttcccgaa   9300
cggcacggtc gatgtgttcc gtggctgggt cagcagtatc ggtaaggcgg tgacggcgaa   9360
ggaagtgatc acccgcacgg tgaaagtcac caatgtggga cgtccgtcga tggcagaaga   9420
tcgcagcacg gtaacagcgg caaccggcat gaccgtgacg cctgccagca cctcggtggt   9480
gaaagggcag agcaccacgc tgaccgtggc cttccagccc gagggcgtaa ccgacaagag   9540
ctttcgtgcg gtgtctgcgg ataaaacaaa agccaccgtg tcggtcagtg gtatgaccat   9600
caccgtgaac ggcgttgctg caggcaaggt caacattccg gttgtatccg gtaatggtga   9660
gtttgctgcg gttgcagaaa ttaccgtcac cgccagttaa tccggagagt cagcgatgtt   9720
cctgaaaacc gaatcatttg aacataacgg tgtgaccgtc acgctttctg aactgtcagc   9780
cctgcagcgc attgagcatc tcgccctgat gaaacggcag gcagaacagg cggagtcaga   9840
cagcaaccgg aagtttactg tggaagacgc catcagaacc ggcgcgtttc tggtggcgat   9900
gtccctgtgg cataaccatc cgcagaagac gcagatgccg tccatgaatg aagccgttaa   9960
acagattgag caggaagtgc ttaccacctg gcccacggag gcaatttctc atgctgaaaa  10020
cgtggtgtac cggctgtctg gtatgtatga gtttgtggtg aataatgccc ctgaacagac  10080
agaggacgcc gggcccgcag agcctgtttc tgcgggaaag tgttcgacgg tgagctgagt  10140
tttgccctga aactggcgcg tgagatgggg cgacccgact ggcgtgccat gcttgccggg  10200
atgtcatcca cggagtatgc cgactggcac cgcttttaca gtacccatta ttttcatgat  10260
gttctgctgg atatgcactt ttccgggctg acgtacaccg tgctcagcct gtttttcagc  10320
gatccggata tgcatccgct ggatttcagt ctgctgaacc ggcgcgaggc tgacgaagag  10380
cctgaagatg atgtgctgat gcagaaagcg gcagggcttg ccggaggtgt ccgctttggc  10440
ccggacggga atgaagttat ccccgcttcc ccggatgtgg cggacatgac ggaggatgac  10500
gtaatgctga tgacagtatc agaagggatc gcaggaggag tccggtatgg ctgaaccggt  10560
aggcgatctg gtcgttgatt tgagtctgga tgcggccaga tttgacgagc agatggccag  10620
agtcaggcgt catttttctg gtacggaaag tgatgcgaaa aaaacagcgg cagtcgttga  10680
acagtcgctg agccgacagg cgctggctgc acagaaagcg gggatttccg tcgggcagta  10740
taaagccgcc atgcgtatgc tgcctgcaca gttcaccgac gtggccacgc agcttgcagg  10800
cgggcaaagt ccgtggctga tcctgctgca acagggggggg caggtgaagg actccttcgg  10860
cgggatgatc cccatgttca gggggcttgc cggtgcgatc accctgccga tggtgggggc  10920
cacctcgctg gcggtggcga ccggtgcgct ggcgtatgcc tggtatcagg gcaactcaac  10980
cctgtccgat ttcaacaaaa cgctggtcct ttccggcaat caggcgggac tgacggcaga  11040
```

tcgtatgctg gtcctgtcca gagccgggca ggcggcaggg ctgacgttta accagaccag 11100
cgagtcactc agcgcactgg ttaaggcggg ggtaagcggt gaggctcaga ttgcgtccat 11160
cagccagagt gtggcgcgtt tctcctctgc atccggcgtg gaggtggaca aggtcgctga 11220
agccttcggg aagctgacca cagacccgac gtcggggctg acggcgatgg ctcgccagtt 11280
ccataacgtg tcggcggagc agattgcgta tgttgctcag ttgcagcgtt ccggcgatga 11340
agccggggca ttgcaggcgg cgaacgaggc cgcaacgaaa gggtttgatg accagacccg 11400
ccgcctgaaa gagaacatgg gcacgctgga gacctgggca gacaggactg cgcgggcatt 11460
caaatccatg tgggatgcgg tgctggatat tggtcgtcct gataccgcgc aggagatgct 11520
gattaaggca gaggctgcgt ataagaaagc agacgacatc tggaatctgc gcaaggatga 11580
ttattttgtt aacgatgaag cgcgggcgcg ttactgggat gatcgtgaaa aggcccgtct 11640
tgcgcttgaa gccgcccgaa agaaggctga gcagcagact caacaggaca aaaatgcgca 11700
gcagcagagc gataccgaag cgtcacggct gaaatatacc gaagaggcgc agaaggctta 11760
cgaacggctg cagacgccgc tggagaaata taccgcccgt caggaagaac tgaacaaggc 11820
actgaaagac gggaaaatcc tgcaggcgga ttacaacacg ctgatggcgg cggcgaaaaa 11880
ggattatgaa gcgacgctga aaaagccgaa acagtccagc gtgaaggtgt ctgcgggcga 11940
tcgtcaggaa gacagtgctc atgctgccct gctgacgctt caggcagaac tccggacgct 12000
ggagaagcat gccggagcaa atgagaaaat cagccagcag cgccgggatt tgtggaaggc 12060
ggagagtcag ttcgcggtac tggaggaggc ggcgcaacgt cgccagctgt ctgcacagga 12120
gaaatccctg ctggcgcata aagatgagac gctggagtac aaacgccagc tggctgcact 12180
tggcgacaag gttacgtatc aggagcgcct gaacgcgctg gcgcagcagg cggataaatt 12240
cgcacagcag caacgggcaa aacgggccgc cattgatgcg aaaagccggg ggctgactga 12300
ccggcaggca gaacgggaag ccacggaaca gcgcctgaag gaacagtatg gcgataatcc 12360
gctggcgctg aataacgtca tgtcagagca gaaaaagacc tgggcggctg aagaccagct 12420
tcgcgggaac tggatggcag gcctgaagtc cggctggagt gagtgggaag agagcgccac 12480
ggacagtatg tcgcaggtaa aaagtgcagc cacgcagacc tttgatggta ttgcacagaa 12540
tatggcggcg atgctgaccg gcagtgagca gaactggcgc agcttcaccc gttccgtgct 12600
gtccatgatg acagaaattc tgcttaagca ggcaatggtg gggattgtcg ggagtatcgg 12660
cagcgccatt ggcggggctg ttggtggcgg cgcatccgcg tcaggcggta cagccattca 12720
ggccgctgcg gcgaaattcc attttgcaac cggaggattt acgggaaccg gcggcaaata 12780
tgagccagcg gggattgttc accgtggtga gtttgtcttc acgaaggagg caaccagccg 12840
gattggcgtg gggaatcttt accggctgat gcgcggctat gccaccggcg gttatgtcgg 12900
tacaccgggc agcatggcag acagccggtc gcaggcgtcc gggacgtttg agcagaataa 12960
ccatgtggtg attaacaacg acggcacgaa cgggcagata ggtccggctg ctctgaaggc 13020
ggtgtatgac atggcccgca agggtgcccg tgatgaaatt cagacacaga tgcgtgatgg 13080
tggcctgttc tccggaggtg gacgatgaag accttccgct ggaaagtgaa acccggtatg 13140
gatgtggctt cggtcccttc tgtaagaaag gtgcgctttg gtgatggcta ttctcagcga 13200
gcgcctgccg ggctgaatgc caacctgaaa acgtacagcg tgacgctttc tgtccccgt 13260
gaggaggcca cggtactgga gtcgtttctg gaagagcacg gggctggaa atcctttctg 13320
tggacgccgc cttatgagtg gcggcagata aaggtgacct gcgcaaaatg gtcgtcgcgg 13380

```
gtcagtatgc tgcgtgttga gttcagcgca gagtttgaac aggtggtgaa ctgatgcagg  13440
atatccggca ggaaacactg aatgaatgca cccgtgcgga gcagtcggcc agcgtggtgc  13500
tctgggaaat cgacctgaca gaggtcggtg gagaacgtta ttttttctgt aatgagcaga  13560
acgaaaaagg tgagccggtc acctggcagg ggcgacagta tcagccgtat cccattcagg  13620
ggagcggttt tgaactgaat ggcaaaggca ccagtacgcg ccccacgctg acggtttcta  13680
acctgtacgg tatggtcacc gggatggcgg aagatatgca gagtctggtc ggcggaacgg  13740
tggtccggcg taaggtttac gcccgttttc tggatgcggt gaacttcgtc aacggaaaca  13800
gttacgccga tccggagcag gaggtgatca gccgctggcg cattgagcag tgcagcgaac  13860
tgagcgcggt gagtgcctcc tttgtactgt ccacgccgac ggaaacggat ggcgctgttt  13920
ttccgggacg tatcatgctg gccaacacct gcacctggac ctatcgcggt gacgagtgcg  13980
gttatagcgg tccggctgtc gcggatgaat atgaccagcc aacgtccgat atcacgaagg  14040
ataaatgcag caaatgcctg agcggttgta agttccgcaa taacgtcggc aactttggcg  14100
gcttcctttc cattaacaaa ctttcgcagt aaatcccatg acacagacag aatcagcgat  14160
tctggcgcac gcccggcgat gtgcgccagc ggagtcgtgc ggcttcgtgg taagcacgcc  14220
ggagggggaa agatatttcc cctgcgtgaa tatctccggt gagccggagg cgtatttccg  14280
tatgtcgccg gaagactggc tgcaggcaga aatgcagggt gagattgtgg cgctggtcca  14340
cagccacccc ggtggtctgc cctggctgag tgaggccgac cggcggctgc aggtgcagag  14400
tgatttgccg tggtggctgg tctgccgggg gacgattcat aagttccgct gtgtgccgca  14460
tctcaccggg cggcgctttg agcacggtgt gacggactgt tacacactgt tccgggatgc  14520
ttatcatctg gcggggattg agatgccgga ctttcatcgt gaggatgact ggtggcgtaa  14580
cggccagaat ctctatctgg ataatctgga ggcgacgggg ctgtatcagg tgccgttgtc  14640
agcggcacag ccgggcgatg tgctgctgtg ctgttttggt tcatcagtgc cgaatcacgc  14700
cgcaatttac tgcggcgacg gcgagctgct gcaccatatt cctgaacaac tgagcaaacg  14760
agagaggtac accgacaaat ggcagcgacg cacacactcc ctctggcgtc accgggcatg  14820
gcgcgcatct gcctttacgg ggatttacaa cgatttggtc gccgcatcga ccttcgtgtg  14880
aaaacggggg ctgaagccat ccgggcactg gccacacagc tcccggcgtt tcgtcagaaa  14940
ctgagcgacg gctggtatca ggtacggatt gccgggcggg acgtcagcac gtccgggtta  15000
acggcgcagt tacatgagac tctgcctgat ggcgctgtaa ttcatattgt tcccagagtc  15060
gccggggcca agtcaggtgg cgtattccag attgtcctgg gggctgccgc cattgccgga  15120
tcattcttta ccgccggagc caccccttgca gcatgggggg cagccattgg ggccggtggt  15180
atgaccggca tcctgttttc tctcggtgcc agtatggtgc tcggtggtgt ggcgcagatg  15240
ctggcaccga aagccagaac tccccgtata cagacaacgg ataacggtaa gcagaacacc  15300
tatttctcct cactggataa catggttgcc cagggcaatg ttctgcctgt tctgtacggg  15360
gaaatgcgcg tggggtcacg cgtggtttct caggagatca gcacggcaga cgaaggggac  15420
ggtggtcagg ttgtggtgat tggtcgctga tgcaaaatgt tttatgtgaa accgcctgcg  15480
ggcggttttg tcatttatgg agcgtgagga atgggtaaag gaagcagtaa ggggcatacc  15540
ccgcgcgaag cgaaggacaa cctgaagtcc acgcagttgc tgagtgtgat cgatgccatc  15600
agcgaagggc cgattgaagg tccggtggat ggcttaaaaa gcgtgctgct gaacagtacg  15660
ccggtgctgg acactgaggg gaataccaac atatccggtg tcacggtggt gttccgggct  15720
ggtgagcagg agcagactcc gccggaggga tttgaatcct ccggctccga gacggtgctg  15780
```

```
ggtacggaag tgaaatatga cacgccgatc acccgcacca ttacgtctgc aaacatcgac  15840
cgtctgcgct ttaccttcgg tgtacaggca ctggtggaaa ccacctcaaa gggtgacagg  15900
aatccgtcgg aagtccgcct gctggttcag atacaacgta acggtggctg ggtgacggaa  15960
aaagacatca ccattaaggg caaaaccacc tcgcagtatc tggcctcggt ggtgatgggt  16020
aacctgccgc cgcgcccgtt taatatccgg atgcgcagga tgacgccgga cagcaccaca  16080
gaccagctgc agaacaaaac gctctggtcg tcatacactg aaatcatcga tgtgaaacag  16140
tgctacccga acacggcact ggtcggcgtg caggtggact cggagcagtt cggcagccag  16200
caggtgagcc gtaattatca tctgcgcggg cgtattctgc aggtgccgtc gaactataac  16260
ccgcagacgc ggcaatacag cggtatctgg gacggaacgt ttaaaccggc atacagcaac  16320
aacatggcct ggtgtctgtg ggatatgctg acccatccgc gctacggcat ggggaaacgt  16380
cttggtgcgg cggatgtgga taaatgggcg ctgtatgtca tcggccagta ctgcgaccag  16440
tcagtgccgg acggctttgg cggcacggag ccgcgcatca cctgtaatgc gtacctgacc  16500
acacagcgta aggcgtggga tgtgctcagc gatttctgct cggcgatgcg ctgtatgccg  16560
gtatggaacg ggcagacgct gacgttcgtg caggaccgac cgtcggataa gacgtggacc  16620
tataaccgca gtaatgtggt gatgccggat gatggcgcgc cgttccgcta cagcttcagc  16680
gccctgaagg accgccataa tgccgttgag gtgaactgga ttgacccgaa caacggctgg  16740
gagacggcga cagagcttgt tgaagatacg caggccattg cccgttacgg tcgtaatgtt  16800
acgaagatgg atgcctttgg ctgtaccagc cgggggcagg cacaccgcgc cgggctgtgg  16860
ctgattaaaa cagaactgct ggaaacgcag accgtggatt tcagcgtcgg cgcagaaggg  16920
cttcgccatg taccgggcga tgttattgaa atctgcgatg atgactatgc cggtatcagc  16980
accggtggtc gtgtgctggc ggtgaacagc cagacccgga cgctgacgct cgaccgtgaa  17040
atcacgctgc catcctccgg taccgcgctg ataagcctgg ttgacggaag tggcaatccg  17100
gtcagcgtgg aggttcagtc cgtcaccgac ggcgtgaagg taaaagtgag ccgtgttcct  17160
gacggtgttg ctgaatacag cgtatgggag ctgaagctgc cgacgctgcg ccagcgactg  17220
ttccgctgcg tgagtatccg tgagaacgac gacggcacgt atgccatcac cgccgtgcag  17280
catgtgccgg aaaaagaggc catcgtggat aacggggcgc actttgacgg cgaacagagt  17340
ggcacggtga atggtgtcac gccgccagcg gtgcagcacc tgaccgcaga agtcactgca  17400
gacagcgggg aatatcaggt gctggcgcga tgggacacac cgaaggtggt gaagggcgtg  17460
agtttcctgc tccgtctgac cgtaacagcg gacgacggca gtgagcggct ggtcagcacg  17520
gcccggacga cggaaaccac ataccgcttc acgcaactgg cgctggggaa ctacaggctg  17580
acagtccggg cggtaaatgc gtgggggcag cagggcgatc cggcgtcggt atcgttccgg  17640
attgccgcac cggcagcacc gtcgaggatt gagctgacgc cgggctattt tcagataacc  17700
gccacgccgc atcttgccgt ttatgacccg acggtacagt ttgagttctg gttctcggaa  17760
aagcagattg cggatatcag acaggttgaa accagcacgc gttatcttgg tacggcgctg  17820
tactggatag ccgccagtat caatatcaaa ccgggccatg attattactt ttatatccgc  17880
agtgtgaaca ccgttggcaa atcggcattc gtggaggccg tcggtcgggc gagcgatgat  17940
gcggaaggtt acctggattt tttcaaaggc aagataaccg aatcccatct cggcaaggag  18000
ctgctggaaa aagtcgagct gacggaggat aacgccagca gactggagga gttttcgaaa  18060
gagtggaagg atgccagtga taagtggaat gccatgtggg ctgtcaaaat tgagcagacc  18120
```

-continued

```
aaagacggca aacattatgt cgcgggtatt ggcctcagca tggaggacac ggaggaaggc  18180
aaactgagcc agtttctggt tgccgccaat cgtatcgcat ttattgaccc ggcaaacggg  18240
aatgaaacgc cgatgtttgt ggcgcagggc aaccagatat tcatgaacga cgtgttcctg  18300
aagcgcctga cggcccccac cattaccagc ggcggcaatc ctccggcctt ttccctgaca  18360
ccggacggaa agctgaccgc taaaaatgcg gatatcagtg gcagtgtgaa tgcgaactcc  18420
gggacgctca gtaatgtgac gatagctgaa aactgtacga taaacggtac gctgagggcg  18480
gaaaaaatcg tcggggacat tgtaaaggcg gcgagcgcgg cttttccgcg ccagcgtgaa  18540
agcagtgtgg actggccgtc aggtacccgt actgtcaccg tgaccgatga ccatcctttt  18600
gatcgccaga tagtggtgct tccgctgacg tttcgcggaa gtaagcgtac tgtcagcggc  18660
aggacaacgt attcgatgtg ttatctgaaa gtactgatga acggtgcggt gatttatgat  18720
ggcgcggcga acgaggcggt acaggtgttc tcccgtattg ttgacatgcc agcgggtcgg  18780
ggaaacgtga tcctgacgtt cacgcttacg tccacacggc attcggcaga tattccgccg  18840
tatacgtttg ccagcgatgt gcaggttatg gtgattaaga aacaggcgct gggcatcagc  18900
gtggtctgag tgtgttacag aggttcgtcc gggaacgggc gttttattat aaaacagtga  18960
gaggtgaacg atgcgtaatg tgtgtattgc cgttgctgtc tttgccgcac ttgcggtgac  19020
agtcactccg gcccgtgcgg aaggtggaca tggtacgttt acggtgggct attttcaagt  19080
gaaaccgggt acattgccgt cgttgtcggg cggggatacc ggtgtgagtc atctgaaagg  19140
gattaacgtg aagtaccgtt atgagctgac ggacagtgtg ggggtgatgg cttccctggg  19200
gttcgccgcg tcgaaaaaga gcagcacagt gatgaccggg gaggatacgt ttcactatga  19260
gagcctgcgt ggacgttatg tgagcgtgat ggccggaccg gttttacaaa tcagtaagca  19320
ggtcagtgcg tacgccatgg ccggagtggc tcacagtcgg tggtccggca gtacaatgga  19380
ttaccgtaag acggaaatca ctcccgggta tatgaaagag acgaccactg ccagggacga  19440
aagtgcaatg cggcatacct cagtggcgtg gagtgcaggt atacagatta atccggcagc  19500
gtccgtcgtt gttgatattg cttatgaagg ctccggcagt ggcgactggc gtactgacgg  19560
attcatcgtt ggggtcggtt ataaattctg attagccagg taacacagtg ttatgacagc  19620
ccgccggaac cggtgggctt ttttgtgggg tgaatatggc agtaaagatt tcaggagtcc  19680
tgaaagacgg cacaggaaaa ccggtacaga actgcaccat tcagctgaaa gccagacgta  19740
acagcaccac ggtggtggtg aacacggtgg gctcagagaa tccggatgaa gccgggcgtt  19800
acagcatgga tgtggagtac ggtcagtaca gtgtcatcct gcaggttgac ggttttccac  19860
catcgcacgc cgggaccatc accgtgtatg aagattcaca accggggacg ctgaatgatt  19920
ttctctgtgc catgacggag gatgatgccc ggccggaggt gctgcgtcgt cttgaactga  19980
tggtggaaga ggtggcgcgt aacgcgtccg tggtggcaca gagtacggca gacgcgaaga  20040
aatcagccgg cgatgccagt gcatcagctg ctcaggtcgc ggcccttgtg actgatgcaa  20100
ctgactcagc acgcgccgcc agcacgtccg ccggacaggc tgcatcgtca gctcaggaag  20160
cgtcctccgg cgcagaagcg gcatcagcaa aggccactga agcggaaaaa agtgccgcag  20220
ccgcagagtc ctcaaaaaac gcggcggcca ccagtgccgg tgcggcgaaa acgtcagaaa  20280
cgaatgctgc agcgtcacaa caatcagccg ccacgtctgc ctccaccgcg gccacgaaag  20340
cgtcagaggc cgccacttca gcacgagatg cggtggcctc aaaagaggca gcaaaatcat  20400
cagaaacgaa cgcatcatca agtgccggtc gtgcagcttc ctcggcaacg gcggcagaaa  20460
attctgccag ggcggcaaaa acgtccgaga cgaatgccag gtcatctgaa acagcagcgg  20520
```

```
aacggagcgc ctctgccgcg gcagacgcaa aaacagcggc ggcggggagt gcgtcaacgg  20580
catccacgaa ggcgacagag gctgcgggaa gtgcggtatc agcatcgcag agcaaaagtg  20640
cggcagaagc ggcggcaata cgtgcaaaaa attcggcaaa acgtgcagaa gatatagctt  20700
cagctgtcgc gcttgaggat gcggacacaa cgagaaaggg gatagtgcag ctcagcagtg  20760
caaccaacag cacgtctgaa acgcttgctg caacgccaaa ggcggttaag gtggtaatgg  20820
atgaaacgaa cagaaaagcc cactggacag tccggcactg accggaacgc caacagcacc  20880
aaccgcgctc aggggaacaa acaataccca gattgcgaac accgcttttg tactggccgc  20940
gattgcagat gttatcgacg cgtcacctga cgcactgaat acgctgaatg aactggccgc  21000
agcgctcggg aatgatccag attttgctac caccatgact aacgcgcttg cgggtaaaca  21060
accgaagaat gcgacactga cggcgctggc agggctttcc acggcgaaaa ataaattacc  21120
gtattttgcg gaaaatgatg ccgccagcct gactgaactg actcaggttg gcagggatat  21180
tctggcaaaa aattccgttg cagatgttct tgaatacctt ggggccggtg agaattcggc  21240
ctttccggca ggtgcgccga tcccgtggcc atcagatatc gttccgtctg gctacgtcct  21300
gatgcagggg caggcgtttg acaaatcagc ctacccaaaa cttgctgtcg cgtatccatc  21360
gggtgtgctt cctgatatgc gaggctggac aatcaagggg aaacccgcca gcggtcgtgc  21420
tgtattgtct caggaacagg atggaattaa gtcgcacacc cacagtgcca gtgcatccgg  21480
tacggatttg gggacgaaaa ccacatcgtc gtttgattac gggacgaaaa caacaggcag  21540
tttcgattac ggcaccaaat cgacgaataa cacgggggct catgctcaca gtctgagcgg  21600
ttcaacaggg gccgcgggtg ctcatgccca cacaagtggt ttaaggatga acagttctgg  21660
ctggagtcag tatggaacag caaccattac aggaagttta tccacagtta aaggaaccag  21720
cacacagggt attgcttatt tatcgaaaac ggacagtcag ggcagccaca gtcactcatt  21780
gtccggtaca gccgtgagtg ccggtgcaca tgcgcataca gttggtattg gtgcgcacca  21840
gcatccggtt gttatcggtg ctcatgccca ttctttcagt attggttcac acggacacac  21900
catcaccgtt aacgctgcgg gtaacgcgga aaacaccgtc aaaaacattg catttaacta  21960
tattgtgagg cttgcataat ggcattcaga atgagtgaac aaccacggac cataaaaatt  22020
tataatctgc tggccggaac taatgaattt attggtgaag gtgacgcata tattccgcct  22080
cataccggtc tgcctgcaaa cagtaccgat attgcaccgc cagatattcc ggctggcttt  22140
gtggctgttt tcaacagtga tgaggcatcg tggcatctcg ttgaagacca tcggggtaaa  22200
accgtctatg acgtggcttc cggcgacgcg ttatttattt ctgaactcgg tccgttaccg  22260
gaaaatttta cctggttatc gccgggaggg gaatatcaga agtggaacgg cacagcctgg  22320
gtgaaggata cggaagcaga aaaactgttc cggatccggg aggcggaaga aacaaaaaaa  22380
agcctgatgc aggtagccag tgagcatatt gcgccgcttc aggatgctgc agatctggaa  22440
attgcaacga aggaagaaac ctcgttgctg gaagcctgga agaagtatcg ggtgttgctg  22500
aaccgtgttg atacatcaac tgcacctgat attgagtggc ctgctgtccc tgttatggag  22560
taatcgtttt gtgatatgcc gcagaaacgt tgtatgaaat aacgttctgc ggttagttag  22620
tatattgtaa agctgagtat tggtttattt ggcgattatt atcttcagga gaataatgga  22680
agttctatga ctcaattgtt catagtgttt acatcaccgc caattgcttt taagactgaa  22740
cgcatgaaat atggtttttc gtcatgtttt gagtctgctg ttgatatttc taaagtcggt  22800
tttttttctt cgttttctct aactattttc catgaaatac atttttgatt attatttgaa  22860
```

-continued

```
tcaattccaa ttacctgaag tctttcatct ataattggca ttgtatgtat tggtttattg  22920
gagtagatgc ttgcttttct gagccatagc tctgatatcc aaatgaagcc ataggcattt  22980
gttattttgg ctctgtcagc tgcataacgc caaaaaatat atttatctgc ttgatcttca  23040
aatgttgtat tgattaaatc aattggatgg aattgtttat cataaaaaat taatgtttga  23100
atgtgataac cgtcctttaa aaaagtcgtt tctgcaagct tggctgtata gtcaactaac  23160
tcttctgtcg aagtgatatt tttaggctta tctaccagtt ttagacgctc tttaatatct  23220
tcaggaatta ttttattgtc atattgtatc atgctaaatg acaatttgct tatggagtaa  23280
tcttttaatt ttaaataagt tattctcctg gcttcatcaa ataaagagtc gaatgatgtt  23340
ggcgaaatca catcgtcacc cattggattg tttatttgta tgccaagaga gttacagcag  23400
ttatacattc tgccatagat tatagctaag gcatgtaata attcgtaatc ttttagcgta  23460
ttagcgaccc atcgtctttc tgatttaata atagatgatt cagttaaata tgaaggtaat  23520
ttcttttgtg caagtctgac taactttttt ataccaatgt ttaacatact ttcatttgta  23580
ataaactcaa tgtcattttc ttcaatgtaa gatgaaataa gagtagcctt tgcctcgcta  23640
tacatttcta aatcgccttg tttttctatc gtattgcgag aatttttagc ccaagccatt  23700
aatggatcat ttttccattt ttcaataaca ttattgttat accaaatgtc atatcctata  23760
atctggtttt tgtttttttg aataataaat gttactgttc ttgcggtttg gaggaattga  23820
ttcaaattca agcgaaataa ttcagggtca aaatatgtat caatgcagca tttgagcaag  23880
tgcgataaat ctttaagtct tctttcccat ggttttttag tcataaaact ctccattttg  23940
ataggttgca tgctagatgc tgatatattt tagaggtgat aaaattaact gcttaactgt  24000
caatgtaata caagttgttt gatctttgca atgattctta tcagaaacca tatagtaaat  24060
tagttacaca ggaaattttt aatattatta ttatcattca ttatgtatta aaattagagt  24120
tgtggcttgg ctctgctaac acgttgctca taggagatat ggtagagccg cagacacgtc  24180
gtatgcagga acgtgctgcg gctggctggt gaacttccga tagtgcgggt gttgaatgat  24240
ttccagttgc taccgatttt acatattttt tgcatgagag aatttgtacc acctcccacc  24300
gaccatctat gactgtacgc cactgtccct aggactgcta tgtgccggag cggacattac  24360
aaacgtcctt ctcggtgcat gccactgttg ccaatgacct gcctaggaat tggttagcaa  24420
gttactaccg gattttgtaa aaacagccct cctcatataa aaagtattcg ttcacttccg  24480
ataagcgtcg taattttcta tctttcatca tattctagat ccctctgaaa aaatcttccg  24540
agtttgctag gcactgatac ataactcttt tccaataatt ggggaagtca ttcaaatcta  24600
taataggttt cagatttgct tcaataaatt ctgactgtag ctgctgaaac gttgcggttg  24660
aactatattt ccttataact tttacgaaag agtttctttg agtaatcact tcactcaagt  24720
gcttccctgc ctccaaacga tacctgttag caatatttaa tagcttgaaa tgatgaagag  24780
ctctgtgttt gtcttcctgc ctccagttcg ccgggcattc aacataaaaa ctgatagcac  24840
ccggagttcc ggaaacgaaa tttgcatata cccattgctc acgaaaaaaa atgtccttgt  24900
cgatataggg atgaatcgct tggtgtacct catctactgc gaaaacttga cctttctctc  24960
ccatattgca gtcgcggcac gatggaacta aattaatagg catcaccgaa aattcaggat  25020
aatgtgcaat aggaagaaaa tgatctatat tttttgtctg tcctatatca ccacaaaatg  25080
gacatttttc acctgatgaa acaagcatgt catcgtaata tgttctagcg ggtttgtttt  25140
tatctcggag attattttca taaagctttt ctaatttaac ctttgtcagg ttaccaacta  25200
ctaaggttgt aggctcaaga gggtgtgtcc tgtcgtaggt aaataactga cctgtcgagc  25260
```

ttaatattct atattgttgt tctttctgca aaaaagtggg gaagtgagta atgaaattat 25320
ttctaacatt tatctgcatc ataccttccg agcatttatt aagcatttcg ctataagttc 25380
tcgctggaag aggtagtttt ttcattgtac tttaccttca tctctgttca ttatcatcgc 25440
ttttaaaacg gttcgacctt ctaatcctat ctgaccatta taattttta gaatggtttc 25500 ataagaaagc tctgaatcaa cggactgcga taataagtgg tggtatccag aatttgtcac 25560
ttcaagtaaa aacacctcac gagttaaaac acctaagttc tcaccgaatg tctcaatatc 25620
cggacggata atatttattg cttctcttga ccgtaggact ttccacatgc aggattttgg 25680
aacctcttgc agtactactg gggaatgagt tgcaattatt gctacaccat tgcgtgcatc 25740
gagtaagtcg cttaatgttc gtaaaaaagc agagagcaaa ggtggatgca gatgaacctc 25800
tggttcatcg aataaaacta atgacttttc gccaacgaca tctactaatc ttgtgatagt 25860
aaataaaaca attgcatgtc cagagctcat tcgaagcaga tatttctgga tattgtcata 25920
aaacaattta gtgaatttat catcgtccac ttgaatctgt ggttcattac gtcttaactc 25980
ttcatattta gaaatgaggc tgatgagttc catatttgaa aagttttcat cactacttag 26040
ttttttgata gcttcaagcc agagttgtct ttttctatct actctcatac aaccaataaa 26100
tgctgaaatg aattctaagc ggagatcgcc tagtgatttt aaactattgc tggcagcatt 26160
cttgagtcca atataaaagt attgtgtacc ttttgctggg tcaggttgtt ctttaggagg 26220
agtaaaagga tcaaatgcac taaacgaaac tgaaacaagc gatcgaaaat atccctttgg 26280
gattcttgac tcgataagtc tattattttc agagaaaaaa tattcattgt tttctgggtt 26340
ggtgattgca ccaatcattc cattcaaaat tgttgtttta ccacacccat tccgcccgat 26400
aaaagcatga atgttcgtgc tgggcataga attaaccgtc acctcaaaag gtatagttaa 26460
atcactgaat ccgggagcac tttttctatt aaatgaaaag tggaaatctg acaattctgg 26520
caaaccattt aacacacgtg cgaactgtcc atgaatttct gaaagagtta cccctctaag 26580
taatgaggtg ttaaggacgc tttcattttc aatgtcggct aatcgatttg gccatactac 26640
taaatcctga atagctttaa gaaggttatg tttaaaacca tcgcttaatt tgctgagatt 26700
aacatagtag tcaatgcttt cacctaagga aaaaaacatt tcagggagtt gactgaattt 26760
tttatctatt aatgaataag tgcttacttc ttctttttga cctacaaaac caattttaac 26820
atttccgata tcgcattttt caccatgctc atcaaagaca gtaagataaa acattgtaac 26880
aaaggaatag tcattccaac catctgctcg taggaatgcc ttattttttt ctactgcagg 26940
aatatacccg cctctttcaa taacactaaa ctccaacata tagtaaccct taattttatt 27000
aaaataaccg caatttattt ggcggcaaca caggatctct cttttaagtt actctctatt 27060
acatacgttt tccatctaaa aattagtagt attgaactta acggggcatc gtattgtagt 27120
tttccatatt tagctttctg cttccttttg gataacccac tgttattcat gttgcatggt 27180
gcactgttta taccaacgat atagtctatt aatgcatata tagtatcgcc gaacgattag 27240
ctcttcaggc ttctgaagaa gcgtttcaag tactaataag ccgatagata gccacggact 27300
tcgtagccat ttttcataag tgttaacttc cgctcctcgc tcataacaga cattcactac 27360
agttatggcg gaaaggtatg catgctgggt gtggggaagt cgtgaaagaa aagaagtcag 27420
ctgcgtcgtt tgacatcact gctatcttct tactggttat gcaggtcgta gtgggtggca 27480
cacaaagctt tgcactggat tgcgaggctt tgtgcttctc tggagtgcga caggtttgat 27540
gacaaaaaat tagcgcaaga agacaaaaat caccttgcgc taatgctctg ttacaggtca 27600
ctaataccat ctaagtagtt gattcatagt gactgcatat gttgtgtttt acagtattat 27660
gtagtctgtt ttttatgcaa aatctaattt aatatattga tatttatatc attttacgtt 27720
tctcgttcag ctttttttata ctaagttggc attataaaaa agcattgctt atcaatttgt 27780
tgcaacgaac aggtcactat cagtcaaaat aaaatcatta tttgatttca attttgtccc 27840
actccctgcc tctgtcatca cgatactgtg atgccatggt gtccgactta tgcccgagaa 27900
gatgttgagc aaacttatcg cttatctgct tctcatagag tcttgcagac aaactgcgca 27960
actcgtgaaa ggtaggcgga tccccttcga aggaaagacc tgatgctttt cgtgcgcgca 28020
taaaatacct tgatactgtg ccggatgaaa gcggttcgcg acgagtagat gcaattatgg 28080
tttctccgcc aagaatctct ttgcatttat caagtgtttc cttcattgat attccgagag 28140
catcaatatg caatgctgtt gggatggcaa tttttacgcc tgttttgctt tgctcgacat 28200
aaagatatcc atctacgata tcagaccact tcatttcgca taaatcacca actcgttgcc 28260
cggtaacaac agccagttcc attgcaagtc tgagccaaca tggtgatgat tctgctgctt 28320
gataaatttt caggtattcg tcagccgtaa gtcttgatct ccttacctct gattttgctg 28380
cgcgagtggc agcgacatgg tttgttgtta tatggccttc agctattgcc tctcggaatg 28440
catcgctcag tgttgatctg attaacttgg ctgacgccgc cttgccctcg tctatgtatc 28500
cattgagcat tgccgcaatt tcttttgtgg tgatgtcttc aagtggagca tcaggcagac 28560
ccctccttat tgctttaatt ttgctcatgt aatttatgag tgtcttctgc ttgattcctc 28620
tgctggccag gatttttttcg tagcgatcaa gccatgaatg taacgtaacg gaattatcac 28680
tgttgattct cgctgtcaga ggcttgtgtt tgtgtcctga aaataactca atgttggcct 28740
gtatagcttc agtgattgcg attcgcctgt ctctgcctaa tccaaactct ttacccgtcc 28800
ttgggtccct gtagcagtaa tatccattgt ttcttatata aaggttaggg ggtaaatccc 28860
ggcgctcatg acttcgcctt cttcccattt ctgatcctct tcaaaaggcc acctgttact 28920
ggtcgattta agtcaacctt taccgctgat tcgtggaaca gatactctct tccatcctta 28980
accggaggtg ggaatatcct gcattcccga acccatcgac gaactgtttc aaggcttctt 29040
ggacgtcgct ggcgtgcgtt ccactcctga agtgtcaagt acatcgcaaa gtctccgcaa 29100
ttacacgcaa gaaaaaaccg ccatcaggcg gcttggtgtt ctttcagttc ttcaattcga 29160
atattggtta cgtctgcatg tgctatctgc gcccatatca tccagtggtc gtagcagtcg 29220
ttgatgttct ccgcttcgat aactctgttg aatggctctc cattccattc tcctgtgact 29280
cggaagtgca tttatcatct ccataaaaca aaacccgccg tagcgagttc agataaaata 29340
aatccccgcg agtgcgagga ttgttatgta atattgggtt taatcatcta tatgttttgt 29400
acagagaggg caagtatcgt ttccaccgta ctcgtgataa taattttgca cggtatcagt 29460
catttctcgc acattgcaga atggggattt gtcttcatta gacttataaa ccttcatgga 29520
atatttgtat gccgactcta tatctatacc ttcatctaca taaacacctt cgtgatgtct 29580
gcatggagac aagacaccgg atctgcacaa cattgataac gcccaatctt tttgctcaga 29640
ctctaactca ttgatactca tttataaact ccttgcaatg tatgtcgttt cagctaaacg 29700
gtatcagcaa tgtttatgta aagaaacagt aagataatac tcaacccgat gtttgagtac 29760
ggtcatcatc tgacactaca gactctggca tcgctgtgaa gacgacgcga aattcagcat 29820
tttcacaagc gttatctttt acaaaaccga tctcactctc ctttgatgcg aatgccagcg 29880
tcagacatca tatgcagata ctcacctgca tcctgaaccc attgacctcc aaccccgtaa 29940
tagcgatgcg taatgatgtc gatagttact aacgggtctt gttcgattaa ctgccgcaga 30000

```
aactcttcca ggtcaccagt gcagtgcttg ataacaggag tcttcccagg atggcgaaca  30060
acaagaaact ggtttccgtc ttcacggact tcgttgcttt ccagtttagc aatacgctta  30120
ctcccatccg agataacacc ttcgtaatac tcacgctgct cgttgagttt tgattttgct  30180
gtttcaagct caacacgcag tttccctact gttagcgcaa tatcctcgtt ctcctggtcg  30240
cggcgtttga tgtattgctg gtttctttcc cgttcatcca gcagttccag cacaatcgat  30300
ggtgttacca attcatggaa aaggtctgcg tcaaatcccc agtcgtcatg cattgcctgc  30360
tctgccgctt cacgcagtgc ctgagagtta atttcgctca cttcgaacct ctctgtttac  30420
tgataagttc cagatcctcc tggcaacttg cacaagtccg acaaccctga acgaccaggc  30480
gtcttcgttc atctatcgga tcgccacact cacaacaatg agtggcagat atagcctggt  30540
ggttcaggcg gcgcattttt attgctgtgt tgcgctgtaa ttcttctatt tctgatgctg  30600
aatcaatgat gtctgccatc tttcattaat ccctgaactg ttggttaata cgcttgaggg  30660
tgaatgcgaa taataaaaaa ggagcctgta gctccctgat gattttgctt ttcatgttca  30720
tcgttcctta aagacgccgt ttaacatgcc gattgccagg cttaaatgag tcggtgtgaa  30780
tcccatcagc gttaccgttt cgcggtgctt cttcagtacg ctacggcaaa tgtcatcgac  30840
gtttttatcc ggaaactgct gtctggcttt ttttgatttc agaattagcc tgacgggcaa  30900
tgctgcgaag ggcgttttcc tgctgaggtg tcattgaaca agtcccatgt cggcaagcat  30960
aagcacacag aatatgaagc ccgctgccag aaaaatgcat tccgtggttg tcatacctgg  31020
tttctctcat ctgcttctgc tttcgccacc atcatttcca gcttttgtga aagggatgcg  31080
gctaacgtat gaaattcttc gtctgtttct actggtattg gcacaaacct gattccaatt  31140
tgagcaaggc tatgtgccat ctcgatactc gttcttaact caacagaaga tgctttgtgc  31200
atacagcccc tcgtttatta tttatctcct cagccagccg ctgtgctttc agtggatttc  31260
ggataacaga aaggccggga aatacccagc ctcgctttgt aacggagtag acgaaagtga  31320
ttgcgcctac ccggatatta tcgtgaggat gcgtcatcgc cattgctccc caaatacaaa  31380
accaatttca gccagtgcct cgtccatttt ttcgatgaac tccggcacga tctcgtcaaa  31440
actcgccatg tacttttcat cccgctcaat cacgacataa tgcaggcctt cacgcttcat  31500
acgcgggtca tagttggcaa agtaccaggc attttttcgc gtcacccaca tgctgtactg  31560
cacctgggcc atgtaagctg actttatggc ctcgaaacca ccgagccgga acttcatgaa  31620
atcccgggag gtaaacgggc atttcagttc aaggccgttg ccgtcactgc ataaaccatc  31680
gggagagcag gcggtacgca tactttcgtc gcgatagatg atcggggatt cagtaacatt  31740
cacgccggaa gtgaattcaa acagggttct ggcgtcgttc tcgtactgtt ttccccaggc  31800
cagtgcttta gcgttaactt ccggagccac accggtgcaa acctcagcaa gcagggtgtg  31860
gaagtaggac attttcatgt caggccactt ctttccggag cggggttttg ctatcacgtt  31920
gtgaacttct gaagcggtga tgacgccgag ccgtaatttg tgccacgcat catccccctg  31980
ttcgacagct ctcacatcga tcccggtacg ctgcaggata atgtccggtg tcatgctgcc  32040
accttctgct ctgcggcttt ctgtttcagg aatccaagag cttttactgc ttcggcctgt  32100
gtcagttctg acgatgcacg aatgtcgcgg cgaaatatct gggaacagag cggcaataag  32160
tcgtcatccc atgttttatc cagggcgatc agcagagtgt taatctcctg catggtttca  32220
tcgttaaccg gagtgatgtc gcgttccggc tgacgttctg cagtgtatgc agtattttcg  32280
acaatgcgct cggcttcatc cttgtcatag ataccagcaa atccgaaggc cagacgggca  32340
```

cactgaatca tggctttatg acgtaacatc cgtttgggat gcgactgcca cggccccgtg 32400
atttctctgc cttcgcgagt tttgaatggt tcgcggcggc attcatccat ccattcggta 32460
acgcagatcg gatgattacg gtccttgcgg taaatccggc atgtacagga ttcattgtcc 32520
tgctcaaagt ccatgccatc aaactgctgg ttttcattga tgatgcggga ccagccatca 32580
acgcccacca ccggaacgat gccattctgc ttatcaggaa aggcgtaaat ttctttcgtc 32640
cacggattaa ggccgtactg gttggcaacg atcagtaatg cgatgaactg cgcatcgctg 32700
gcatcacctt taaatgccgt ctggcgaaga gtggtgatca gttcctgtgg gtcgacagaa 32760
tccatgccga cacgttcagc cagcttccca gccagcgttg cgagtgcagt actcattcgt 32820
tttatacctc tgaatcaata tcaacctggt ggtgagcaat ggtttcaacc atgtaccgga 32880
tgtgttctgc catgcgctcc tgaaactcaa catcgtcatc aaacgcacgg gtaatggatt 32940
ttttgctggc cccgtggcgt tgcaaatgat cgatgcatag cgattcaaac aggtgctggg 33000
gcaggccttt ttccatgtcg tctgccagtt ctgcctcttt ctcttcacgg gcgagctgct 33060
ggtagtgacg cgcccagctc tgagcctcaa gacgatcctg aatgtaataa gcgttcatgg 33120
ctgaactcct gaaatagctg tgaaaatatc gcccgcgaaa tgccgggctg attaggaaaa 33180
caggaaaggg ggttagtgaa tgcttttgct tgatctcagt ttcagtatta atatccattt 33240
tttataagcg tcgacggctt cacgaaacat cttttcatcg ccaataaaag tggcgatagt 33300
gaatttagtc tggatagcca taagtgtttg atccattctt tgggactcct ggctgattaa 33360
gtatgtcgat aaggcgtttc catccgtcac gtaatttacg ggtgattcgt tcaagtaaag 33420
attcggaagg gcagccagca acaggccacc ctgcaatggc atattgcatg gtgtgctcct 33480
tatttataca taacgaaaaa cgcctcgagt gaagcgttat tggtatgcgg taaaaccgca 33540
ctcaggcggc cttgatagtc atatcatctg aatcaaatat tcctgatgta tcgatatcgg 33600
taattcttat tccttcgcta ccatccattg gaggccatcc ttcctgacca tttccatcat 33660
tccagtcgaa ctcacacaca acaccatatg catttaagtc gcttgaaatt gctataagca 33720
gagcatgttg cgccagcatg attaatacag catttaatac agagccgtgt ttattgagtc 33780
ggtattcaga gtctgaccag aaattattaa tctggtgaag tttttcctct gtcattacgt 33840
catggtcgat ttcaatttct attgatgctt tccagtcgta atcaatgatg tatttttga 33900
tgtttgacat ctgttcatat cctcacagat aaaaaatcgc cctcacactg gagggcaaag 33960
aagatttcca ataatcagaa caagtcggct cctgtttagt tacgagcgac attgctccgt 34020
gtattcactc gttggaatga atacacagtg cagtgtttat tctgttattt atgccaaaaa 34080
taaaggccac tatcaggcag ctttgttgtt ctgtttacca agttctctgg caatcattgc 34140
cgtcgttcgt attgcccatt tatcgacata tttcccatct tccattacag gaaacatttc 34200
ttcaggctta accatgcatt ccgattgcag cttgcatcca ttgcatcgct tgaattgtcc 34260
acaccattga tttttatcaa tagtcgtagt catacggata gtcctggtat tgttccatca 34320
catcctgagg atgctcttcg aactcttcaa attcttcttc catatatcac cttaaatagt 34380
ggattgcggt agtaaagatt gtgcctgtct tttaaccaca tcaggctcgg tggttctcgt 34440
gtacccctac agcgagaaat cggataaact attacaaccc ctacagtttg atgagtatag 34500
aaatggatcc actcgttatt ctcggacgag tgttcagtaa tgaacctctg gagagaacca 34560
tgtatatgat cgttatctgg gttggacttc tgcttttaag cccagataac tggcctgaat 34620
atgttaatga gagaatcggt attcctcatg tgtggcatgt tttcgtcttt gctcttgcat 34680
tttcgctagc aattaatgtg catcgattat cagctattgc cagcgccaga tataagcgat 34740

-continued

```
ttaagctaag aaaacgcatt aagatgcaaa acgataaagt gcgatcagta attcaaaacc  34800
ttacagaaga gcaatctatg gttttgtgcg cagcccttaa tgaaggcagg aagtatgtgg  34860
ttacatcaaa acaattccca tacattagtg agttgattga gcttggtgtg ttgaacaaaa  34920
ctttttcccg atggaatgga aagcatatat tattccctat tgaggatatt tactggactg  34980
aattagttgc cagctatgat ccatataata ttgagataaa gccaaggcca atatctaagt  35040
aactagataa gaggaatcga ttttccctta attttctggc gtccactgca tgttatgccg  35100
cgttcgccag gcttgctgta ccatgtgcgc tgattcttgc gctcaatacg ttgcaggttg  35160
ctttcaatct gtttgtggta ttcagccagc actgtaaggt ctatcggatt tagtgcgctt  35220
tctactcgtg atttcggttt gcgattcagc gagagaatag ggcggttaac tggttttgcg  35280
cttaccccaa ccaacagggg atttgctgct ttccattgag cctgtttctc tgcgcgacgt  35340
tcgcggcggc gtgtttgtgc atccatctgg attctcctgt cagttagctt tggtggtgtg  35400
tggcagttgt agtcctgaac gaaaaccccc cgcgattggc acattggcag ctaatccgga  35460
atcgcactta cggccaatgc ttcgtttcgt atcacacacc ccaaagcctt ctgctttgaa  35520
tgctgccctt cttcagggct taatttttaa gagcgtcacc ttcatggtgg tcagtgcgtc  35580
ctgctgatgt gctcagtatc accgccagtg gtatttatgt caacaccgcc agagataatt  35640
tatcaccgca gatggttatc tgtatgtttt ttatatgaat ttattttttg caggggggca  35700
ttgtttggta ggtgagagat ctgaattgct atgtttagtg agttgtatct atttattttt  35760
caataaatac aattggttat gtgttttggg ggcgatcgtg aggcaaagaa aacccggcgc  35820
tgaggccggg ttattcttgt tctctggtca aattatatag ttggaaaaca aggatgcata  35880
tatgaatgaa cgatgcagag gcaatgccga tggcgatagt gggtatcatg tagccgctta  35940
tgctggaaag aagcaataac ccgcagaaaa acaaagctcc aagctcaaca aaactaaggg  36000
catagacaat aactaccgat gtcatatacc catactctct aatcttggcc agtcggcgcg  36060
ttctgcttcc gattagaaac gtcaaggcag caatcaggat tgcaatcatg gttcctgcat  36120
atgatgacaa tgtcgcccca agaccatctc tatgagctga aaaagaaaca ccaggaatgt  36180
agtggcggaa aaggagatag caaatgctta cgataacgta aggaattatt actatgtaaa  36240
caccaggcat gattctgttc cgcataatta ctcctgataa ttaatcctta actttgccca  36300
cctgcctttt aaaacattcc agtatatcac ttttcattct tgcgtagcaa tatgccatct  36360
cttcagctat ctcagcattg gtgaccttgt tcagaggcgc tgagagatgg cctttttctg  36420
atagataatg ttctgttaaa atatctccgg cctcatcttt tgcccgcagg ctaatgtctg  36480
aaaattgagg tgacgggtta aaaataatat ccttggcaac ctttttttata tccctttttaa  36540
attttggctt aatgactata tccaatgagt caaaaagctc cccttcaata tctgttgccc  36600
ctaagacctt taatatatcg ccaaatacag gtagcttggc ttctaccttc accgttgttc  36660
ggccgatgaa atgcatatgc ataacatcgt ctttggtggt tcccctcatc agtggctcta  36720
tctgaacgcg ctctccactg cttaatgaca ttcctttccc gattaaaaaa tctgtcagat  36780
cggatgtggt cggcccgaaa acagttctgg caaaaccaat ggtgtcgcct tcaacaaaca  36840
aaaaagatgg gaatcccaat gattcgtcat ctgcgaggct gttcttaata tcttcaactg  36900
aagctttaga gcgatttatc ttctgaacca gactcttgtc atttgttttg gtaaagagaa  36960
aagtttttcc atcgatttta tgaatataca aataattgga gccaacctgc aggtgatgat  37020
tatcagccag cagagaatta aggaaaacag acaggtttat tgagcgctta tctttccctt  37080
```

tatttttgct gcggtaagtc gcataaaaac cattcttcat aattcaatcc atttactatg 37140
ttatgttctg aggggagtga aaattcccct aattcgatga agattcttgc tcaattgtta 37200
tcagctatgc gccgaccaga acaccttgcc gatcagccaa acgtctcttc aggccactga 37260
ctagcgataa ctttccccac aacggaacaa ctctcattgc atgggatcat tgggtactgt 37320
gggtttagtg gttgtaaaaa cacctgaccg ctatccctga tcagtttctt gaaggtaaac 37380
tcatcacccc caagtctggc tatgcagaaa tcacctggct caacagcctg ctcagggtca 37440
acgagaatta acattccgtc aggaaagctt ggcttggagc ctgttggtgc ggtcatggaa 37500
ttaccttcaa cctcaagcca gaatgcagaa tcactggctt ttttggttgt gcttacccat 37560
ctctccgcat cacctttggt aaaggttcta agcttaggtg agaacatccc tgcctgaaca 37620
tgagaaaaaa cagggtactc atactcactt ctaagtgacg gctgcatact aaccgcttca 37680
tacatctcgt agatttctct ggcgattgaa gggctaaatt cttcaacgct aactttgaga 37740
atttttgtaa gcaatgcggc gttataagca tttaatgcat tgatgccatt aaataaagca 37800
ccaacgcctg actgccccat ccccatcttg tctgcgacag attcctggga taagccaagt 37860
tcatttttct ttttttcata aattgcttta aggcgacgtg cgtcctcaag ctgctcttgt 37920
gttaatggtt tcttttttgt gctcatacgt taaatctatc accgcaaggg ataaatatct 37980
aacaccgtgc gtgttgacta ttttacctct ggcggtgata atggttgcat gtactaagga 38040
ggttgtatgg aacaacgcat aaccctgaaa gattatgcaa tgcgctttgg gcaaaccaag 38100
acagctaaag atctcggcgt atatcaaagc gcgatcaaca aggccattca tgcaggccga 38160
aagatttttt taactataaa cgctgatgga agcgtttatg cggaagaggt aaagcccttc 38220
ccgagtaaca aaaaaacaac agcataaata accccgctct tacacattcc agccctgaaa 38280
aagggcatca aattaaacca cacctatggt gtatgcattt atttgcatac attcaatcaa 38340
ttgttatcta aggaaatact tacatatggt tcgtgcaaac aaacgcaacg aggctctacg 38400
aatcgagagt gcgttgctta acaaaatcgc aatgcttgga actgagaaga cagcggaagc 38460
tgtgggcgtt gataagtcgc agatcagcag gtggaagagg gactggattc caaagttctc 38520
aatgctgctt gctgttcttg aatggggggt cgttgacgac gacatggctc gattggcgcg 38580
acaagttgct gcgattctca ccaataaaaa acgcccggcg gcaaccgagc gttctgaaca 38640
aatccagatg gagttctgag gtcattactg gatctatcaa caggagtcat tatgacaaat 38700
acagcaaaaa tactcaactt cggcagaggt aactttgccg gacaggagcg taatgtggca 38760
gatctcgatg atggttacgc cagactatca aatatgctgc ttgaggctta ttcgggcgca 38820
gatctgacca agcgacagtt taaagtgctg cttgccattc tgcgtaaaac ctatgggtgg 38880
aataaaccaa tggacagaat caccgattct caacttagcg agattacaaa gttacctgtc 38940
aaacggtgca atgaagccaa gttagaactc gtcagaatga atattatcaa gcagcaaggc 39000
ggcatgtttg gaccaaataa aaacatctca gaatggtgca tccctcaaaa cgagggaaaa 39060
tcccctaaaa cgagggataa aacatccctc aaattggggg attgctatcc ctcaaaacag 39120
ggggacacaa aagacactat tacaaaagaa aaaagaaaag attattcgtc agagaattct 39180
ggcgaatcct ctgaccagcc agaaaacgac ctttctgtgg tgaaaccgga tgctgcaatt 39240
cagagcggca gcaagtgggg gacagcagaa gacctgaccg ccgcagagtg gatgtttgac 39300
atggtgaaga ctatcgcacc atcagccaga aaaccgaatt ttgctgggtg ggctaacgat 39360
atccgcctga tgcgtgaacg tgacggacgt aaccaccgcg acatgtgtgt gctgttccgc 39420
tgggcatgcc aggacaactt ctggtccggt aacgtgctga gcccggccaa actccgcgat 39480
aagtggaccc aactcgaaat caaccgtaac aagcaacagg caggcgtgac agccagcaaa 39540
ccaaaactcg acctgacaaa cacagactgg atttacgggg tggatctatg aaaaacatcg 39600
ccgcacagat ggttaacttt gaccgtgagc agatgcgtcg gatcgccaac aacatgccgg 39660
aacagtacga cgaaaagccg caggtacagc aggtagcgca gatcatcaac ggtgtgttca 39720
gccagttact ggcaactttc ccggcgagcc tggctaaccg tgaccagaac gaagtgaacg 39780
aaatccgtcg ccagtgggtt ctggcttttc gggaaaacgg gatcaccacg atggaacagg 39840
ttaacgcagg aatgcgcgta gcccgtcggc agaatcgacc atttctgcca tcacccgggc 39900
agtttgttgc atggtgccgg gaagaagcat ccgttaccgc cggactgcca aacgtcagcg 39960
agctggttga tatggtttac gagtattgcc ggaagcgagg cctgtatccg gatgcggagt 40020
cttatccgtg gaaatcaaac gcgcactact ggctggttac caacctgtat cagaacatgc 40080
gggccaatgc gcttactgat gcggaattac gccgtaaggc cgcagatgag cttgtccata 40140
tgactgcgag aattaaccgt ggtgaggcga tccctgaacc agtaaaacaa cttcctgtca 40200
tgggcggtag acctctaaat cgtgcacagg ctctggcgaa gatcgcagaa atcaaagcta 40260
agttcggact gaaaggagca agtgtatgac gggcaaagag gcaattattc attacctggg 40320
gacgcataat agcttctgtg cgccggacgt tgccgcgcta acaggcgcaa cagtaaccag 40380
cataaatcag gccgcggcta aaatggcacg ggcaggtctt ctggttatcg aaggtaaggt 40440
ctggcgaacg gtgtattacc ggtttgctac cagggaagaa cgggaaggaa agatgagcac 40500
gaacctggtt tttaaggagt gtcgccagag tgccgcgatg aaacgggtat tggcggtata 40560
tggagttaaa agatgaccat ctacattact gagctaataa caggcctgct ggtaatcgca 40620
ggccttttta tttgggggag agggaagtca tgaaaaaact aacctttgaa attcgatctc 40680
cagcacatca gcaaaacgct attcacgcag tacagcaaat ccttccagac ccaaccaaac 40740
caatcgtagt aaccattcag gaacgcaacc gcagcttaga ccaaaacagg aagctatggg 40800
cctgcttagg tgacgtctct cgtcaggttg aatggcatgg tcgctggctg gatgcagaaa 40860
gctggaagtg tgtgtttacc gcagcattaa agcagcagga tgttgttcct aaccttgccg 40920
ggaatggctt tgtggtaata ggccagtcaa ccagcaggat gcgtgtaggc gaatttgcgg 40980
agctattaga gcttatacag gcattcggta cagagcgtgg cgttaagtgg tcagacgaag 41040
cgagactggc tctggagtgg aaagcgagat ggggagacag ggctgcatga taaatgtcgt 41100
tagtttctcc ggtggcagga cgtcagcata tttgctctgg ctaatggagc aaaagcgacg 41160
ggcaggtaaa gacgtgcatt acgttttcat ggatacaggt tgtgaacatc caatgacata 41220
tcggtttgtc agggaagttg tgaagttctg ggatataccg ctcaccgtat tgcaggttga 41280
tatcaacccg gagcttggac agccaaatgg ttatacggta tgggaaccaa aggatattca 41340
gacgcgaatg cctgttctga agccatttat cgatatggta aagaaatatg gcactccata 41400
cgtcggcggc gcgttctgca ctgacagatt aaaactcgtt cccttcacca aatactgtga 41460
tgaccatttc gggcgaggga attacaccac gtggattggc atcagagctg atgaaccgaa 41520
gcggctaaag ccaaagcctg gaatcagata tcttgctgaa ctgtcagact ttgagaagga 41580
agatatcctc gcatggtgga agcaacaacc attcgatttg caaataccgg aacatctcgg 41640
taactgcata ttctgcatta aaaaatcaac gcaaaaaatc ggacttgcct gcaaagatga 41700
ggagggattg cagcgtgttt ttaatgaggt catcacggga tcccatgtgc gtgacggaca 41760
tcgggaaacg ccaaaggaga ttatgtaccg aggaagaatg tcgctggacg gtatcgcgaa 41820

-continued

```
aatgtattca gaaaatgatt atcaagccct gtatcaggac atggtacgag ctaaaagatt  41880
cgataccggc tcttgttctg agtcatgcga aatatttgga gggcagcttg atttcgactt  41940
cgggagggaa gctgcatgat gcgatgttat cggtgcggtg aatgcaaaga agataaccgc  42000
ttccgaccaa atcaacctta ctggaatcga tggtgtctcc ggtgtgaaag aacaccaaca  42060
ggggtgttac cactaccgca ggaaaaggag gacgtgtggc gagacagcga cgaagtatca  42120
ccgacataat ctgcgaaaac tgcaaatacc ttccaacgaa acgcaccaga aataaaccca  42180
agccaatccc aaaagaatct gacgtaaaaa ccttcaacta cacggctcac ctgtgggata  42240
tccggtggct aagacgtcgt gcgaggaaaa caaggtgatt gaccaaaatc gaagttacga  42300
acaagaaagc gtcgagcgag ctttaacgtg cgctaactgc ggtcagaagc tgcatgtgct  42360
ggaagttcac gtgtgtgagc actgctgcgc agaactgatg agcgatccga atagctcgat  42420
gcacgaggaa gaagatgatg gctaaaccag cgcgaagacg atgtaaaaac gatgaatgcc  42480
gggaatggtt tcaccctgca ttcgctaatc agtggtggtg ctctccagag tgtggaacca  42540
agatagcact cgaacgacga agtaaagaac gcgaaaaagc ggaaaaagca gcagagaaga  42600
aacgacgacg agaggagcag aaacagaaag ataaacttaa gattcgaaaa ctcgccttaa  42660
agccccgcag ttactggatt aaacaagccc aacaagccgt aaacgccttc atcagagaaa  42720
gagaccgcga cttaccatgt atctcgtgcg gaacgctcac gtctgctcag tgggatgccg  42780
gacattaccg gacaactgct gcggcacctc aactccgatt taatgaacgc aatattcaca  42840
agcaatgcgt ggtgtgcaac cagcacaaaa gcggaaatct cgttccgtat cgcgtcgaac  42900
tgattagccg catcgggcag gaagcagtag acgaaatcga atcaaaccat aaccgccatc  42960
gctggactat cgaagagtgc aaggcgatca aggcagagta ccaacagaaa ctcaaagacc  43020
tgcgaaatag cagaagtgag gccgcatgac gttctcagta aaaaccattc cagacatgct  43080
cgttgaaaca tacggaaatc agacagaagt agcacgcaga ctgaaatgta gtcgcggtac  43140
ggtcagaaaa tacgttgatg ataaagacgg gaaaatgcac gccatcgtca acgacgttct  43200
catggttcat cgcggatgga gtgaaagaga tgcgctatta cgaaaaaatt gatggcagca  43260
aataccgaaa tatttgggta gttggcgatc tgcacggatg ctacacgaac ctgatgaaca  43320
aactggatac gattggattc gacaacaaaa aagacctgct tatctcggtg ggcgatttgg  43380
ttgatcgtgg tgcagagaac gttgaatgcc tggaattaat cacattcccc tggttcagag  43440
ctgtacgtgg aaaccatgag caaatgatga ttgatggctt atcagagcgt ggaaacgtta  43500
atcactggct gcttaatggc ggtggctggt tctttaatct cgattacgac aaagaaattc  43560
tggctaaagc tcttgcccat aaagcagatg aacttccgtt aatcatcgaa ctggtgagca  43620
aagataaaaa atatgttatc tgccacgccg attatccctt tgacgaatac gagtttggaa  43680
agccagttga tcatcagcag gtaatctgga accgcgaacg aatcagcaac tcacaaaacg  43740
ggatcgtgaa agaaatcaaa ggcgcggaca cgttcatctt tggtcatacg ccagcagtga  43800
aaccactcaa gtttgccaac caaatgtata tcgataccgg cgcagtgttc tgcggaaacc  43860
taacattgat tcaggtacag ggagaaggcg catgagactc gaaagcgtag ctaaatttca  43920
ttcgccaaaa agcccgatga tgagcgactc accacgggcc acggcttctg actctctttc  43980
cggtactgat gtgatggctg ctatggggat ggcgcaatca caagccggat tcggtatggc  44040
tgcattctgc ggtaagcacg aactcagcca gaacgacaaa caaaaggcta tcaactatct  44100
gatgcaattt gcacacaagg tatcggggaa ataccgtggt gtggcaaagc ttgaaggaaa  44160
tactaaggca aaggtactgc aagtgctcgc aacattcgct tatgcggatt attgccgtag  44220
```

tgccgcgacg ccgggggcaa gatgcagaga ttgccatggt acaggccgtg cggttgatat 44280
tgccaaaaca gagctgtggg ggagagttgt cgagaaagag tgcggaagat gcaaaggcgt 44340
cggctattca aggatgccag caagcgcagc atatcgcgct gtgacgatgc taatcccaaa 44400
ccttacccaa cccacctggt cacgcactgt taagccgctg tatgacgctc tggtggtgca 44460
atgccacaaa gaagagtcaa tcgcagacaa cattttgaat gcggtcacac gttagcagca 44520
tgattgccac ggatggcaac atattaacgg catgatattg acttattgaa taaaattggg 44580
taaatttgac tcaacgatgg gttaattcgc tcgttgtggt agtgagatga aaagaggcgg 44640
cgcttactac cgattccgcc tagttggtca cttcgacgta tcgtctggaa ctccaaccat 44700
cgcaggcaga gaggtctgca aaatgcaatc ccgaaacagt tcgcaggtaa tagttagagc 44760
ctgcataacg gtttcgggat tttttatatc tgcacaacag gtaagagcat tgagtcgata 44820
atcgtgaaga gtcggcgagc ctggttagcc agtgctcttt ccgttgtgct gaattaagcg 44880
aataccggaa gcagaaccgg atcaccaaat gcgtacaggc gtcatcgccg cccagcaaca 44940
gcacaaccca aactgagccg tagccactgt ctgtcctgaa ttcattagta atagttacgc 45000
tgcggccttt tacacatgac cttcgtgaaa gcgggtggca ggaggtcgcg ctaacaacct 45060
cctgccgttt tgcccgtgca tatcggtcac gaacaaatct gattactaaa cacagtagcc 45120
tggatttgtt ctatcagtaa tcgaccttat tcctaattaa atagagcaaa tccccttatt 45180
gggggtaaga catgaagatg ccagaaaaac atgacctgtt ggccgccatt ctcgcggcaa 45240
aggaacaagg catcggggca atccttgcgt ttgcaatggc gtaccttcgc ggcagatata 45300
atggcggtgc gtttacaaaa acagtaatcg acgcaacgat gtgcgccatt atcgcctagt 45360
tcattcgtga ccttctcgac ttcgccggac taagtagcaa tctcgcttat ataacgagcg 45420
tgtttatcgg ctacatcggt actgactcga ttggttcgct tatcaaacgc ttcgctgcta 45480
aaaaagccgg agtagaagat ggtagaaatc aataatcaac gtaaggcgtt cctcgatatg 45540
ctggcgtggt cggagggaac tgataacgga cgtcagaaaa ccagaaatca tggttatgac 45600
gtcattgtag gcggagagct atttactgat tactccgatc accctcgcaa acttgtcacg 45660
ctaaacccaa aactcaaatc aacaggcgcc ggacgctacc agcttctttc ccgttggtgg 45720
gatgcctacc gcaagcagct tggcctgaaa gacttctctc cgaaaagtca ggacgctgtg 45780
gcattgcagc agattaagga gcgtggcgct ttacctatga ttgatcgtgg tgatatccgt 45840
caggcaatcg accgttgcag caatatctgg gcttcactgc cgggcgctgg ttatggtcag 45900
ttcgagcata aggctgacag cctgattgca aaattcaaag aagcgggcgg aacggtcaga 45960
gagattgatg tatgagcaga gtcaccgcga ttatctccgc tctggttatc tgcatcatcg 46020
tctgcctgtc atgggctgtt aatcattacc gtgataacgc cattacctac aaagcccagc 46080
gcgacaaaaa tgccagagaa ctgaagctgg cgaacgcggc aattactgac atgcagatgc 46140
gtcagcgtga tgttgctgcg ctcgatgcaa aatacacgaa ggagttagct gatgctaaag 46200
ctgaaaatga tgctctgcgt gatgatgttg ccgctggtcg tcgtcggttg cacatcaaag 46260
cagtctgtca gtcagtgcgt gaagccacca ccgcctccgg cgtggataat gcagcctccc 46320
cccgactggc agacaccgct gaacgggatt atttcaccct cagagagagg ctgatcacta 46380
tgcaaaaaca actggaagga acccagaagt atattaatga gcagtgcaga tagagttgcc 46440
catatcgatg ggcaactcat gcaattattg tgagcaatac acacgcgctt ccagcggagt 46500
ataaatgcct aaagtaataa aaccgagcaa tccatttacg aatgtttgct gggtttctgt 46560

```
tttaacaaca ttttctgcgc cgccacaaat tttggctgca tcgacagttt tcttctgccc  46620
aattccagaa acgaagaaat gatgggtgat ggtttccttt ggtgctactg ctgccggttt  46680
gttttgaaca gtaaacgtct gttgagcaca tcctgtaata agcagggcca gcgcagtagc  46740
gagtagcatt tttttcatgg tgttattccc gatgcttttt gaagttcgca gaatcgtatg  46800
tgtagaaaat taaacaaacc ctaaacaatg agttgaaatt tcatattgtt aatatttatt  46860
aatgtatgtc aggtgcgatg aatcgtcatt gtattcccgg attaactatg tccacagccc  46920
tgacggggaa cttctctgcg ggagtgtccg ggaataatta aaacgatgca cacagggttt  46980
agcgcgtaca cgtattgcat tatgccaacg ccccggtgct gacacggaag aaaccggacg  47040
ttatgattta gcgtggaaag atttgtgtag tgttctgaat gctctcagta aatagtaatg  47100
aattatcaaa ggtatagtaa tatcttttat gttcatggat atttgtaacc catcggaaaa  47160
ctcctgcttt agcaagattt tccctgtatt gctgaaatgt gatttctctt gatttcaacc  47220
tatcatagga cgtttctata agatgcgtgt ttcttgagaa tttaacattt acaacctttt  47280
taagtccttt tattaacacg gtgttatcgt tttctaacac gatgtgaata ttatctgtgg  47340
ctagatagta aatataatgt gagacgttgt gacgttttag ttcagaataa aacaattcac  47400
agtctaaatc ttttcgcact tgatcgaata tttctttaaa aatggcaacc tgagccattg  47460
gtaaaacctt ccatgtgata cgagggcgcg tagtttgcat tatcgttttt atcgtttcaa  47520
tctggtctga cctccttgtg ttttgttgat gatttatgtc aaatattagg aatgttttca  47580
cttaatagta ttggttgcgt aacaaagtgc ggtcctgctg gcattctgga gggaaataca  47640
accgacagat gtatgtaagg ccaacgtgct caaatcttca tacagaaaga tttgaagtaa  47700
tattttaacc gctagatgaa gagcaagcgc atggagcgac aaaatgaata aagaacaatc  47760
tgctgatgat ccctccgtgg atctgattcg tgtaaaaaat atgcttaata gcaccatttc  47820
tatgagttac cctgatgttg taattgcatg tatagaacat aaggtgtctc tggaagcatt  47880
cagagcaatt gaggcagcgt tggtgaagca cgataataat atgaaggatt attccctggt  47940
ggttgactga tcaccataac tgctaatcat tcaaactatt tagtctgtga cagagccaac  48000
acgcagtctg tcactgtcag gaaagtggta aaactgcaac tcaattactg caatgccctc  48060
gtaattaagt gaatttacaa tatcgtcctg ttcggaggga agaacgcggg atgttcattc  48120
ttcatcactt ttaattgatg tatatgctct cttttctgac gttagtctcc gacggcaggc  48180
ttcaatgacc caggctgaga aattcccgga cccttttttgc tcaagagcga tgttaatttg  48240
ttcaatcatt tggttaggaa agcggatgtt gcgggttgtt gttctgcggg ttctgttctt  48300
cgttgacatg aggttgcccc gtattcagtg tcgctgattt gtattgtctg aagttgtttt  48360
tacgttaagt tgatgcagat caattaatac gatacctgcg tcataattga ttatttgacg  48420
tggtttgatg gcctccacgc acgttgtgat atgtagatga taatcattat cactttacgg  48480
gtcctttccg gtgatccgac aggttacggg gcggcgacct cgaaaa                 48526
```

<210> SEQ ID NO 4
<211> LENGTH: 5955
<212> TYPE: DNA
<213> ORGANISM: Artificial Sequence
<220> FEATURE:
<223> OTHER INFORMATION: Artificial Operon

<400> SEQUENCE: 4

```
attaggcctg tttggccgtg acaccggaca atgagtaatg tcgcaaaatg tgtacattgt     60
ctcaaccgca cgcactccga ttggctcctt ccaaggctcg ttgtcttcta agacggccgt    120
```

```
agaactgggc gcggtggcgt taaaaggagc actggcgaag gtgccggaac tggatgcctc    180
taaggatttt gacgaaatta tttttggcaa tgtgctctcg gcaaacctgg gacaggcgcc    240
cgcacgccag gtggcgctgg cggcaggcct gagcaaccat atagtggcca gtacggtgaa    300
taaggtttgc gcctctgcga tgaaggccat aattctgggc gcgcagtcta taaaatgcgg    360
caacgcggat gtggttgtcg cgggcggctg cgaatcgatg accaatgccc cgtactacat    420
gccggccgca cgggctggcg caaaatttgg acagaccgtg ctcgtggatg gcgttgaacg    480
cgatgggctg aatgatgctt acgatggctt ggcaatgggc gtccacgccg aaaagtgcgc    540
acgggattgg gatattaccc gcgaacagca ggacaacttt gcaatagaat cttaccagaa    600
atcgcagaaa tcgcagaagg aaggcaaatt cgacaacgaa attgtcccag tgactattaa    660
gggttttcgc ggcaagccag atacccaggt tacaaaggac gaggaaccag cgcgcttaca    720
cgtggaaaaa ctgcgctcgg cccgtaccgt gttccagaaa gaaaatggca ccgtgaccgc    780
agcgaatgcg tcgccgataa atgatggcgc ggccgcagtt atactggtgt ctgaaaaagt    840
gctgaaggaa aagaacctga agccactggc gattataaaa ggctggggcg aggcagcgca    900
tcagccggcg gattttacgt gggcgccgtc gctcgccgtg ccgaaggcgc tgaaacatgc    960
gggaatagaa gacataaact cggtggatta ctttgaattc aacgaagcat tttcagtggt   1020
tggcctggta aataccaaga ttctgaagtt ggacccgtcg aaggtgaacg tctatggcgg   1080
cgcggtggcg ttgggccacc cgctgggctg ctcgggcgcg cgcgtagtgg tgacgctttt   1140
gtctatatta caacaggaag gtggcaagat aggcgtggca gcaatttgca acggcggcgg   1200
cggcgcgtct tcgattgtta ttgaaaagat ctaaggcctt gatggccaac gcgggagatt   1260
tttcatgaaa ctatccacca aactctgctg gtgcggcatt aaaggtcgcc tccgtcccca   1320
gaagcagcag cagttacaca acacgaatct gcagatgacc gaattgaaaa aacagaagac   1380
tgcggaacag aaaactcgcc cacagaacgt tggcattaaa ggcatacaga tttacatacc   1440
gacccagtgc gttaatcagt cggagttgga gaaatttgat ggagtgtcgc agggcaaata   1500
cacgattggc cttggacaga ctaatatgtc gtttgttaac gaccgcgaag atatatactc   1560
aatgtctttg accgtgctgt cgaagctgat aaagagctac aatatagaca ctaataaaat   1620
tggccgctta gaagttggca ccgaaaccct tattgacaag tctaagtcgg ttaagtcggt   1680
tctgatgcag ctgtttggcg aaaataccga cgttgaaggc attgacacac tcaacgcatg   1740
ctacggcggc actaatgctc tgttcaattc gctgaattgg attgaatcga atgcctggga   1800
tggccgcgac gcaattgtcg tgtgtggcga tattgcaata tacgataagg gcgcagcccg   1860
cccgactggc ggcgcaggca ccgtggcgat gtggataggc ccagatgcgc cgattgtctt   1920
tgactcggtc cgcgcgtcgt acatggaaca cgcatacgat ttttacaagc cggatttcac   1980
tagtgaatat ccatacgttg atggccattt ttccttaacc tgctacgtta aggcgctcga   2040
tcaggtgtac aagagctatt ctaagaaggc gatttcgaaa gggctggtga gtgatcctgc   2100
gggctcagat gcgctgaatg tgctgaaata tttcgactac aatgtgttcc atgtgccgac   2160
ttgcaaactg gttacgaaat cctacggccg cttattgtat aatgatttcc gcgcaaaccc   2220
acagctgttc ccggaagtgg acgcagaatt agcgaccaga gattatgacg aatcgttaac   2280
tgataagaat attgaaaaaa cctttgtgaa cgtggcgaag ccgttccaca aagagcgcgt   2340
ggcacagtcg ctgattgtgc cgacgaatac gggcaatatg tacactgcct cggtgtatgc   2400
agcatttgcc tcgttgttaa attatgtggg ttcggacgac ttacagggaa agcgggtggg   2460
```

-continued

```
cttattttcg tacggctctg gcttagcggc ctcgttgtat tcgtgtaaaa ttgtgggcga   2520
cgttcagcat attataaagg aattagatat taccaataaa ttagcaaagc gcataactga   2580
aaccccgaag gattacgaag cggcaataga actgcgcgaa aacgcacatc tgaagaagaa   2640
tttcaaacca cagggctcta ttgagcatct gcagagcggc gtgtactacc tgactaatat   2700
agatgacaaa tttcgccgct cgtacgatgt gaaaaaataa ggcctcgatg gccgtgaact   2760
ggatagtgaa ataatgcccc ccttgttcaa gggtcttaaa caaatggcca agccgattgc   2820
atatgtgtcc cgcttttcag ctaaacgacc gattcatatc atcctctttt cgttgataat   2880
ctctgccttc gcgtatttgt ctgttattca atattacttc aacggctggc agttggattc   2940
caacagcgtg tttgaaaccg cgccgaacaa agactctaat accttgtttc aggaatgctc   3000
tcattactac cgcgattctt cgttggatgg ctgggtctcc ataactgctc atgaagcgag   3060
cgagttaccg gcaccgcacc attactattt gttaaatctt aatttcaaca gcccaaacga   3120
aaccgactct attccggaat tggcgaatac agtgtttgag aaagataaca cgaaatatat   3180
tcttcaggaa gatctaagcg tgtctaaaga aatttcgtcg accgatggta caaaatggcg   3240
tttacgcagc gaccgcaaaa gcctcttcga cgtcaagaca ttagcctatt cgctatacga   3300
tgtcttttcc gaaaacgtca ctcaggccga ccccttttgac gttctcatta tggtgaccgc   3360
atacttgatg atgttctaca ctatcttcgg actattcaac gacatgcgta agactgggtc   3420
caacttttgg ctgagtgcat cgacggtagt taactcggcc tcctccctct tcttagccct   3480
gtatgttact cagtgcattt tgggaaaaga agtgtctgcc ttaaccctct ttgaaggcct   3540
gccattcatt gtcgtggtgg tgggcttcaa gcacaaaata aagattgcac aatatgcact   3600
tgagaaattt gaacgcgttg gcttatcgaa acgtattacc actgatgaaa tagtgtttga   3660
atctgtaagt gaagagggcg gccggctgat tcaggaccat ctgctctgca tttttgcatt   3720
tataggttgt tcgatgtatg cgcaccagct gaagaccctg acgaatttct gtatcttatc   3780
cgcctttata ttgatttttg aactgatttt aaccccaacg ttttattcgg cgatattagc   3840
tctccgcctt gaaatgaacg tgatacaccg ctcgaccatt ataaagcaga cgttagaaga   3900
agacggcgtg gtgccgtcga cggcccgcat aatttcgaaa gccgaaaaga aatctgtctc   3960
gtcgttctta aacctaagcg tagtggttat tataatgaaa ctatcggtta tccttctgtt   4020
tgttttcata aatttttata attttggcgc caactgggtt aacgatgcat tcaactccct   4080
gtacttcgat aaggaacggg tgtcgttgcc ggattttatt acttcaaacg catcggaaaa   4140
ttttaaagag caggcgattg tgagcgttac tccgttatta tattacaaac ctattaagtc   4200
ttaccagaga attgaggata tggtgctctt gctgctccgg aacgttagcg tggcaattcg   4260
ggatcgtttc gttagcaaat tagtgctctc tgcattagtc tgtagcgcgg ttataaacgt   4320
atatttactg aacgcggcgc gcattcatac tagctatacc gccgaccagc tggtaaaaac   4380
cgaagttact aagaagtcgt ttaccgcgcc agtccagaag gcgtcgacgc cggtgttaac   4440
taacaaaacg gttatttcgg gttcaaaagt taaaagctta tcctcggctc agtcaagttc   4500
ctccggtcca tcctcctcga gcgaggaaga tgattctaga gatattgaaa gtctggataa   4560
gaaaatccgg ccattagaag aattagaagc cttattaagc agcggtaaca cgaaacagct   4620
gaagaataaa gaggttgcgg cactggtgat tcacggcaag ttaccactgt acgcgctgga   4680
gaaaaaatta ggcgatacca cacgcgctgt ggctgtccgg cgtaaggcgc tctccattct   4740
ggccgaagcg ccagtcttag cctcggatcg gttaccgtat aaaaactatg actacgacag   4800
agtctttgga gcgtgctgcg aaaacgtgat cggctacatg ccactgcctg tgggcgtgat   4860
```

cggacctctg gtgatagatg gcacgtcgta tcatatcccg atggccacca cggagggctg 4920
cctggtcgcg tcggcaatgc ggggatgcaa ggccataaac gcgggaggcg gcgccacgac 4980
cgtgttaacc aaggatggca tgacgcgcgg accggtcgtt cggttcccga ccctgaaacg 5040
ctcgggcgca tgcaagatct ggttagactc cgaagagggt cagaatgcca ttaaaaaagc 5100
gtttaattcg acgtcccgct ttgcccggct tcagcatatt cagacctgct tggccggtga 5160
tttactattc atgcgctttc gcacgaccac cggcgacgcc atgggcatga acatgatttc 5220
gaaaggcgtt gaatactcct taaagcagat ggtcgaagag tatggatggg aagatatgga 5280
ggtggtttct gtgtcgggca attactgcac tgacaaaaaa ccggcggcaa taaattggat 5340
agaaggccgg ggcaagagcg ttgttgccga agcgaccatt ccaggcgatg tggttcgcaa 5400
agtattaaaa agcgatgtgt ctgccctggt ggagctgaat attgcgaaga acctggtggg 5460
ttcggccatg gcggggtcgg tgggcggttt taatgcccat gccgcgaact tagtaacggc 5520
ggtgttcctg gccttaggtc aggatccagc ccagaacgtg gaaagctcta attgcatcac 5580
gctgatgaaa gaagtagacg gcgatctgcg catttctgtc tctatgccgt ctatagaagt 5640
cggcactata ggcggcggca ccgtgttgga accgcagggc gcaatgctgg acttattagg 5700
cgtccgcgga ccccatgcga ctgcgccagg cactaatgcc cggcagttag cccgcatcgt 5760
ggcatgcgca gttctggccg gcgaattatc tttatgcgcg gcattggccg caggacatct 5820
ggtgcagagc catatgactc acaatcgtaa accagcggaa ccgacgaaac caaataacct 5880
ggacgcaacc gatatcaacc ggctgaaaga tgggtctgtt acttgtatta aatcttaagg 5940
ccttcttggc caaaa 5955

<210> SEQ ID NO 5
<211> LENGTH: 26
<212> TYPE: DNA
<213> ORGANISM: Artificial Sequence
<220> FEATURE:
<223> OTHER INFORMATION: Artificial Primer

<400> SEQUENCE: 5
tagggtctca aagcggccgc aagctt 26

<210> SEQ ID NO 6
<211> LENGTH: 25
<212> TYPE: DNA
<213> ORGANISM: Artificial Sequence
<220> FEATURE:
<223> OTHER INFORMATION: Artificial Primer

<400> SEQUENCE: 6
tagggtctca gcggccaaga aggcc 25

<210> SEQ ID NO 7
<211> LENGTH: 30
<212> TYPE: DNA
<213> ORGANISM: Artificial Sequence
<220> FEATURE:
<223> OTHER INFORMATION: Artificial Primer

<400> SEQUENCE: 7
tagggtctca ccgcccttcc cggtcgatat 30

<210> SEQ ID NO 8
<211> LENGTH: 42
<212> TYPE: DNA

<213> ORGANISM: Artificial Sequence
<220> FEATURE:
<223> OTHER INFORMATION: Artificial Primer

<400> SEQUENCE: 8
tagggtctca tattagctta attgttatcc gctcacaatt cc 42

<210> SEQ ID NO 9
<211> LENGTH: 43
<212> TYPE: DNA
<213> ORGANISM: Artificial Sequence
<220> FEATURE:
<223> OTHER INFORMATION: Artificial Primer

<400> SEQUENCE: 9
tagggtctca aataactgga aaaaattagt gtctcatggt tcg 43

<210> SEQ ID NO 10
<211> LENGTH: 33
<212> TYPE: DNA
<213> ORGANISM: Artificial Sequence
<220> FEATURE:
<223> OTHER INFORMATION: Artificial Primer

<400> SEQUENCE: 10
tagggtctca gcttaagtgg tgggtagttg acc 33

<210> SEQ ID NO 11
<211> LENGTH: 127
<212> TYPE: DNA
<213> ORGANISM: Artificial Sequence
<220> FEATURE:
<223> OTHER INFORMATION: MEV001

<400> SEQUENCE: 11
cacctgcacg tattaggcct gtttggccgt gacaccggac aatgagtaat gtcgcaaaat 60
gtgtacattg tctcaaccgc acgcactccg attggctcct tccaaggctc gttgtcacgt 120
gcaggtg 127

<210> SEQ ID NO 12
<211> LENGTH: 140
<212> TYPE: DNA
<213> ORGANISM: Artificial Sequence
<220> FEATURE:
<223> OTHER INFORMATION: MEV002

<400> SEQUENCE: 12
cacctgcacg ttgtcttcta agacggccgt agaactgggc gcggtggcgt taaaaggagc 60
actggcgaag gtgccggaac tggatgcctc taaggatttt gacgaaatta tttttggcaa 120
tgtgctctca cgtgcaggtg 140

<210> SEQ ID NO 13
<211> LENGTH: 129
<212> TYPE: DNA
<213> ORGANISM: Artificial Sequence
<220> FEATURE:
<223> OTHER INFORMATION: MEV003

<400> SEQUENCE: 13
cacctgcacg ttctcggcaa acctgggaca ggcgcccgca cgccaggtgg cgctggcggc 60
aggcctgagc aaccatatag tggccagtac ggtgaataag gtttgcgcct ctgcgatgac 120
gtgcaggtg 129

<210> SEQ ID NO 14
<211> LENGTH: 136
<212> TYPE: DNA
<213> ORGANISM: Artificial Sequence
<220> FEATURE:
<223> OTHER INFORMATION: MEV004

<400> SEQUENCE: 14
cacctgcacg tgatgaaggc cataattctg ggcgcgcagt ctataaaatg cggcaacgcg 60
gatgtggttg tcgcgggcgg ctgcgaatcg atgaccaatg ccccgtacta catgccggcc 120
gcacgacgtg caggtg 136

<210> SEQ ID NO 15
<211> LENGTH: 136
<212> TYPE: DNA
<213> ORGANISM: Artificial Sequence
<220> FEATURE:
<223> OTHER INFORMATION: MEV005

<400> SEQUENCE: 15
cacctgcacg tcacgggctg gcgcaaaatt tggacagacc gtgctcgtgg atggcgttga 60
acgcgatggg ctgaatgatg cttacgatgg cttggcaatg ggcgtccacg ccgaaaagtg 120
cgcacacgtg caggtg 136

<210> SEQ ID NO 16
<211> LENGTH: 131
<212> TYPE: DNA
<213> ORGANISM: Artificial Sequence
<220> FEATURE:
<223> OTHER INFORMATION: MEV006

<400> SEQUENCE: 16
cacctgcacg tgcacgggat tgggatatta cccgcgaaca gcaggacaac tttgcaatag 60
aatcttacca gaaatcgcag aaatcgcaga aggaaggcaa attcgacaac gaaattgtcc 120
acgtgcaggt g 131

<210> SEQ ID NO 17
<211> LENGTH: 135
<212> TYPE: DNA
<213> ORGANISM: Artificial Sequence
<220> FEATURE:
<223> OTHER INFORMATION: MEV007

<400> SEQUENCE: 17
cacctgcacg tgtcccagtg actattaagg gttttcgcgg caagccagat acccaggtta 60
caaaggacga ggaaccagcg cgcttacacg tggaaaaact gcgctcggcc cgtaccgtgt 120
tccaacgtgc aggtg 135

<210> SEQ ID NO 18
<211> LENGTH: 138
<212> TYPE: DNA
<213> ORGANISM: Artificial Sequence
<220> FEATURE:
<223> OTHER INFORMATION: MEV008

<400> SEQUENCE: 18
cacctgcacg ttccagaaag aaaatggcac cgtgaccgca gcgaatgcgt cgccgataaa 60
tgatggcgcg gccgcagtta tactggtgtc tgaaaaagtg ctgaaggaaa agaacctgaa 120
gccactgacg tgcaggtg 138

<210> SEQ ID NO 19
<211> LENGTH: 139
<212> TYPE: DNA
<213> ORGANISM: Artificial Sequence
<220> FEATURE:
<223> OTHER INFORMATION: MEV009

<400> SEQUENCE: 19
cacctgcacg tactggcgat tataaaaggc tggggcgagg cagcgcatca gccggcggat 60
tttacgtggg cgccgtcgct cgccgtgccg aaggcgctga aacatgcggg aatagaagac 120
ataaactcac gtgcaggtg 139

<210> SEQ ID NO 20
<211> LENGTH: 133
<212> TYPE: DNA
<213> ORGANISM: Artificial Sequence
<220> FEATURE:
<223> OTHER INFORMATION: MEV010

<400> SEQUENCE: 20
cacctgcacg tactcggtgg attactttga attcaacgaa gcattttcag tggttggcct 60
ggtaaatacc aagattctga agttggaccc gtcgaaggtg aacgtctatg gcggcgcggt 120
ggacgtgcag gtg 133

<210> SEQ ID NO 21
<211> LENGTH: 130
<212> TYPE: DNA
<213> ORGANISM: Artificial Sequence
<220> FEATURE:
<223> OTHER INFORMATION: MEV011

<400> SEQUENCE: 21
cacctgcacg tgtggcgttg ggccacccgc tgggctgctc gggcgcgcgc gtagtggtga 60
cgcttttgtc tatattacaa caggaaggtg gcaagatagg cgtggcagca atttgcaaca 120
cgtgcaggtg 130

<210> SEQ ID NO 22
<211> LENGTH: 140
<212> TYPE: DNA
<213> ORGANISM: Artificial Sequence
<220> FEATURE:
<223> OTHER INFORMATION: MEV012

<400> SEQUENCE: 22
cacctgcacg tcaacggcgg cggcggcgcg tcttcgattg ttattgaaaa gatctaaggc 60
cttgatggcc aacgcgggag atttttcatg aaactatcca ccaaactctg ctggtgcggc 120
attaaaggta cgtgcaggtg 140

<210> SEQ ID NO 23
<211> LENGTH: 129
<212> TYPE: DNA
<213> ORGANISM: Artificial Sequence
<220> FEATURE:
<223> OTHER INFORMATION: MEV013

<400> SEQUENCE: 23
cacctgcacg taggtcgcct ccgtccccag aagcagcagc agttacacaa cacgaatctg 60
cagatgaccg aattgaaaaa acagaagact gcggaacaga aaactcgccc acagaacgac 120
gtgcaggtg 129

<210> SEQ ID NO 24
<211> LENGTH: 136
<212> TYPE: DNA
<213> ORGANISM: Artificial Sequence
<220> FEATURE:
<223> OTHER INFORMATION: MEV014

<400> SEQUENCE: 24
cacctgcacg taacgttggc attaaaggca tacagattta cataccgacc cagtgcgtta 60
atcagtcgga gttggagaaa tttgatggag tgtcgcaggg caaatacacg attggccttg 120
gacagacgtg caggtg 136

<210> SEQ ID NO 25
<211> LENGTH: 130
<212> TYPE: DNA
<213> ORGANISM: Artificial Sequence
<220> FEATURE:
<223> OTHER INFORMATION: MEV015

<400> SEQUENCE: 25
cacctgcacg tacagactaa tatgtcgttt gttaacgacc gcgaagatat atactcaatg 60
tctttgaccg tgctgtcgaa gctgataaag agctacaata tagacactaa taaaattgga 120
cgtgcaggtg 130

<210> SEQ ID NO 26
<211> LENGTH: 136
<212> TYPE: DNA
<213> ORGANISM: Artificial Sequence
<220> FEATURE:
<223> OTHER INFORMATION: MEV016

<400> SEQUENCE: 26
cacctgcacg tttggccgct tagaagttgg caccgaaacc cttattgaca agtctaagtc 60
ggttaagtcg gttctgatgc agctgtttgg cgaaaatacc gacgttgaag gcattgacac 120
actcaacgtg caggtg 136

<210> SEQ ID NO 27
<211> LENGTH: 137
<212> TYPE: DNA
<213> ORGANISM: Artificial Sequence
<220> FEATURE:
<223> OTHER INFORMATION: MEV017

<400> SEQUENCE: 27
cacctgcacg tctcaacgca tgctacggcg gcactaatgc tctgttcaat tcgctgaatt 60
ggattgaatc gaatgcctgg gatggccgcg acgcaattgt cgtgtgtggc gatattgcaa 120
tatacgacgt gcaggtg 137

<210> SEQ ID NO 28
<211> LENGTH: 131
<212> TYPE: DNA
<213> ORGANISM: Artificial Sequence
<220> FEATURE:
<223> OTHER INFORMATION: MEV018

<400> SEQUENCE: 28
cacctgcacg ttacgataag ggcgcagccc gcccgactgg cggcgcaggc accgtggcga 60
tgtggatagg cccagatgcg ccgattgtct ttgactcggt ccgcgcgtcg tacatggaac 120
acgtgcaggt g 131

<210> SEQ ID NO 29
<211> LENGTH: 135
<212> TYPE: DNA
<213> ORGANISM: Artificial Sequence
<220> FEATURE:
<223> OTHER INFORMATION: MEV019

<400> SEQUENCE: 29
cacctgcacg tgaacacgca tacgattttt acaagccgga tttcactagt gaatatccat 60
acgttgatgg ccatttttcc ttaacctgct acgttaaggc gctcgatcag gtgtacaaga 120
gctaacgtgc aggtg 135

<210> SEQ ID NO 30
<211> LENGTH: 134
<212> TYPE: DNA
<213> ORGANISM: Artificial Sequence
<220> FEATURE:
<223> OTHER INFORMATION: MEV020

<400> SEQUENCE: 30
cacctgcacg tgctattcta agaaggcgat ttcgaaaggg ctggtgagtg atcctgcggg 60
ctcagatgcg ctgaatgtgc tgaaatattt cgactacaat gtgttccatg tgccgacttg 120
caaacgtgca ggtg 134

<210> SEQ ID NO 31
<211> LENGTH: 135
<212> TYPE: DNA
<213> ORGANISM: Artificial Sequence
<220> FEATURE:
<223> OTHER INFORMATION: MEV021

<400> SEQUENCE: 31
cacctgcacg tgcaaactgg ttacgaaatc ctacggccgc ttattgtata atgatttccg 60
cgcaaaccca cagctgttcc cggaagtgga cgcagaatta gcgaccagag attatgacga 120
atcgacgtgc aggtg 135

<210> SEQ ID NO 32
<211> LENGTH: 139
<212> TYPE: DNA
<213> ORGANISM: Artificial Sequence
<220> FEATURE:
<223> OTHER INFORMATION: MEV022

<400> SEQUENCE: 32
cacctgcacg tatcgttaac tgataagaat attgaaaaaa cctttgtgaa cgtggcgaag 60
ccgttccaca aagagcgcgt ggcacagtcg ctgattgtgc cgacgaatac gggcaatatg 120
tacactgcac gtgcaggtg 139

<210> SEQ ID NO 33
<211> LENGTH: 132
<212> TYPE: DNA
<213> ORGANISM: Artificial Sequence
<220> FEATURE:
<223> OTHER INFORMATION: MEV023

<400> SEQUENCE: 33
cacctgcacg tctgcctcgg tgtatgcagc atttgcctcg ttgttaaatt atgtgggttc 60
ggacgactta cagggaaagc gggtgggctt attttcgtac ggctctggct tagcggcctc 120
gacgtgcagg tg 132

<210> SEQ ID NO 34
<211> LENGTH: 131
<212> TYPE: DNA
<213> ORGANISM: Artificial Sequence
<220> FEATURE:
<223> OTHER INFORMATION: MEV024

<400> SEQUENCE: 34
cacctgcacg tctcgttgta ttcgtgtaaa attgtgggcg acgttcagca tattataaag 60
gaattagata ttaccaataa attagcaaag cgcataactg aaaccccgaa ggattacgaa 120
acgtgcaggt g 131

<210> SEQ ID NO 35
<211> LENGTH: 134
<212> TYPE: DNA
<213> ORGANISM: Artificial Sequence
<220> FEATURE:
<223> OTHER INFORMATION: MEV025

<400> SEQUENCE: 35
cacctgcacg tcgaagcggc aatagaactg cgcgaaaacg cacatctgaa gaagaatttc 60
aaaccacagg gctctattga gcatctgcag agcggcgtgt actacctgac taatatagat 120
gacacgtgca ggtg 134

<210> SEQ ID NO 36
<211> LENGTH: 131
<212> TYPE: DNA
<213> ORGANISM: Artificial Sequence
<220> FEATURE:
<223> OTHER INFORMATION: MEV026

<400> SEQUENCE: 36
cacctgcacg ttgacaaatt tcgccgctcg tacgatgtga aaaaataagg cctcgatggc 60
cgtgaactgg atagtgaaat aatgcccccc ttgttcaagg gtcttaaaca aatggccaag 120
acgtgcaggt g 131

<210> SEQ ID NO 37
<211> LENGTH: 143
<212> TYPE: DNA
<213> ORGANISM: Artificial Sequence
<220> FEATURE:
<223> OTHER INFORMATION: MEV027

<400> SEQUENCE: 37
cacctgcacg tcaagccgat tgcatatgtg tcccgctttt cagctaaacg accgattcat 60
atcatcctct tttcgttgat aatctctgcc ttcgcgtatt tgtctgttat tcaatattac 120
ttcaacggct ggacgtgcag gtg 143

<210> SEQ ID NO 38
<211> LENGTH: 135
<212> TYPE: DNA
<213> ORGANISM: Artificial Sequence
<220> FEATURE:
<223> OTHER INFORMATION: MEV028

<400> SEQUENCE: 38

-continued

```
cacctgcacg tctggcagtt ggattccaac agcgtgtttg aaaccgcgcc gaacaaagac      60

tctaatacct tgtttcagga atgctctcat tactaccgcg attcttcgtt ggatggctgg     120

gtctacgtgc aggtg                                                      135
```

<210> SEQ ID NO 39
<211> LENGTH: 127
<212> TYPE: DNA
<213> ORGANISM: Artificial Sequence
<220> FEATURE:
<223> OTHER INFORMATION: MEV029

<400> SEQUENCE: 39

```
cacctgcacg tgtctccata actgctcatg aagcgagcga gttaccggca ccgcaccatt      60

actatttgtt aaatcttaat ttcaacagcc caaacgaaac cgactctatt ccggaaacgt     120

gcaggtg                                                               127
```

<210> SEQ ID NO 40
<211> LENGTH: 141
<212> TYPE: DNA
<213> ORGANISM: Artificial Sequence
<220> FEATURE:
<223> OTHER INFORMATION: MEV030

<400> SEQUENCE: 40

```
cacctgcacg tggaattggc gaatacagtg tttgagaaag ataacacgaa atatattctt      60

caggaagatc taagcgtgtc taaagaaatt tcgtcgaccg atggtacaaa atggcgttta     120

cgcagcgacc acgtgcaggt g                                               141
```

<210> SEQ ID NO 41
<211> LENGTH: 126
<212> TYPE: DNA
<213> ORGANISM: Artificial Sequence
<220> FEATURE:
<223> OTHER INFORMATION: MEV031

<400> SEQUENCE: 41

```
cacctgcacg tgaccgcaaa agcctcttcg acgtcaagac attagcctat tcgctatacg      60

atgtcttttc cgaaaacgtc actcaggccg accccttga cgttctcatt atggtacgtg      120

caggtg                                                                126
```

<210> SEQ ID NO 42
<211> LENGTH: 136
<212> TYPE: DNA
<213> ORGANISM: Artificial Sequence
<220> FEATURE:
<223> OTHER INFORMATION: MEV032

<400> SEQUENCE: 42

```
cacctgcacg ttggtgaccg catacttgat gatgttctac actatcttcg gactattcaa      60

cgacatgcgt aagactgggt ccaacttttg gctgagtgca tcgacggtag ttaactcggc     120

ctcctacgtg caggtg                                                     136
```

<210> SEQ ID NO 43
<211> LENGTH: 135
<212> TYPE: DNA
<213> ORGANISM: Artificial Sequence
<220> FEATURE:
<223> OTHER INFORMATION: MEV033

<400> SEQUENCE: 43
cacctgcacg ttcctccctc ttcttagccc tgtatgttac tcagtgcatt ttgggaaaag 60
aagtgtctgc cttaaccctc tttgaaggcc tgccattcat tgtcgtggtg gtgggcttca 120
agcaacgtgc aggtg 135

<210> SEQ ID NO 44
<211> LENGTH: 141
<212> TYPE: DNA
<213> ORGANISM: Artificial Sequence
<220> FEATURE:
<223> OTHER INFORMATION: MEV034

<400> SEQUENCE: 44
cacctgcacg tagcacaaaa taaagattgc acaatatgca cttgagaaat ttgaacgcgt 60
tggcttatcg aaacgtatta ccactgatga aatagtgttt gaatctgtaa gtgaagaggg 120
cggccggctg acgtgcaggt g 141

<210> SEQ ID NO 45
<211> LENGTH: 124
<212> TYPE: DNA
<213> ORGANISM: Artificial Sequence
<220> FEATURE:
<223> OTHER INFORMATION: MEV035

<400> SEQUENCE: 45
cacctgcacg tgctgattca ggaccatctg ctctgcattt ttgcatttat aggttgttcg 60
atgtatgcgc accagctgaa gaccctgacg aatttctgta tcttatccgc cttacgtgca 120
ggtg 124

<210> SEQ ID NO 46
<211> LENGTH: 139
<212> TYPE: DNA
<213> ORGANISM: Artificial Sequence
<220> FEATURE:
<223> OTHER INFORMATION: MEV036

<400> SEQUENCE: 46
cacctgcacg tcctttatat tgatttttga actgatttta accccaacgt tttattcggc 60
gatattagct ctccgccttg aaatgaacgt gatacaccgc tcgaccatta taaagcagac 120
gttagaagac gtgcaggtg 139

<210> SEQ ID NO 47
<211> LENGTH: 136
<212> TYPE: DNA
<213> ORGANISM: Artificial Sequence
<220> FEATURE:
<223> OTHER INFORMATION: MEV037

<400> SEQUENCE: 47
cacctgcacg tgaagaagac ggcgtggtgc cgtcgacggc ccgcataatt tcgaaagccg 60
aaaagaaatc tgtctcgtcg ttcttaaacc taagcgtagt ggttattata atgaaactat 120
cggttacgtg caggtg 136

<210> SEQ ID NO 48
<211> LENGTH: 131
<212> TYPE: DNA
<213> ORGANISM: Artificial Sequence
<220> FEATURE:
<223> OTHER INFORMATION: MEV038

<400> SEQUENCE: 48
cacctgcacg tggttatcct tctgtttgtt ttcataaatt tttataattt tggcgccaac 60
tgggttaacg atgcattcaa ctccctgtac ttcgataagg aacgggtgtc gttgccggat 120
acgtgcaggt g 131

<210> SEQ ID NO 49
<211> LENGTH: 140
<212> TYPE: DNA
<213> ORGANISM: Artificial Sequence
<220> FEATURE:
<223> OTHER INFORMATION: MEV039

<400> SEQUENCE: 49
cacctgcacg tggattttat tacttcaaac gcatcggaaa attttaaaga gcaggcgatt 60
gtgagcgtta ctccgttatt atattacaaa cctattaagt cttaccagag aattgaggat 120
atggtgctca cgtgcaggtg 140

<210> SEQ ID NO 50
<211> LENGTH: 129
<212> TYPE: DNA
<213> ORGANISM: Artificial Sequence
<220> FEATURE:
<223> OTHER INFORMATION: MEV040

<400> SEQUENCE: 50
cacctgcacg tgctcttgct gctccggaac gttagcgtgg caattcggga tcgtttcgtt 60
agcaaattag tgctctctgc attagtctgt agcgcggtta taaacgtata tttactgaac 120
gtgcaggtg 129

<210> SEQ ID NO 51
<211> LENGTH: 131
<212> TYPE: DNA
<213> ORGANISM: Artificial Sequence
<220> FEATURE:
<223> OTHER INFORMATION: MEV041

<400> SEQUENCE: 51
cacctgcacg tctgaacgcg gcgcgcattc atactagcta taccgccgac cagctggtaa 60
aaaccgaagt tactaagaag tcgtttaccg cgccagtcca gaaggcgtcg acgccggtgt 120
acgtgcaggt g 131

<210> SEQ ID NO 52
<211> LENGTH: 143
<212> TYPE: DNA
<213> ORGANISM: Artificial Sequence
<220> FEATURE:
<223> OTHER INFORMATION: MEV042

<400> SEQUENCE: 52
cacctgcacg tgtgttaact aacaaaacgg ttatttcggg ttcaaaagtt aaaagcttat 60
cctcggctca gtcaagttcc tccggtccat cctcctcgag cgaggaagat gattctagag 120
atattgaaag tcacgtgcag gtg 143

<210> SEQ ID NO 53
<211> LENGTH: 127
<212> TYPE: DNA
<213> ORGANISM: Artificial Sequence
<220> FEATURE:
<223> OTHER INFORMATION: MEV043

<400> SEQUENCE: 53
cacctgcacg tagtctggat aagaaaatcc ggccattaga agaattagaa gccttattaa 60
gcagcggtaa cacgaaacag ctgaagaata aagaggttgc ggcactggtg attcacacgt 120
gcaggtg 127

<210> SEQ ID NO 54
<211> LENGTH: 136
<212> TYPE: DNA
<213> ORGANISM: Artificial Sequence
<220> FEATURE:
<223> OTHER INFORMATION: MEV044

<400> SEQUENCE: 54
cacctgcacg ttcacggcaa gttaccactg tacgcgctgg agaaaaaatt aggcgatacc 60
acacgcgctg tggctgtccg gcgtaaggcg ctctccattc tggccgaagc gccagtctta 120
gcctcacgtg caggtg 136

<210> SEQ ID NO 55
<211> LENGTH: 132
<212> TYPE: DNA
<213> ORGANISM: Artificial Sequence
<220> FEATURE:
<223> OTHER INFORMATION: MEV045

<400> SEQUENCE: 55
cacctgcacg tcctcggatc ggttaccgta taaaaactat gactacgaca gagtctttgg 60
agcgtgctgc gaaaacgtga tcggctacat gccactgcct gtgggcgtga tcggacctct 120
gacgtgcagg tg 132

<210> SEQ ID NO 56
<211> LENGTH: 135
<212> TYPE: DNA
<213> ORGANISM: Artificial Sequence
<220> FEATURE:
<223> OTHER INFORMATION: MEV046

<400> SEQUENCE: 56
cacctgcacg ttctggtgat agatggcacg tcgtatcata tcccgatggc caccacggag 60
ggctgcctgg tcgcgtcggc aatgcgggga tgcaaggcca taaacgcggg aggcggcgcc 120
acgaacgtgc aggtg 135

<210> SEQ ID NO 57
<211> LENGTH: 138
<212> TYPE: DNA
<213> ORGANISM: Artificial Sequence
<220> FEATURE:
<223> OTHER INFORMATION: MEV047

<400> SEQUENCE: 57
cacctgcacg tacgaccgtg ttaaccaagg atggcatgac gcgcggaccg gtcgttcggt 60
tcccgaccct gaaacgctcg ggcgcatgca agatctggtt agactccgaa gagggtcaga 120
atgccatacg tgcaggtg 138

<210> SEQ ID NO 58
<211> LENGTH: 132
<212> TYPE: DNA
<213> ORGANISM: Artificial Sequence
<220> FEATURE:

<223> OTHER INFORMATION: MEV048

<400> SEQUENCE: 58
cacctgcacg tccattaaaa aagcgtttaa ttcgacgtcc cgctttgccc ggcttcagca 60
tattcagacc tgcttggccg gtgatttact attcatgcgc tttcgcacga ccaccggcga 120
cacgtgcagg tg 132

<210> SEQ ID NO 59
<211> LENGTH: 140
<212> TYPE: DNA
<213> ORGANISM: Artificial Sequence
<220> FEATURE:
<223> OTHER INFORMATION: MEV049

<400> SEQUENCE: 59
cacctgcacg tcgacgccat gggcatgaac atgatttcga aaggcgttga atactcctta 60
aagcagatgg tcgaagagta tggatgggaa gatatggagg tggtttctgt gtcgggcaat 120
tactgcacta cgtgcaggtg 140

<210> SEQ ID NO 60
<211> LENGTH: 128
<212> TYPE: DNA
<213> ORGANISM: Artificial Sequence
<220> FEATURE:
<223> OTHER INFORMATION: MEV050

<400> SEQUENCE: 60
cacctgcacg tcactgacaa aaaaccggcg gcaataaatt ggatagaagg ccggggcaag 60
agcgttgttg ccgaagcgac cattccaggc gatgtggttc gcaaagtatt aaaaagcacg 120
tgcaggtg 128

<210> SEQ ID NO 61
<211> LENGTH: 137
<212> TYPE: DNA
<213> ORGANISM: Artificial Sequence
<220> FEATURE:
<223> OTHER INFORMATION: MEV051

<400> SEQUENCE: 61
cacctgcacg taagcgatgt gtctgccctg gtggagctga atattgcgaa gaacctggtg 60
ggttcggcca tggcggggtc ggtgggcggt tttaatgccc atgccgcgaa cttagtaacg 120
gcggtgacgt gcaggtg 137

<210> SEQ ID NO 62
<211> LENGTH: 133
<212> TYPE: DNA
<213> ORGANISM: Artificial Sequence
<220> FEATURE:
<223> OTHER INFORMATION: MEV052

<400> SEQUENCE: 62
cacctgcacg tggtgttcct ggccttaggt caggatccag cccagaacgt ggaaagctct 60
aattgcatca cgctgatgaa agaagtagac ggcgatctgc gcatttctgt ctctatgccg 120
tcacgtgcag gtg 133

<210> SEQ ID NO 63
<211> LENGTH: 134
<212> TYPE: DNA
<213> ORGANISM: Artificial Sequence

<220> FEATURE:
<223> OTHER INFORMATION: MEV053

<400> SEQUENCE: 63
cacctgcacg tcgtctatag aagtcggcac tataggcggc ggcaccgtgt tggaaccgca 60
gggcgcaatg ctggacttat taggcgtccg cggaccccat gcgactgcgc caggcactaa 120
tgcacgtgca ggtg 134

<210> SEQ ID NO 64
<211> LENGTH: 130
<212> TYPE: DNA
<213> ORGANISM: Artificial Sequence
<220> FEATURE:
<223> OTHER INFORMATION: MEV054

<400> SEQUENCE: 64
cacctgcacg tatgcccggc agttagcccg catcgtggca tgcgcagttc tggccggcga 60
attatcttta tgcgcggcat tggccgcagg acatctggtg cagagccata tgactcacaa 120
cgtgcaggtg 130

<210> SEQ ID NO 65
<211> LENGTH: 138
<212> TYPE: DNA
<213> ORGANISM: Artificial Sequence
<220> FEATURE:
<223> OTHER INFORMATION: MEV055

<400> SEQUENCE: 65
cacctgcacg tcacaatcgt aaaccagcgg aaccgacgaa accaaataac ctggacgcaa 60
ccgatatcaa ccggctgaaa gatgggtctg ttacttgtat taaatcttaa ggccttcttg 120
gccaaaaacg tgcaggtg 138

<210> SEQ ID NO 66
<211> LENGTH: 60
<212> TYPE: DNA
<213> ORGANISM: Artificial Sequence
<220> FEATURE:
<223> OTHER INFORMATION: T1-1

<400> SEQUENCE: 66
tgagacgtct cggcctgttt ggccattacg gggcggcgac ctcgcgggtt ttcgctattt 60

<210> SEQ ID NO 67
<211> LENGTH: 60
<212> TYPE: DNA
<213> ORGANISM: Artificial Sequence
<220> FEATURE:
<223> OTHER INFORMATION: T1-2

<400> SEQUENCE: 67
tgcccgtgtc ggttattcca aaatgctgct gggtgtttat gcctacttta tagagcataa 60

<210> SEQ ID NO 68
<211> LENGTH: 60
<212> TYPE: DNA
<213> ORGANISM: Artificial Sequence
<220> FEATURE:
<223> OTHER INFORMATION: T1-3

<400> SEQUENCE: 68
gactcccagc tggaccgcta cgaaatgcgc gtatggggat gggggccggg tgaggaaagc 60

<210> SEQ ID NO 69
<211> LENGTH: 60
<212> TYPE: DNA
<213> ORGANISM: Artificial Sequence
<220> FEATURE:
<223> OTHER INFORMATION: T1-4

<400> SEQUENCE: 69
acatcgctgc gcgaatatgc cggttatcac ggcggtggca gcggatttgg agggcagttg 60

<210> SEQ ID NO 70
<211> LENGTH: 60
<212> TYPE: DNA
<213> ORGANISM: Artificial Sequence
<220> FEATURE:
<223> OTHER INFORMATION: T1-5

<400> SEQUENCE: 70
tgaacctgca gacggctcag gatacggata acggctactc cgtgtttgag cagtcactgc 60

<210> SEQ ID NO 71
<211> LENGTH: 60
<212> TYPE: DNA
<213> ORGANISM: Artificial Sequence
<220> FEATURE:
<223> OTHER INFORMATION: T1-6

<400> SEQUENCE: 71
ggatggtggc gggggcattt gactgcgctg acatcatcgc ccgtgtgcgt gacataaaac 60

<210> SEQ ID NO 72
<211> LENGTH: 60
<212> TYPE: DNA
<213> ORGANISM: Artificial Sequence
<220> FEATURE:
<223> OTHER INFORMATION: T1-7

<400> SEQUENCE: 72
cagtgacccg gctcataccg caaccgcgcc cggcggattg agtgcgaaag cgcctgcaat 60

<210> SEQ ID NO 73
<211> LENGTH: 60
<212> TYPE: DNA
<213> ORGANISM: Artificial Sequence
<220> FEATURE:
<223> OTHER INFORMATION: T1-8

<400> SEQUENCE: 73
ttccttcaaa gccgtcaagg agaagctgga tacccgtcgt ggctctaatt ccgagctgga 60

<210> SEQ ID NO 74
<211> LENGTH: 60
<212> TYPE: DNA
<213> ORGANISM: Artificial Sequence
<220> FEATURE:
<223> OTHER INFORMATION: T1-9

<400> SEQUENCE: 74
tggtgttttt gatgaccctg aaaatatcag ctatgccgga cagggcgtgc gcgttgaagg 60

<210> SEQ ID NO 75
<211> LENGTH: 60
<212> TYPE: DNA
<213> ORGANISM: Artificial Sequence
<220> FEATURE:
<223> OTHER INFORMATION: T1-10

<400> SEQUENCE: 75
cgaagagctg gacagcgata cctggcaggc ggagctgcat atcgaagttt tcctgcctgc 60

<210> SEQ ID NO 76
<211> LENGTH: 60
<212> TYPE: DNA
<213> ORGANISM: Artificial Sequence
<220> FEATURE:
<223> OTHER INFORMATION: T1-11

<400> SEQUENCE: 76
agaaattacc gtcaccgcca gttaatccgg agagtcagcg atgttcctga aaaccgaatc 60

<210> SEQ ID NO 77
<211> LENGTH: 60
<212> TYPE: DNA
<213> ORGANISM: Artificial Sequence
<220> FEATURE:
<223> OTHER INFORMATION: T1-12

<400> SEQUENCE: 77
gaaagtgatg cgaaaaaaac agcggcagtc gttgaacagt cgctgagccg acaggcgctg 60

<210> SEQ ID NO 78
<211> LENGTH: 60
<212> TYPE: DNA
<213> ORGANISM: Artificial Sequence
<220> FEATURE:
<223> OTHER INFORMATION: T1-13

<400> SEQUENCE: 78
gggatgatcg tgaaaaggcc cgtcttgcgc ttgaagccgc ccgaaagaag gctgagcagc 60

<210> SEQ ID NO 79
<211> LENGTH: 60
<212> TYPE: DNA
<213> ORGANISM: Artificial Sequence
<220> FEATURE:
<223> OTHER INFORMATION: T1-14

<400> SEQUENCE: 79
cacccgttcc gtgctgtcca tgatgacaga aattctgctt aagcaggcaa tggtggggat 60

<210> SEQ ID NO 80
<211> LENGTH: 60
<212> TYPE: DNA
<213> ORGANISM: Artificial Sequence
<220> FEATURE:
<223> OTHER INFORMATION: T1-15

<400> SEQUENCE: 80
gcagaacgaa aaaggtgagc cggtcacctg gcaggggcga cagtatcagc cgtatcccat 60

<210> SEQ ID NO 81
<211> LENGTH: 60
<212> TYPE: DNA
<213> ORGANISM: Artificial Sequence
<220> FEATURE:
<223> OTHER INFORMATION: T1-16

<400> SEQUENCE: 81
tctggcgggg attgagatgc cggactttca tcgtgaggat gactggtggc gtaacggcca 60

<210> SEQ ID NO 82

<211> LENGTH: 60
<212> TYPE: DNA
<213> ORGANISM: Artificial Sequence
<220> FEATURE:
<223> OTHER INFORMATION: T1-17

<400> SEQUENCE: 82
atggagcgtg aggaatgggt aaaggaagca gtaaggggca taccccgcgc gaagcgaagg 60

<210> SEQ ID NO 83
<211> LENGTH: 60
<212> TYPE: DNA
<213> ORGANISM: Artificial Sequence
<220> FEATURE:
<223> OTHER INFORMATION: T1-18

<400> SEQUENCE: 83
ggagccgcgc atcacctgta atgcgtacct gaccacacag cgtaaggcgt gggatgtgct 60

<210> SEQ ID NO 84
<211> LENGTH: 60
<212> TYPE: DNA
<213> ORGANISM: Artificial Sequence
<220> FEATURE:
<223> OTHER INFORMATION: T1-19

<400> SEQUENCE: 84
acaccgaagg tggtgaaggg cgtgagtttc ctgctccgtc tgaccgtaac agcggacgac 60

<210> SEQ ID NO 85
<211> LENGTH: 60
<212> TYPE: DNA
<213> ORGANISM: Artificial Sequence
<220> FEATURE:
<223> OTHER INFORMATION: T1-20

<400> SEQUENCE: 85
tgaatgcgaa ctccgggacg ctcagtaatg tgacgatagc tgaaaactgt acgataaacg 60

<210> SEQ ID NO 86
<211> LENGTH: 60
<212> TYPE: DNA
<213> ORGANISM: Artificial Sequence
<220> FEATURE:
<223> OTHER INFORMATION: T1-21

<400> SEQUENCE: 86
tggattaccg taagacggaa atcactcccg ggtatatgaa agagacgacc actgccaggg 60

<210> SEQ ID NO 87
<211> LENGTH: 60
<212> TYPE: DNA
<213> ORGANISM: Artificial Sequence
<220> FEATURE:
<223> OTHER INFORMATION: T1-22

<400> SEQUENCE: 87
aggccgccac ttcagcacga gatgcggtgg cctcaaaaga ggcagcaaaa tcatcagaaa 60

<210> SEQ ID NO 88
<211> LENGTH: 60
<212> TYPE: DNA
<213> ORGANISM: Artificial Sequence
<220> FEATURE:
<223> OTHER INFORMATION: T1-23

<400> SEQUENCE: 88
tttgacaaat cagcctaccc aaaacttgct gtcgcgtatc catcgggtgt gcttcctgat 60

<210> SEQ ID NO 89
<211> LENGTH: 60
<212> TYPE: DNA
<213> ORGANISM: Artificial Sequence
<220> FEATURE:
<223> OTHER INFORMATION: T1-24

<400> SEQUENCE: 89
aggggaatat cagaagtgga acggcacagc ctgggtgaag gatacggaag cagaaaaact 60

<210> SEQ ID NO 90
<211> LENGTH: 60
<212> TYPE: DNA
<213> ORGANISM: Artificial Sequence
<220> FEATURE:
<223> OTHER INFORMATION: T1-25

<400> SEQUENCE: 90
aatgacaatt tgcttatgga gtaatctttt aattttaaat aagttattct cctggcttca 60

<210> SEQ ID NO 91
<211> LENGTH: 60
<212> TYPE: DNA
<213> ORGANISM: Artificial Sequence
<220> FEATURE:
<223> OTHER INFORMATION: T1-26

<400> SEQUENCE: 91
gggtgttgaa tgatttccag ttgctaccga ttttacatat tttttgcatg agagaatttg 60

<210> SEQ ID NO 92
<211> LENGTH: 60
<212> TYPE: DNA
<213> ORGANISM: Artificial Sequence
<220> FEATURE:
<223> OTHER INFORMATION: T1-27

<400> SEQUENCE: 92
actactaagg ttgtaggctc aagagggtgt gtcctgtcgt aggtaaataa ctgacctgtc 60

<210> SEQ ID NO 93
<211> LENGTH: 60
<212> TYPE: DNA
<213> ORGANISM: Artificial Sequence
<220> FEATURE:
<223> OTHER INFORMATION: T1-28

<400> SEQUENCE: 93
tccaatataa aagtattgtg taccttttgc tgggtcaggt tgttctttag gaggagtaaa 60

<210> SEQ ID NO 94
<211> LENGTH: 60
<212> TYPE: DNA
<213> ORGANISM: Artificial Sequence
<220> FEATURE:
<223> OTHER INFORMATION: T1-29

<400> SEQUENCE: 94
tctgcttcct tttggataac ccactgttat tcatgttgca tggtgcactg tttataccaa 60

<210> SEQ ID NO 95
<211> LENGTH: 60
<212> TYPE: DNA

<213> ORGANISM: Artificial Sequence
<220> FEATURE:
<223> OTHER INFORMATION: T1-30

<400> SEQUENCE: 95
ttatcaagtg tttccttcat tgatattccg agagcatcaa tatgcaatgc tgttgggatg 60

<210> SEQ ID NO 96
<211> LENGTH: 60
<212> TYPE: DNA
<213> ORGANISM: Artificial Sequence
<220> FEATURE:
<223> OTHER INFORMATION: T1-31

<400> SEQUENCE: 96
aagtacatcg caaagtctcc gcaattacac gcaagaaaaa accgccatca ggcggcttgg 60

<210> SEQ ID NO 97
<211> LENGTH: 60
<212> TYPE: DNA
<213> ORGANISM: Artificial Sequence
<220> FEATURE:
<223> OTHER INFORMATION: T1-32

<400> SEQUENCE: 97
caggatggcg aacaacaaga aactggtttc cgtcttcacg gacttcgttg ctttccagtt 60

<210> SEQ ID NO 98
<211> LENGTH: 60
<212> TYPE: DNA
<213> ORGANISM: Artificial Sequence
<220> FEATURE:
<223> OTHER INFORMATION: T1-33

<400> SEQUENCE: 98
ctggtttctc tcatctgctt ctgctttcgc caccatcatt tccagctttt gtgaaaggga 60

<210> SEQ ID NO 99
<211> LENGTH: 60
<212> TYPE: DNA
<213> ORGANISM: Artificial Sequence
<220> FEATURE:
<223> OTHER INFORMATION: T1-34

<400> SEQUENCE: 99
agctctcaca tcgatcccgg tacgctgcag gataatgtcc ggtgtcatgc tgccaccttc 60

<210> SEQ ID NO 100
<211> LENGTH: 60
<212> TYPE: DNA
<213> ORGANISM: Artificial Sequence
<220> FEATURE:
<223> OTHER INFORMATION: T1-35

<400> SEQUENCE: 100
gcgttgcaaa tgatcgatgc atagcgattc aaacaggtgc tggggcaggc ctttttccat 60

<210> SEQ ID NO 101
<211> LENGTH: 60
<212> TYPE: DNA
<213> ORGANISM: Artificial Sequence
<220> FEATURE:
<223> OTHER INFORMATION: T1-36

<400> SEQUENCE: 101
agataaaaaa tcgccctcac actggagggc aaagaagatt tccaataatc agaacaagtc 60

<210> SEQ ID NO 102
<211> LENGTH: 60
<212> TYPE: DNA
<213> ORGANISM: Artificial Sequence
<220> FEATURE:
<223> OTHER INFORMATION: T1-37

<400> SEQUENCE: 102
ttgagcttgg tgtgttgaac aaaacttttt cccgatggaa tggaaagcat atattattcc 60

<210> SEQ ID NO 103
<211> LENGTH: 60
<212> TYPE: DNA
<213> ORGANISM: Artificial Sequence
<220> FEATURE:
<223> OTHER INFORMATION: T1-38

<400> SEQUENCE: 103
aacaaggatg catatatgaa tgaacgatgc agaggcaatg ccgatggcga tagtgggtat 60

<210> SEQ ID NO 104
<211> LENGTH: 60
<212> TYPE: DNA
<213> ORGANISM: Artificial Sequence
<220> FEATURE:
<223> OTHER INFORMATION: T1-39

<400> SEQUENCE: 104
aacaaaaaag atgggaatcc caatgattcg tcatctgcga ggctgttctt aatatcttca 60

<210> SEQ ID NO 105
<211> LENGTH: 60
<212> TYPE: DNA
<213> ORGANISM: Artificial Sequence
<220> FEATURE:
<223> OTHER INFORMATION: T1-40

<400> SEQUENCE: 105
cctgactgcc ccatccccat cttgtctgcg acagattcct gggataagcc aagttcattt 60

<210> SEQ ID NO 106
<211> LENGTH: 60
<212> TYPE: DNA
<213> ORGANISM: Artificial Sequence
<220> FEATURE:
<223> OTHER INFORMATION: T1-41

<400> SEQUENCE: 106
acgccagact atcaaatatg ctgcttgagg cttattcggg cgcagatctg accaagcgac 60

<210> SEQ ID NO 107
<211> LENGTH: 60
<212> TYPE: DNA
<213> ORGANISM: Artificial Sequence
<220> FEATURE:
<223> OTHER INFORMATION: T1-42

<400> SEQUENCE: 107
agcctggcta accgtgacca gaacgaagtg aacgaaatcc gtcgccagtg ggttctggct 60

<210> SEQ ID NO 108
<211> LENGTH: 60
<212> TYPE: DNA
<213> ORGANISM: Artificial Sequence
<220> FEATURE:

<223> OTHER INFORMATION: T1-43

<400> SEQUENCE: 108
aaatccttcc agacccaacc aaaccaatcg tagtaaccat tcaggaacgc aaccgcagct 60

<210> SEQ ID NO 109
<211> LENGTH: 60
<212> TYPE: DNA
<213> ORGANISM: Artificial Sequence
<220> FEATURE:
<223> OTHER INFORMATION: T1-44

<400> SEQUENCE: 109
gcctgcaaag atgaggaggg attgcagcgt gtttttaatg aggtcatcac gggatcccat 60

<210> SEQ ID NO 110
<211> LENGTH: 60
<212> TYPE: DNA
<213> ORGANISM: Artificial Sequence
<220> FEATURE:
<223> OTHER INFORMATION: T1-45

<400> SEQUENCE: 110
ttaaagcccc gcagttactg gattaaacaa gcccaacaag ccgtaaacgc cttcatcaga 60

<210> SEQ ID NO 111
<211> LENGTH: 60
<212> TYPE: DNA
<213> ORGANISM: Artificial Sequence
<220> FEATURE:
<223> OTHER INFORMATION: T1-46

<400> SEQUENCE: 111
aaaaatatgt tatctgccac gccgattatc cctttgacga atacgagttt ggaaagccag 60

<210> SEQ ID NO 112
<211> LENGTH: 60
<212> TYPE: DNA
<213> ORGANISM: Artificial Sequence
<220> FEATURE:
<223> OTHER INFORMATION: T1-47

<400> SEQUENCE: 112
atgggttaat tcgctcgttg tggtagtgag atgaaaagag gcggcgctta ctaccgattc 60

<210> SEQ ID NO 113
<211> LENGTH: 60
<212> TYPE: DNA
<213> ORGANISM: Artificial Sequence
<220> FEATURE:
<223> OTHER INFORMATION: T1-48

<400> SEQUENCE: 113
cggacgtcag aaaaccagaa atcatggtta tgacgtcatt gtaggcggag agctatttac 60

<210> SEQ ID NO 114
<211> LENGTH: 60
<212> TYPE: DNA
<213> ORGANISM: Artificial Sequence
<220> FEATURE:
<223> OTHER INFORMATION: T1-49

<400> SEQUENCE: 114
tacgaatgtt tgctgggttt ctgttttaac aacattttct gcgccgccac aaattttggc 60

<210> SEQ ID NO 115
<211> LENGTH: 60
<212> TYPE: DNA
<213> ORGANISM: Artificial Sequence
<220> FEATURE:
<223> OTHER INFORMATION: T1-50

<400> SEQUENCE: 115
ttttatcgtt tcaatctggt ctgacctcct tgtgttttgt tgatgattta tgtcaaatat 60

<210> SEQ ID NO 116
<211> LENGTH: 60
<212> TYPE: DNA
<213> ORGANISM: Artificial Sequence
<220> FEATURE:
<223> OTHER INFORMATION: T1-51

<400> SEQUENCE: 116
acgggtcctt tccggtgatc cgacaggtta cggggcggcg acctcgaaaa ggccttcttg 60

<210> SEQ ID NO 117
<211> LENGTH: 36
<212> TYPE: DNA
<213> ORGANISM: Artificial Sequence
<220> FEATURE:
<223> OTHER INFORMATION: F1-1

<400> SEQUENCE: 117
cgatgcggcc gcaagcttgg atccgcggcc gcccgg 36

<210> SEQ ID NO 118
<211> LENGTH: 167
<212> TYPE: DNA
<213> ORGANISM: Artificial Sequence
<220> FEATURE:
<223> OTHER INFORMATION: F1-2

<400> SEQUENCE: 118
cgatgcggcc gcaagcttga agagctcttc tttcagaacg ctcggttgcc gccgggcgtt 60
ttttatgaga cgtctcggcc tgtttggcct taacgtgcag gtggatccag atctaagctt 120
ctatagaagc ttggtaccga cgtctcggcc tgtttggccc gccgcat 167

<210> SEQ ID NO 119
<211> LENGTH: 49
<212> TYPE: DNA
<213> ORGANISM: Artificial Sequence
<220> FEATURE:
<223> OTHER INFORMATION: F1-3

<400> SEQUENCE: 119
gtgccacctg gatccacctg cacgtaaaag gccttcttgg ccaccccgg 49

<210> SEQ ID NO 120
<211> LENGTH: 18
<212> TYPE: DNA
<213> ORGANISM: Artificial Sequence
<220> FEATURE:
<223> OTHER INFORMATION: F2-1

<400> SEQUENCE: 120
ttccagccgg agggcgta 18

<210> SEQ ID NO 121
<211> LENGTH: 18
<212> TYPE: DNA

```
<213> ORGANISM: Artificial Sequence
<220> FEATURE:
<223> OTHER INFORMATION: F2-2

<400> SEQUENCE: 121

ttccagcccg agggcgta                                                    18
```

METHOD FOR PREPARING DNA UNIT COMPOSITION, AND METHOD FOR CREATING CONCATENATED DNA

CROSS REFERENCE TO RELATED APPLICATIONS

The present application is a continuation application of U.S. patent application Ser. No. 15/113,222, filed on Jul. 21, 2016, the entire contents of which are incorporated herein by reference and priority to which is hereby claimed. Application Ser. No. 15/113,222 is the U.S. national stage of application No. PCT/JP2014/073579 filed on Sep. 5, 2014. Priority under 35 U.S.C. § 119(a) and 35 U.S.C. § 365 (b) is claimed from Japanese Application No. 2014-008690, filed Jan. 21, 2014, the disclosure of which is also incorporated herein by reference.

TECHNICAL FIELD

The present invention relates to a method of preparing a DNA unit fragment composition and a method of constructing a DNA concatemer.

BACKGROUND ART

In recent years, techniques for DNA synthesis have been increasingly developed, for example, in order to construct a long chain DNA molecule having a size of a genome. Known such techniques include assembly of chemically synthesized DNA fragments and PCR-amplified DNA unit fragments. The synthesis process of the chemical synthesized DNA and the PCR method, however, are known to be accompanied by random mutation introduced into synthesized DNA molecules. Therefore, the sequences of the DNA molecules need to be always checked somewhere from the start to the end of the gene-assembling process so as to select a DNA molecule having a desired sequence.

Checking base sequences is usually conducted by Sanger base sequencing on an automated fluorescence sequencer. This method can determine about 800 consecutive bases in a single session of base sequencing. When the number of base sequencing sessions for checking base sequences of chemically- or PCR-synthesized DNA unit fragments prior to gene-assembling is reduced, time and cost can be saved. For this reason, the chemically- or PCR-synthesized DNA unit fragments to be used for gene-assembling are preferably short.

As the DNA unit fragments to be used for gene-assembling become shorter, however, the number of them to be assembled needs to be increased.

A currently known method to assemble a plurality of DNA unit fragments is a gene-assembling method employing a plasmid transformation system in *Bacillus subtilis* (the OGAB method). Patent Document 1, for example, discloses a method that adopts the OGAB method for constructing a DNA plasmid for use in transforming a *Bacillus subtilis* cell.

The OGAB method employs a so-called multimeric plasmid, in which multiple plasmid units exist within one molecule by homologous recombination between plasmid molecules. In the OGAB method, the DNA plasmid molecule for transformation is not necessarily circular, but it only has to have a tandem-repeat structure in which a plasmid unit and a DNA unit fragment used for assembling to be assembled appear repeatedly with each unit maintaining a same direction.

In the OGAB method, to prepare a DNA molecule having a tandem-repeat structure as above described, multiple DNA unit fragments, when used, need to be joined to their corresponding plasmids. As the number of kinds of DNA unit fragments increases, it becomes more difficult to join them to their corresponding plasmids and to construct a tandem-repeat structure. To join many DNA unit fragments together, the molar ratio among DNA unit fragments in ligation is desirably made close to 1.

Patent Document 1: Japanese Patent No. 4479199

DISCLOSURE OF THE INVENTION

Problems to be Solved by the Invention

In reality, however, it is difficult to precisely control the number of moles of each kind of DNA unit fragment. One of the reasons for this is that no method that quantifies DNA with a fluorescent double-stranded DNA intercalater such as SYBR Green I has reproducibility better than about ±20% because, for example, the color of a fluorescent substance fades during measurement. These measurement method measures the weight of DNA per unit volume and therefore when followed by the OGAB method in which the number of moles of DNA per unit volume is required for calculating the amount of each DNA unit fragment, the weight of DNA measured by the above mentioned measurement method needs to be converted to the corresponding molarity. The weight of a DNA unit fragment is proportional to the length thereof. Therefore, when the DNA unit fragment molecules are broadly varied in length and accordingly have their weight measurements varying by several folds or greater for the equal number of moles, calculation based on the measurement value often includes large errors. The method of Patent Document 1 attempts to adjust the molar ratio among DNA unit fragments to 1, but fails to precisely control the molar ratio due to the broad distribution of the lengths of the DNA unit fragments.

The present invention is devised based on the above circumstances, and an object of the present invention is to provide a method of preparing a DNA unit fragment composition and a method of constructing a DNA concatemer, in either of which methods the numbers of moles of multiple kinds of DNA unit fragments are substantially the same.

Means for Solving the Problems

The inventors of the present invention have found that measurement errors occurring in the measurement of the number of moles of each kind of DNA unit fragment are reduced when a corresponding auxiliary sequence is attached to each DNA unit fragment, and the present invention has now been completed. More specifically, the present invention subsumes the following embodiments.

(1) A method of preparing a DNA unit fragment composition, comprising:

a step of preparing solutions containing multiple kinds of DNA unit fragments, each solution containing one of the multiple kinds of DNA unit fragments, each DNA unit fragment being attached to a corresponding auxiliary sequence; and a step of, after preparing each solution, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is close to the number of moles of DNA unit fragment in another portion.

(2) The method of preparing a DNA unit fragment composition according to (1), wherein each DNA unit fragment with the corresponding auxiliary sequence attached thereto has a circular structure, and each corresponding auxiliary sequence is a plasmid DNA sequence harboring an origin of replication.

(3) The method of preparing a DNA unit fragment composition according to (1) or (2), wherein the distribution of the sum of the lengths of the base sequence of each DNA unit fragment and the base sequence of the corresponding auxiliary sequence attached to the DNA unit fragment has a standard deviation ranging from −20% to 20% with relative to the average value of the sum of the lengths.

(4) The method of preparing a DNA unit fragment composition according to any one of (1) to (3), wherein the average length of the base sequence of the corresponding auxiliary sequence attached to each DNA unit fragment is twice or greater than the average length of the base sequence of the DNA unit fragment.

(5) The method of preparing a DNA unit fragment composition according to any one of (1) to (4), wherein each DNA unit fragment is not longer than 1600 bp.

(6) The method of preparing a DNA unit fragment composition according to any one of (1) to (5), wherein the DNA unit fragments are used to construct a DNA concatemer, the DNA concatemer comprising DNA assemblies each comprising the DNA unit fragments, and the step of preparing solutions containing multiple kinds of DNA unit fragments comprises a step of designing each DNA unit fragment, the designing being conducted in a way that the base sequence of each DNA assembly when divided by the number of kinds of its constituent DNA unit fragments into equal parts has a non-palindromic sequence near each boundary between two adjacent equal parts, and that each DNA unit fragment has such a non-palindromic sequence at an end and is separated by the non-palindromic sequence from an adjacent DNA unit fragment.

(7) A method of constructing a DNA concatemer to be used for microbial cell transformation, the DNA concatemer comprising more than one DNA assembly unit, each of the more than one DNA assembly unit comprising a DNA vector harboring an origin of replication effective in a host microorganism and a DNA assembly, the method comprising:

a step of preparing a DNA unit fragment composition in a solution by the method as claimed in any one of (1) to (6);

a step of preparing the DNA vector;

a step of removing with a restriction enzyme a corresponding auxiliary sequence from each DNA unit fragment with the corresponding auxiliary sequence attached thereto contained in the solution after preparation; and a step of, after the removal step, joining the DNA vector and each of the DNA unit fragment together, wherein each of the DNA vector and the DNA unit fragment is structurally capable of being joined repeatedly while maintaining a certain order, and each DNA assembly comprises of a DNA molecule in which the DNA unit fragment is joined to one another.

(8) The method of constructing a DNA concatemer according to (7), further comprising: a step of, based on a relation between the yield of a DNA fragment comprising a target number of DNA unit fragments joined together and a coefficient of variation for the concentration of this DNA fragment, the yield being equal to the product of the number of DNA unit fragments per assembly unit and the number of the assembly unit, adjusting a coefficient of variation for the concentrations of the DNA vector and each DNA unit fragment in the joining step.

(9) The method of constructing a DNA concatemer according to (7) or (8), wherein the restriction enzyme is a Type II restriction enzyme.

(10) The method of constructing a DNA concatemer according to any one of (7) to (9), further comprising: a step of, before the removal step, mixing two or more solutions containing DNA unit fragments selected from the solutions containing DNA unit fragments.

(11) The method of constructing a DNA concatemer according to any one of (7) to (10), further comprising: a step of, after the removal step and before the joining step, inactivating the restriction enzyme.

(12) The method of constructing a DNA concatemer according to any one of (7) to (11), wherein the microorganism is *Bacillus subtilis.*

Effects of the Invention

The present invention provides a method of preparing a DNA unit fragment composition and a method of constructing a DNA concatemer, in either of which methods the numbers of moles of multiple kinds of DNA unit fragments are substantially the same.

BRIEF DESCRIPTION OF THE DRAWINGS

FIG. 1 an illustration showing DNA vectors according to an embodiment of the present invention.

FIG. 15 a photograph showing the result of electrophoresis in Example 2 of the present invention, conducted after transforming *Bacillus subtilis* with a DNA concatemer obtained by ligation of a DNA unit fragment and a DNA vector, extracting plasmids from the resulting plurality of transformant strains of *Bacillus subtilis*, and subjecting the resulting plasmids to restriction enzyme treatment.

FIG. 18 a graph showing the appearance number of transformants obtained by transformation of *Bacillus subtilis* competent cells with the DNA (A) to the DNA (H) used in Test Example 1.

FIGS. 19A-19D are graphs showing the relationship between CV (%) indicating variation in the concentrations of DNA unit fragments and the relative amount of each kind of DNA unit fragment, analyzed for each gene assembly size in simulation 1. FIG. 19A is a graph for a 6-fragment assembly, FIG. 19B is a graph for a 13-fragment assembly, FIG. 19C is a graph for a 26-fragment assembly, and FIG. 19D is a graph for a 51-fragment assembly.

FIG. 21B is a graph showing λ function of CV (%) indicating variation in the concentrations of DNA unit fragments determined from the average N value of virtual ligation product.

FIG. 24A is a graph comparing with simulation with a ligation-eligible rate of 95%, FIG. 24B is a graph comparing with simulation with a ligation-eligible rate of 96%, FIG. 24C is a graph comparing with simulation with a ligation-eligible rate of 97%, FIG. 24D is a graph comparing with simulation with a ligation-eligible rate of 98%, FIG. 24E is a graph comparing with simulation with a ligation-eligible rate of 99%, and FIG. 24F is a graph comparing with simulation with a ligation-eligible rate of 100%.

PREFERRED MODE FOR CARRYING OUT THE INVENTION

Figure 2:
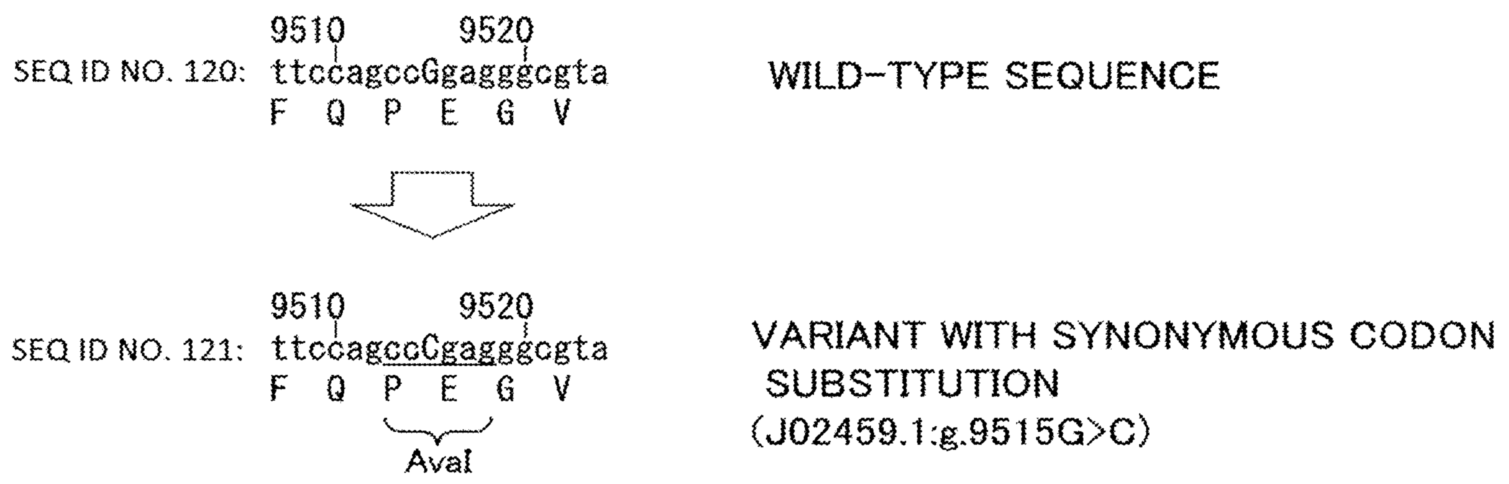
FIG. 2 an illustration showing the structure of a synonymous codon variant of Fragment No. 10 among DNA unit fragments of Example 1 of the present invention.

Embodiments of the present invention are described below. The scope of the present invention, however, is not limited to these embodiments.

<Method of Preparing DNA Unit Fragment Composition>

A method of preparing a DNA unit fragment composition of the present invention comprises: a step of preparing solutions containing multiple kinds of DNA unit fragments, each solution containing one of the multiple kinds of DNA unit fragments, each DNA unit fragment being attached to a corresponding auxiliary sequence; and a step of, after the preparation step, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is close to the number of moles of DNA unit fragment in another portion. In the present specification, different kinds of "DNA unit fragments" are distinguished from each other by the difference in the base sequences. The "DNA unit fragment" refers to one with or without a restriction enzyme recognition site introduced thereinto.

In the present invention, when the concentration of each kind of DNA unit fragment in the solution containing the DNA unit fragment is measured, the DNA unit fragment being measured has the corresponding auxiliary sequence attached thereto. The corresponding auxiliary sequences thus attached contribute to reduction in distribution of the lengths of different base sequences when the concentration of the solution is measured. As a result, when the measurement result is used to calculate the number of moles of each kind of DNA unit fragment, errors in the calculation are reduced. Then, when the resulting measurement result is used for taking a portion from each of the solutions so that the number of moles of DNA unit fragment in each portion is substantially the same, the molar ratio among different portions tends to be close to 1. The "concentration of the DNA unit fragment in the solution" thus measured refers to the molarity of the DNA unit fragment. The method of measuring the molarity of the DNA unit fragment in the solution is not particularly limited, but examples of the method include measuring the mass ratio (% by mass) of the DNA unit fragment in the solution and then using the measurement (% by mass) to calculate the molarity of the DNA unit fragment in the solution. In the method of measuring the molarity of the DNA unit fragment in the solution, a means capable of measuring the DNA concentration by weight with ±20% precision is preferably used, and, more specifically, a microspectrophotometer for measuring ultraviolet absorption spectra is preferably used.

The step of preparing solutions containing DNA unit fragments each with the corresponding auxiliary sequence attached thereto is not particularly limited and may be conducted, for example, by preparing each DNA unit fragment and then attaching the corresponding auxiliary sequence to the DNA unit fragment.

Preparation of the DNA unit fragment may be conducted by using the DNA unit fragment synthesized in advance or newly constructed. Construction of each DNA unit fragment can be achieved by a well-known conventional method including polymerase chain reaction (PCR) and chemical synthesis. Addition of a restriction enzyme recognition sequence to each DNA unit fragment can be achieved by constructing the DNA unit fragment by PCR in which, for example, a primer having a restriction enzyme recognition sequence for forming a protruding end in the base sequence of the template DNA is used, or by constructing the DNA unit fragment by chemical synthesis in which a restriction enzyme recognition sequence is incorporated in advance for forming a certain protruding sequence at an end of the DNA unit fragment. The base sequence of the DNA unit fragment thus constructed can be confirmed by a well-known conventional method, for example, by incorporating the DNA unit fragment into a plasmid and then conducting Sanger base sequencing on an automated fluorescence sequencer.

The corresponding auxiliary sequence is not particularly limited and may be a linear DNA molecule or a circular plasmid. When a circular plasmid DNA sequence is used, the DNA unit fragment with the corresponding auxiliary sequence attached thereto has a circular structure and therefore can be used, for example, to transform a host such as *Escherichia coli.*

The DNA plasmid is not particularly limited in its kind, but for replication of the DNA plasmid in the transformed host, the plasmid DNA sequence preferably has an origin of replication. Specifically, a high-copy *Escherichia coli* plasmid vector, pUC19, or a derivative plasmid thereof is preferable. In order to reduce the distribution of the lengths between DNA unit fragments each attached to the corresponding auxiliary sequence so that the numbers of moles of the DNA unit fragments can be made close to one another, all the DNA unit fragments are preferably cloned into the same kind of plasmid vector.

Attaching the corresponding auxiliary sequence to each DNA unit fragment may be conducted, for example, by ligation with DNA ligase, or by TA cloning in the case of attaching the DNA unit fragment to the DNA plasmid.

The standard deviation of the distribution of the sum of the lengths of the base sequence of each DNA unit fragment and the base sequence of the corresponding auxiliary sequence attached to the DNA unit fragment is not particularly limited. When the standard deviation is small, calculation errors are reduced in the calculation of the number of moles of each DNA unit fragment conducted based on the measurement result of the DNA concentration in the solution, and, as a result, the number of moles of the DNA unit fragment contained in one solution can be close to the number of moles of DNA unit fragment in another solution. Specifically, the standard deviation of the distribution of the sum of the lengths of the base sequence of each DNA unit fragment and the base sequence of the corresponding auxiliary sequence attached to the DNA unit fragment preferably ranges from −20% to 20%, more preferably ranges from −15% to 15%, further more preferably ranges from −10% to 10%, further preferably ranges from −5% to 5%, even further preferably ranges from −1% to 1%, and most preferably ranges from −0.5% to 0.5% with relative to the average value of the sum of the lengths.

The average length of the base sequence of the corresponding auxiliary sequence attached to each DNA unit fragment is not particularly limited. When the average length of the base sequence of the corresponding auxiliary sequence attached to each DNA unit fragment is greater than the average length of the base sequence of the DNA unit fragment, calculation errors are reduced in the calculation of the number of moles of the DNA unit fragment conducted based on the measurement result of the DNA concentration in the solution, and, as a result, the number of moles of the DNA unit fragment contained in one solution can be close to the number of moles of DNA unit fragment in another solution. Specifically, the average length of the base sequence of the corresponding auxiliary sequence attached to the DNA unit fragment is preferably not smaller than twice, further preferably not smaller than 5 times, further preferably not smaller than 10 times, and most preferably not smaller than 20 times the average length of the base sequence of the DNA unit fragment. When the average length of the base sequence of the corresponding auxiliary sequence attached to each DNA unit fragment is too great, handling of the DNA unit fragment with the corresponding auxiliary sequence attached thereto is difficult. Therefore, the average length of the base sequence of the corresponding auxiliary sequence attached to each DNA unit fragment is preferably not greater than 10000 times (specifically, for example, not greater than 5000 times, not greater than 3000 times, not greater than 1000 times, not greater than 500 times, not greater than 250 times, and not greater than 100 times) the average length of the base sequence of the DNA unit fragment, for example.

The length of each DNA unit fragment is not particularly limited. However, the number of sessions of base sequencing required for determining the base sequence of each DNA unit fragment is preferably small in order to save time and cost. Therefore, each DNA unit fragment is preferably short, and specifically, it is preferably not longer than 1600 bp and further preferably not longer than 1200 bp. Particularly when base sequencing is conducted by Sanger base sequencing on an automated fluorescence sequencer, which can determine about 800 consecutive bases in a single session of base sequencing, each DNA unit fragment is most preferably not longer than 800 bp (specifically, not longer than 600 bp, not longer than 500 bp, not longer than 400 bp, not longer than 200 bp, and not longer than 100 bp, for example). As the DNA unit fragments thus become shorter, however, the number of them needed for constructing a DNA concatemer described below increases. Here, many DNA unit fragments can be joined together when they are prepared by the method of the present invention as described below. But, again, when each DNA unit fragment is too short, the number of the DNA unit fragments to be joined increases and, as a result, operation efficiency decreases. For this reason, each DNA unit fragment is preferably not shorter than 20 bp, more preferably not shorter than 30 bp, and further preferably not shorter than 50 bp.

Applications of the DNA unit fragment composition prepared by the method of the present invention are not particularly limited. The DNA unit fragment composition prepared by the method of the present invention can be used to construct a DNA concatemer comprising DNA assemblies each comprising the DNA unit fragments. When the DNA unit fragment composition prepared by the method of the present invention is used to construct a DNA concatemer by a method described below, many kinds of DNA unit fragments (50 kinds or more, for example) can be joined together. This is achieved probably for a reason that the numbers of moles of DNA unit fragments contained in the DNA unit fragment composition prepared by the method of the present invention are close to one another with high precision.

In the present invention, the step of preparing solutions containing DNA unit fragments may comprise a step of designing each DNA unit fragment. Designing each DNA unit fragment is not particularly limited. In the case, for example, where the DNA unit fragment composition is used to construct a DNA concatemer comprising DNA assemblies, the designing may be conducted in a way that the base sequence of each DNA assembly when divided by the number of kinds of its constituent DNA unit fragments into equal parts has a non-palindromic sequence near each boundary between two adjacent equal parts, and that each DNA unit fragment is separated by the non-palindromic sequence from an adjacent DNA unit fragment. The DNA unit fragments thus designed have substantially the same length. This characteristic is preferable in terms of operation efficiency because when the DNA unit fragments are to be used for DNA concatemer construction as described below and are therefore subjected to removal of corresponding auxiliary sequences with restriction enzymes and to subsequent electrophoresis for size-based selection, the DNA unit fragments are observed substantially as a single band, allowing recovery of all the DNA unit fragments to be completed in a single session of size-based selection. The area referred to by the expression "near each boundary between two adjacent equal parts" is not particularly limited, and may be determined, as needed, based on the length of the base sequence. When the base sequence of each DNA unit fragment is 1000-bp long, for example, the area "near each boundary between two adjacent equal parts" may be determined, for example, as an area within 100 bp (specifically, within 90 bp, within 80 bp, within 70 bp, within 60 bp, within 50 bp, within 30 bp, within 20 bp, within 10 bp, within 5 bp) of each "boundary between two adjacent equal parts".

When the DNA unit fragment is thus designed for constructing a DNA concatemer comprising target DNA assemblies, the DNA unit fragment is preferably designed to have a non-palindromic sequence (a sequence that is not a palindromic sequence) at an end of the DNA unit fragment. The non-palindromic sequence of the DNA unit fragment thus designed is converted into a protruding sequence that is structurally capable of being joined repeatedly while maintaining a certain order as described below.

<Method of Constructing DNA Concatemer>

The present invention also subsumes a method of constructing a DNA concatemer. The method of constructing a DNA concatemer of the present invention comprises: a step of preparing the DNA unit fragment composition in the solution by the method described above; a step of preparing a DNA vector; a step of removing with a restriction enzyme the corresponding auxiliary sequence from each DNA unit fragment with the corresponding auxiliary sequence attached thereto contained in the solution; and a step of, after the removal step, joining the DNA vector and the DNA unit fragment together.

The DNA concatemer comprises more than one DNA assembly unit and is to be used for microbial cell transformation. Each DNA assembly unit comprises the DNA vector and the DNA assembly. The number of DNA assembly units in one DNA concatemer is not particularly limited provided that it is greater than 1. However, for enhanced efficiency in transformation, the number is preferably not smaller than 1.5, more preferably not smaller than 2, further preferably not smaller than 3, and most preferably not smaller than 4.

Each DNA vector harbors an origin of replication effective in a host microorganism that is to be transformed. The DNA vector is not particularly limited provided that it harbors a sequence that allows DNA replication to occur in a microorganism to be transformed with the DNA concatemer. For example, the DNA vector harbors a sequence coding for an origin of replication effective in a bacterium of the genus *Bacillus* (*Bacillus subtilis*). The sequence coding for an origin of replication effective in *Bacillus subtilis* is not particularly limited. Examples of sequences coding for the origin of replication include sequences coding for, for example, an origin of replication harbored by plasmids such as pTB19 (Imanaka, T., et al. J. Gen. Microbioi. 130, 1399-1408. (1984)), pLS32 (Tanaka, T and Ogra, M. FEBS Lett. 422, 243-246. (1998)), and pAMβ1 (Swinfield, T. J., et al. Gene 87, 79-90. (1990)).

Each DNA assembly is a DNA molecule in which the DNA unit fragment described above is joined to one another. The DNA referred to in the present invention is a DNA molecule to be cloned, and is not particularly limited in its kind or size. Specifically, the DNA referred to in the present invention may have a sequence naturally occurring in a prokaryote, a eukaryote, a virus, or the like or an artificial sequence, for example. In the method of the present invention capable of joining many DNA unit fragments to a plasmid as described above, a DNA molecule having a long base sequence is preferably used. The DNA molecule having a long base sequence is, for example, a group of genes coding for an entire metabolic pathway or a complete or partial genomic DNA of a phage or the like.

Each DNA assembly unit may or may not comprise an additional proper base sequence, where appropriate, besides the DNA vector and the DNA assembly. In the case of constructing a plasmid for use in expression of a constituent gene of the DNA assembly, the DNA assembly unit may comprise a base sequence capable of controlling transcription and translation, such as a promoter, an operator, an activator, and a terminator. Specific examples of a promoter for *Bacillus subtilis* as a host include Pspac promoter (Yansura, D. and Henner, D. J. Pro. Natl. Acad. Sci, USA 81, 439-443. (1984)), the expression of which can be controlled by IPTG (isopropyl s-D-thiogalactopyranoside), and Pr promoter (Itaya, M. Biosci. Biotechnol. Biochem. 63, 602-604. (1999)).

Each of the DNA vector and the DNA unit fragment is structurally capable of being joined repeatedly while maintaining a certain order. In the present specification, the expression "joined while maintaining a certain order" refers to that a DNA unit fragment is joined in a certain order and orientation to another DNA unit fragment or to a DNA vector adjacent within a DNA assembly unit. The expression "joined repeatedly" refers to that the 5' end of a DNA unit fragment or a DNA vector harboring its 5' base sequence is joined to the 3' end of a DNA unit fragment or a DNA vector harboring its 3' base sequence. Specific examples of such a DNA unit fragment include a DNA unit fragment having an end capable of being joined repeatedly to a partner while maintaining a certain order due to complementation between the base sequences of their protruding ends. Such protrusion is not particularly limited in its structure, or in the difference in shape between one on the 5' protruding end and one on the 3' protruding end, provided that it has a non-palindromic sequence.

Each protruding end is preferably formed by the step of removing the corresponding auxiliary sequence from the DNA unit fragment with a restriction enzyme. Therefore, in construction of a DNA concatemer by the method of the present invention, the DNA unit fragment preferably comprises a restriction enzyme recognition sequence that allows removal of the corresponding auxiliary sequence with a restriction enzyme. The preparation of the DNA vector can also be conducted, for example, by restriction enzyme treatment that forms a protruding end and allows the DNA vector and the DNA unit fragment to join repeatedly while maintaining a certain order.

The restriction enzyme used above for removal of the corresponding auxiliary sequence is not particularly limited, but is preferably a Type II restriction enzyme, and is more preferably a Type IIS restriction enzyme that can form a protruding end having a certain sequence at a locus at a certain distance outside its recognition sequence, such as AarI, BbsI, BbvI, BcoDI, BfuAI, Bsal, BsaXI, BsmAI, BsmBI, BsmFI, BspMI, BspQI, BtgZI, FokI, and SfaNI. A Type IIS restriction enzyme can form different protruding ends for a single DNA unit fragment, and consequently can maintain the order in which DNA unit fragments are joined. Not only in the preparation of the DNA unit fragment but also in the preparation of the DNA vector, a Type IIS restriction enzyme is preferably used for forming a protruding end that allows the DNA vector and the DNA unit fragment to join repeatedly while maintaining a certain order.

The DNA unit fragments can be divided into groups, each group for a single restriction enzyme to be used for removal of the corresponding auxiliary sequence. In this case, each group can consist of two or more solutions each containing a different DNA unit fragment. The two or more solutions can be mixed together before the removal step. As a result, a separate session of restriction enzyme treatment is not required for respective DNA unit fragment, but, instead, a single session of restriction enzyme treatment is enough to treat an entire restriction-enzyme group. Especially when the DNA unit fragments are fractionated by electrophoresis, the DNA unit fragments can be recovered in a single session of fractionation and, as a result, operation efficiency is further enhanced. However, when there are multiple groups of the DNA unit fragments, fractionation is conducted for each group. When the DNA unit fragments are recovered, the recovered amounts can vary between different groups. Accordingly, the numbers of moles of DNA unit fragments that have been made substantially the same can also vary. For this reason, the number of groups each for a single restriction enzyme to be used for removal of the corresponding auxiliary sequence is preferably small, in other words, the number of kinds of restriction enzymes to be used for removal of the corresponding auxiliary sequence is preferably small. The number of kinds of restriction enzymes to be used is preferably not greater than 5, more preferably not greater than 3, and most preferably 1. Specifically, when only a single kind of restriction enzyme is used, all the solutions containing DNA unit fragments can be mixed together, leading to significant enhancement in operation efficiency and then to decreased probability of variation occurring in the number of moles of DNA unit fragments that have been made substantially the same. The number of moles of many DNA unit fragments are made substantially the same when mixed together, and therefore these many DNA unit fragments can be joined together as described above with a restriction enzyme.

When a Type IIS restriction enzyme recognition sequence is added to the sequence of the DNA unit fragment, the Type IIS restriction enzyme to be used is selected so that it recognizes none of the sequences of the DNA unit fragments in the same group. In other words, when a certain Type IIS restriction enzyme is used, each restriction enzyme recognition is designed such that the Type IIS restriction enzyme does not recognizes the sequence of one DNA unit fragment but recognizes the sequence of another DNA unit fragment, a different Type IIS restriction enzyme is selected for the another DNA unit fragment. In case of such design, different Type IIS restriction enzymes are used for different DNA unit fragments, and that the DNA unit fragments can then be divided into groups each for a different Type IIS restriction enzyme. If a Type IIS restriction enzyme is available that recognizes none of the sequences of the DNA unit fragments used, the recognition sequence of the Type IIS restriction enzyme can be added to the DNA unit fragments so that the corresponding auxiliary sequences can be removed from the DNA unit fragments all at once with the single Type IIS restriction enzyme.

The step of joining the DNA vector and the DNA unit fragment is not particularly limited, but can be conducted by, after restriction enzyme treatment, fractionating the DNA unit fragment from its corresponding auxiliary sequence treated with the restriction enzyme and then joining the DNA unit fragment thus fractionated and the DNA vector with DNA ligase or the like (ligation). In this way, a DNA concatemer to be used for microbial transformation can be constructed. It is noted that the DNA unit fragment used in the joining step has no restriction enzyme recognition sequence added thereinto.

The method of fractionation between the DNA unit fragment and its corresponding auxiliary sequence is not particularly limited. It is preferable that the molar ratio between the DNA unit fragments is maintained after restriction enzyme treatment, and agarose gel electrophoresis is specifically preferable.

The method of joining the DNA unit fragment and the DNA vector is not particularly limited, but the joining is preferably conducted in the presence of polyethylene glycol and a salt. The salt is more preferably a monovalent alkali metal salt. More specifically, the joining is further preferably conducted in a ligation reaction solution containing 10% polyethylene glycol 6000 and 250-mM sodium chloride. The concentration of each DNA unit fragment in the ligation reaction solution is not particularly limited, but is preferably not lower than 1 fmol/μl. The reaction temperature and the reaction time for ligation are not particularly limited, but are preferably 37° C. and for 30 minutes or longer. Preferably, the concentration of the DNA vector in the ligation reaction solution is measured before reaction and then the number of moles of the DNA vector and the number of moles of the DNA unit fragment are adjusted to be the same.

The method of preparing a DNA concatemer according to the present invention may or may not comprise, and preferably comprise a step of, based on a relation between the yield of a DNA fragment comprising a target number of DNA unit fragments joined together and a coefficient of variation for the concentration of this DNA fragment (hereinafter in the present specification, the coefficient is called "coefficient of variation 1") (hereinafter in the present specification, the relation is called "relation"), the yield being equal to the product of the number of DNA unit fragments per assembly unit and the number of the more than one assembly unit, adjusting a coefficient of variation for the concentrations of the DNA vector and each DNA unit fragment (hereinafter in the present specification, the coefficient is called "coefficient of variation 2") in the joining step. It is noted that the coefficient of variation 1 is a coefficient of variation used in the relation for convenience, and the coefficient of variation 2 is the coefficient of variation for the concentrations of each DNA unit fragment and the DNA vector in the actual joining step. By including this adjustment step, the coefficient of variation 2 is adjusted to fall within the range shown by the relation, a desired number of DNA unit fragments (for example, 50 DNA unit fragments) can be joined in the joining step.

The target number of DNA unit fragments joined together refers to the number of DNA fragments intended to be joined in the joining step, and more specifically refers to the product of the number of DNA unit fragments per assembly unit to be joined and the number of the more than one assembly unit. The "yield of a DNA fragment comprising a target number of DNA unit fragments joined together" refers to the proportion of the number of DNA fragments per DNA assembly unit joined together to the total number of DNA fragments used for joining.

The relation according to the present invention is a formula showing the relationship between the yield of a DNA fragment comprising a target number of DNA unit fragments joined together and the coefficient of variation 1. A formula determined by computer simulation of ligation, for example, can be used. More specifically, the relation can be obtained by conducting simulation of ligation, for example, for each of DNA unit fragment groups having a coefficient of variation 1 varying by 1% starting from 0% to 20% (10 to 30 groups, for example), determining the distribution of the number of DNA unit fragments per each resulting DNA concatemer (exponential distribution, for example), plotting a fitting curve of the resulting distributions, and using the fitting curve. A specific tool for use in ligation simulation is not particularly limited and a conventional known means can be used. For example, VBA (Visual Basic for Applications) of spreadsheet software Excel (registered trademark) 2007 can be used for programming as well as constructing algorithms to conduct simulation. The fitting curve can be plotted, for example, with a function of spreadsheet software Excel (registered trademark) 2007 that helps plotting exponential approximation curves. Adjustment of the coefficient of variation 2 based on the relation can be conducted, for example, after designing the relation, by substituting the yield of a target DNA fragment into the relation thus obtained, and adjusting the process in each pre-joining step so that the DNA fragment being joined has a coefficient of variation 1 equal to the thus-calculated coefficient of variation 1. The method of adjustment is not particularly limited. For example, the adjustment may be conducted by selecting, in a step such as the step of preparing the DNA vector, the step of preparing the DNA unit fragment, and/or the step of joining the DNA vector and the DNA unit fragment together, a measuring instrument (a spectrophotometer, a spectrofluorophotometer, or a real-time PCR apparatus, for example), that has its measurement errors known in advance for use in determining the concentration of the DNA vector or the DNA unit fragment in order to obtain the desired coefficient of variation 2.

The coefficient of variation 2 is not particularly limited. As the variation in the concentrations of the DNA unit fragments being joined is reduced, the number of DNA unit fragments that can be joined increases. Therefore, the coefficient of variation 2 is preferably not greater than 20%, more preferably not greater than 15%, further preferably not greater than 10%, further more preferably not greater than 8%, and most preferably not greater than 5%.

The method of preparing a DNA concatemer of the present invention may further comprise a step of inactivating the restriction enzyme after the removal step and before the joining step. A certain DNA unit fragment can have a restriction enzyme cleavage site that is the same as a restriction enzyme cleavage site for separating another DNA unit fragment from its corresponding auxiliary sequence. In this case, it is difficult to mix together different DNA unit fragment groups with their corresponding auxiliary sequences attached thereto while the restriction enzyme or enzymes are still active. Accordingly, the DNA unit fragments cannot be fractionated in a single session by combining these DNA unit fragment groups together. In contrast, when the restriction enzyme or enzymes have been inactivated, different DNA unit fragment groups with their corresponding auxiliary sequences attached thereto can be combined together after the inactivation, and, as a result, the DNA unit fragments can be fractionated in a single session. This advantage makes it easier to construct a DNA concatemer comprising even a greater number of DNA assemblies in the joining step, and, as a result, makes it easier to transform *Bacillus subtilis*. Inactivation of the restriction enzymes can be conducted by a well-known conventional method, for example, phenol-chloroform treatment.

The host microorganism to be transformed is not particularly limited provided that it has ability to undergo spontaneous transformation. Examples of the ability to undergo spontaneous transformation include ability to process DNA into a single strand prior to taking it up. Specific examples of the host microorganism include bacteria of the genus *Bacillus*, bacteria of the genus *Streptococcus*, bacteria of the genus *Haemophilus*, a bacteria of the genus *Neisseria*, and the like. Examples of the bacteria of the genus *Bacillus* include *B. subtilis* (*Bacillus subtilis*), *B. megaterium* (*Bacillus megaterium*), *B. stearothermophilus* (*Bacillus stearothermophilus*), and the like. Examples of the most preferable microorganisms, among these, include *Bacillus subtilis* that has excellent ability to undergo spontaneous transformation and recombination.

The DNA concatemer constructed by the method of the present invention can be used for microbial cell transformation. The method of giving competency to a microorganism that is to be transformed can be a known method that is suitable for the selected microorganism. Specifically, for *Bacillus subtilis*, a method described in Anagnostopoulou, C. and Spizizen, J. J. Bacteriol., 81, 741-746(1961) is preferably used. Similarly, as the method of transformation, a known method that is suitable for the selected microorganism can be used. The amount of ligation product solution to give to the competent cell is not particularly limited, but is preferably from 1/20 to 20/20 and more preferably half the amount of the competent cell culture. The method of purifying the resulting plasmid from the transformant can also be a known method.

The presence of DNA assemblies in the plasmid purified from the transformant can be confirmed by checking the size-based patterns of fragments cleaved by a restriction enzyme or enzymes, PCR, or base sequencing. When the DNA insert for a substance-producing function, it can be confirmed by detecting the function.

EXAMPLES

The present invention will be described below more specifically by examples. The examples merely illustrate embodiments of the present invention, and therefore do not limit the scope of the present invention.

(Materials)

The microbial cells used for transformation were *Bacillus subtilis* cells. The strains of *Bacillus subtilis* used were strain RM125 (Uozumi, T., et al. Moi. Gen. Genet., 152, 65-69 (1977)) and its derivative strain BUSY9797. As a DNA vector capable of replication in *Bacillus subtilis*, pGETS118-AarI-pBR (see SEQ ID NO:1) constructed as described below by using pGET118 (Kaneko, S., et al. Nucleic Acids Res. 31, e112 (2003)) as well as pGETS151-pBR (see SEQ ID NO:2) were used. As a DNA assembly, lambda phage DNA (manufactured by Toyobo Co., Ltd.) (see SEQ ID NO:3) and an artificial operon of the mevalonate pathway described below (see SEQ ID NO:4) were used. For selecting an *Escherichia coli* having a DNA plasmid into which a DNA unit fragment is incorporated, the antibiotic carbenicillin (Wako Pure Chemical Industries, Ltd.) was used. For selecting *Bacillus subtilis*, the antibiotic tetracycline (Sigma) was used. As a Type IIS restriction enzyme, AarI (Thermo), BbsI (NEB), BsmBI (NEB), and SfiI (NEB) were used. The restriction enzymes Hindlll, PvuII, and T4 DNA Ligase used were manufactured by Takara Bio Inc. For ligation that was normally conducted for constructing an *Escherichia coli* plasmid, Takara Ligation Kit (Mighty) (Takara Bio Inc.) was used. For PCR reaction for preparing a DNA unit fragment, KOD plus polymerase manufactured by Toyobo Co., Ltd. was used. For colony PCR for base sequencing DNA cloned in a plasmid, Ex-Taq HS manufactured by Takara Bio Inc. was used. As a DNA plasmid that was a corresponding auxiliary sequence to be attached to a DNA unit fragment, pMD-19 (simple) (Takara Bio Inc.) was used. The enzyme used for purifying a circular plasmid was Plasmid Safe manufactured by EPICENTRE. As the agarose gel for electrophoresis, 2-Hydroxyethyl agarose (Sigma), which was agarose gel for DNA electrophoresis having low melting temperature, or UltraPure Agarose (Invitrogen Limited) was used. For inactivation of a restriction enzyme, phenol:chloroform:isoamyl alcohol 25:24:1 and TE saturated phenol (containing 8-quinolinol) manufactured by Nacalai Tesque, Inc. were used. The lambda terminase used was manufactured by EPICENTRE. For lambda phage packaging, Gigapack III Plus Packaging Extract from Agilent Technologies was used. The lysozyme used was manufactured by Wako Pure Chemical Industries, Ltd. The medium component of the LB medium and the agar-agar manufactured by Becton, Dickinson and Company were used. The IPTG (isopropyl s-D-thiogalactopyranoside) used was manufactured by Wako Pure Chemical Industries, Ltd. All the medium components and biochemical reagents other than those described above manufactured by Wako Pure Chemical Industries, Ltd were used. For construction of a plasmid other than those particularly mentioned, one of *Escherichia coli* strains DH5a, JM109, and TOP10 was used. For purification of a small amount of constructed plasmid from *Escherichia coli*, QIAprep Spin Miniprep Kit from QIAGEN was used, while for purification of a large amount, QIAfilter Midi Kit from QIAGEN was used. For DNA cleanup from an enzymatic reaction solution, MinElute Reaction Cleanup Kit from QIAGEN or QIAquick PCR purification Kit from QIAGEN was used. For purification of a gel block resulting from ordinary agarose gel electrophoresis separation, MinElute Gel Extraction Kit from QIAGEN was used. As a spectrophotometer for trace amount detection, nano-drop 2000 from Thermo was used. For base sequencing, the automated fluorescence sequencer 3130xl Genetic Analyzer manufactured by Applied Biosystems Inc. was used. Other common DNA handling was conducted according to a standard protocol (Sambrook, J., et al., Molecular Cloning: A Laboratory Manual. Cold Spring Harbor Laboratory Press, Cold Spring Harbor, N.Y. (1989)). *Bacillus subtilis* transformation and plasmid extraction were conducted according to a known method (Tsuge, K., et al., Nucleic Acids Res. 31, e133. (2003)).

(Construction of DNA Vector Used in Assembly)

The DNA vector used in lambda phage DNA assembly, pGETS118-AarI-pBR (SEQ ID NO:1), was a plasmid constructed through multiple steps starting from the *Escherichia coli-Bacillus subtilis* shuttle plasmid vector pGETS118 harboring an origin of replication in *Escherichia coli* F factor, oriS, and an origin of replication in *Bacillus subtilis*, repA (Kaneko, et. al., Nucleic Acids Res., 31, e112. (2003)). The structure thereof is shown in FIG. 1. The cloning site for a gene assembly was the area between two AarI cleavage sites. This area between the two AarI cleavage sites, which was to be removed at the time of assembling, had an origin of replication of the *Escherichia coli* multicopy plasmid pBR322 for facilitating vector acquisition in *Escherichia coli*, as well as an ampicillin resistance gene, introduced thereinto. As for the AarI cleavage site naturally occurring in a tetracycline resistance gene of pGETS118, its recognition site was rendered ineffective by single base mutation that had no influence on the amino acid sequence of the tetracycline resistance gene (tetL). The DNA vector used in assembly of an artificial mevalonate-pathway operon, pGETS151-pBR (SEQ ID NO:2), was constructed by joining together fragments amplified from the pGETS118-AarI-pBR DNA described above as a template with three pairs of primers, PartA (5'-TAGGGTCTCAaagcggccgcaagctt-3' (see SEQ ID NO:5) and 5'-TAGGGTCTCAGCggccaagaaggcc-3' (see SEQ ID NO:6)), PartB (5'-TAGGGTCTCAccGCCCTTCCCGGTCGATAT-3' (see SEQ ID NO:7) and 5'-TAGGGTCTCAtaTTAGCTTAATTGTTATCCGCTCACAATTCC-3' (see SEQ ID NO:8)), and PartC (5'-TAGGGTCTCAAAtaactggaaaaaattagtgtctcatggttcg-3' (see SEQ ID NO:9) and 5'-TAGGGTCTCAgcttaagtggtgggtagttgacc-3' (see SEQ ID NO:10)). Unlike the template plasmid, this DNA vector pGETS151-pBR did not have gene regions functioning only in *Escherichia coli* (the region between cat and oriS, and the region between parA and parC) (FIG. 1). Although this DNA vector with a gene assembly was capable of replicating only in *Bacillus subtilis*, it shared the same characteristics with pGETS118-AarI-pBR in terms of the gene-assembling process. To about 10 μl of a solution each containing one of the plasmids (equivalent to 5 μg), 29 μl of sterilized water, 5 μl of 10× Buffer_for_AarI that came with a restriction enzyme used, 1 μl of 50× Oligonucleotide for activation of cleavage that also came with the restriction enzyme used, and 5 μl of the restriction enzyme AarI (Thermo) were added, followed by reaction at 37° C. for 2 hours. The resulting liquid was subjected to separation by electrophoresis in agarose gel having low melting temperature. From the gel, a fragment of about 15 kb (in the case of pGETS118-AarI-pBR) or of 4.3 kb (in the case of pGETS151-pBR) attributed to the vector was cut out, followed by purification of the DNA vector in question, which was then dissolved in 20 μl of TE. The concentration of the DNA vector was measured by taking a 1-μl sample from the TE solution and subjecting the sample to measurement with a spectrophotometer for trace amount detection.

(Designing DNA Unit Fragment's Border Regions)

The number of different combinations of 4-base protruding was 4 raised to the 4th power, which was equal to 256. From these, protruding sequences used in the present invention were selected according to the following criterion. First, all the 16 palindromic sequences (Group 0) (AATT, ATAT, TATA, TTAA, CCGG, CGCG, GCGC, GGCC, ACGT, AGCT, TCGA, TGCA, CATG, CTAG, GATC, GTAC) were excluded because their complementary sequences had the same sequences as their own and therefore there was a possibility that identical fragments would join together, which was not appropriate in the present invention. The remaining 240 sequences included both a certain sequence (CCTA, for example) and its complementary sequence (TAGG), and therefore the theoretical number of combinations of protruding sequences applicable to DNA concatenation was 240/2=120 combinations. Then, based on the GC content and the appearance order in which the constituent G and C bases were aligned, these combinations were divided into groups of combinations of protruding ends as follows.

(Group I) 6 combinations of protruding ends consisting of A and T alone (AAAA/TTTT, TAAA/TTTA, ATAA/TTAT, AATA/TATT, AAAT/ATTT, ATTA/TAAT).

(Group II) All 32 combinations consisting of 3 bases selected from A and T and 1 base selected from C and G (CAAA/TTTG, ACAA/TTGT, AACA/TGTT, AAAC/GTTT, GAAA/TTTC, AGAA/TTCT, AAGA/TCTT, AAAG/CTTT, CAAT/ATTG, ACAT/ATGT, AACT/AGTT, AATC/GATT, GAAT/ATTC, AGAT/ATCT, AAGT/ACTT, AATG/CATT, CATA/TATG, ACTA/TAGT, ATCA/TGAT, ATAC/GTAT, GATA/TATC, AGTA/TACT, ATGA/TCAT, ATAG/CTAT, CTTA/TAAG, TCTA/TAGA, TTCA/TGAA, TTAC/GTAA, GTTA/TAAC, TGTA/TACA, TTGA/TCAA, TTAG/CTAA).

(Group III) 44 combinations, left by subtracting 8 palindromic combinations from all 52 combinations consisting of 2 bases selected from A and T and 2 bases selected from C and G (AACC/GGTT, AACG/CGTT, AAGC/GCTT, AAGG/CCTT, ACAC/GTGT, ACAG/CTGT, ACCA/TGGT, ACCT/AGGT, ACGA/TCGT, ACTC/GAGT, ACTG/CAGT, AGAC/GTCT, AGAG/CTCT, AGCA/TGCT, AGGA/TCCT, AGTC/GACT, AGTG/CACT, ATCC/GGAT, ATCG/CGAT, ATGC/GCAT, ATGG/CCAT, CAAC/GTTG, CAAG/CTTG, CACA/TGTG, CAGA/TCTG, CATC/GATG, CCAA/TTGG, CCTA/TAGG, CGAA/TTCG, CGTA/TACG, CTAC/GTAG, CTCA/TGAG, CTGA/TCAG, CTTC/GAAG, GAAC/GTTC, GACA/TGTC, GAGA/TCTC, GCAA/TTGC, GCTA/TAGC, GGAA/TTCC, GGTA/TACC, GTCA/TGAC, GTGA/TCAC, TCCA/TGGA).

(Group IV) 16 combinations with no 3 consecutive bases selected from C and G, out of all 32 combinations consisting of 1 base selected from A and T and 3 bases selected from C and G (CACC/GGTG, CCAC/GTGG, CTCC/GGAG, CCTC/GAGG, CACG/CGTG, CCAG/CTGG, CTCG/CGAG, CCTG/CAGG, CAGC/GCTG, CGAC/GTCG, CTGC/GCAG, CGTC/GACG, GAGC/GCTC, GGAC/GTCC, GTGC/GCAC, GGTC/GACC).

(Group V) All 16 combinations with 3 consecutive bases selected from C and G, out of all 32 combinations consisting of 1 base selected from A and T and 3 bases selected from C and G (ACCC/GGGT, CCCA/TGGG, TCCC/GGGA, CCCT/AGGG, ACCG/CGGT, CCGA/TCGG, TCCG/CGGA, CCGT/ACGG, ACGC/GCGT, CGCA/TGCG, TCGC/GCGA, CGCT/AGCG, AGGC/GCCT, GGCA/TGCC, TGGC/GCCA, GGCT/AGCC).

(Group VI) All 6 combinations consisting of bases selected from C and G alone (CCCC/GGGG, GCCC/GGGC, CGCC/GGCG, CCGC/GCGG, CCCG/CGGG, CGGC/GCCG).

Boundaries between a DNA vector and a DNA unit fragment in Examples 1 and 2 were selected from Group 1 among the groups divided as above. Boundaries between two DNA unit fragments as candidates were selected from 60 combinations in total of protruding ends included in Group III (44 combinations) and Group IV (16 combinations). Selection of a combination of protruding ends was conducted by determining the full-length final base sequence made up by the sequences to be assembled and then determining ideal dividing boundaries that divided the full-length base sequence into equal parts. The base sequence used in Example 1 is described below referring to specific examples.

Example 1 is an experiment of reconstruction of a 48522-bp molecule consisting of the 48502-bp full-length lambda phage genome, to which a 16-bp cos site and a 4-bp protruding sequence required for assembly are added. Table 1 below shows ideal dividing boundaries and actual dividing boundaries within DNA assemblies and protruding base sequences of the DNA assemblies in Example 1. Reconstruction was attempted by first dividing the molecule devoid of a plasmid vector for assembly into 50 DNA unit fragments having substantially the same size, and then joining these 50 DNA unit fragments together. Ideally, all of the 50 fragments are divided to have the same length. In order to avoid changing any base in the sequences to be assembled, it was necessary to construct 5' end protruding of 4 bases to be used for assembly, depending on the originally existing sequence. In reality, there was almost no chance that each single one of the ideal dividing boundaries had one of the protruding sequences described above, which means that it was impossible to divide the original sequence into equal DNA unit fragments at the ideal dividing boundaries. Therefore, in this example, in order to make the size of the unit as close to the size of the ideal dividing unit as possible, simulation was conducted to assign a protruding-end combination to each boundary. The simulation was conducted as follows: first, the full-length original molecule (48522 bp) was divided into 50 equal-sized ideal DNA unit fragments of 970 bp, which were then named as Fragment No. 01, Fragment No. 02, Fragment No. 03, . . . , and Fragment No. 50 in order of increasing absolute base number; and, then, the presence of any 4-base protruding end candidate was searched for within a 4-base sequence that extended the same distance from an absolute position of each ideal boundary (the ideal dividing boundaries lay between the 970th base and the 971th base, between the 1940th base and the 1941th base, between the 2910th base and the 2911th base, . . . , and between the 47530th base and the 47531th base), with the 4-base sequence being sequentially enlarged by 1 base at a time to each side of the ideal dividing boundary, namely, the 4-base sequence becoming sequentially enlarged to a 6-base sequence, an 8-base sequence, a 10-base sequence, a 12-base sequence, a 14-base sequence, a 16-base sequence, an 18-base sequence, a 20-base sequence, a 22-base sequence, and a 24-base sequence. This procedure is explained in the following specific example (Table 1). The ideal dividing boundary between Fragment No. 01 and Fragment No. 02 lay between the 970th base and the 971th base. Within the 16-base sequence extending the same distance from the ideal dividing boundary (the base sequence from the 963th base to the 988th base, namely, 5'-ATGCTGCTGGGTGTTT-3'), 7 protruding-end combination candidates were found (ACAC/GTGT, AGCA/TGCT, ATGC/GCAT, CACC/GGTG, CAGC/GCTG, CCAG/CTGG, CTGC/GCAG). This procedure was conducted for all the 49 ideal dividing boundaries, in an attempt to find at least one protruding sequence candidate within each base sequence of a certain length lying near each of the ideal dividing boundaries. When the length was extended to 24 bp, each base sequence had at least one 4-base protruding sequence candidate. Then, for each base sequence, a specific protruding sequence was selected from the protruding candidates, as follows: the least common protruding-end combination found (or not taken yet) in all of the (remaining) base sequences was assigned, preferentially, to the base sequence with the least number of protruding-end combination candidates; and this procedure was repeated so that a unique protruding-end combination was assigned to all the boundaries.

TABLE 1

| Ideal dividing boundary | 60 Bases near ideal ("\|" indicates each ideal diving boundary) | Actual dividing | Protrudung sequence | Complementary sequence | SEQ ID NO: |
|---|---|---|---|---|---|
| -1\|1 | tgagacgtctcggcctgtttggccattaCG\|GGGCGGCGACCTCGCGGGTTTTCGCTATTT | -7/-6 | ATTA | TAAT | 66 |
| 970\|971 | TGCCCGTGTCGGTTATTCCAAAATGCTGCT\|GGCTGTTTATGCCTACTTTATAGAGGATAA | 962/963 | ATGC | GCAT | 67 |
| 1940\|1941 | GACTCCCAGCTGGACCGCTACGAAATGCGC\|GTATGGGGATGGGGGCCGGGTGAGGAAAGC | 1942/1943 | ATGG | CCAT | 68 |
| 2910\|2911 | ACATCGCTGCGCGAATATGCCGGTTATCAC\|GGCGGTGGCAGCGGATTTGGAGGGCAGTTG | 2907/2908 | CACG | CCTG | 69 |
| 3880\|3881 | TGAACCTGCAGACGGCTCAGGATACGGATA\|ACGGCTACTCCGTGTTTGAGCAGTCACTGC | 3879/3880 | AACG | CGTT | 70 |
| 4850\|4851 | GGATGGTGGCGGGGGCATTTGACTCCGCTG\|ACATCATCGCCCGIGTGCGTGACATAAAAC | 4847/4848 | CTGA | TCAG | 71 |
| 5820\|5821 | CAGTGACCCGGCTCATACCGCAACCGCGCC\|CGGCGGATTGAGTGCGAAAGCGCCTGCAAT | 5824/5825 | GCAT | ATCC | 72 |
| 6790\|6791 | TTCCTTCAAAGCCGTCAAGGAGAAGCTGGA\|TACCCGTCGTGGCTCTAATTCCGAGCTGGA | 6790/6791 | TACC | GGTA | 73 |
| 7760\|7761 | TGGTGTTTTTGATGACCCTGAAAATATCAG\|CTATGCCGGACAGGGCGTGCGCGTTGAAGC | 7759/7760 | GCTA | TAGC | 74 |
| 8730\|8731 | CGAAGAGCTGGACAGCGATACCTGGCAGGC\|GGAGCTGCATATCGAAGTTTTCCTGCCTGC | 8731/8732 | GAGC | GCTC | 75 |
| 9700\|9701 | AGAAATTACCGTCACCGCCAGTTAATCCGG\|AGAGTCAGCGATGTTCCTGAAAACCGAATC | 9700/9701 | AGAG | CTCT | 76 |
| 10670\|10671 | GAAAGTGATGCGAAAAAAACAGCGGCAGTC\|GTTGAACAGTCGCTGAGCCGACAGGCGCTG | 10666/10667 | AGTC | GACT | 77 |
| 11640\|11641 | GGGATGATCGTGAAAAGGCCCGTCTTGCGC\|TTGAAGCCGCCCGAAAGAAGGCTGAGCAGC | 11642/11643 | GAAG | CTTC | 78 |
| 12610\|12611 | CACCCGTTCCGTCCTGTCCATGATGACAGA\|AATTCTGCTTAAGCAGGCAATGGTGGGGAT | 12606/12607 | GAGA | TCTG | 79 |
| 13580\|13581 | GCAGAACGAAAAAGGTGAGCCGGTCACCTG\|GCAGGGGCGACAGTATCAGCCGTATCCCAT | 13577/13578 | CTGG | CCAG | 80 |
| 14550\|14551 | TCTGGCGGGGATTGAGATGCCGGACTTTCA\|TCGTGAGGATGACTGGTGGCGTAACCGCCA | 14550/14551 | TCGT | ACGA | 81 |
| 15520\|15521 | ATGGAGCGTGAGGAATGGGTAAAGGAAGCA\|GTAAGGGGCATACCCCGCGCGAAGCGAAGG | 15516/15517 | AGCA | TCCT | 82 |
| 16490\|16491 | GGAGCCGCGCATCACCTGTAATGCGTACCT\|GACCACACAGCGTAAGGCGTGGGATGTGCT | 16487/16488 | CCTG | CAGG | 83 |
| 17460\|17461 | ACACCGAAGGTGCTGAAGGGCCTGAGTTTC\|CTGCTCCGTCTGACCGTAACAGCGGACGAC | 17452/17453 | TCAG | CTCA | 84 |
| 18430\|18431 | TGAATGCGAACTCCGGGACGCTCAGTAATG\|TGACGATAGCTGAAAACTGTACGATAAACG | 18428/18429 | TGTG | CACA | 85 |
| 19400\|19401 | TGGATTACCGTAAGACGGAAATCACTCCCG\|GGTATATGAAAGAGACGACCACTGCCAGGG | 19394/19395 | CTCC | GGAG | 86 |
| 20370\|20371 | AGGCCGCCACTTCAGCACGAGATGCGGTGG\|CCTCAAAAGAGGCAGCAAAATCATCAGAAA | 20366/20367 | GTGG | CCAC | 87 |
| 21340\|21341 | TTTGACAAATCAGCCTACCCAAAACTTGCT\|GTCGCGTATCCATCGGGIGTGCTTCCTGAT | 21340/21341 | GTCG | CGAC | 88 |
| 22310\|22311 | AGGGGAATATCAGAAGTGGAACGGCACAGC\|CTGGGTGAAGGATACGGAAGCAGAAAAACT | 22303/22304 | GCAC | GTGC | 89 |

TABLE 1 -continued

<table>
<tr><th>Ideal dividing boundary</th><th>60 Bases near ideal ("|" indicates each ideal diving boundary)</th><th>Actual dividing</th><th>Protrudung sequence</th><th>Complementary sequence</th><th>SEQ ID NO:</th></tr>
<tr><td>23280|23281</td><td>AATGACAATTTGCTTATGGAGTAATCTTTT|AATTTTAAATAAGTTATTCTCCTGGCTTCA</td><td>23268/23269</td><td>GAGT</td><td>ACTC</td><td>90</td></tr>
<tr><td>24250|24251</td><td>GGGTGTTGAATGATTTCCAGTTGCTACCGA|TTTTACATATTTTTTGCATGAGAGAATTTG</td><td>24243/24244</td><td>CTAC</td><td>GTAG</td><td>91</td></tr>
<tr><td>25220|25221</td><td>ACTACTAAGGTTGTAGGCTCAAGAGGGTGT|GTCCTGTCGTAGGTAAATAACTGACCTGTC</td><td>25220/25221</td><td>GTCC</td><td>GGAC</td><td>92</td></tr>
<tr><td>26190|26191</td><td>TCCAATATAAAAGTATTGTGTACCTTTTGC|TGGGTCAGGTTGTTCTTTAGGAGGAGTAAA</td><td>26192/26193</td><td>GGTC</td><td>GACC</td><td>93</td></tr>
<tr><td>27160|27161</td><td>TCTGCTTCCTTTTGGATAACCCACTGTTAT|TCATGTTGCATGGTGCACTGTTTATACCAA</td><td>27152/27153</td><td>ACTG</td><td>CAGT</td><td>94</td></tr>
<tr><td>28130|28131</td><td>TTATCAAGTGTTTCCTTCATTGATATTCCG|AGAGCATCAATATCCAATGCTGTTGGGATG</td><td>28128/28129</td><td>CGAG</td><td>CTCG</td><td>95</td></tr>
<tr><td>29100|29101</td><td>AACTACATCGCAAAGTCTCCGCAATTACAC|GCAAGAAAAAACCGCCATCAGGCGGCTTGG</td><td>29096/29097</td><td>ACAC</td><td>GTCT</td><td>96</td></tr>
<tr><td>30070|30071</td><td>CAGGATGGCGAACAACAAGAAACTGGTTTC|CGTCTTCACGGACTTCGTTGCTTTCCAGTT</td><td>30071/30072</td><td>GTCT</td><td>AGAC</td><td>97</td></tr>
<tr><td>31040|31041</td><td>CTGGTTTCTCTCATCTCCTTCTGCTTTCGC|CACCATCATTTCCACCTTTTGTGAAAGGGA</td><td>31041/31042</td><td>ACCA</td><td>TGGT</td><td>98</td></tr>
<tr><td>32010|32011</td><td>AGCTCTCACATCGATCCCGGTACGCTGCAG|GATAATGTCCCGTGTCATGCTGCCACCTTC</td><td>32008/32009</td><td>AGGA</td><td>TCCT</td><td>99</td></tr>
<tr><td>32980|32981</td><td>GCGTTGCAAATGATCGATGCATAGCGATTC|AAACAGGTCCTGGGGCAGGCCTTTTTCCAT</td><td>32984/32985</td><td>AGGT</td><td>ACCT</td><td>100</td></tr>
<tr><td>33950|33951</td><td>AGATAAAAAATCGCCCTCACACTGGAGGGC|AAAGAAGATTTCCAATAATCAGAACAAGTC</td><td>33942/33943</td><td>TGGA</td><td>TCCA</td><td>101</td></tr>
<tr><td>34920|34921</td><td>TTGAGCTTGGTGTGTTGAACAAAACTTTTT|CCCGATGGAATGGAAAGCATATATTATTCC</td><td>34918/34919</td><td>TTCC</td><td>GGAA</td><td>102</td></tr>
<tr><td>35890|35891</td><td>AACAAGGATGCATATATGAATGAACGATGC|AGAGGCAATGCCGATGGCGATAGTGGGTAT</td><td>35894/35895</td><td>GCAA</td><td>TTGC</td><td>103</td></tr>
<tr><td>36860|36861</td><td>AACAAAAAAGATGGGAATCCCAATGATTCG|TCATCTCCGAGGCTGTTCTTAATATCTTCA</td><td>36858/36859</td><td>CGTC</td><td>GACG</td><td>104</td></tr>
<tr><td>37830|37831</td><td>CCTGACTGCCCCATCCCCATCTTGTCTGCG|ACAGATTCCTCGGATAAGCCAAGTTCATTT</td><td>37822/37823</td><td>TGTC</td><td>GAGA</td><td>105</td></tr>
<tr><td>38800|38801</td><td>ACGCCAGACTATCAAATATGCTGCTTGAGG|CTTATTCGCCCGCAGATCTGACCAAGCGAC</td><td>38804/38805</td><td>TTCG</td><td>CGAA</td><td>106</td></tr>
<tr><td>39770|39771</td><td>AGCCTGGCTAACCGTGACCAGAACGAAGTG|AACGAAATCCGTCGCCAGTGGGTTCTGGCT</td><td>39760/39761</td><td>GAAC</td><td>GTTC</td><td>107</td></tr>
<tr><td>40740|40741</td><td>AAATCCTTCCAGACCCAACCAAACCAATCG|TAGTAACCATTCACGAACGCAACCGCAGCT</td><td>40738/40739</td><td>CGTA</td><td>TACC</td><td>108</td></tr>
<tr><td>41710|41711</td><td>GCCTGCAAAGATGAGGAGGGATTCCAGCGT|GTTTTTAATGAGGTCATCACCGGATCCCAT</td><td>41704/41705</td><td>CAGC</td><td>GCTG</td><td>109</td></tr>
<tr><td>42680|42681</td><td>TTAAAGCCCCGCAGTTACTGGATTAAACAA|GCCCAACAAGCCGTAAACGCCTTCATCAGA</td><td>42682/42683</td><td>CCAA</td><td>TTGG</td><td>110</td></tr>
<tr><td>43650|43651</td><td>AAAAATATGTTATCTCCCACGCCGATTATC|CCTTTGACGAATACGAGTTTGGAAAGCCAG</td><td>43650/43651</td><td>CCTT</td><td>AAGG</td><td>111</td></tr>
<tr><td>44620|44621</td><td>ATGGGTTAATTCGCTCGTTGTGGTAGTGAG|ATGAAAAGAGGCGGCGCTTACTACCGATTC</td><td>44614/44615</td><td>AGTG</td><td>CACT</td><td>112</td></tr>
<tr><td>45590|45591</td><td>CGGACGTCAGAAAACCAGAAATCATGGTTA|TGACGTCATTGTAGGCGGAGAGCTATTTAC</td><td>45590/45591</td><td>TGAC</td><td>GTCA</td><td>113</td></tr>
</table>

TABLE 1 -continued

| Ideal dividing boundary | 60 Bases near ideal ("\|" indicates each ideal diving boundary) | Actual dividing | Protrudung sequence | Complementary sequence | SEQ ID NO: |
|---|---|---|---|---|---|
| 46560\|46561 | TACGAATGTTTGCTGGGTTTCTGTTTTAAC\|AACATTTTCTGCGCCGCCACAAATTTTGGC | 46559/46560 | CAAC | GTTG | 114 |
| 47530\|47531 | TTTTATCGTTTCAATCTGGTCTGACCTCCT\|TGTGTTTTGTTGATGATTTATGTCAAATAT | 47528/47529 | CTTG | CAAG | 115 |
| 48516\|48517 | ACGGGTCCTTTCCGGTGATCCGACAGGTTA\|CGGGGCGGCGACCTCGaaaaggccttattg | 48516/48517 | AAAA | TTTT | 116 |

isoschizomer), BsmBI (5'-CGTCTCN/-3',5'-/(N)5 GAGACG-3'), BsmFI (5'-GGGAC(N)10/-3',5'-/(N)14 GTCCC-3'), BspMI (a BfuAI isoschizomer), BtgZI (5'-GCGATG(N)10/-3',5'-/(N)14CATCGC-3'), FokI (5'-GGATG(N)9/-3'5'-/(N)13CATCC-5'), and SfaNI (5'-GCATC(N)9/-3',5'-/(N)13 GATGC-5'). These restriction enzymes were screened for any restriction enzyme that did not have its recognition site in an *Escherichia coli* plasmid vector used for gene fragment subcloning (pMD19, Simple, TAKARA), or any restriction enzyme that had its recognition site in there but was capable of forming a fragment longer enough or shorter enough than the ideal dividing unit. As a result, a total of 6 kinds of restriction enzyme candidates were found, including 5 restriction enzymes (AarI, BbsI, BfuAI, BsmFI, and BtgZI) that did not had no cleavage and 1 restriction enzyme (BsmBI) that had its recognition sequence in the vector but was capable of forming a fragment longer enough or shorter enough than the ideal dividing unit. As for these restriction enzyme site candidates, the distribution of the restriction enzyme site within the entire lambda phage, namely, across Fragment No. 01 to Fragment No. 50 was searched. As a result, each of these restriction enzymes had its restriction enzyme recognition sites within the lambda phage genome, namely, 12 sites for AarI, 24 sites for BbsI, 41 sites for BfuAI, 38 sites for BsmFI, 45 sites for BtgZI, and 14 sites for BsmBI. Then, for each DNA unit fragment, a restriction enzyme that did not cleave inside the DNA unit fragment itself was used. It was confirmed that it is sufficient that the fewest number of the kinds of restriction enzymes to be used was only 3, namely, BbsI, AarI, and BsmBI. Each of these Type IIS restriction enzymes was assigned for cleaving a certain group of DNA unit fragments, as follows.

The group of fragments to be cleaved with BbsI consisted of Fragments Nos. 01 to 08, 12, 16 to 22, 24, 27, 28, 33 to 39, 43, and 45 to 50, a total of 33 fragments; the group to be cleaved with AarI consisted of Fragments Nos. 09 to 11, 13, 23, 25.30, 32, and 44, a total of 9 fragments; and the group to be cleaved with BsmBI consisted of Fragments Nos. 14, 15, 26, 29, 31, and 40 to 42, a total of 8 fragments.

<Cloning of Gene Fragment>

All of the 50 fragments, from Fragment No. 01 to Fragment No. 50, were amplified from the full-length lambda phage genome by PCR. First, to the 5' end of a primer for amplifying a DNA sequence between combinations of protruding-end sequences determined above, a corresponding restriction enzyme recognition site among those determined above was attached so that a protruding end was to be formed at the intended position. Then, to the resulting 5' end, a primer to which a TAG sequence was further attached was used. A pair of these primers made in this way was used to amplify a certain DNA fragment in the specified region from the full-length lambda phage genome. PCR reaction was allowed to proceed under the conditions where 50 μl for one cycle consisted of 5 μl of KOD Plus 10× buffer Ver.2, 3 μl of 25-mM MgSO4, 5 μl of dNTP (2 mM each), 1 μl of KOD Plus (1 unit/μl), 48 pg of lambda phage DNA (Toyobo Co., Ltd.), 15 pmol of primers (an F primer and an R primer respectively), and sterilized water, and on a GeneAmp PCR System 9700 (Applied Biosystems Inc.) programmed as follows.

One cycle consisted of incubation at 94° C. for 2 min, at 98° C. for 10 s, 55° C. for 30 s, and then at 68° C. for 1 min. The cycle was repeated 30 times, followed by incubation at 68° C. for 7 min. The amplified DNA unit fragments were separated in 1% agarose gel (UltraPure Agarose, Invitrogen Ltd.) made of 1×TAE buffer (prepared by diluting "Tris-acetate-EDTA stock buffer (50× concentrated) pH8.3 (at 25° C.)" manufactured by Nacalai Tesque, Inc. 50 times with milliQ water) containing 2 mg/ml of Crystal Violet (Wako Pure Chemical Industries, Ltd.), on an electrophoresis system (i-MyRun. NC, Cosmo Bio Co., Ltd.) at a voltage of 100 V for 10 min of electrophoresis. The DNA band in question was cut out from the electrophoresis gel with a razor to recover as the gel segment weighed about 200 mg. From this gel segment, a DNA unit fragment was purified with a Concert Rapid Gel Extraction System (Life Technologies). The specific procedure was as follows: L1 Buffer having a volume 3 times the weight of the gel segment was added to the gel segment; the gel segment was dissolved at 45° C. in a block incubator for about 10 min; the resulting solution was added into a spin column cartridge supplied (a 2-ml centrifuge tube into which a spin column was attached); centrifugation was conducted at 20,000×g for 1 min and the flow-through was discarded; 750 μl of L2 Buffer was then added to the spin column; and centrifugation was conducted at 20,000×g for 1 min and the flow-through was discarded. In order to remove as much residue such as the L2 Buffer remaining in the spin column as possible, the following procedure was conducted: the spin column was centrifuged at 20,000×g for 1 min; the spin column was transferred from the 2-ml centrifuge tube which was discarded to a 1.5-ml centrifuge tube; into the spin column, 30 μl of TE buffer (10 mM Tris-HCl, 1 mM EDTA, pH8.0) was added; and the spin column was left for 2 min and was then centrifuged at 20,000×g for 1 min to recover a DNA solution. The resulting DNA was preserved at −20° C. until it was used. The resulting DNA unit fragment was cloned into the *Escherichia coli* plasmid vector by the following TA cloning method.

To 8 μl of the DNA unit fragment solution, 1 μl of 10× Ex-Taq Buffer that came with TAKARA PCR reaction enzyme Ex-Taq, 0.5 μl of 100-mM dATP, and 0.5 μl of Ex-Taq was added, followed by incubation at 65° C. at 10 min. As a result, a protrusion of A was added to the 3' end of the DNA unit fragment. To 1 μl of the DNA unit fragment solution, 1 μl of TAKARA pMD19-Simple and 3 μl of sterilized water were added and mixed, and thereto, 5 μl of TAKARA Ligation (Mighty) Mix was added, followed by incubation at 16° C. for 30 min. A 5-μl portion of the ligation solution was added to 50 μl of *Escherichia coli* DH5α chemically competent cell, followed by incubation on ice for 15 min, heat shock at 42° C. for 30 sec, and then being left on ice for 2 min. Thereto, 200 μl of an LB medium was added, followed by incubation at 37° C. for 1 h. The culture was streaked onto an LB plate supplemented with carbenicillin (100 μg/ml) and containing 1.5% agar-agar, followed by overnight culture at 37° C. As a result, a transformant transformed with the plasmid was obtained. A resulting colony was treated with a PCR template DNA preparation reagent (Cica Geneus DNA preparation reagent, KANTO CHEMICAL CO., INC.), and a PCR template DNA molecule was prepared. Specifically, Reagent a and Reagent b in the reagent kit were mixed in a ratio of 1:10, and into 2.5 μl of the resulting solution, a fraction of a colony taken from the plate with a toothpick was suspended, followed by treatment at 72° C. for 6 min and then at 94° C. for 3 min. To the resulting liquid, 2.5 μl of TAKARA Ex-Taq 10× enzyme, 2 μl of 2.5-mM dNTP solution, 0.25 μl of 10-pmol/μl M13F primer, 0.25 μl of 10-pmol/μl M13R primer, 17 μl of sterilized water, and 0.5 μl of Ex-TaqHS were added, followed by incubation at 94° C. for 5 min. A cycle of incubation at 98° C. for 20 sec, at 55° C. for 30 sec, and at 72° C. for 1 min was repeated 30 times for DNA amplification. The base sequence of the PCR product was analyzed to confirm complete agreement of it with the intended sequence. Consequently, all the clones gave the correct sequences. In this process, one of the variants obtained from Fragment No. 10 was found to have synonymous substitution within its gene-V-coding region (g.9515 G>C). Due to this mutation, in the phage genome, a restriction enzyme Aval recognition site newly appears (FIG. 2). In this example, for the purpose of clearly demonstrating that the phage was artificially constructed, this variant with synonymous substitution (g.9515 G>C) was used instead of the wild-type one, as for Fragment No. 10.

<High-Purity Purification of Plasmid Harboring DNA Unit Fragment>

Figure 3:
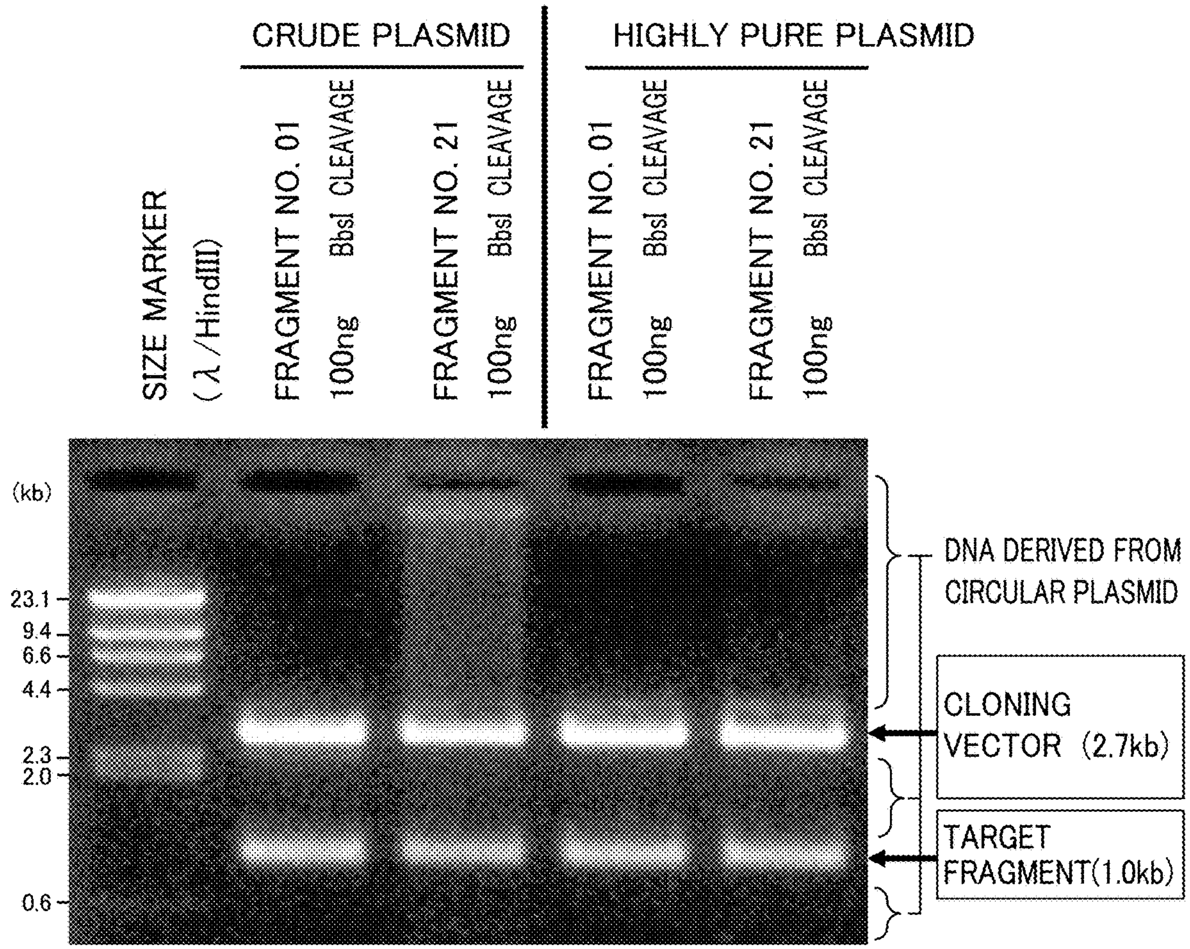
FIG. 3 a photograph showing the result of electrophoresis analyzing crude plasmids each harboring Fragment No. 01 or Fragment No. 21 among DNA unit fragments of Example 1 of the present invention, and highly pure plasmids resulting from purification of these crude plasmids, after restriction enzyme treatment.

Each of the all 50 kinds of *Escherichia coli* transformants each harboring a plasmid into which a corresponding one of Fragments Nos. 01 to 50 having the intended sequence had been cloned was cultured overnight at 37° C. for 120 spm in 50 ml of an LB medium supplemented with 100 μg/ml of carbenicillin. The resulting bacterial cells were subjected to purification with QIAfilter Plasmid Midi Kit (QIAGEN). To 50 μl of the resulting crude plasmid solution, 5 μl of a 3-M potassium acetate-acetic acid buffer solution (pH5.2) and 125 μl of ethanol were added, followed by centrifugation at 20,000×g for 10 min for ethanol precipitation of the DNA. The resulting precipitate was rinsed with 70% ethanol, and the residue was removed, followed by re-dissolution in 50 μl of TE (pH8.0). A 1-μl sample was taken from the crude plasmid solution for measurement of the DNA concentration with a spectrophotometer for trace amount detection (ND-2000, Thermo). The amount of DNA in the crude plasmid solution at this time was about 0.5 μg/μl to 4 μg/μl. Referring to the measurement value, 5 μg of DNA was taken from each crude plasmid solution and collected into a 1.5-ml tube, into which sterilized water was added so as to achieve a total volume of 50 μl. Thereto, 6 μl of Plasmid Safe (Epicentre) 10× reaction buffer, 2.4 μl of 25-mM ATP solution, and 2 μl of Plasmid Safe enzyme solution were added and mixed, followed by incubation at 37° C. for 1 h in the programmable block incubator BI-526T (ASTEC) and then incubation at 75° C. for 30 min for enzyme inactivation. The resulting solution was purified with PCR purification kit (QIAGEN). In the final step of purification with the kit, the DNA adsorbed on the column was eluted off not with the elution buffer that came with the kit but with 25 μl of TE buffer (pH8.0) so as to give a highly-pure plasmid solution. The plasmid harboring Fragment No. 01 and the plasmid harboring Fragment No. 21 before and after purification were analyzed by DNA electrophoresis (UltraPure Agarose, Invitrogen Limited), confirming incorporation of the intended fragments (DNA unit fragments) (FIG. 3).

<Precisely Adjusting Concentrations of Plasmids Each Harboring DNA Unit Fragment, and Combining Equal Moles of Plasmids>

The resulting DNA solution was reanalyzed with a spectrophotometer for trace amount detection so as to determine the concentration of the highly-pure plasmid solution. The concentration of each sample was within the range from about 100 ng/μl to 200 ng/μl reflecting the degree of purification of the crude plasmid solution, where the theoretical maximum concentration was 200 ng/μl. Based on the measurement result, 15 μl of each plasmid solution was taken into a 1.5-ml tube, to which TE was added so as to achieve a concentration of each plasmid of 100 ng/μl. Reanalysis of the concentration of the resulting highly-pure plasmid solution with a spectrophotometer for trace amount detection showed variation from the target value of 100 ng/μl within the range of about several percent. As for each highly-pure plasmid solution, the volume (μl) of the solution containing 500 ng of the DNA was accurately calculated to the second decimal place. A portion of the DNA solution in an amount of this volume (about 5 μl) was combined with the other such portions that were to be cleaved later with the same kind of restriction enzyme (the BbsI group, the AarI group, and the BsmBI group). Between the portions combined together, the numbers of moles of the DNA unit fragments were adjusted to be substantially the same.

<Cleavage of Same-Mole-Number Plasmids Combined Together, in One Session with Restriction Enzyme>

The total volume of the combined same-mole-number plasmid solution was about 165 μl for the BbsI group, about 45 μl for the AarI group, and about 40 μl for the BsmBI group. The combined solution of each group was tripled in volume with sterilized water, giving a highly-pure plasmid solution having a volume of 495 μl, 135 μl, or 120 μl, which was cleaved with the corresponding kind of restriction enzyme as follows.

Figure 4:
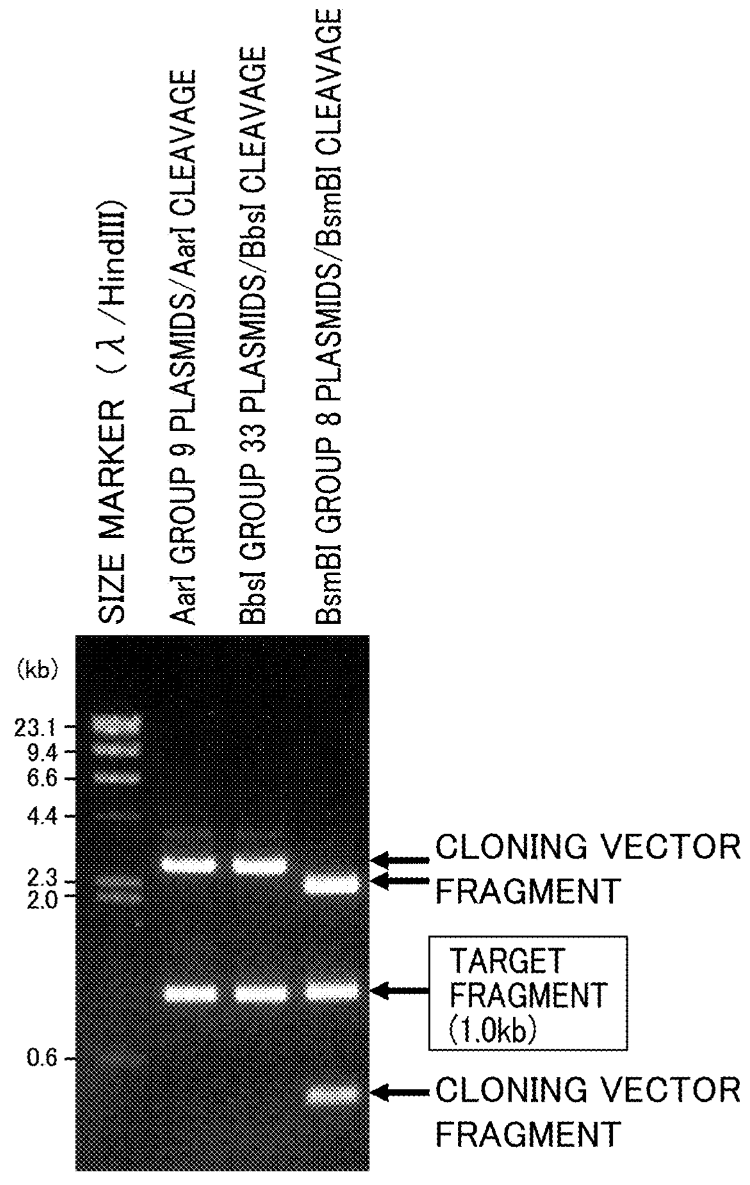
FIG. 4 a photograph showing the result of electrophoresis analyzing a group of plasmids to be treated with BbsI, a group of plasmids to be treated with AarI, and a group of plasmids to be treated with BsmBI, among plasmids harboring DNA unit fragments after purification in Example 1 of the present invention. Each group of plasmids had been treated with each restriction enzyme in one session prior to electrophoresis.

To the highly-pure plasmid solution of the BbsI group, 55 μl of 10×NEB buffer #2 and 27.5 μl of the restriction enzyme BbsI (NEB) were added to give about 577 μl of the resulting plasmid solution, which was subjected to reaction at 37° C. for 2 h. To the highly-pure plasmid solution of the AarI group, 15 μl of 10× Buffer_for_AarI that came with the restriction enzyme, 3 μl of 50× Oligonucleotide for activation of cleavage that also came with the restriction enzyme, and 7.5 μl of the restriction enzyme AarI (Thermo) were added to give about 160 μl of the resulting plasmid solution, which was subjected to reaction at 37° C. for 2 h. To the highly-pure plasmid solution of the BsmBI group, 13.3 μl of 10×NEB Buffer #3 and 6.3 μl of the restriction enzyme BsmBI (NEB) were added to give about 140 μl of the resulting plasmid solution, which was subjected to reaction at 55° C. for 2 h. After 2 h, a portion was taken from each plasmid solution without the same-mole-number relationship being lost, in other words, 33 μl from the BbsI group, 9 μl from the AarI group, and 8 μl from the BsmBI group were taken. A 5-μl sample from each portion was analyzed by DNA electrophoresis, and cleavage of the plasmids with the corresponding restriction enzyme was confirmed (FIG. 4).

<Fractionation, in One Session, of 50 DNA Unit Fragments by Agarose Gel Electrophoresis, and Purification>

Figure 5:
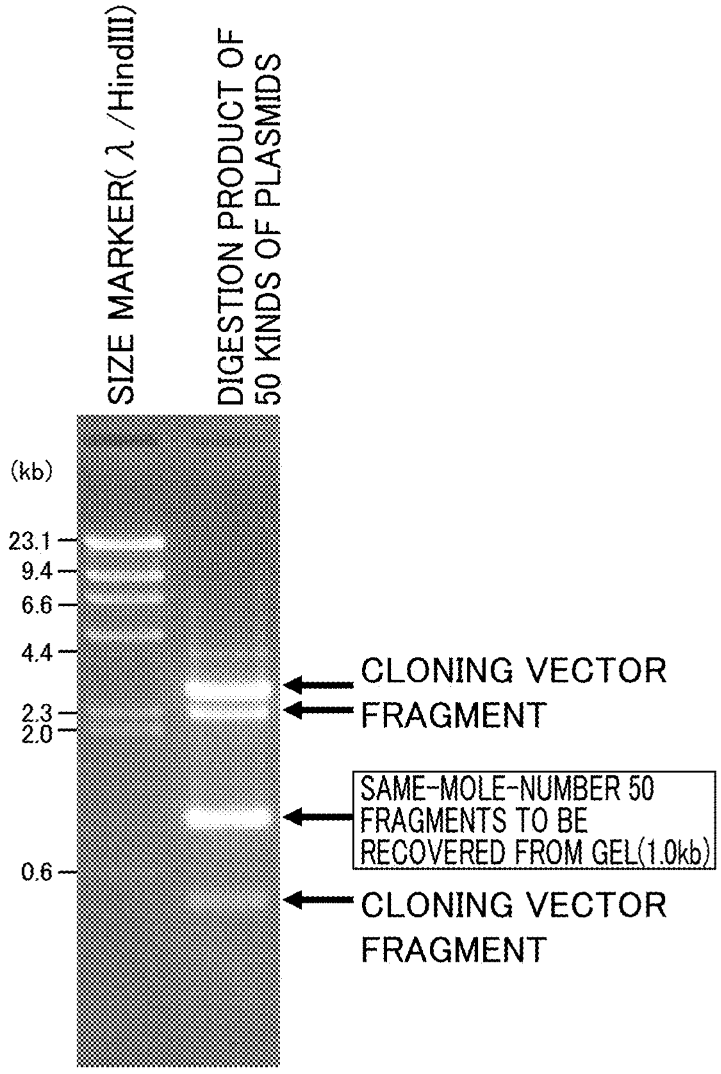
FIG. 5 a photograph showing the result of electrophoresis analyzing a group of plasmids to be treated with BbsI, a group of plasmids to be treated with AarI, and a group of plasmids to be treated with BsmBI, among plasmids harboring DNA unit fragments after purification in Example 1 of the present invention. Each group of plasmids had been treated with each restriction enzyme in one session and then combined together prior to electrophoresis.

After the confirmation above, an equal amount of phenol-chloroform-isoamyl alcohol (25:24:1) (Nacalai Tesque, Inc.) was added to and mixed well with each plasmid solution for restriction enzyme inactivation. The resulting mixture of the plasmid solution and phenol-chloroform-isoamyl alcohol (25:24:1) was combined with the other mixtures into a single tube, followed by centrifugation (20,000×g, 10 min) for separation into a phenol phase and an aqueous phase. The aqueous phase (about 900 μl) was transferred to another 1.5-ml tube, to which 500 μl of 1-butanol (Wako Pure Chemical Industries, Ltd.) was added and mixed well, and the resultant was centrifuged (20,000×g, 1 min) so as to remove water-saturated 1-butanol. This series of procedure was repeated until the aqueous phase was reduced to a volume of 450 μl or lower. To the resultant, 50 μl of a 3-M potassium acetate-acetic acid buffer (pH5.2) and 900 μl of ethanol were added, followed by centrifugation (20,000×g, 10 min) to precipitate the DNA, which was rinsed with 70% ethanol and dissolved in 20 μl of TE. To the resultant, 2 μl of 10× Dye for electrophoresis was added. The entire mixture was subjected to electrophoresis in 0.7% agarose gel with low melting temperature (2-Hydroxyethyl Agarose Type VII, Sigma) in the presence of 1×TAE (Tris-Acetate-EDTA Buffer) buffer on a commercially available agarose gel electrophoresis system (i-MyRun. N, nucleic acid electrophoresis system, Cosmo Bio Co., Ltd.) at a voltage of 35 V (about 2 V/cm) for 4 h of electrophoresis. As a result, Fragments Nos. 01 to 50 were separated from the plasmid vectors (FIG. 5). The gel after electrophoresis was stained in 100 ml of 1×TAE buffer containing 1 μg/ml of ethidium bromide (Sigma) for 30 min, followed by irradiation with ultraviolet having a long wavelength (366 mn). The band attributed to Fragments Nos. 01 to 50 (near about 1 kb) thus visualized was cut out with a razor, and was transferred into a 1.5-ml tube. To the agarose gel with low melting temperature (about 300 mg), 1×TAE buffer was added to achieve a total volume of about 700 μl, followed by incubation at 65° C. for 10 min for gel dissolution. To the resulting gel solution, 500 μl of 1-butanol was added, and centrifugation (20,000×g, 1 min) was conducted for separation into an aqueous phase and a butanol phase, followed by discarding water-saturated butanol. This series of procedure was repeated until the aqueous phase was reduced to a volume of 450 μl or lower. To the resulting liquid, 50 μl of a 3-M potassium acetate-acetic acid buffer solution (pH 5.2) and 900 μl of ethanol were added, followed by centrifugation (20,000×g, 1 min) to precipitate the DNA, which was rinsed with 70% ethanol and dissolved in 20 μl of TE. A 1-μl sample was taken from the resultant for measurement of the concentration with a spectrophotometer for trace amount detection.

Figure 6:
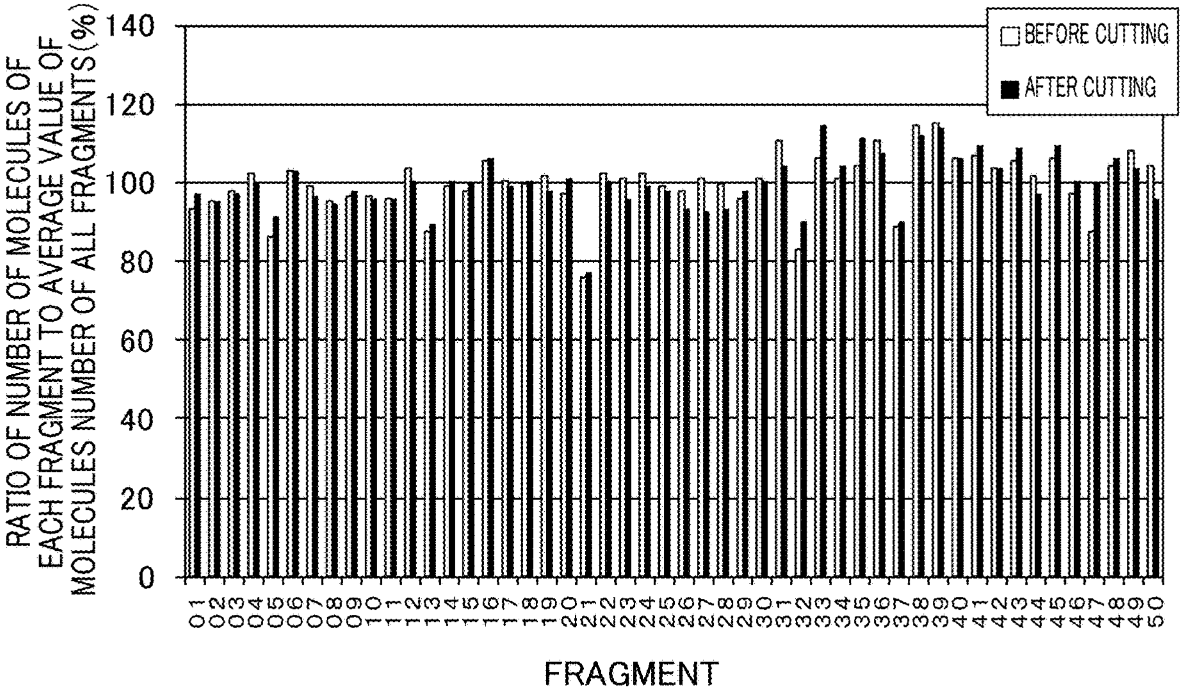
FIG. 6 an illustration showing the distribution of the number of molecules of each kind of DNA unit fragment before and after size-based selection. A group of plasmids to be treated with BbsI, a group of plasmids to be treated with AarI, and a group of plasmids to be treated with BsmBI, among plasmids harboring DNA unit fragments in Example 1 of the present invention, had been treated with each restriction enzyme in one session and then combined together.
Figure 7:
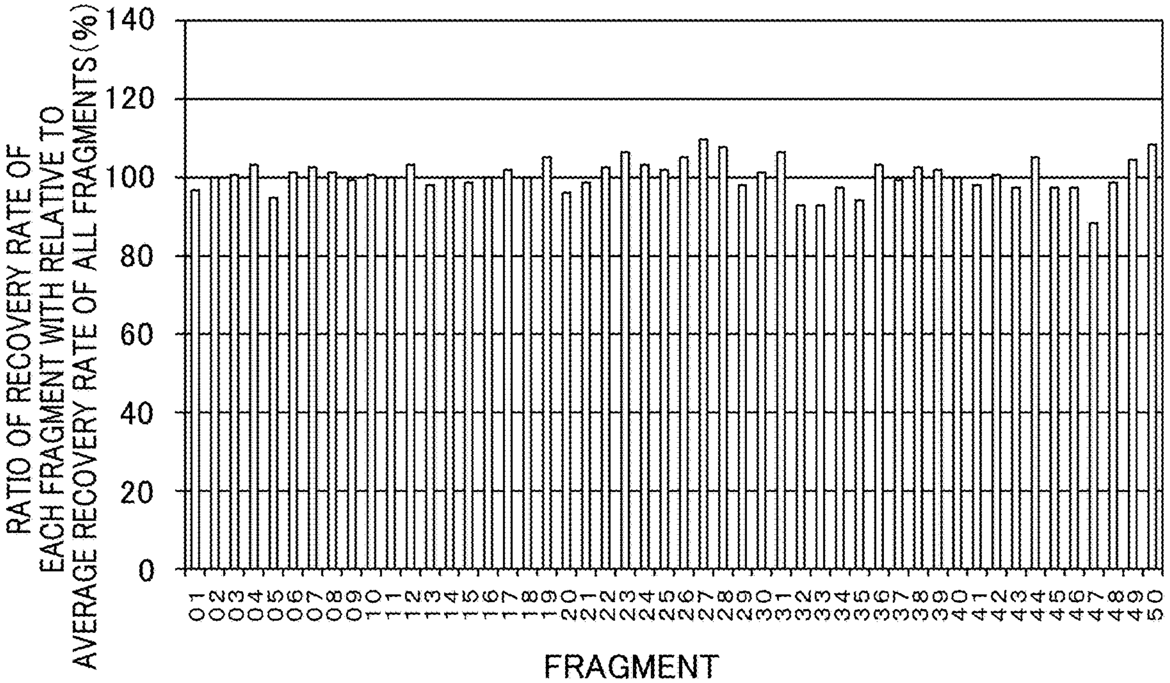
FIG. 7 an illustration showing the percentage change in the numbers of molecules of each kind of DNA unit fragment before and after size-based selection. A group of plasmids to be treated with BbsI, a group of plasmids to be treated with AarI, and a group of plasmids to be treated with BsmBI, among plasmids harboring DNA unit fragments in Example 1 of the present invention, had been treated with each restriction enzyme in one session and then combined together.

In order to confirm the number of moles contained in each group before and after size-based selection was determined by quantitative PCR. FIG. 6 shows distribution of the number of molecules of each DNA unit fragment before and after size-based selection, and FIG. 7 shows the percentage change in the number of molecules of each DNA unit fragment. It was confirmed that the molar ratio between the 50 fragments was substantially the same and was maintained after recovery.

<Gene Assembly>

Figure 8:
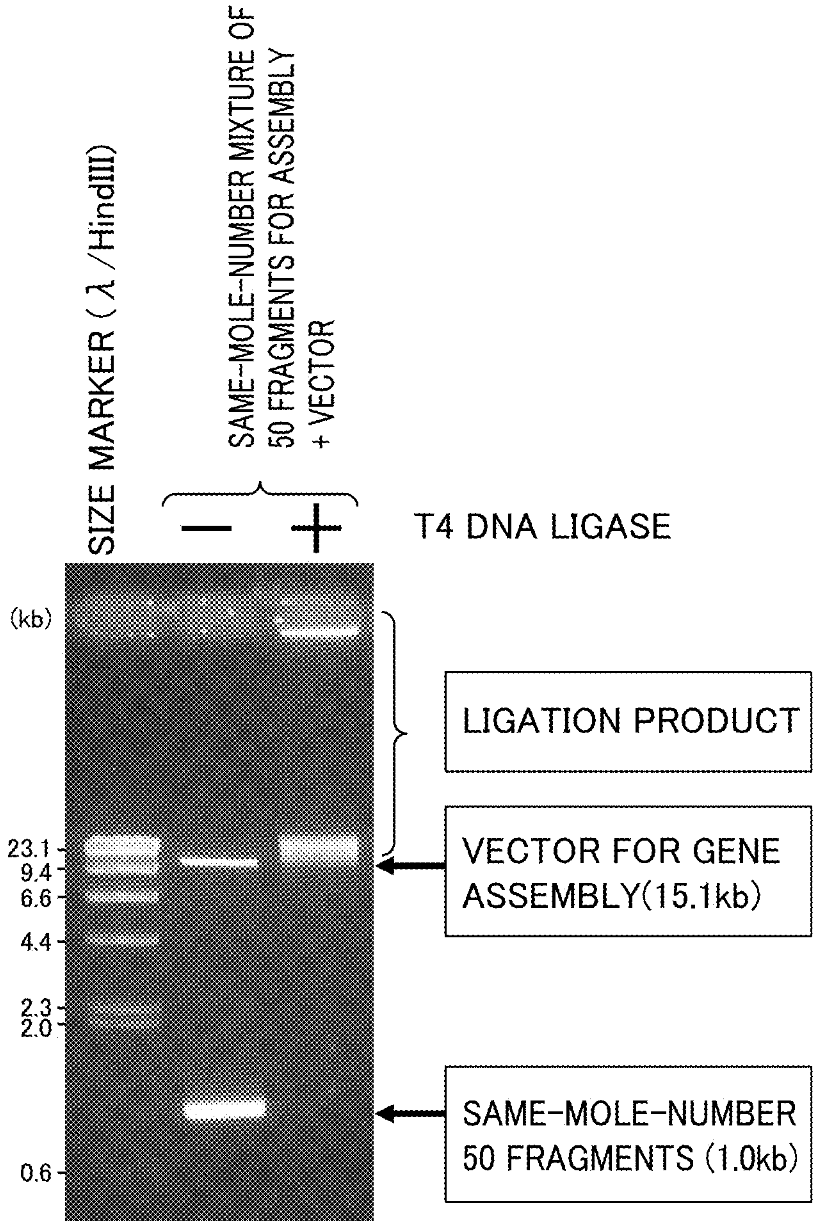
FIG. 8 a photograph showing the result of electrophoresis analyzing the product of ligation of a DNA unit fragment and a DNA vector in Example 1 of the present invention.

The resulting same-mole-number mixture of Fragments Nos. 01 to 50 had a DNA concentration by weight of 98 ng/μl and a sum of the lengths of the base sequences of 48,522 bp. On the other hand, the DNA vector (pGETS118-AarI/AarI) had a DNA concentration by weight of 190 ng/μl, and its full length was 15,139 bp. This length-weight ratio was used for obtaining a same-mole-number mixture of the both DNA molecules, in other words, the same-mole-number mixture of Fragments Nos. 01 to 50 was mixed with the DNA vector at a ratio of 6.21 μl:1.00 μl. To 7.2 μl of the resulting same-mole-number mixed solution, 8.2 μl of 2× ligation buffer was added, and the entire mixture was incubated at 37° C. for 5 min. Thereto, 1 μl of T4 DNA ligase (Takara) was added, followed by incubation at 37° C. for 4 h. A portion of the resulting mixture was analyzed by electrophoresis, and successful ligation was confirmed (FIG. 8). An 8-μl portion of the mixture was collected to a tube, to which 100 μl of a *Bacillus subtilis* competent cell was added, followed by rotation culture at 37° C. for 30 min in a duck rotor. After 300 μl of an LB medium was added thereto, another session of rotation culture was conducted at 37° C. for 1 h in a culture rotator. The resulting culture medium was spread onto an LB plate supplemented with 10 μg/ml tetracycline, followed by overnight culture at 37° C. As a result, 250 colonies were obtained.

<Checking Structures of Plasmid in Transformant>

Figure 9:
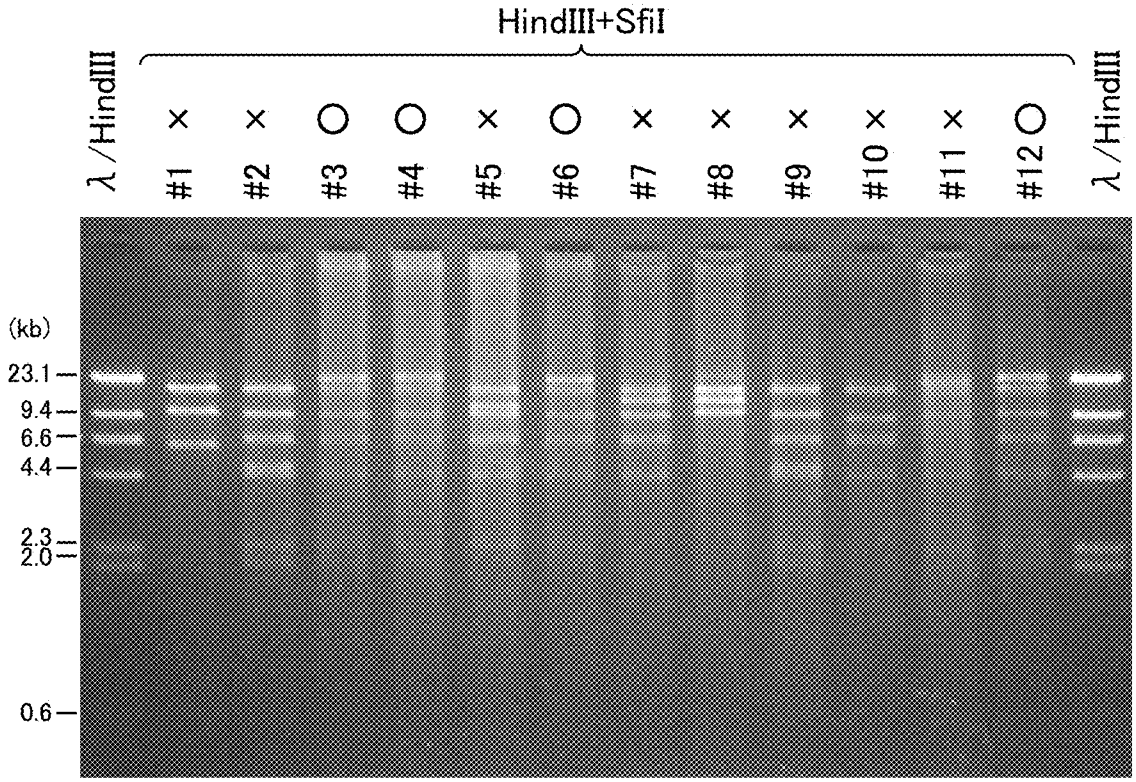
FIG. 9 a photograph showing the result of electrophoresis in Example 1 of the present invention, conducted after transforming *Bacillus subtilis* with a DNA concatemer obtained by ligation of a DNA unit fragment and a DNA vector, extracting plasmids from the resulting plurality of transformant strains of *Bacillus subtilis*, and subjecting the resulting plasmids to restriction enzyme treatment.
Figure 10:
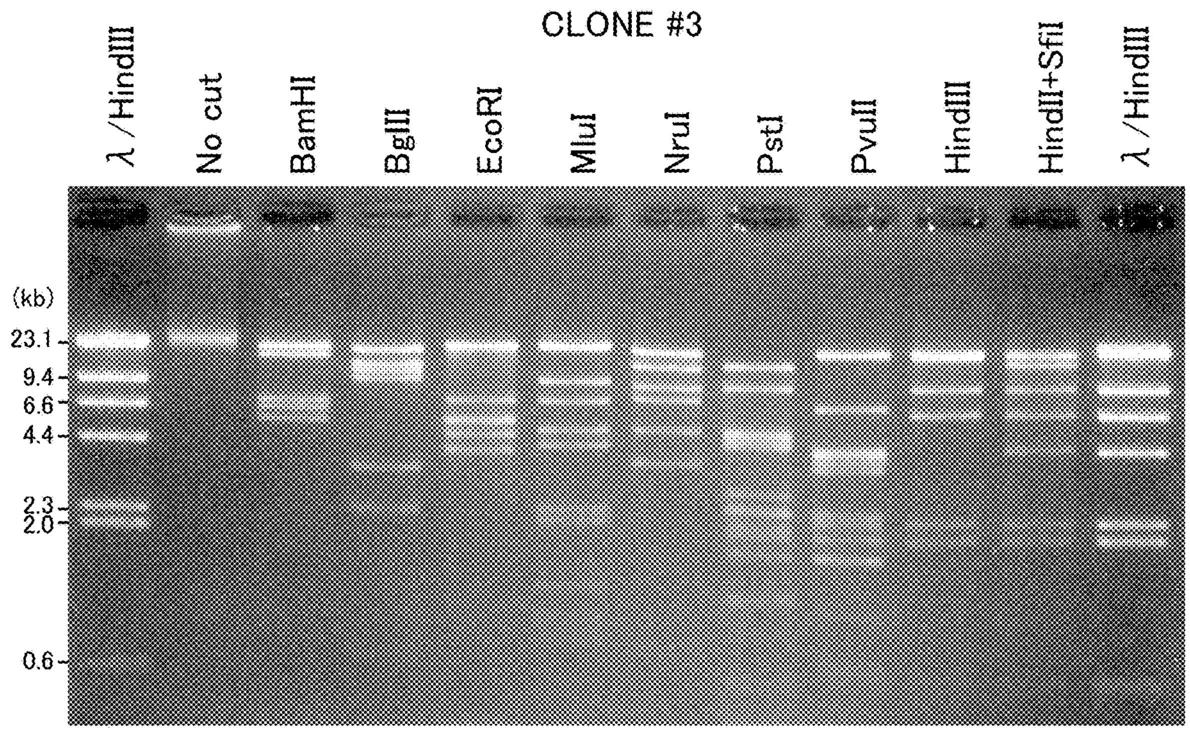
FIG. 10 a photograph showing the result of electrophoresis in Example 1 of the present invention, conducted after extracting plasmids from a plurality of transformant strains of *Bacillus subtilis*, subjecting the resulting plasmids to restriction enzyme treatment and electrophoresis, selecting a *Bacillus subtilis* clone containing a target DNA assembly based on the electrophoresis photograph, and conducting restriction enzyme treatment.

12 strains of colonies were randomly selected, and each of them was cultured overnight in an LB medium supplemented with 2 ml of 10 μg/ml tetracycline. For increasing the number of copies of the plasmid inside, IPTG was added to achieve a final concentration of 1 mM, followed by culturing at 37° C. for 3 h. The plasmid was extracted from the resulting bacterial cells, followed by double digestion with the restriction enzymes HindIII and SfiI. Electrophoresis analysis was conducted, and 4 out of the 12 strains gave the desired cleavage pattern (FIG. 9). Each of these 4 strains was subjected to cesium chloride-ethidium bromide density gradient ultracentrifugation to give a large amount of the plasmid, and the plasmid was cleaved with 13 kinds of restriction enzymes. Electrophoresis analysis revealed that all the cleaved fragments derived from each of the 4 strains gave expected patterns (FIG. 10). Further, the entire region, except for the vector region, of the plasmid derived from each of the 4 strains was sequenced, and, as a result, the resulting base sequence was in complete agreement with the expected base sequence.

<Checking Functions of Gene Assemblies>

Figure 11:
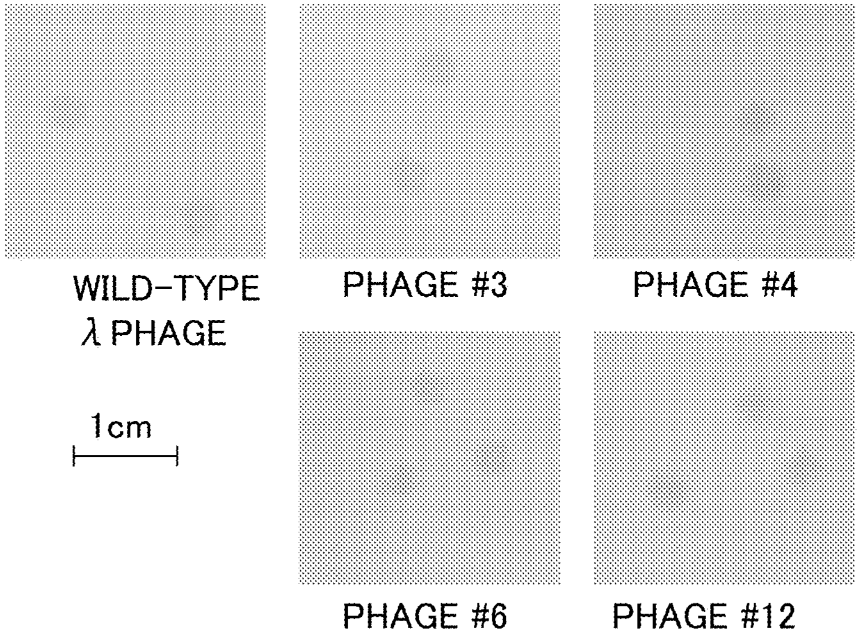
FIG. 11 an illustration showing that selected DNA assemblies formed lambda phage DNA plaques in Example 1 of the present invention.
Figure 12:
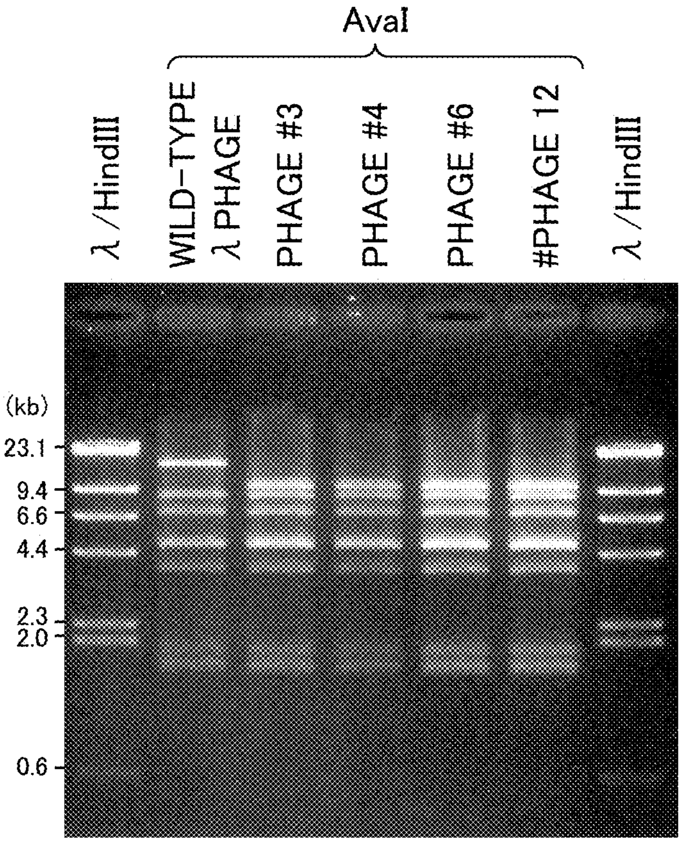
FIG. 12 a photograph showing genomes of selected DNA assemblies and wild-type lambda phage after treated with the restriction enzyme AvaI, in Example 1 of the present invention.

Lambda phage functions of the plasmid derived from each of the 4 strains were checked in terms of plaque-forming ability, as follows. Each of the assembly-harboring plasmids called #3, #4, #6, and #12 was cleaved with lambda terminase (Lambda terminase, Epicentre) to give a vector part and a gene assembly part. The latter was added to a lambda packaging extract (Gigapack III Plus Packaging Extract, Agilent Technologies). *Escherichia coli* (strain VCS257) was infected with the resultant, and was spread on an LB plate, followed by overnight culture at 37° C. As a result, plaque formation was observed. It was confirmed that the shape of the plaques was similar to that of the plaques concurrently obtained by lambda phage DNA manufactured by Toyobo Co., Ltd. (FIG. 11). Phage DNA was purified from the plaques formed by the plasmid, and was cleaved with the restriction enzyme AvaI for checking the presence of the mutation introduced. As shown in FIG. 12, the resulting cleavage pattern displayed was different from the one displayed by the lambda phage DNA manufactured by Toyobo Co., Ltd., and the presence of an AvaI site was confirmed in each phage as planned. Thus, it was confirmed that the lambda phage genome constructed by assembling all the 50 fragments, namely, Fragments Nos. 01 to 50, was fully adequate in terms of its base sequence and its plaque-forming ability.

These results showed that the 50 DNA unit fragments as constituents of lambda phage DNA and the DNA vector (pGETS118-AarI/AarI), a total of 51 DNA fragments, were successfully joined together.

Example 2, Construction of Artificial Operon of Mevalonate Pathway by Assembling 55 DNA Unit Fragments and DNA Vector The isoprenoids are known to be a large class of compounds having an isoprene unit as a skeleton and are synthesized from a common starting compound, which is isopentenyl diphosphate (IPP). There are two pathways known for IPP production starting from the glycolytic pathway, namely, the mevalonate pathway and the non-mevalonate pathway. Both of these pathways may be present in a single living organism, but *Escherichia coli* only has the non-mevalonate pathway. In order to enhance the ability of *Escherichia coli* to produce IPP, a part of the genes coding for the mevalonate pathway in yeast, a eukaryote, was artificially constructed by assembling synthetic DNA fragments according to the frequency in use of codons occurring in *Escherichia coli*, as follows.

<Designing Sequence of Artificial Operon of Mevalonate>

There are 3 genes (ERG10 (1.2 kb), ERG13 (1.5 kb), and HMG1 (3.2 kb)) necessary in the first half of the mevalonate pathway in yeast, namely, the metabolic pathway starting from acetyl CoA to mevalonic acid. The codons in these 3 genes were redesigned according to the frequency in use of codons occurring in *Escherichia coli* to give 3 artificial genes, which were then made into an artificial operon (5,951 bp) (SEQ ID NO:4) (the full-length sequence shown under SEQ ID NO:4 had a size of 5,955 bp including 4 bases to serve as a protruding end), as described below. The redesigning of the gene codons in yeast to gene codons in *Escherichia coli* was conducted by ranking yeast synonymous codons based on the frequency in appearance of them occurring among all genes in yeast, also ranking *Escherichia coli* synonymous codons based on the frequency in appearance of them occurring among all genes in *Escherichia coli*, and exchanging between codons in the same rank.

<Designing DNA Unit Fragment>

A restriction enzyme that had no potential to cleave the 5,951-bp DNA sequence after the exchange between synonymous codons was looked for, in the same manner as in Example 1. The result showed that the DNA sequence contained no recognition sequence of the restriction enzyme AarI and therefore had no potential to be cleaved with AarI. Therefore, AarI was selected for cleaving in the process of all clone preparation. The full-length sequence (5,951 bp) was divided into 55 fragments, each of which was 108 bp long on average. This size was designated as the size of each ideal dividing unit. Near boundaries between these dividing units, the presence of any one of particular sequences (60 combinations in total, consisting of 44 combinations left by subtracting 8 palindromic combinations from all 52 combinations consisting of 2 bases in total selected from A and T and 2 bases in total selected from C and G (Group III described above) and all 16 combinations with no 3 consecutive bases selected from C and G out of all 32 combinations consisting of 1 base in total selected from A and T and 3 bases in total selected from C and G (Group IV described above)) was searched for. As a result, one of these particular sequences were found to be occurred within ±7 bp to each side of the ideal dividing boundary. Based on these results, the full-length sequence was divided into 55 fragments, each having a size from 98 bp to 115 bp. Table 2 shows the dividing units and the protruding base sequences within a DNA assembly in Example 2. To the boundary between a mevalonate-pathway gene group and a gene-assembling vector, the protruding sequences (ATTA and AAAA) consisting only of A and/or T were utilized.

TABLE 2

| Fragment | Sequence (Including AarI site. Four nucleotides underlined indicates protrusion sequence. 5'→3') | Full-length (bp) | SEQ ID NO: |
|---|---|---|---|
| MEV001 | cacctgcacgtattaGGCCTgttTGGCCGTGACACCGGACAATGAGTAatgTCGCAAAATGTGTACATTGTCTCAACCGCACGCACTCCGATTGGCTCCTTCCAAGGCTCGTTGTCacgtgcaggtg | 127 | 11 |
| MEV002 | cacctgcacgtTGTCTTCTAAGACGGCCGTAGAACTGGGCGCGGTGGCGTTAAAAGGAGCACTGGCGAAGGTGCCGGAACTGGATGCCTCTAAGGATTTTGACGAAATTATTTTTGGCAATGTGCTCTCacgtgcaggtg | 140 | 12 |
| MEV003 | cacctgcacgtTCTCGGCAAACCTGGGACAGGCGCCCGCACGCCAGGTGGCGCTGGCGGCAGGCCTGAGCAACCATATAGTGGCCAGTACGGTGAATAAGGTTTGCGCCTCTGCGATGacgtgcaggtg | 129 | 13 |
| MEV004 | cacctgcacgtGATGAAGGCCATAATTCTGGGCGCGCAGTCTATAAAATGCGGCAACGCGGATGTGGTTGTCGCGGGCGGCTGCGAATCGATGACCAATGCCCCGTACTACATGCCGGCCGCACGacgtgcaggtg | 136 | 14 |
| MEV005 | cacctgcacgtCACGGGCTGGCGCAAAATTTGGACAGACCGTGCTCGTGGATGGCGTTGAACGCGATGGGCTGAATGATGCTTACGATGGCTTGGCAATGGGCGTCCACGCCGAAAAGTGCGCACacgtgcaggtg | 136 | 15 |
| MEV006 | cacctgcacgtGCACGGGATTGGGATATTACCCGCGAACAGCAGGACAACTTTGCAATAGAATCTTACCAGAAATCGCAGAAATCGCAGAAGGAAGGCAAATTCGACAACGAAATTGTCCacgtgcaggtg | 131 | 16 |
| MEV007 | cacctgcacgtGTCCCAGTGACTATTAAGGGTTTTCGCGGCAAGCCAGATACCCAGGTTACAAAGGACGAGGAACCAGCGCGCTTACACGTGGAAAAACTGCGCTCGGCCCGTACCGTGTTCCAacgtgcaggtg | 135 | 17 |
| MEV008 | cacctgcacgtTCCAGAAAGAAAATGGCACCGTGACCGCAGCGAATGCGTCGCCGATAAATGATGGCGCGGCCGCAGTTATACTGGTGTCTGAAAAAGTGCTGAAGGAAAAGAACCTGAAGCCACTGacgtgcaggtg | 138 | 18 |
| MEV009 | cacctgcacgtACTGGCGATTATAAAAGGCTGGGGCGAGGCAGCGCATCAGCCGGCGGATTTTACGTGGGCGCCGTCGCTCGCCGTGCCGAAGGCGCTGAAACATGCGGGAATAGAAGACATAAACTCacgtgcaggtg | 139 | 19 |
| MEV010 | cacctgcacgtACTCGGTGGATTACTTTGAATTCAACGAAGCATTTTCAGTGGTTGGCCTGGTAAATACCAAGATTCTGAAGTTGGACCCGTCGAAGGTGAACGTCTATGGCGGCGCGGTGGacgtgcaggtg | 133 | 20 |
| MEV011 | cacctgcacgtGTGGCGTTGGGCCACCCGCTGGGCTGCTCGGGCGCGCGTAGTGGTGACGCTTTTGTCTATATTACAACAGGAAGGTGGCAAGATAGGCGTGGCAGCAATTTGCAACacgtgcaggtg | 130 | 21 |
| MEV012 | cacctgcacgtCAACGGCGGCGGCGGCGCGTCTTCGATTGTTATTGAAAAGATCtaaGGCCTtgaTGGCCAACGCGGGAGATTTTTCatgAAACTATCCACCAAACTCTGCTGGTGCGGCATTAAAGGTacgtgcaggtg | 140 | 22 |

TABLE 2 -continued

| Fragment | Sequence (Including AarI site. Four nucleotides underlined indicates protrusion sequence. 5'→3') | Full-length (bp) | SEQ ID NO: |
|---|---|---|---|
| MEV013 | cacctgcacgtAGGTCGCCTCCGTCCCCAGAAGCAGCAGCAGTTACACAACACGAATCTGCAGATGACCGAATTGAAAAAACAGAAGACTGCGGAACAGAAAACTCGCCCACAGAACGacgtgcaggtg | 129 | 23 |
| MEV014 | cacctgcacgtAACGTTGGCATTAAAGGCATACAGATTTACATACCGACCCAGTGCGTTAATCAGTCGGAGTTGGAGAAATTTGATGGAGTGTCGCAGGGCAAATACACGATTGGCCTTGGACAGacgtgcaggtg | 136 | 24 |
| MEV015 | cacctgcacgtACAGACTAATATGTCGTTTGTTAACGACCGCGAAGATATATACTCAATGTCTTTGACCGTGCTGTCGAAGCTGATAAAGAGCTACAATATAGACACTAATAAAATTGGacgtgcaggtg | 130 | 25 |
| MEV016 | cacctgcacgtTTGGCCGCTTAGAAGTTGGCACCGAAACCCTTATTGACAAGTCTAAGTCGGTTAAGTCGGTTCTGATGCAGCTGTTTGGCGAAAATACCGACGTTGAAGGCATTGACACACTCAacgtgcaggtg | 136 | 26 |
| MEV017 | cacctgcacgtCTCAACGCATGCTACGGCGGCACTAATGCTCTGTTCAATTCGCTGAATTGGATTGAATCGAATGCCTGGGATGGCCGCGACGCAATTGTCGTGTGTGGCGATATTGCAATATACGacgtgcaggtg | 137 | 27 |
| MEV018 | cacctgcacgtTACGATAAGGGCGCAGCCCGCCCGACTGGCGGCGCAGGCACCGTGGCGATGTGGATAGGCCCAGATGCGCCGATTGTCTTTGACTCGGTCCGCGCGTCGTACATGGAACacgtgcaggtg | 131 | 28 |
| MEV019 | cacctgcacgtGAACACGCATACGATTTTTACAAGCCGGATTTCACTAGTGAATATCCATACGTTGATGGCCATTTTTCCTTAACCTGCTACGTTAAGGCGCTCGATCAGGTGTACAAGAGCTAacgtgcaggtg | 135 | 29 |
| MEV020 | cacctgcacgtGCTATTCTAAGAAGGCGATTTCGAAAGGGCTGGTGAGTGATCCTGCGGGCTCAGATGCGCTGAATGTGCTGAAATATTTCGACTACAATGTGTTCCATGTGCCGACTTGCAAacgtgcaggtg | 134 | 30 |
| MEV021 | cacctgcacgtGCAAACTGGTTACGAAATCCTACGGCCGCTTATTGTATAATGATTTCCGCGCAAACCCACAGCTGTTCCCGGAAGTGGACGCAGAATTAGCGACCAGAGATTATGACGAATCGacgtgcaggtg | 135 | 31 |
| MEV022 | cacctgcacgtATCGTTAACTGATAAGAATATTGAAAAAACCTTTGTGAACGTGGCGAAGCCGTTCCACAAAGAGCGCGTGGCACAGTCGCTGATTGTGCCGACGAATACGGGCAATATGTACACTGCacgtgcaggtg | 139 | 32 |
| MEV023 | cacctgcacgtCTGCCTCGGTGTATGCAGCATTTGCCTCGTTGTTAAATTATGTGGGTTCGGACGACTTACAGGGAAAGCGGGTGGGCTTATTTTCGTACGGCTCTGGCTTAGCGGCCTCGacgtgcaggtg | 132 | 33 |
| MEV024 | cacctgcacgtCTCGTTGTATTCGTGTAAAATTGTGGGCGACGTTCAGCATATTATAAAGGAATTAGATATTACCAATAAATTAGCAAAGCGCATAACTGAAACCCCGAAGGATTACGAAacgtgcaggtg | 131 | 34 |
| MEV025 | cacctgcacgtCGAAGCGGCAATAGAACTGCGCGAAAACGCACATCTGAAGAAGAATTTCAAACCACAGGGCTCTATTGAGCATCTGCAGAGCGGCGTGTACTACCTGACTAATATAGATGACacgtgcaggtg | 134 | 35 |
| MEV026 | cacctgcacgtTGACAAATTTCGCCGCTCGTACGATGTGAAAAAAtaaGGCCTcgaTGGCCGTGAACTGGATAGTGAAATAatgCCCCCCTTGTTCAAGGGTCTTAAACAAATGGCCAAGacgtgcaggtg | 131 | 36 |
| MEV027 | cacctgcacgtCAAGCCGATTGCATATGTGTCCCGCTTTTCAGCTAAACGACCGATTCATATCATCCTCTTTTCGTTGATAATCTCTGCCTTCGCGTATTTGTCTGTTATTCAATATTACTTCAACGGCTGGacgtgcaggtg | 143 | 37 |
| MEV028 | cacctgcacgtCTGGCAGTTGGATTCCAACAGCGTGTTTGAAACCGCGCCGAACAAAGACTCTAATACCTTGTTTCAGGAATGCTCTCATTACTACCGCGATTCTTCGTTGGATGGCTGGGTCTacgtgcaggtg | 135 | 38 |
| MEV029 | cacctgcacgtGTCTCCATAACTGCTCATGAAGCGAGCGAGTTACCGGCACCGCACCATTACTATTTGTTAAATCTTAATTTCAACAGCCCAAACGAAACCGACTCTATTCCGGAAacgtgcaggtg | 127 | 39 |
| MEV030 | cacctgcacgtGGAATTGGCGAATACAGTGTTTGAGAAAGATAACACGAAATATATTCTTCAGGAAGATCTAAGCGTGTCTAAAGAAATTTCGTCGACCGATGGTACAAAATGGCGTTTACGCAGCGACCacgtgcaggtg | 141 | 40 |
| MEV031 | cacctgcacgtGACCGCAAAAGCCTCTTCGACGTCAAGACATTAGCCTATTCGCTATACGATGTCTTTTCCGAAAACGTCACTCAGGCCGACCCCTTTGACGTTCTCATTATGGTacgtgcaggtg | 126 | 41 |
| MEV032 | cacctgcacgtTGGTGACCGCATACTTGATGATGTTCTACACTATCTTCGGACTATTCAACGACATGCGTAAGACTGGGTCCAACTTTTGGCTGAGTGCATCGACGGTAGTTAACTCGGCCTCCTacgtgcaggtg | 136 | 42 |

TABLE 2 -continued

| Fragment | Sequence (Including AarI site. Four nucleotides underlined indicates protrusion sequence. 5'→3') | Full-length (bp) | SEQ ID NO: |
|---|---|---|---|
| MEV033 | cacctgcacgtTCCTCCCTCTTCTTAGCCCTGTATGTTACTCAGTGCATTTTGGGAAAAGAAGTGTCTGCCTTAACCCTCTTTGAAGGCCTGCCATTCATTGTCGTGGTGGTGGGCTTCAAGCAacgtgcaggtg | 135 | 43 |
| MEV034 | cacctgcacgtAGCACAAAATAAAGATTGCACAATATGCACTTGAGAAATTTGAACGCGTTGGCTTATCGAAACGTATTACCACTGATGAAATAGTGTTTGAATCTGTAAGTGAAGAGGGCGGCCGGCTGacgtgcaggtg | 141 | 44 |
| MEV035 | cacctgcacgtGCTGATTCAGGACCATCTGCTCTGCATTTTTGCATTTATAGGTTGTTCGATGTATGCGCACCAGCTGAAGACCCTGACGAATTTCTGTATCTTATCCGCCTTacgtgcaggtg | 124 | 45 |
| MEV036 | cacctgcacgtCCTTTATATTGATTTTTGAACTGATTTTAACCCCAACGTTTTATTCGGCGATATTAGCTCTCCGCCTTGAAATGAACGTGATACACCGCTCGACCATTATAAAGCAGACGTTAGAAGacgtgcaggtg | 139 | 46 |
| MEV037 | cacctgcacgtGAAGAAGACGGCGTGGTGCCGTCGACGGCCCGCATAATTTCGAAAGCCGAAAAGAAATCTGTCTCGTCGTTCTTAAACCTAAGCGTAGTGGTTATTATAATGAAACTATCGGTTacgtgcaggtg | 136 | 47 |
| MEV038 | cacctgcacgtGGTTATCCTTCTGTTTGTTTTCATAAATTTTTATAATTTTGGCGCCAACTGGGTTAACGATGCATTCAACTCCCTGTACTTCGATAAGGAACGGGTGTCGTTGCCGGATacgtgcaggtg | 131 | 48 |
| MEV039 | cacctgcacgtGGATTTTATTACTTCAAACGCATCGGAAAATTTTAAAGAGCAGGCGATTGTGAGCGTTACTCCGTTATTATATTACAAACCTATTAAGTCTTACCAGAGAATTGAGGATATGGTGCTCacgtgcaggtg | 140 | 49 |
| MEV040 | cacctgcacgtGCTCTTGCTGCTCCGGAACGTTAGCGTGGCAATTCGGGATCGTTTCGTTAGCAAATTAGTGCTCTCTGCATTAGTCTGTAGCGCGGTTATAAACGTATATTTACTGAacgtgcaggtg | 129 | 50 |
| MEV041 | cacctgcacgtCTGAACGCGGCGCGCATTCATACTAGCTATACCGCCGACCAGCTGGTAAAAACCGAAGTTACTAAGAAGTCGTTTACCGCGCCAGTCCAGAAGGCGTCGACGCCGGTGTacgtgcaggtg | 131 | 51 |
| MEV042 | cacctgcacgtGTGTTAACTAACAAAACGGTTATTTCGGGTTCAAAAGTTAAAAGCTTATCCTCGGCTCAGTCAAGTTCCTCCGGTCCATCCTCCTCGAGCGAGGAAGATGATTCTAGAGATATTGAAAGTCacgtgcaggtg | 143 | 52 |
| MEV043 | cacctgcacgtAGTCTGGATAAGAAAATCCGGCCATTAGAAGAATTAGAAGCCTTATTAAGCAGCGGTAACACGAAACAGCTGAAGAATAAAGAGGTTGCGGCACTGGTGATTCACacgtgcaggtg | 127 | 53 |
| MEV044 | cacctgcacgtTCACGGCAAGTTACCACTGTACGCGCTGGAGAAAAAATTAGGCGATACCACACGCGCTGTGGCTGTCCGGCGTAAGGCGCTCTCCATTCTGGCCGAAGCGCCAGTCTTAGCCTCacgtgcaggtg | 136 | 54 |
| MEV045 | cacctgcacgtCCTCGGATCGGTTACCGTATAAAAACTATGACTACGACAGAGTCTTTGGAGCGTGCTGCGAAAACGTGATCGGCTACATGCCACTGCCTGTGGGCGTGATCGGACCTCTGacgtgcaggtg | 132 | 55 |
| MEV046 | cacctgcacgtTCTGGTGATAGATGGCACGTCGTATCATATCCCGATGGCCACCACGGAGGGCTGCCTGGTCGCGTCGGCAATGCGGGGATGCAAGGCCATAAACGCGGGAGGCGGCGCCACGAacgtgcaggtg | 135 | 56 |
| MEV047 | cacctgcacgtACGACCGTGTTAACCAAGGATGGCATGACGCGCGGACCGGTCGTTCGGTTCCCGACCCTGAAACGCTCGGGCGCATGCAAGATCTGGTTAGACTCCGAAGAGGGTCAGAATGCCATacgtgcaggtg | 138 | 57 |
| MEV048 | cacctgcacgtCCATTAAAAAAGCGTTTAATTCGACGTCCCGCTTTGCCCGGCTTCAGCATATTCAGACCTGCTTGGCCGGTGATTTACTATTCATGCGCTTTCGCACGACCACCGGCGACacgtgcaggtg | 132 | 58 |
| MEV049 | cacctgcacgtCGACGCCATGGGCATGAACATGATTTCGAAAGGCGTTGAATACTCCTTAAAGCAGATGGTCGAAGAGTATGGATGGGAAGATATGGAGGTGGTTTCTGTGTCGGGCAATTACTGCACTacgtgcaggtg | 140 | 59 |
| MEV050 | cacctgcacgtCACTGACAAAAAACCGGCGGCAATAAATTGGATAGAAGGCCGGGGCAAGAGCGTTGTTGCCGAAGCGACCATTCCAGGCGATGTGGTTCGCAAAGTATTAAAAAGCacgtgcaggtg | 128 | 60 |
| MEV051 | cacctgcacgtAAGCGATGTGTCTGCCCTGGTGGAGCTGAATATTGCGAAGAACCTGGTGGGTTCGGCCATGGCGGGGTCGGTGGGCGGTTTTAATGCCCATGCCGCGAACTTAGTAACGGCGGTGacgtgcaggtg | 137 | 61 |
| MEV052 | cacctgcacgtGGTGTTCCTGGCCTTAGGTCAGGATCCAGCCCAGAACGTGGAAAGCTCTAATTGCATCACGCTGATGAAAGAAGTAGACGGCGATCTGCGCATTTCTGTCTCTATGCCGTCacgtgcaggtg | 133 | 62 |

TABLE 2 -continued

| Fragment | Sequence (Including AarI site. Four nucleotides underlined indicates protrusion sequence. 5'→3') | Full-length (bp) | SEQ ID NO: |
|---|---|---|---|
| MEV053 | cacctgcacgtCGTCTATAGAAGTCGGCACTATAGGCGGCGGCACCGTGTTGGAACCGCAGGGCG<br>CAATGCTGGACTTATTAGGCGTCCGCGGACCCCATGCGACTGCGCCAGGCACTAATGCacgtgc<br>aggtg | 134 | 63 |
| MEV054 | cacctgcacgtATGCCCGGCAGTTAGCCCGCATCGTGGCATGCGCAGTTCTGGCCGGCGAATTATC<br>TTTATGCGCGGCATTGGCCGCAGGACATCTGGTGCAGAGCCATATGACTCACAacgtgcaggtg | 130 | 64 |
| MEV055 | cacctgcacgtCACAATCGTAAACCAGCGGAACCGACGAAACCAAATAACCTGGACGCAACCGA<br>TATCAACCGGCTGAAAGATGGGTCTGTTACTTGTATTAAATCTtaaGGCCTTCTTGGCCaaaaacg<br>tgcaggtg | 138 | 65 |

<Construction of DNA Unit Fragment from Synthetic DNA>

Each of the divided fragments obtained was prepared with 2 molecules of chemically synthesized 80-base DNA, according to a method by Rossi et al. (Rossi, J. J., and Itakura, K. 1982. J. Biol. Chem. 257, 9226-9229 (1982)). Specifically, each of the resulting divided fragments had these 2 chemically synthesized DNA molecules hybridizing to each other at the 3' end for a span of several tens bp, and also had an AarI recognition site introduced to the 5' end side so that the above-designed protruding sequence was to be formed between the AarI cleavage site and the 5' end by digestion. The hybridization between these 2 synthetic DNA molecules followed by template-dependent elongation reaction gave a double-stranded DNA unit fragment, which was then amplified by PCR in the way to be described below. The resultant double-stranded DNA unit fragment as well as a pair of PCR primers designed to hybridize with the AarI recognition site on each end, namely, a total of 3 kinds of DNA molecules, were used to be added in the PCR reaction, and consequently a DNA unit fragment flanked by AarI cleavage sites was obtained. The resultant DNA unit fragment was joined to *Escherichia coli* plasmid vector pMD19 by TA cloning method, followed by transformation of *Escherichia coli* for cloning method. Sequencing was then conducted to select a clone having a base sequence desirable for each fragment.

<Mixing Same Mole Numbers of Plasmids Each Harboring DNA Unit Fragment>

Each of the 55 strains of *Escherichia coli* each harboring the resulting desired clone was cultured and then subjected to treatment with Plasmid mini-prep (QIAGEN), whereby 50 μl of a crude plasmid solution was obtained. A 1-μl sample of the resultant was analyzed with a spectrophotometer for trace amount detection, and the DNA concentration of it was determined as 82 ng/μl to 180 ng/μl. Each plasmid weighing about 5 μg was treated with Plasmid Safe, followed by enzyme inactivation by heating. Purification with Minielute PCR purification Kit (QIAGEN) gave 25 μl of a highly-pure plasmid solution. A 1-μl sample of the resultant was analyzed with a spectrophotometer for trace amount detection, and the concentration of it was determined as 108 ng/μl to 213 ng/μl. A 20-μl portion of the highly-pure plasmid solution was transferred into a separate tube and diluted with TE so as to make the concentration of the plasmid be mathematically 100 ng/μl. The resulting purified plasmid solution was reanalyzed with a microspectrophotometer to calculate the concentration, and, based on the concentration measurement, the volume (μl) of the solution containing 500 ng of the highly pure plasmid was accurately calculated to the second decimal place. A portion of each plasmid solution in an amount of this volume (about 5 μl) was separated into one tube, where this portion was combined with the other such portions. To the resulting same-mole-number plasmid mixture solution, which was about 275 μl in total volume, sterilized water having a volume twice the volume of the same-mole-number plasmid mixture solution, 137.5 μl of 10× Buffer_for_AarI, and 67.5 μl of the restriction enzyme AarI were added, followed by reaction at 37° C. overnight.

<Size-Based Selection of 55 DNA Unit Fragments in One Session>

Figure 13:
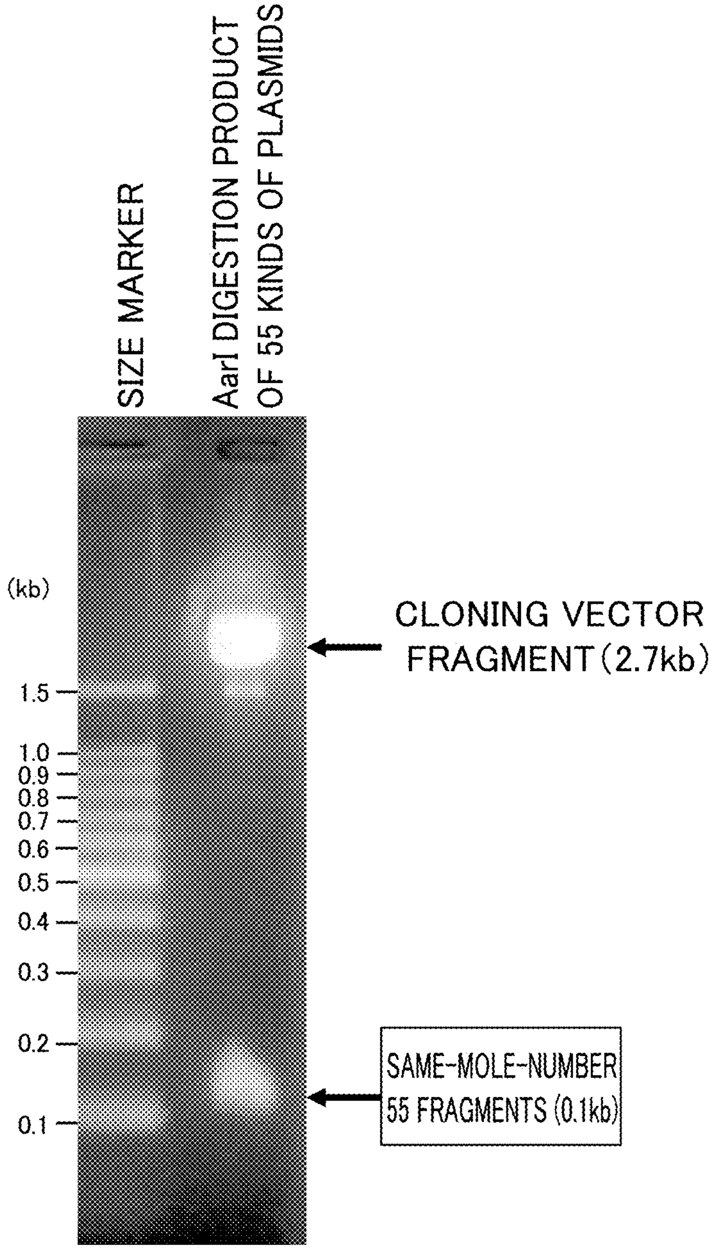
FIG. 13 a photograph showing the result of electrophoresis analyzing plasmids harboring DNA unit fragments after purification in Example 2 of the present invention. The plasmids had been treated with the restriction enzyme AarI in one session prior to electrophoresis.

To the resulting reaction solution, an equal amount of phenol-chloroform-isoamyl alcohol (25:24:1) was added for AarI inactivation, followed by centrifugation. The resulting supernatant was purified by ethanol precipitation, and the precipitate was dissolved in 20 μl of TE. The resultant, combined with xylene cyanol as a coloring agent for electrophoresis, was subjected to electrophoresis in 2.5% agarose gel with TAE buffer for 30 minutes at 100 V so as to separate the DNA vector pMD19 and the insert DNA unit fragment (FIG. 13). The gel was divided with a razor into segments, and one segment was stained with ethidium bromide to check the position of the target band that was attributed to the same-mole-number mixture of the 55 fragments. Then, from another segment of the gel left unstained, the target DNA band was cut out.

<Purification of Same-Mole-Number Mixture of DNA Unit Fragments>

DNA purification from the obtained gel segment was conducted with MiniElute Gel Extraction Kit (QIAGEN) as follows.

The volume of the gel was measured from the weight thereof, and CG Buffer having a volume 15 times the volume thus calculated was added, followed by incubation at 50° C. for 10 min for dissolving the gel. Thereto, isopropyl alcohol having a volume 5 times the volume of the gel segment was added, and the resulting liquid was placed in the column, followed by centrifugation to make the DNA adsorbed on the column. To the column, 500 of CG Buffer was added, followed by centrifugation for washing, and then 750 μl of PE Buffer was further added, followed by centrifugation for washing. In this way, the column was washed. The column was centrifuged one more time for complete removal of any residue. To the column, 10 μl of TE buffer was added, followed by centrifugation. Thus, a mixed solution of substantially the same number of moles of the 55 DNA unit fragments was obtained.

<Addition of DNA Having Origin of Replication, to Same-Mole-Number Mixed Solution of DNA Unit Fragments>

The mixed solution was analyzed with a spectrophotometer for trace amount detection to measure the concentration, and the DNA concentration thereof was determined as 20 ng/μl. pGET151/AarI was also prepared at the same time in a concentration of 67 ng/μl. In consideration of these results as well as the ratio between the lengths of these (5955 bp:4306 bp), the same-mole-number mixed solution of the 55 fragments and the pGETS151/AarI were mixed in a ratio of 4.63:1.

<Gene Assembling>

Figure 14:
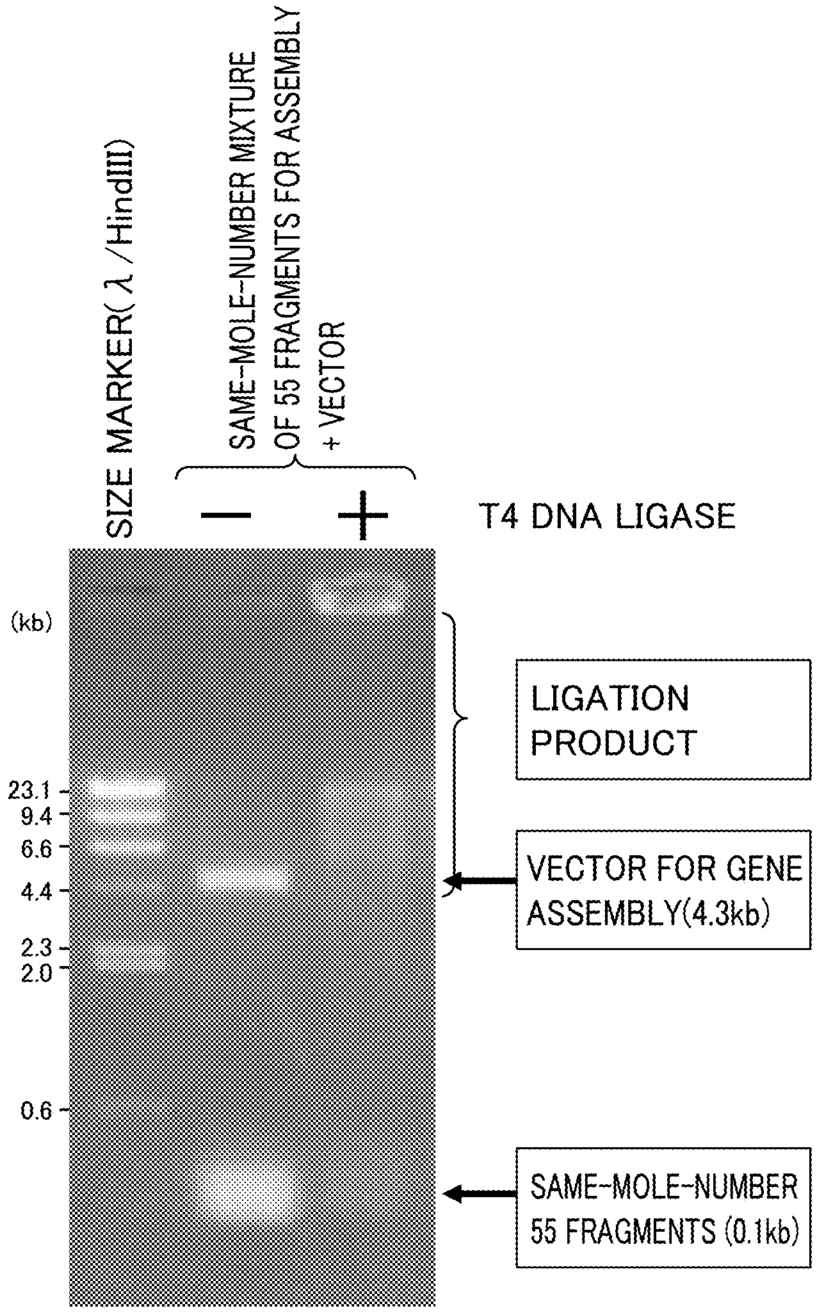
FIG. 14 a photograph showing the result of electrophoresis analyzing the product of ligation of a DNA unit fragment and a DNA vector in Example 2 of the present invention.

To 5.63 μl of the resulting same-mole-number mixed solution, 6.63 μl of 2× ligation buffer was added, followed by incubation at 37° C. for 5 min Thereto, 1 μl of T4 DNA ligase (Takara) was added, followed by incubation at 37° C. for 4 h. A sample of the resultant was analyzed by electrophoresis for checking whether or not ligation between the DNA unit fragments and the DNA vector in a tandem-repeat structure was successful (FIG. 14). After ligation, 8 μl of the resulting solution was added to a separate tube, to which 100 of a *Bacillus subtilis* competent cell was added, followed by rotation culture at 37° C. for 30 min in a duck rotor. Then, after 300 μl of an LB medium was added thereto, another session of rotation culture was conducted at 37° C. for 1 h in a culture rotator. The resulting culture medium was spread onto an LB plate supplemented with 10 μg/ml tetracycline.

<Transformation, and Checking Structures of Assembly>

Figure 16:
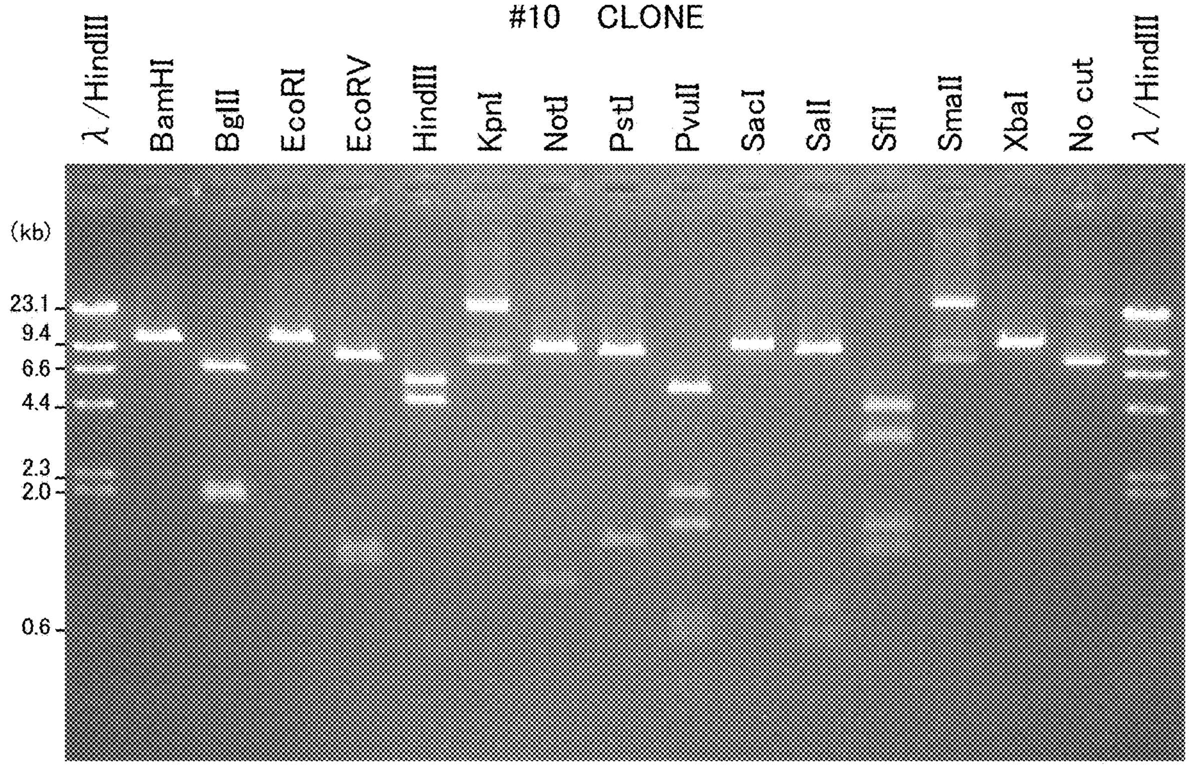
FIG. 16 a photograph showing the result of electrophoresis in Example 2 of the present invention, conducted after extracting plasmids from a plurality of transformant strains of *Bacillus subtilis*, subjecting the resulting plasmids to restriction enzyme treatment and electrophoresis, selecting a *Bacillus subtilis* clone containing a target DNA assembly based on the electrophoresis photograph, and conducting restriction enzyme treatment.

From the resulting 154 colonies, 24 clones were randomly selected and inoculated into an LB medium supplemented with 10 μg/ml tetracycline. IPTG was added thereto so as to achieve a final concentration of 1 mM during the logarithmic phase, followed by culturing to reach the stationary phase. The DNA plasmid was extracted and was treated with the restriction enzyme PvuII, followed by electrophoresis for checking the cleavage pattern (FIG. 15). As a result, 2 clones (#10 and #20) were found to have the expected base sequence, and these plasmids were subjected to treatment with other restriction enzymes and then to electrophoresis for determining their structures in more detail, which were found to be in agreement with the target structure (FIG. 16). It was confirmed that sequencing these plasmids indicated that these clones #10 and #20 had base sequences as designed.

These results showed that the 55 DNA unit fragments as constituents of the artificial operon of the mevalonate pathway and the DNA vector (pGETS151-pBR), a total of 56 DNA fragments, were successfully joined together.

Thus, it was confirmed that the method of the present invention of constructing a DNA concatemer was capable of joining 50 or more DNA fragments together. The reason for this many DNA fragments being successfully joined together was probably that the numbers of moles of DNA unit fragments are close to one another more accurately.

The reason that the numbers of moles of DNA unit fragments in the DNA unit fragment composition prepared by the method of the present invention were close to one another more accurately was probably the following.

When the concentration of each DNA unit fragment in the solution containing the DNA unit fragment was measured in Examples 1 and 2, the DNA unit fragment being measured had the corresponding auxiliary sequence attached thereto (specifically, a circular DNA plasmid). Even if the base sequences of different kinds of DNA unit fragments varied greatly, the corresponding auxiliary sequences thus attached contributed to reduction in distribution of the lengths of different base sequences being measured. As a result, when the measurement result was used to calculate the number of moles of each kind of DNA unit fragment, errors in the calculation were reduced. Then, when the resulting measurement result was used for taking a portion from each of the solutions so that the number of moles of DNA unit fragment in each portion was adjusted to be substantially the same, the molar ratio between different portions tended to be close to 1. Probably for this reason, the numbers of moles of DNA unit fragments became more accurately substantially the same.

In Example 1, the standard deviation of the distribution of the sum of the lengths of the base sequence of each DNA unit fragment and the base sequence of the corresponding auxiliary sequence attached to the DNA unit fragment was 3691.4 bp±6.6 bp, and ranged from −0.18% to 0.18% of the average value of the sum of the lengths. In Example 2, the standard deviation of the distribution of the sum of the lengths of the base sequence of each DNA unit fragment and the base sequence of the corresponding auxiliary sequence attached to the DNA unit fragment was 2828.2 bp±4.5 bp, and ranged from −0.16% to 0.16% of the average value of the sum of the lengths. In Examples 1 and 2, the standard deviation was smaller than the average value of the sum of the lengths, and probably for this reason, errors in the calculation of the number of moles of each DNA unit fragment conducted based on the measurement result of the DNA concentration in the solution were reduced.

The ratio of the average length of the base sequence of the corresponding auxiliary sequence attached to each DNA unit fragment to the average length of the base sequence of the DNA unit fragment was about 2.7 in Example 1 and about 27 in Example 2. Because the average length of the base sequence of the corresponding auxiliary sequence attached to each DNA unit fragment was longer than the average length of the base sequence of the DNA unit fragment, errors in the calculation of the number of moles of each DNA unit fragment conducted based on the measurement of the DNA concentration in the solution were further reduced, and probably for this reason, errors in the calculation of the number of moles of each DNA unit fragment conducted based on the measurement of the DNA concentration in the solution were further reduced.

In Example 1 and Example 2, designing each DNA unit fragment was conducted in a way that the base sequence of each DNA assembly when divided by the number of kinds of its constituent DNA unit fragments into equal parts had a non-palindromic sequence near each boundary between two adjacent equal parts, and that each DNA unit fragment was separated by the non-palindromic sequence from an adjacent DNA unit fragment. The DNA unit fragments thus designed had substantially the same length. When the DNA unit fragments were subjected to removal of corresponding auxiliary sequences with restriction enzymes and to subsequent electrophoresis for size-based selection, the DNA unit fragments were observed as a band at substantially the same position, allowing recovery of all the DNA unit fragments to be completed in a single session of size-based selection. Therefore, operation efficiency was enhanced.

In Example 1, the DNA unit fragments were divided into groups, each group for a single restriction enzyme to be used for removal of the corresponding auxiliary sequence (3 kinds of restriction enzymes in Example 1, 1 kind of restriction enzyme in Example 2). In this case, each group consisted of two or more solutions each containing a different DNA unit fragment. The two kinds or more solutions could be mixed together before the removal step. As a result, a separate session of restriction enzyme treatment was not required for respective DNA unit fragment, but, instead, a single session of restriction enzyme treatment was enough to treat an entire restriction-enzyme group. Consequently, the operation efficiency of DNA concatemer construction was enhanced. It was confirmed that even such mixture is used, the number of moles of many DNA unit fragments were substantially the same when mixed together, and therefore the many DNA unit fragments were successfully joined together as described above.

(Test Example 1, Checking level of repeating unit of redundancy (r) of DNA assembly unit required for transformation of *Bacillus subtilis* DNA plasmid)

In order to check the level of the repeating number (redundancy) r of DNA assembly unit required for transformation of *Bacillus subtilis* DNA plasmid, the following test was conducted.

The plasmid pGETS118-t0-Pr-SfiI-pBR (SEQ ID NO:1) harboring an origin of replication effective in *Bacillus subtilis* was used to prepare the following DNA molecules (A) to (H).

<Preparation of DNA (A)>

The DNA (A) was a circular monomeric DNA plasmid with redundancy of r=1. First, *Escherichia coli* was transformed with pGETS118-t0-Pr-SfiI-pBR. Most of the plasmids obtained from the resulting transformant were the DNA (A), but a small amount of multimers were also contained. In order to remove the multimers, all the plasmids obtained were subjected to electrophoresis in agarose gel with low melting temperature for DNA-size-based selection, and only the monomeric DNA plasmid region was cut out from the gel and purified. Thus, the DNA (A) was prepared.

<Preparation of DNA (B)>

The DNA (B) was a linear monomeric DNA plasmid with redundancy of r=1. The DNA (B) was prepared by treating the DNA (A) with the restriction enzyme BlpI (the recognition site thereof was (5'-GC/TNAGC-3')).

<Preparation of DNA (C)>

The DNA (C) was a tandem-repeat linear multimeric DNA plasmid with redundancy of r>1. BlpI used for preparing the DNA (B) above formed a 3-base non-palindromic protruding sequence at the 5' end. Accordingly, by joining molecules of the DNA (B) to each other with DNA ligase, a continuous linear multimeric DNA plasmid having its plasmid units arranged in a certain orientation was prepared, which was the DNA (C).

<Preparation of DNA (D)>

The DNA (D) was a linear monomeric DNA plasmid with redundancy of r=1. The DNA (D) was prepared by treating the DNA (A) with the restriction enzyme EcoRI (the recognition site thereof was (5'-G/AATTC-3')).

<Preparation of DNA (E)>

The DNA (E) was a linear multimeric DNA plasmid including a portion with partially redundancy of r>1 and composed of molecules of the DNA (D) joined together in a random orientation. EcoRI used for preparing the DNA (D) above formed a 3-base palindromic protruding sequence at the 5' end. Accordingly, by joining DNA plasmids that were cleaved with EcoRI, it was possible to construct a multimeric DNA plasmid having its plasmid units joined in a random orientation. The DNA (E) was prepared by joining molecules of the DNA (D) above to each other with DNA ligase.

<Preparation of DNA (F)>

The DNA (F) was a linear semi-monomeric mixture with r 1. The DNA (F) was prepared as follows: the DNA (A) was cleaved only at a single site with the restriction enzyme KasI, dephosphorylated, and then cleaved with BlpI at a site near the above-cleaved site to give a DNA fragment; the DNA (A) was cleaved only at a single site with the restriction enzyme Afel, dephosphorylated, and then cleaved with BlpI at a site near the above-cleaved site to give a DNA fragment; and mixing both of these resulting DNA fragments in equal amount. Each of the DNA fragments in the mixture (F) had redundancy r which is slightly lower than 1.

<Preparation of DNA (G)>

The DNA (G) was a linear semi-dimer DNA plasmid with redundancy of r=1.98. The DNA (G) was prepared by joining 2 DNA fragments (F) above with DNA ligase, and the orientation therein was regulated by its BlpI sites alone.

<Preparation of DNA (H)>

The cleavage site in the DNA (B) and the cleavage site in the DNA (D) were away from each other. The DNA (H) was a mixture prepared by not joining but mixing the DNA (B) and the DNA (D) in equal number of moles.

<Transformation of *Bacillus subtilis* Competent Cell with DNA (A) to DNA (H)>

Figure 17:
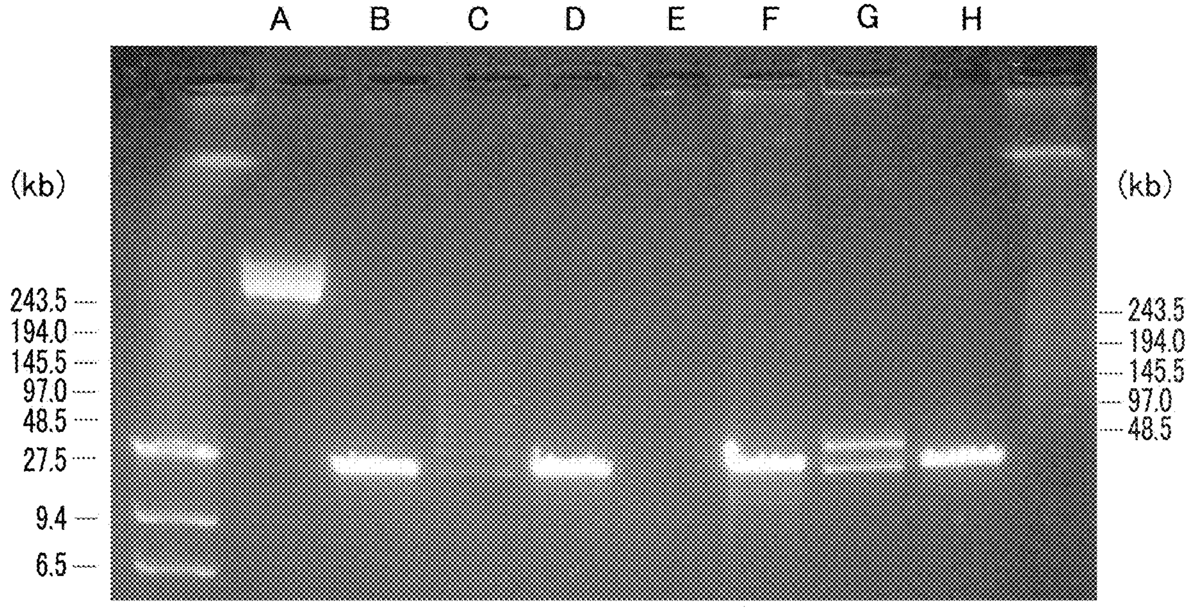
FIG. 17 a photograph showing the result of electrophoresis analyzing a DNA (A) to a DNA (H) used in Test Example 1.

A *Bacillus subtilis* competent cell was transformed with each of the DNA (A) to the DNA (H). Based on the appearance number of the tetracycline-resistant strains as index, the number of transformants per 1 μg was determined. Each of the DNA (A) to the DNA (H) for use in transformation was dissolved in ligation buffer regardless of whether the DNA was to be subjected to ligation reaction. FIG. 17 is a photograph showing the result of electrophoresis analyzing the DNA (A) to the DNA (H), and FIG. 18 shows the appearance number of transformants obtained by transformation of *Bacillus subtilis* competent cell with the DNA (A) to the DNA (H). It is noted that in the photograph of electrophoresis in FIG. 17, the lanes of the DNA (C) and the DNA (E) had DNA molecules of various sizes widely distributed across each lane, making the bands difficult to distinguish. As for the lane "G" in FIG. 17, the upper band was attributed to the DNA (G) with redundancy of r=1.97, and the lower band was attributed to DNA with redundancy of r=0.95 as a contaminant in the DNA (G).

It was confirmed that these results showed that transformants were obtained only with the ligation, namely, the DNA (C), the DNA (E), and the DNA (G), with the circular DNA (A) not counted. As indicated by these results, no transformant would be obtained with redundancy being r=1 or r<1 even when the DNA molecule was prepared by mixing 2 kinds of linear plasmid molecules having different cleavage sites that would be able to compensate for each other. As a result, it was indicated that redundancy of a linear DNA molecule needed to satisfy r>1 at lowest.

(Simulation 1, Ligation Simulation)

<Setting Algorithm for Ligation Simulation>

Simulation was programmed on VBA of spreadsheet software Excel (registered trademark) 2007. The DNA fragment F used in virtual ligation was expressed as 3 parameters, Fi(Ni, Li, Ri). "i" referred to the identification number of the fragment, more specifically the number on the cell in the row i on Excel. "N" referred to the number of DNA unit fragments in a single ligation DNA fragment molecule in virtual ligation. "L" referred to an arbitrary natural number that represented the sequence of the left protruding end of the ligation product. Similarly to "L", "R" referred to an arbitrary natural number that represented the sequence of the right protruding end of the ligation product. When L=R, the 2 protruding sequences were complementary to each other. Therefore, the relationship L=R defines that ligation was eligible to occur. Ligation simulation was conducted as follows.

The random number j that satisfied i≠j was obtained by generating a uniform random number between 0 and 1 by the RAND 0 method, multiplying the resulting number by m (described below), and rounding off the resulting number to give an integer. This resulting integer was applied to the fragment Fi(Ni, Li, Ri) to give the fragment Fj(Nj, Lj, Rj). Whether these 2 fragments were to be successfully joined together was determined according to the following discrimination formulae, and when they were to be successfully joined together, the parameters of these fragments were converted as follows.

When Li=Rj was satisfied, in other words, when the left end of Fi and the right end of Fj were to be successfully joined together, conversion was made to give the fragment Fi(new)(Ni(old)+Nj(old), Lj(old), Ri(old)) and the fragment Fj(new)(0, 0, 0). In contrast, when Ri=Lj was satisfied, in other words, when the right end of the fragment Fi and the left end of the fragment Fj were to be successfully joined together, conversion was made to give the fragment Fi(new)(Ni(old)+Nj(old), Li(old), Rj(old)) and the fragment Fj(new)(0, 0, 0). When Li≠Rj and Ri≠Lj were satisfied, no conversion was made (giving (the fragment Fi(new)(Ni(old), Li(old), Ri(old)) and the fragment Fj(new)(Nj(old), Lj(old), Rj(old))), where no virtual ligation was to occur. The same calculation conducted sequentially with i=1 m was defined as 1 cycle of virtual ligation. Here, the variable m referred to the total number of DNA fragments in the virtual ligation cycles, and for the 1st simulation cycle, the variable m referred to the total number of DNA unit fragments to start with. After calculation for the 1st cycle of virtual ligation, calculation for the next cycle of virtual ligation was conducted by rearranging the fragments Fi by the sorting function (the Sort method) in the VBA command of Excel 2007 so that the values Li were arranged in descending order, counting the total number of the fragments Fi except for the fragment F(0, 0, 0), and using the resulting total number as a variable m for the new cycle. Virtual ligation was repeated until the number of fragments reached the minimum mmin where there were no more protruding fragments complementary to each other and therefore no more cycle of virtual ligation was possibly conducted. The value mmin was determined according to the following calculation based on data about the starting DNA unit fragments, namely, the pre-ligation DNA unit fragments.

mmin=(total number of DNA unit fragments)−(total number, across entire system, of 1 out of 2 kinds of DNA unit fragments both satisfying L=R, that was fewer than the other)

<Ligation Simulation>

Virtual DNA unit fragment groups each of which consisted of 6 fragments, 13 fragments, 26 fragments, or 51 fragments assembled together were formed as follows. The virtual DNA unit fragment groups contained a fixed number, 640, of DNA unit fragments on average, and had a coefficient of variation (CV) that was set to increase sequentially by 1% from 0% to 20%.

The virtual DNA unit fragment groups were formed respectively by generating a group of random numbers from 0 to 1 corresponding to each assembly size by the uniform random number command RAND ( ) of Excel, standardizing the group of random numbers with average value of 0 and variance of 1, multiplying each standardized random number by (fragment average value*CV (%)/100), and adding the average value of fragments to the resulting number. For each assembly size, independent 20 groups of random numbers were constructed each for one of the CV (%) values. Each of these groups of random numbers underwent virtual ligation by the simulation, which was conducted until mmin was reached. The resulting 20 virtual ligation fragments were combined together, and the total number of ligation fragments for each N value was obtained. The ratio of (N value×number of ligation fragments) to the total number of DNA unit fragments used in ligation was determined. A 100-% stacked graph was created such that the value attributed to a molecule with a higher N value was plotted lower in the graph. Such graphs are shown in FIG. 19. FIG. 19 shows distribution of the sizes of ligation products to which the starting DNA unit fragments were eventually taken up. FIG. 19A is a graph for the 6-fragment assembly, FIG. 19B is a graph for the 13-fragment assembly, FIG. 19C is a graph for the 26-fragment assembly, and FIG. 19D is a graph for the 51-fragment assembly. In the case of the 6-fragment assembly, redundancy of r=1 region was reached at n=6 and the upper right region indicated where redundancy satisfied r<1. These results showed that: in the case of the 6-fragment assembly, most DNA unit fragments were taken up by DNA fragments that had redundancy of r>1, at any CV value; and, in contrast, in the case of the 51-fragment assembly, redundancy was lower than 1 in most of the region except for the region where CV was near 0%.

<Obtaining Theoretical Formula for Ligation from Ligation Simulation>

Figure 20:
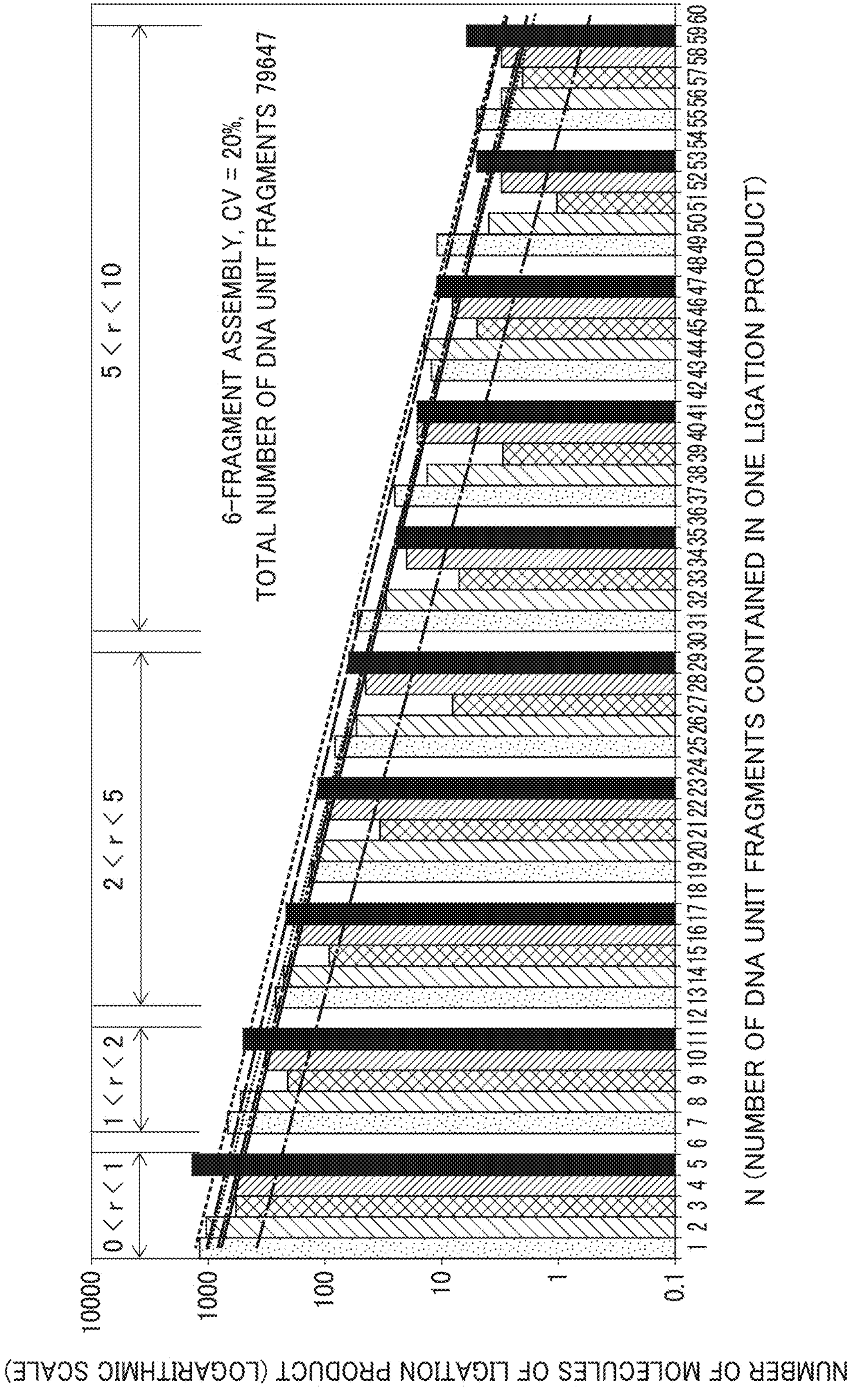
FIG. 20 a graph showing the relationship between N (the number of DNA unit fragments in one ligation product) and the number of molecules of ligation products, analyzed for a 6-fragment assembly in simulation 1 with CV=20%.

The results of the ligation simulation were numerically analyzed in order to obtain a general formula for the ligation mechanism. First, whether it was possible to plot a fitting curve for the distribution of the sizes of ligation products for each CV value for each assembly size was evaluated. FIG. 20 is a diagram for the case of the 6-fragment assembly comprising 640 fragments on average, and it shows distribution of the number of DNA unit fragments contained in a ligation product at CV=20%. In FIG. 20, different patterns that filled the rectangles drawn for the same redundancy (0<r<1, 1<r<2, 2<r<5, or 5<r<10) indicated the different components generated by dividing N for each pattern by r for each redundancy range (5 components in the case of the 6-fragment assembly, calculated by subtracting 1 component that gave a reminder of 0 when dividing N by r and therefore was not eligible for logarithmic transformation, from 6 components each of which gave a remainder of 0, 1, 2, 3, 4, or 5). Rectangles with the same pattern across different redundancy ranges were attributed to the same kind of component generated by dividing N value by r. Each linear approximation curve in the diagram shown in FIG. 20 was plotted for components that shared the same pattern.

The number of molecules contained in a ligation product for each N value shown in the histogram had a general tendency to exponentially decrease as N value increased, and appeared to be close to geometric distribution, which was one type of discrete probability distribution. Microscopically, however, the histogram displayed a periodic model consisting of cycles each of the size of the gene assembly, namely, the size of one redundancy unit (6 in the case of the 6-fragment assembly). The histogram displayed a characteristic pattern where no fragment occurred for N value being equal to an integral multiple of the size of the gene assembly. This particular characteristic was not in complete agreement with geometric distribution or with exponential distribution regarded as continuous probability distribution. However, when converting the axis that showed the number of molecules in a ligation product into logarithmic expression, selecting and taking out, from each cycle, the components that constituted the same microscopic cycle, in other words, the components that gave the same remainder when N was divided by 6 or the size of the assembly, and plotting a linear approximation curve, the resulting linear approximation curve had the second power of a very high correlation coefficient (0.94 or greater). Therefore, it was considered that there was no problem when a linear approximation curve created for each component displayed exponential distribution. The same distribution as displayed by the case of the 6-fragment assembly where CV value as variation in the concentration was 20%, shown in FIG. 20, was also observed for other assembly sizes and other CVs. Thus, based on the assumption that this mechanism was eligible to be heuristically approximated to exponential distribution, fitting to exponential distribution function ($f(n)=\lambda*\exp(-\lambda*n)$) was conducted hereinafter.

Figure 21A:
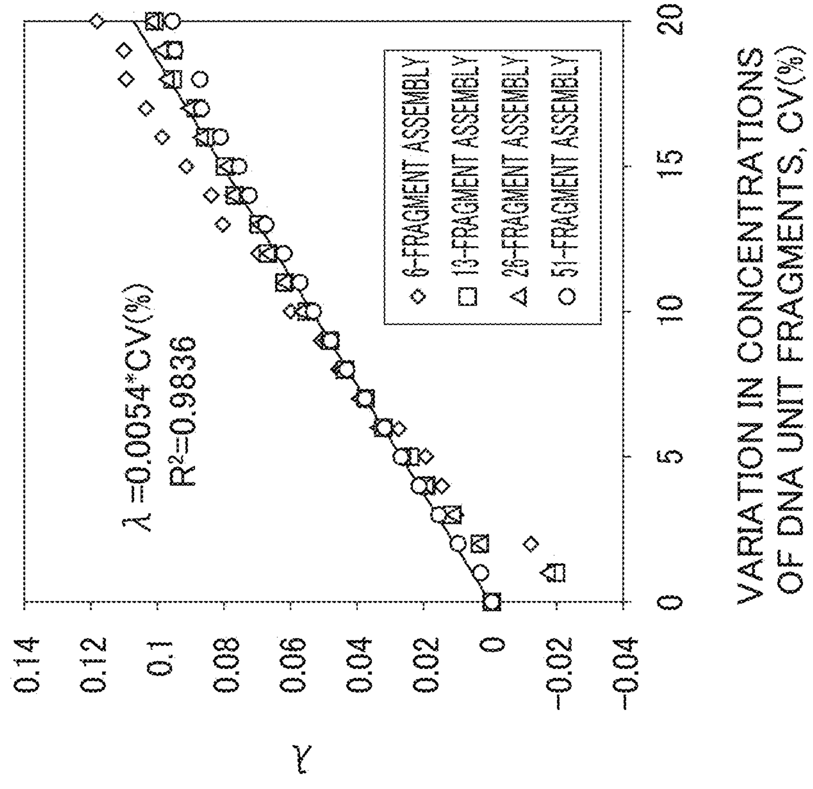
FIGS. 21A-21B FIG. 21A is a graph showing λ function of CV (%) indicating variation in the concentrations of DNA unit fragments obtained from fitting to an exponential distribution curve in simulation 1.
Figure 21B:
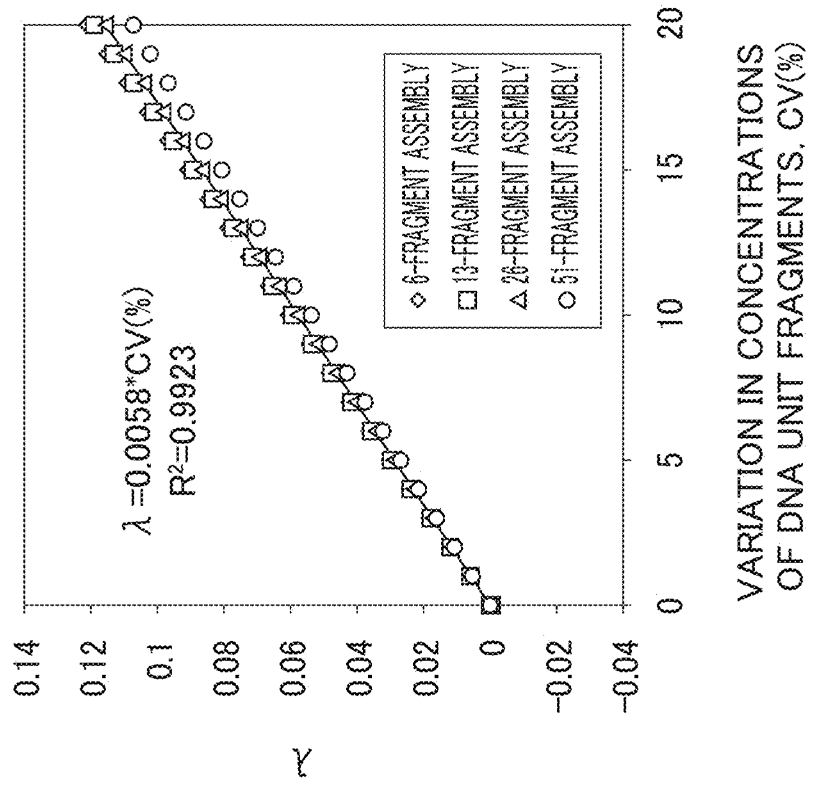

Specific procedure was as follows: (1) in the results of simulation conducted for each assembly size described above, the number of molecules for about 3 cycles as for each of the components that gave the same remainder when N was divided by the size of the assembly was subjected to logarithmic transformation, and the resulting values were used to create a linear approximation curve, followed by determining the slope ($-\lambda$) of the straight line and calculating the value $\lambda$;

and (2) next, in consideration that the average value of f(N) in the exponential distribution function was the reciprocal of the parameter $\lambda$, namely, $1/\lambda$, the average value of N of ligation products for the 20 groups of random numbers was determined, and the reciprocal of the resulting average value was used to determine $\lambda$ for each CV (%) (CV (%)). The results of (1) and (2) were plotted, with setting the abscissa showing the CV (%) value of variation of concentrations of DNA unit fragments and the ordinate showing the $\lambda$ value. As a result, it was shown that all the plottings for each size of the gene assembly were on a direct proportional straight line passing through a certain original point. A linear approximation curve was determined for each set of these plottings, as shown in FIG. 21. In FIG. 21, A is a graph showing the relationship between the slope X determined for the 3 cycles in (1) and variation in the concentrations of DNA unit fragments, and B is a graph showing the relationship between X determined from the reciprocal of the average N value in (2) and variation in the concentrations of DNA unit fragments. From (2) with higher accuracy, the general formula of these linear approximation curves was derived: $f(N)=0.0058*CV\ (\%)*\exp(-0.0058*CV\ (\%)*N)$. From FIG. 21, it was found that the second power of correlation coefficient of $\lambda=0.0058*CV$ (%) was expressed as 0.99, indicating high correlation. Thus, this general formula was confirmed to have no problem.

<Qualitative Analysis of Reaction Rate of Ligation>

The ligation simulation described above was intended to represent a state where ligation between all reasonable protruding-end combinations had been fully completed. Here, in order to examine how close the ligation reaction conditions in actual gene assembly were to reaction conditions in simulation, the kinetics of ligation reaction were analyzed.

First, in ligation reaction conducted under the conditions in actual gene assembly, samples of the ligation products were taken at various reaction times. A 51-fragment concatemer for $\lambda$ phage reconstruction was used, and all the 51 joints were qualitatively analyzed to evaluate the degree of actual joining. The average concentration of the DNA unit fragments used in ligation was about 0.2 fmol/μl. To the DNA unit fragment solution, T4 DNA ligase was added. After 0 minute, 1.25 minutes, 2.5 minutes, 5 minutes, 10 minutes, 20 minutes, 40 minutes, 80 minutes, 160 minutes, and 320 minutes at 37° C., a sample of each reaction solution was taken. Then the progress of ligation of each fragment was evaluated using a primer set for quantitative PCR designed to amplify DNA stretching across the joint between 2 DNA unit fragments being reasonably joined, a primer set for quantitative PCR designed to amplify only inside each DNA unit fragment, and, as an indicator, the dilution series of DNA that was produced by cleaving with a restriction enzyme a commercially available $\lambda$ phage genomic DNA (Toyobo Co., Ltd.) or an assembly-harboring plasmid constructed in advance and then rendering the resulting DNA fragment linear. The results showed that ligation had been completed in about 10 minutes at any joint under these reaction conditions, indicating that ligation would be substantially fully completed in the actual reaction time of 4 hours (240 minutes). The results also showed that the ratio of the number of joints after sufficient time (after 40 minutes) to the number of the kind of the DNA unit fragments that was fewer than the other was substantially 1, indicating that most of the ligated DNA fragments joined to their correct ligation partners.

<Estimation of Misligation Rate>

Figure 22:
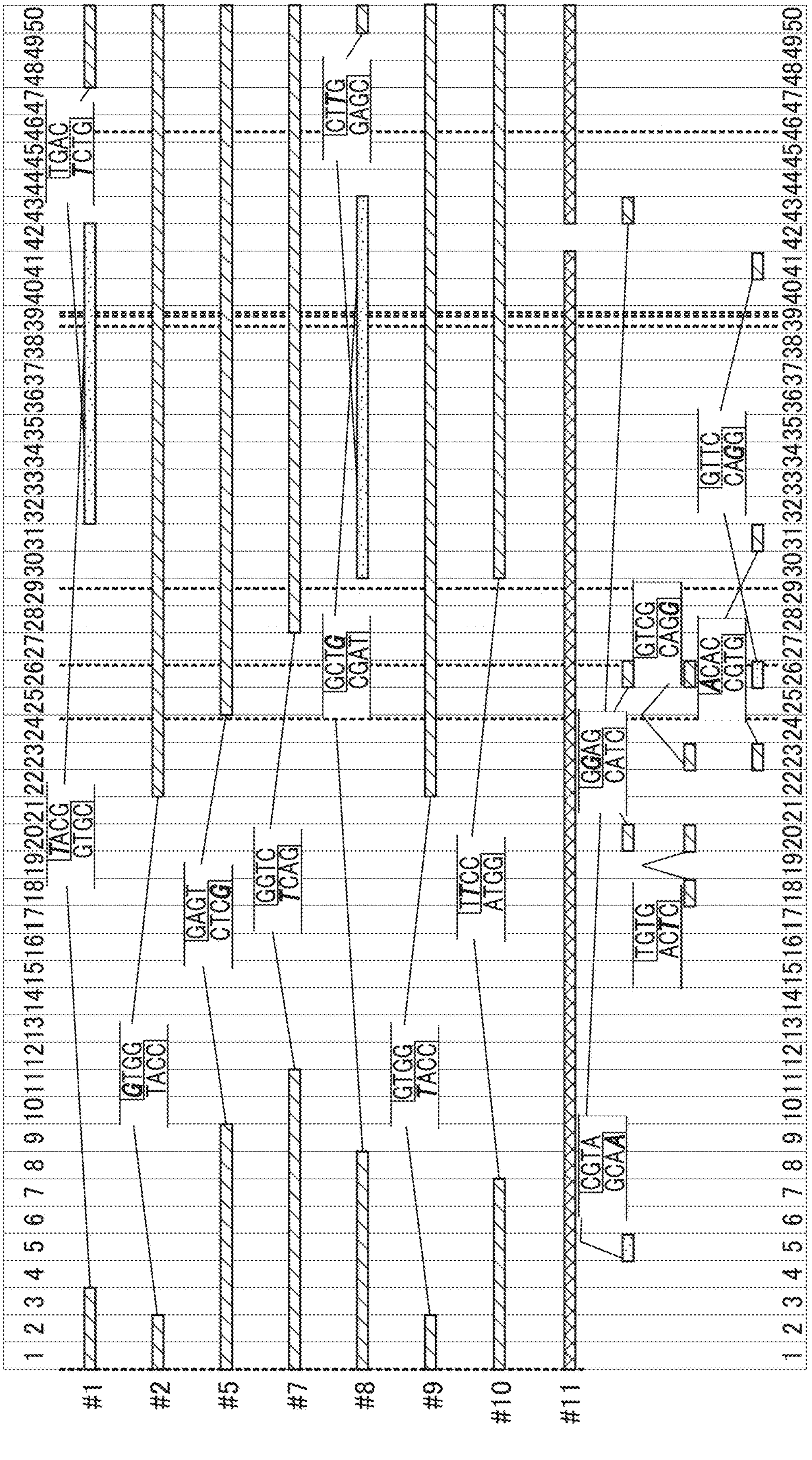
FIG. 22 an illustration showing misligation sites in assemblies #1, #2, #5, #7, #8, #9, #10, and #11 among assemblies resulting from experiment of reconstruction of λ phage genome in simulation 1.

The state of ligation was studied in more detail. Among the assemblies obtained in the experiment above of reconstruction of $\lambda$ phage genome, all the clones except for clones #3, #4, #6, and #12 with their entire base sequences completely determined (namely, clones #1, #2, #5, #7, #8, #9, #10, and #11) were subjected to base sequencing in order to identify ligation site between a wrong combination. FIG. 22 shows misligation sites for each of these clones. The results showed that each of the 7 clones except for the clone #11 had 1 or 2 misligation sites within the sequence, and all of these misligation sites were successfully identified. The clone #11 had the same DNA unit fragments occurring repeatedly within the DNA assembly and was found to have 6 misligation sites in total. No thorough structural identification was conducted. As for all the clones except for the clone #11 with its accurate number of DNA unit fragments unknown, the appearance frequency of misligation was determined. As a result, the rate of misligation was found to be about 1 in 46 joints, which was equal to a relatively low rate of misligation of about 2.2%. These results were in agreement with the results from quantitative PCR above.

<Distribution of Sizes of Actual Ligation Products, and Verification of Agreement with Simulation>

From these two analyses described above, namely, estimation of the misligation rate and qualitative analysis of reaction rate of ligation, it was presumed that ligation would be substantially fully completed in actual ligation reaction after a sufficient amount of time of 4 hours and that the probability of misligation was low. Then, as for actual DNA unit fragment groups with variation occurring in the concentration of the starting DNA unit fragments, whether distribution of the sizes of actual ligation products was predictable by simulation was studied, as follows.

Figure 23:
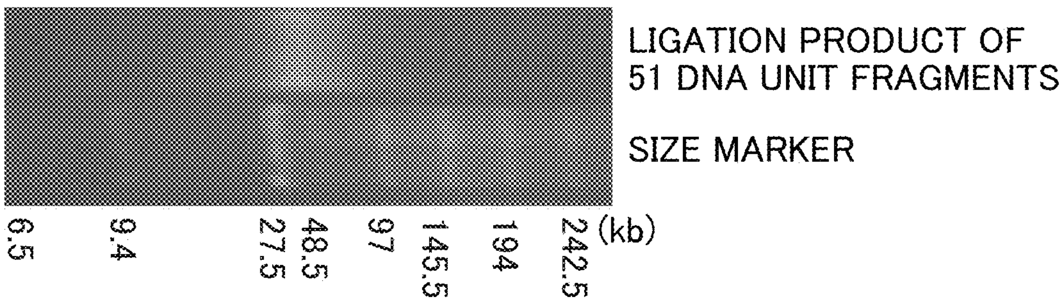
FIG. 23 a photograph showing the result of pulsed-field gel electrophoresis analyzing the product of ligation of 51 DNA unit fragments with CV=6.6% variation in the number of fragments in experiment of reconstruction of λ phage genome in simulation 1.
Figure 24A:
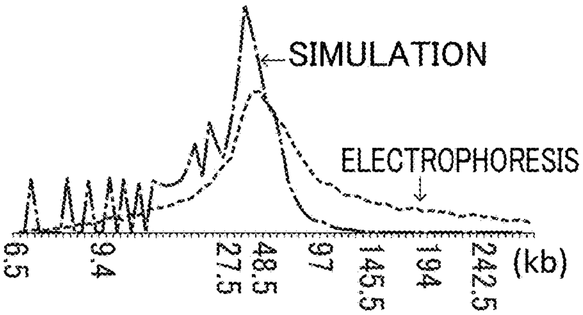
FIGS. 24A-24F are graphs comparing actual ligation efficiency and ligation efficiency in ligation simulation in simulation 1.
Figure 24D:
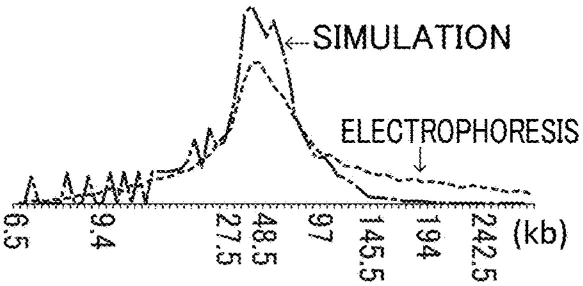
Figure 24B:
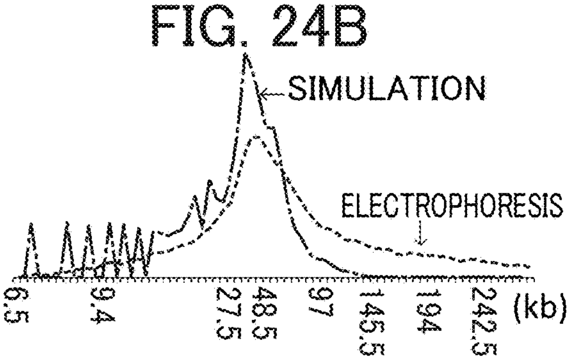
Figure 24E:
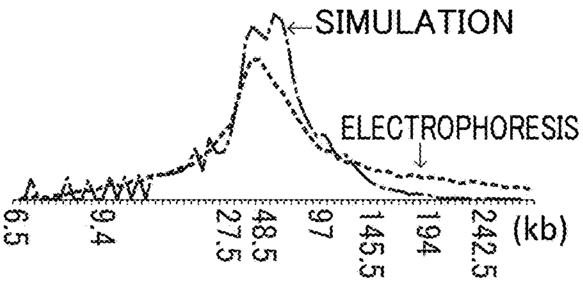
Figure 24C:
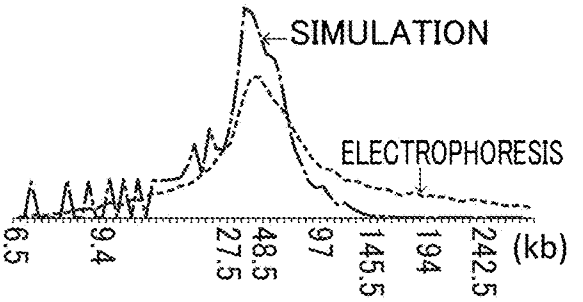
Figure 24F:
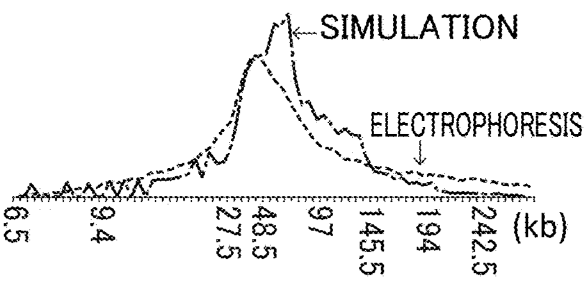

Analysis was conducted on the groups used in the experiment of reconstruction of $\lambda$ phage genome. The groups had variation in the concentrations of DNA unit fragments with 7.5% of CV as observed by quantitative PCR. An observed value resulting from quantitative PCR involved measurement errors of CV=3.6%. Therefore, the true CV value for DNA unit fragment variation was presumably and possibly lower than CV=7.5%. Simulation was conducted to determine a CV value that was potentially the true CV value. As a result, when the true CV value was 6.6%, the observed value was presumably and possibly CV=7.5% due to measurement errors of CV=3.6%. In consideration of the true DNA unit fragment variation being CV=6.6%, simulation was conducted so as to simulate ligation of 51 kinds of starting DNA unit fragments under conditions of average 640 fragments prepared for the RAND 0 method and CV=6.6%. The simulation reaction was conducted until not only mmin indicating 100% reaction rate was reached but also a designated m value was reached. The designated m value was obtained by determining m values for ligation-eligible rates of 95%, 96%, 97%, 98%, and 99% ligation, preparing 100 independent groups of random numbers for each m value, and determining the designated m value. The distribution patterns of obtained ligation products displayed by these 100 groups were combined together, and the length (bp) of DNA of each virtual ligation product of DNA unit fragments was determined by using the parameters F(N, L, R). Then, the actual DNA unit fragment groups used in experiment of reconstruction of λ phage genome with variation in the number of fragments of CV=6.6% were, as described in the paragraph "Qualitative analysis of reaction rate of ligation" above, subjected to reaction at 37° C. for 4 hours, followed by electrophoresis on a CHEF-type pulsed-field gel electrophoresis system (manufactured by Bio Craft Co., Ltd.) for 16 hours under electrophoresis conditions of 0.5×TBE, 5 V/cm, and 30 sec per cycle, in order to see the actual distribution of the molecular weight of DNA. FIG. 23 is a photograph showing the result of the electrophoresis. From the resulting electrophoresis photograph, a DNA density distribution pattern was acquired on NIH image software, and the pattern thus acquired was overlaid with expected DNA distribution patterns obtained for each ligation efficiency determined from simulation, for comparison. The results are shown in FIG. 24. FIG. 24 showed that the distribution pattern of the molecular weight of DNA resulting from the electrophoresis was in near agreement with the expected DNA distribution patterns for ligation efficiency from 98% to 100%. In particular, the maximum molecular weight indicating the maximum concentration was in excellent agreement with the expected DNA distribution pattern for ligation efficiency of 98%. These simulation results showed that ligation was substantially fully completed within 4 hours of ligation reaction and simulation was able to nearly perfectly reproduce ligation with mere misligation of about 2%.

<Generalization of Ligation Simulation>

Figure 25:
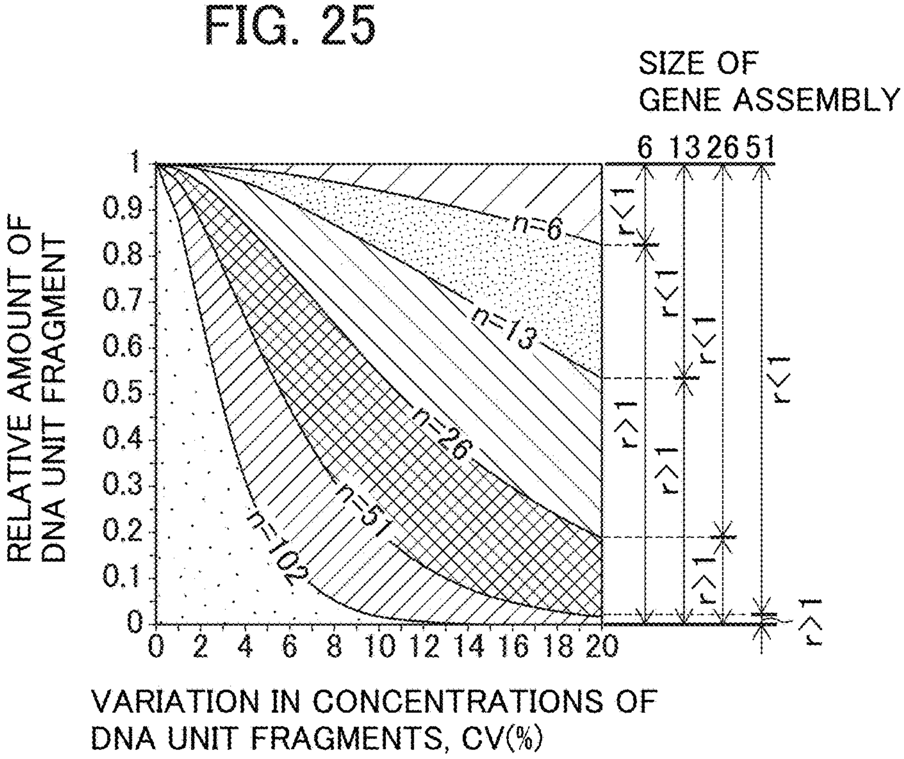
FIG. 25 a graph showing the relationship between CV (%) indicating variation in the concentrations of DNA unit fragments and the relative amount of each kind of DNA unit fragment, obtained by using the formula f(N)=0.0058*CV (%)*exp(−0.058*CV (%)*N). The analysis was conducted for each gene assembly size in simulation 1.
Figure 26:
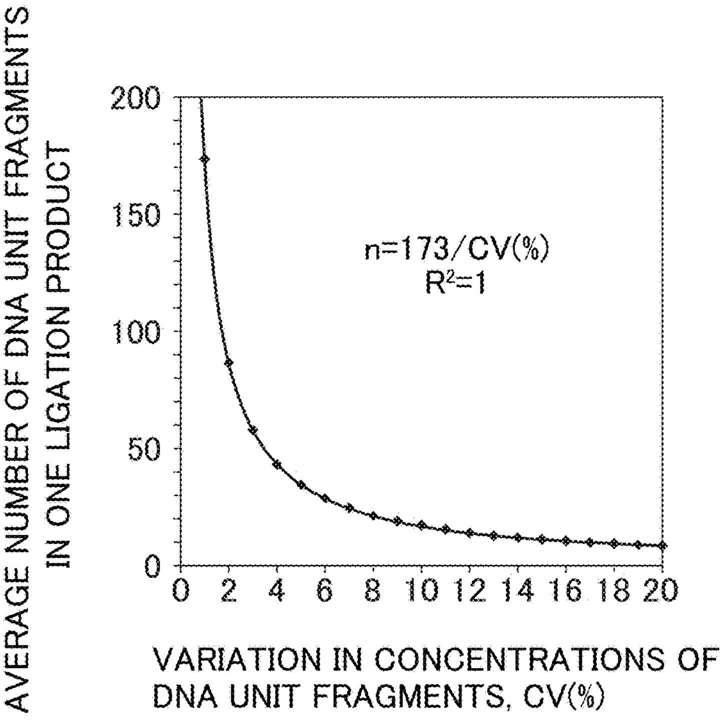
FIG. 26 a graph showing the relationship between variation in the concentrations of DNA unit fragments and the average number of DNA unit fragments in one ligation product, obtained by using the formula f(N)=0.0058*CV (%)*exp(−0.0058*CV (%)*N).

DNA unit fragments used in actual assembly cannot be free from variation in the concentration. How well actual variation in the concentrations of DNA unit fragments needed to be regulated was summarized based on the general formula f(N)=0.0058*CV (%)*exp(−0.0058*CV (%)*N) determined above, and was shown in FIG. 25. Although variation in DNA concentration was approximately CV (%)=6.6 in the gene-assembling experiment above, FIG. 25 shows that, when CV (%)=6.6, about 40% of the DNA unit fragments used in the 51-fragment assembly was taken up by a ligation product with an r value of greater than 1. FIG. 25 also shows that, when a novel 102-fragment gene assembly, twice the size of the 51-fragment assembly, is designed, it is necessary to achieve CV (%)=3.3 in order to obtain the same level of assembly efficiency as for the 51-fragment assembly. By the formula f(N)=0.0058*CV (%)*exp(−0.0058*CV (%)*N), the relationship between variation in the concentrations of DNA unit fragments and the average number of DNA unit fragments in one ligation product was determined. The results are shown in FIG. 26. It was shown that, the formula f(N)=0.0058*CV (%)*exp(−0.0058*CV (%)*N) made it possible to easily presume the average number of DNA unit fragments contained in one ligation product with a CV (%) value.

SEQUENCE LISTING

The invention claimed is:

1. A method of preparing a DNA unit fragment composition, comprising:

preparing solutions containing multiple kinds of DNA unit fragments, each solution containing one of the multiple kinds of DNA unit fragments, each DNA unit fragment being attached to a corresponding auxiliary sequence; and after preparing each solution, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is substantially the same as the number of moles of DNA unit fragment in another portion, and combining each of the portions to prepare the DNA unit fragment composition, wherein the DNA unit fragments are used to construct a DNA concatemer, the DNA concatemer comprising DNA assemblies each comprising the DNA unit fragments, and the preparing solutions containing multiple kinds of DNA unit fragments comprises a step of designing each DNA unit fragment, the designing being conducted in a way that in the base sequence of each DNA assembly a non-palindromic sequence is present between two adjacent DNA unit fragments, and each DNA unit fragment has the non-palindromic sequence at an end and is separated by the non-palindromic sequence from an adjacent DNA unit fragment.

2. The method of preparing a DNA unit fragment composition according to claim 1, wherein each DNA unit fragment with the corresponding auxiliary sequence attached thereto has a circular structure, and each corresponding auxiliary sequence is a plasmid DNA sequence harboring an origin of replication.

3. The method of preparing a DNA unit fragment composition according to claim 1, wherein a standard deviation of the sum of the length of the base sequence of each DNA unit fragment and the length of the base sequence of the corresponding auxiliary sequence attached to the DNA unit fragment is within −20% plus or minus the average value of the sum of the lengths.

4. The method of preparing a DNA unit fragment composition according to claim 1, wherein the average length of the base sequence of the corresponding auxiliary sequence attached to each DNA unit fragment is twice or greater than the average length of the base sequence of the DNA unit fragment.

5. The method of preparing a DNA unit fragment composition according to claim 1, wherein each DNA unit fragment is not longer than 1600 bp.

6. A method of constructing a DNA concatemer to be used for microbial cell transformation, the DNA concatemer comprising more than one DNA assembly unit, each of the more than one DNA assembly unit comprising a DNA vector harboring an origin of replication effective in a host microorganism and a DNA assembly, the method comprising:

preparing a DNA unit fragment composition in a solution by the method as claimed in claim 1;

preparing the DNA vector;

removing with a restriction enzyme a corresponding auxiliary sequence from each DNA unit fragment with the corresponding auxiliary sequence attached thereto contained in the solution after preparation; and after the removal step, joining the DNA vector and each of the DNA unit fragment together, wherein each of the DNA vector and the DNA unit fragment is structurally capable of being joined repeatedly while maintaining a certain order, and each DNA assembly comprises of a DNA molecule in which the DNA unit fragment is joined to one another.

7. The method of constructing a DNA concatemer according to claim 6, further comprising:

based on a relation between the yield of a DNA fragment comprising a target number of DNA unit fragments joined together and a coefficient of variation for the concentration of this DNA fragment, the yield being equal to the product of the number of DNA unit fragments per assembly unit and the number of the assembly unit, adjusting a coefficient of variation for the concentrations of the DNA vector and each DNA unit fragment in the joining step.

8. The method of constructing a DNA concatemer according to claim 6, wherein the restriction enzyme is a Type II restriction enzyme.

9. The method of constructing a DNA concatemer according to claim 6, further comprising:

before the removal step, mixing two or more solutions containing DNA unit fragments selected from the solutions containing DNA unit fragments.

10. The method of constructing a DNA concatemer according to claim 6, further comprising:

after the removal step and before the joining step, inactivating the restriction enzyme.

11. The method of constructing a DNA concatemer according to claim 6, wherein the microorganism is *Bacillus subtilis*.

12. The method of claim 1, wherein a molar ratio among each of the different portions is 1.

13. A method of preparing a DNA unit fragment composition, comprising:

preparing solutions containing multiple kinds of DNA unit fragments, each solution containing one of the multiple kinds of DNA unit fragments, each DNA unit fragment being attached to a corresponding auxiliary sequences; and after preparing each solution, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is substantially the same as the number of moles of DNA unit fragment in another portion, and combining each of the portions to prepare the DNA unit fragment composition, wherein the average length of the base sequence of the corresponding auxiliary sequence attached to each DNA unit fragment is twice or greater than the average length of the base sequence of the DNA unit fragment.

14. The method of preparing a DNA unit fragment composition according to claim 13, wherein a standard deviation of the sum of the length of the base sequence of each DNA unit fragment and the length of the base sequence of the corresponding auxiliary sequence attached to the DNA unit fragment is within 20% plus or minus the average value of the sum of the lengths.

15. The method of preparing a DNA unit fragment composition according to claim 13, wherein each DNA unit fragment is not longer than 1600 bp.

16. The method of claim 13, wherein the number of moles of DNA unit fragment in one portion is the same as the number of moles of DNA unit fragment in another portion.

* * * * *